(12) United States Patent
Mitsudera

(10) Patent No.: US 8,247,596 B2
(45) Date of Patent: Aug. 21, 2012

(54) HALOGEN-CONTAINING ORGANOSULFUR COMPOUND AND USE THEREOF

(75) Inventor: Hiromasa Mitsudera, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 164 days.

(21) Appl. No.: 12/665,670

(22) PCT Filed: Jun. 26, 2008

(86) PCT No.: PCT/JP2008/062035
§ 371 (c)(1),
(2), (4) Date: Feb. 4, 2010

(87) PCT Pub. No.: WO2009/005110
PCT Pub. Date: Jan. 8, 2009

(65) Prior Publication Data
US 2010/0160422 A1 Jun. 24, 2010

(30) Foreign Application Priority Data

Jun. 29, 2007 (JP) ................................. 2007-171883
Mar. 19, 2008 (JP) ................................. 2008-071102

(51) Int. Cl.
*C07C 317/10* (2006.01)
*C07C 317/18* (2006.01)
*C07C 317/24* (2006.01)
*A01N 41/10* (2006.01)

(52) U.S. Cl. ........ 560/150; 562/503; 562/505; 562/506; 568/74; 514/706; 514/708; 514/710

(58) Field of Classification Search .................. None
See application file for complete search history.

(56) References Cited

U.S. PATENT DOCUMENTS

| 4,118,389 A | 10/1978 | Magee |
| 2011/0160251 A1 * | 6/2011 | Nishiguchi et al. ........... 514/357 |

FOREIGN PATENT DOCUMENTS

| JP | 2005-179321 A | 7/2005 |
| SU | 1007338 A1 * | 4/1992 |
| WO | WO 2008/143332 A1 | 11/2008 |

OTHER PUBLICATIONS

Vidugiriene, et al., Lietuvos TSR Mokslu Akademijos Darbai, Serija B: Chemija, Technika, Fizine Geografija (1970), (4), 171-177.*
International Preliminary Report on Patentablity (Form PCT/IB/373) and Written Opinion of the International Searching Authority (Form PCT/ISA/237) issued in PCT/JP2008/062035, Jan. 5, 2010.
Office Action in Egyptian Application No. PCT1915/2009 mailed May 17, 2011, including an English translation.
Database Caplus Chemical Abstracts Service, Columbus, Ohio, US:XP002507465 retrieved from STN Database accession No. 2005:587220 abstract.
Office Action for corresponding Egyptian Patent Application No. PCT 2009121915, dated Dec. 12, 2011.

* cited by examiner

*Primary Examiner* — Kamal Saeed
*Assistant Examiner* — Nyeemah A Grazier
(74) *Attorney, Agent, or Firm* — Birch, Stewart, Kolasch & Birch, LLP

(57) ABSTRACT

There is provided a halogen-containing organosulfur compound having an excellent controlling effect on arthropod pests represented by the formula (I): wherein, m represents 0, 1 or 2, n represents 0, 1 or 2, A represents optionally substituted C3-C7 cycloalkyl or optionally substituted C5-C7 cycloalkenyl group, Q represents a C1-C5 haloalkyl group containing at least one fluorine atom, or a fluorine atom, $R^1$ and $R^3$ independently represent optionally substituted C1-C4 chain hydrocarbon, halogen or hydrogen, $R^2$ and $R^4$ independently represent optionally substituted C1-C4 chain hydrocarbon, —C(=G)$R^5$, cyano, halogen or hydrogen, G represents oxygen or sulfur, and $R^5$ represents optionally substituted C1-C4 alkyl, hydroxyl, optionally substituted C1-C4 alkoxy, optionally substituted C3-C6 alkenyloxy, optionally substituted C3-C6 alkynyloxy, amino, optionally substituted C1-C4 alkylamino, optionally substituted di(C1-C4 alkyl)amino, C2-C5 cyclic amino or hydrogen.

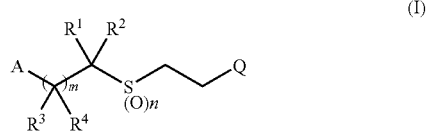

(I)

22 Claims, No Drawings

HALOGEN-CONTAINING ORGANOSULFUR COMPOUND AND USE THEREOF

TECHNICAL FIELD

The present invention relates to a halogen-containing organosulfur compound and its use for controlling arthropod pests.

BACKGROUND ART

Hitherto, many pesticidal compositions for controlling arthropod pests have been developed and used practically. Further, JP-A 2004-130306 discloses a certain halogen-containing organosulfur compound.

DISCLOSURE OF THE INVENTION

An object of the present invention is to provide a novel compound having an excellent controlling effect on arthropod pests and its use.

The present inventors have intensively studied to find out a compound having an excellent controlling effect on arthropod pests. As a result, they have found that a halogen-containing organosulfur compound represented by the following formula (I) has an excellent controlling effect on arthropod pests such as harmful insects and harmful mites. Thus, the present invention has been completed.

That is, the present invention provides:
(1) A halogen-containing organosulfur compound represented by the formula (I):

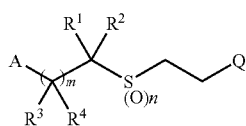

wherein m represents 0, 1 or 2, n represents 0, 1 or 2,

A represents a C3-C7 cycloalkyl group optionally substituted with a group selected from the groups E1 to E3, or a C5-C7 cycloalkenyl group optionally substituted with a group selected from the groups E1 to E3;

Q represents a C1-C5 haloalkyl group containing at least one fluorine atom, or a fluorine atom;

$R^1$ and $R^3$ are the same as or different from each other, and represent a C1-C4 chain hydrocarbon group optionally substituted with a halogen atom, a halogen atom, or a hydrogen atom;

$R^2$ and $R^4$ are the same as or different from each other, and represent a C1-C4 chain hydrocarbon group optionally substituted with a halogen atom, —C(=G)$R^5$, a cyano group, a halogen atom, or a hydrogen atom;

G represents an oxygen atom or a sulfur atom;

$R^5$ represents a C1-C4 alkyl group optionally substituted with a halogen atom, a hydroxyl group, a C1-C4 alkoxy group optionally substituted with a halogen atom, a C3-C6 alkenyloxy group optionally substituted with a halogen atom, a C3-C6 alkynyloxy group optionally substituted with a halogen atom, an amino group, a C1-C4 alkylamino group optionally substituted with a halogen atom, a di(C1-C4 alkyl)amino group optionally substituted with a halogen atom, a C2-C5 cyclic amino group, or a hydrogen atom;

the group E1 is a group of monovalent substituents consisting of a C1-C6 chain hydrocarbon group optionally substituted with a group selected from the group L, a C3-C6 cycloalkyl group optionally substituted with a halogen atom, —O$R^6$, —S$R^6$, —S(=O)$R^6$, —S(=O)$_2R^6$, —C(=O)$R^7$, —OC(=O)$R^8$, a halogen atom, a cyano group, and a hydroxyl group;

the group E2 is a group of bivalent substituents of which two valences are derived from one atom, consisting of =O, =NO—$R^6$, =C=CH$_2$, and =C($R^{11}$)$R^{12}$;

the group E3 is a group of bivalent substituents of which two valences are derived from different atoms, consisting of a C2-C6 alkylene group optionally substituted with a group selected from the group L, a C4-C6 alkenylene group optionally substituted with a group selected from the group L, -G-$T^1$-G-, and -G-$T^1$-G-$T^2$-; wherein $T^1$ and $T^2$ are the same as or different from each other, and represent a methylene group or an ethylene group;

the group L consists of a hydroxyl group, a C1-C4 alkoxy group optionally substituted with a halogen atom, a C3-C6 alkenyloxy group optionally substituted with a halogen atom, a C3-C6 alkynyloxy group optionally substituted with a halogen atom, —N($R^9$)$R^{10}$, a C2-C5 cyclic amino group, —C(=O)$R^7$, —OC(=O)$R^8$ and a halogen atom;

$R^6$ represents a C1-C4 chain hydrocarbon group optionally substituted with a group selected from the group L, or a C3-C6 cycloalkyl group optionally substituted with a group selected from the group L;

$R^7$ represents a hydroxyl group, a C1-C4 alkoxy group optionally substituted with a halogen atom, a C3-C6 alkenyloxy group optionally substituted with a halogen atom, a C3-C6 alkynyloxy group optionally substituted with a halogen atom, an amino group, a C1-C4 alkylamino group optionally substituted with a halogen atom, a di(C1-C4 alkyl)amino group optionally substituted with a halogen atom, a C2-C5 cyclic amino group, a C1-C4 alkyl group optionally substituted with a halogen atom, or a hydrogen atom;

$R^8$ represents a C1-C4 alkoxy group optionally substituted with a halogen atom, a C3-C6 alkenyloxy group optionally substituted with a halogen atom, a C3-C6 alkynyloxy group optionally substituted with a halogen atom, an amino group, a C1-C4 alkylamino group optionally substituted with a halogen atom, a di(C1-C4 alkyl)amino group optionally substituted with a halogen atom, a C2-C5 cyclic amino group, a C1-C4 alkyl group optionally substituted with a halogen atom, or a hydrogen atom;

$R^9$ and $R^{10}$ are the same as or different from each other, and represent a C1-C4 alkyl group optionally substituted with a halogen atom, a C3-C6 alkenyl group optionally substituted with a halogen atom, a C3-C6 alkynyl group optionally substituted with a halogen atom, a C3-C6 cycloalkyl group optionally substituted with a halogen atom, a phenyl group optionally substituted with a halogen atom, or a hydrogen atom; and $R^{11}$ and $R^{12}$ are the same as or different from each other, and represent a C1-C4 alkoxy group optionally substituted with a halogen atom, a C1-C4 chain hydrocarbon group optionally substituted with a halogen atom, a halogen atom, or a hydrogen atom (hereinafter, referred to as "the compound of the present invention");

(2) The halogen-containing organosulfur compound according to the above (1), wherein Q is a C1-C3 haloalkyl group containing at least one fluorine atom;

(3) The halogen-containing organosulfur compound according to the above (1), wherein Q is a C1-C5 fluoroalkyl group;

(4) The halogen-containing organosulfur compound according to the above (1), wherein Q is a C1-C3 fluoroalkyl group;

(5) The halogen-containing organosulfur compound according to any one of the above (1) to (4), wherein m is 0;
(6) The halogen-containing organosulfur compound according to any one of the above (1) to (4), wherein m is 1;
(7) The halogen-containing organosulfur compound according to any one of the above (1) to (6), wherein n is 0;
(8) The halogen-containing organosulfur compound according to any one of the above (1) to (6), wherein n is 1;
(9) The halogen-containing organosulfur compound according to any one of the above (1) to (6), wherein n is 2;
(10) The halogen-containing organosulfur compound according to any one of the above (1) to (9), wherein $R^2$ is a hydrogen atom;
(11) The halogen-containing organosulfur compound according to any one of the above (1) to (9), wherein $R^2$ is a C1-C4 alkyl group;
(12) The halogen-containing organosulfur compound according to any one of the above (1) to (9), wherein $R^2$ is a cyano group;
(13) The halogen-containing organosulfur compound according to any one of the above (1) to (9), wherein $R^2$ is —C(=G)$R^5$;
(14) The halogen-containing organosulfur compound according to any one of the above (1) to (9), wherein $R^2$ is —C(=G)$R^5$, G is an oxygen atom, and $R^5$ is an amino group, a C1-C4 alkylamino group optionally substituted with a halogen atom, a di(C1-C4 alkyl)amino group optionally substituted with a halogen atom, or a C2-C5 cyclic amino group;
(15) The halogen-containing organosulfur compound according to any one of the above (1) to (9), wherein $R^2$ is —C(=G)$R^5$, G is an oxygen atom, and $R^5$ is an amino group;
(16) The halogen-containing organosulfur compound according to any one of the above (1) to (15), wherein $R^1$ is a hydrogen atom, or a C1-C4 alkyl group optionally substituted with a halogen atom;
(17) The halogen-containing organosulfur compound according to any one of the above (1) to (15), wherein $R^1$ is a halogen atom;
(18) The halogen-containing organosulfur compound according to any one of the above (1) to (17), wherein A is a cyclohexyl group optionally substituted with a group selected from the groups E1 to E3, or a cyclohexenyl group optionally substituted with a group selected from the groups E1 to E3;
(19) The halogen-containing organosulfur compound according to any one of the above (1) to (17), wherein A is a cyclohexyl or cyclohexenyl group which is optionally substituted with a monovalent group selected from the group consisting of a C2-C6 alkynyl group optionally substituted with a group selected from the group L, a C2-C6 alkynyl group optionally substituted with a group selected from the group L, a halogen atom, and a cyano group;
(20) The halogen-containing organosulfur compound according to any one of the above (1) to (17), wherein A is a cyclohexyl group optionally substituted with a group selected from the group E2;
(21) A pesticidal composition which comprises the halogen-containing organosulfur compound according to any one of the above (1) to (20) as an active ingredient; and
(22) A method of controlling an arthropod pest which comprises applying an effective amount of the halogen-containing organosulfur compound according to any one of the above (1) to (20) to the arthropod pest or a place where the arthropod pest inhabits.

Illustrative Embodiment for Carrying Out the Invention

The "haloalkyl group", as used herein, means an alkyl group substituted with one or more of halogen atoms selected from the group consisting of fluorine, chlorine, bromine and iodine. The expression "C1-C6" or the like, as used herein, means the total number of carbon atoms constituting each substituent group.

The C3-C7 cycloalkyl group of the "C3-C7 cycloalkyl group optionally substituted with a group selected from the groups E1 to E3" in the formula (I) is a 3- to 7-membered saturated carbocyclic group, and examples thereof include a cyclopropyl group, a cyclobutyl group, a cyclopentyl group, a cyclohexyl group, a cycloheptyl group and a cyclooctyl group.

The C5-C7 cycloalkenyl group of the "C5-C7 cycloalkenyl group optionally substituted with a group selected from the groups E1 to E3" in the formula (I) is a 5- to 7-membered unsaturated carbocyclic group not containing the maximum number of double bonds, and examples thereof include a 1-cyclopentenyl group, a 2-cyclopentenyl group, a 3-cyclopentenyl group, a 1-cyclohexenyl group, a 2-cyclohexenyl group, a 3-cyclohexenyl group, a 1-cycloheptenyl group, a 2-cycloheptenyl group, a 3-cycloheptenyl group and a 4-cycloheptenyl group.

The C3-C7 cycloalkyl group or the C5 to C7 cycloalkenyl group may be substituted with two or more monovalent groups selected from the group E1 at different carbon atoms or the same carbon atom on the ring, and the two or more monovalent substituents selected from the group E1 may be the same as or different from each other. Examples of a cyclohexyl group substituted with two groups selected from the group E1 are shown below.

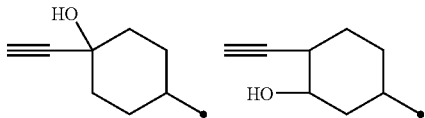

In addition, the C3-C7 cycloalkyl group or the C5 to C7 cycloalkenyl group may be substituted with a bivalent group selected from the group E3 at different carbon atoms or the same carbon atom on the ring. Examples of a cyclohexyl group substituted with a group selected from the group E3 are shown below.

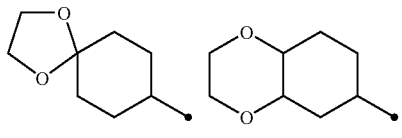

In the group E1, examples of the "C1-C6 chain hydrocarbon group optionally substituted with a group selected from the group L" include a C1-C6 alkyl group optionally substituted with a group selected from the group L, such as a methyl group, a fluoromethyl group, a difluoromethyl group, a trifluoromethyl group, a 2-propynyloxymethyl group, a 2-butynyloxymethyl group, a hydroxymethyl group and the like; a C2-C6 alkenyl group optionally substituted with a group selected from the group L, such as a vinyl group, a 2,2-difluorovinyl group, a 1-propenyl group, a 2-propenyl group and the like; and a C2-C6 alkynyl group optionally substituted with a group selected from the group L, such as a 3-methoxy-1-propynyl group, a 3-methoxy-1-butynyl group, a 4-methoxy-1-butynyl group, a 4-methoxy-2-butynyl group, a 3-methoxy-1-pentynyl group, a 4-methoxy-1-pentynyl group, a 5-methoxy-1-pentynyl group, a 4-methoxy-2-pentynyl group, a 5-methoxy-2-pentynyl group, 5-methoxy-3-pentynyl group, a 3-hydroxy-1-propynyl group, a 3-hydroxy-1-butynyl group, a 4-hydroxy-1-butynyl group, a 4-hydroxy-2-butynyl group, a 3-hydroxy-1-pentynyl group, a 4-hydroxy-1-pentynyl group, a 5-hydroxy-1-pentynyl group, a 4-hydroxy-2-pentynyl group, a 5-hydroxy-2-pentynyl group, a 5-hydroxy-3-pentynyl group, a 3-methylamino-1-propynyl group, a 3-methylamino-1-butynyl group, a 4-methylamino-1-butynyl group, a 4-methylamino-2-butynyl group, a 3-methylamino-1-pentynyl group, a 4-methylamino-1-pentynyl group, a 5-methylamino-1-pentynyl group, a 4-methylamino-2-pentynyl group, a 5-methylamino-2-pentynyl group, a 5-methylamino-3-pentynyl group, a 3-dimethylamino-1-propynyl group, a 3-dimethylamino-1-butynyl group, a 4-dimethylamino-1-butynyl group, a 4-dimethylamino-2-butynyl group, a 3-dimethylamino-1-pentynyl group, a 4-dimethylamino-1-pentynyl group, a 5-dimethylamino-1-pentynyl group, a 4-dimethylamino-2-pentynyl group, a 5-dimethylamino-2-pentynyl group, a 5-dimethylamino-3-pentynyl group, a 3-phenylamino-1-propynyl group, a 3-phenylamino-1-butynyl group, a 4-phenylamino-1-butynyl group, a 4-phenylamino-2-butynyl group, a 3-phenylamino-1-pentynyl group, a 4-phenylamino-1-pentynyl group, a 5-phenylamino-1-pentynyl group, a 4-phenylamino-2-pentynyl group, a 5-phenylamino-2-pentynyl group, a 5-phenylamino-3-pentynyl group, a 3-methylphenylamino-1-propynyl group, a 3-methylphenylamino-1-butynyl group, a 4-methylphenylamino-1-butynyl group, a 4-methylphenylamino-2-butynyl group, 3-methylphenylamino-1-pentynyl group, a 4-methylphenylamino-1-pentynyl group, a 5-methylphenylamino-1-pentynyl group, a 4-methylphenylamino-2-pentynyl group, a 5-methylphenylamino-2-pentynyl group, a 5-methylphenylamino-3-pentynyl group, a 3-(1-pyrrolidinyl)-1-propynyl group, a 3-(1-pyrrolidinyl)-1-butynyl group, a 4-(1-pyrrolidinyl)-1-butynyl group, a 4-(1-pyrrolidinyl)-2-butynyl group, a 3-(1-pyrrolidinyl)-1-pentynyl group, a 4-(1-pyrrolidinyl)-1-pentynyl group, a 5-(1-pyrrolidinyl)-1-pentynyl group, a 4-(1-pyrrolidinyl)-2-pentynyl group, a 5-(1-pyrrolidinyl)-2-pentynyl group, a 5-(1-pyrrolidinyl)-3-pentynyl group, a 3-(1-piperidinyl)-1-propynyl group, a 3-(1-piperidinyl)-1-butynyl group, a 4-(1-piperidinyl)-1-butynyl group, a 4-(1-piperidinyl)-2-butynyl group, a 3-(1-piperidinyl)-1-pentynyl group, a 4-(1-piperidinyl)-1-pentynyl group, a 5-(1-piperidinyl)-1-pentynyl group, a 4-(1-piperidinyl)-2-pentynyl group, a 5-(1-piperidinyl)-2-pentynyl group, a 5-(1-piperidinyl)-3-pentynyl group, a 3-(1-morpholinyl)-1-propynyl group, a 3-(1-morpholinyl)-1-butynyl group, a 4-(1-morpholinyl)-1-butynyl group, a 4-(1-morpholinyl)-2-butynyl group, a 3-(1-morpholinyl)-1-pentynyl group, a 4-(1-morpholinyl)-1-pentynyl group, a 5-(1-morpholinyl)-1-pentynyl group, a 4-(1-morpholinyl)-2-pentynyl group, a 5-(1-morpholinyl)-2-pentynyl group, a 5-(1-morpholinyl)-3-pentynyl group, a 3-methoxycarbonyl-1-propynyl group, a 3-methoxycarbonyl-1-butynyl group, a 4-methoxycarbonyl-1-butynyl group, a 4-methoxycarbonyl-2-butynyl group, a 3-methoxycarbonyl-1-pentynyl group, a 4-methoxycarbonyl-1-pentynyl group, a 5-methoxycarbonyl-1-pentynyl group, a 4-methoxycarbonyl-2-pentynyl group, a 5-methoxycarbonyl-2-pentynyl group, a 5-methoxycarbonyl-3-pentynyl group, a 3-dimethylaminocarbonyl-1-propynyl group, a 3-dimethylaminocarbonyl-1-butynyl group, a 4-dimethylaminocarbonyl-1-butynyl group, a 4-dimethylaminocarbonyl-2-butynyl group, a 3-dimethylaminocarbonyl-1-pentynyl group, a 4-dimethylaminocarbonyl-1-pentynyl group, a 5-dimethylaminocarbonyl-1-pentynyl group, a 4-dimethylaminocarbonyl-2-pentynyl group, a 5-dimethylaminocarbonyl-2-pentynyl group, a 5-dimethylaminocarbonyl-3-pentynyl group, a 3-(1-pyrrolidinyl)carbonyl-1-propynyl group, a 3-(1-pyrrolidinyl)carbonyl-1-butynyl group, a 4-(1-pyrrolidinyl)carbonyl-1-butynyl group, a 4-(1-pyrrolidinyl)carbonyl-2-butynyl group, a 3-(1-pyrrolidinyl)carbonyl-1-pentynyl group, a 4-(1-pyrrolidinyl)carbonyl-1-pentynyl group, a 5-(1-pyrrolidinyl)carbonyl-1-pentynyl group, a 4-(1-pyrrolidinyl)carbonyl-2-pentynyl group, a 5-(1-pyrrolidinyl)carbonyl-2-pentynyl group, a 5-(1-pyrrolidinyl)carbonyl-3-pentynyl group, a 3-(1-piperidinyl)carbonyl-1-propynyl group, a 3-(1-piperidinyl)carbonyl-1-butynyl group, a 4-(1-piperidinyl)carbonyl-1-butynyl group, a 4-(1-piperidinyl)carbonyl-2-butynyl group, a 3-(1-piperidinyl)carbonyl-1-pentynyl group, a 4-(1-piperidinyl)carbonyl-1-pentynyl group, a 5-(1-piperidinyl)carbonyl-1-pentynyl group, a 4-(1-piperidinyl)carbonyl-2-pentynyl group, a 5-(1-piperidinyl)carbonyl-2-pentynyl group, a 5-(1-piperidinyl)carbonyl-3-pentynyl group, a 3-(1-morpholinyl)carbonyl-1-propynyl group, a 3-(1-morpholinyl)carbonyl-1-butynyl group, a 4-(1-morpholinyl)carbonyl-1-butynyl group, a 4-(1-morpholinyl)carbonyl-2-butynyl group, a 3-(1-morpholinyl)carbonyl-1-pentynyl group, a 4-(1-morpholinyl)carbonyl-1-pentynyl group, a 5-(1-morpholinyl)carbonyl-1-pentynyl group, a 4-(1-morpholinyl)carbonyl-2-pentynyl group, a 5-(1-morpholinyl)carbonyl-2-pentynyl group, a 5-(1-morpholinyl)carbonyl-3-pentynyl group, a 3-carboxy-1-propynyl group, a 3-carboxy-1-butynyl group, a 4-carboxy-1-butynyl group, a 4-carboxy-2-butynyl group, a 3-carboxy-1-pentynyl group, a 4-carboxy-1-pentynyl group, a 5-carboxy-1-pentynyl group, a 4-carboxy-2-pentynyl group, a 5-carboxy-2-pentynyl group, a 5-carboxy-3-pentynyl group, a 3-acetoxy-1-propynyl group, a 3-acetoxy-1-butynyl group, a 4-acetoxy-1-butynyl group, a 4-acetoxy-2-butynyl group, a 3-acetoxy-1-pentynyl group, a 4-acetoxy-1-pentynyl group, a 5-acetoxy-1-pentynyl group, a 4-acetoxy-2-pentynyl group, a 5-acetoxy-2-pentynyl group, a 5-acetoxy-3-pentynyl group, a 3-methoxycarbonyloxy-1-propynyl group, a 3-methoxycarbonyloxy-1-butynyl group, a 4-methoxycarbonyloxy-1-butynyl group, a 4-methoxycarbonyloxy-2-butynyl group, a 3-methoxycarbonyloxy-1-pentynyl group, a 4-methoxycarbonyloxy-1-pentynyl group, a 5-methoxycarbonyloxy-1-pentynyl group, a 4-methoxycarbonyloxy-2-pentynyl group, a 5-methoxycarbonyloxy-2-pentynyl group, a 5-methoxycarbonyloxy-3-pentynyl group, a 2-bromoethynyl group, a 2-iodoethynyl group, a 3-fluoro-1-propynyl group, a 3,3-difluoro-1-propynyl group, a 3,3,3-tridifluoro-1-propynyl group, a 3-fluoro-1-propynyl group, a 3,3-difluoro-1-propynyl group, a 3,3,3-trifluoro-1-propynyl group, a 1-fluoro-2-propynyl group, a 1,1-difluoro-2-propynyl group, a 3-fluoro-1-butynyl group, a 4-fluoro-1-butynyl group, a 3-fluoro-1-pentynyl group, a 4-fluoro-1-pentynyl group, a 5-fluoro-1-pentynyl group, an ethynyl group, a 1-propynyl group, a 2-propynyl group, a 1-butynyl group, a 2-butynyl group, a 3-butynyl group, a 1-pentynyl group, a 2-pentynyl group, a 3-pentynyl group and the like.

Examples of the "C3-C6 cycloalkyl group optionally substituted with a halogen atom" in the group E1 include a cyclopropyl group.

Examples of a group represented by "—$OR^6$" in the group E1 include a C1-C4 alkoxy group optionally substituted with a halogen atom, such as a 2-propynyloxy group, a 2-butynyloxy group and the like; a C3-C6 alkenyloxy group optionally substituted with a halogen atom; and a C3-C6 alkynyloxy group optionally substituted with a halogen atom.

Examples of a group represented by "—SR$^6$" in the group E1 include a C1-C4 alkylthio group optionally substituted with a halogen atom.

Examples of a group represented by "—S(=O)R$^6$" in the group E1 include a C1-C4 alkylsulfinyl group optionally substituted with a halogen atom.

Examples of a group represented by "—S(=O)$_2$R$^6$" in the group E1 include a C1-C4 alkylsulfonyl group optionally substituted with a halogen atom.

Examples of a group represented by "—C(=O)R$^7$" in the group E1 include a group in which R$^7$ is a C1-C4 alkyl group optionally substituted with a halogen atom; a group in which R$^7$ is a C1-C4 alkoxy group optionally substituted with a halogen atom; a group in which R$^7$ is a C3-C6 alkenyloxy group optionally substituted with a halogen atom; a group in which R$^7$ is a C3-C6 alkynyloxy group, optionally substituted with a halogen atom; a group in which R$^7$ is an amino group, a C1-C4 alkylamino group optionally substituted with a halogen atom, or a di(C1-C4 alkyl)amino group optionally substituted with a halogen atom; a group in which R$^7$ is a C2-C5 cyclic amino group; a group in which R$^7$ is a hydroxyl group; and a group in which R$^7$ is a hydrogen atom.

Examples of a group represented by "—OC(=O)R$^8$" in the group E1 include a group in which R$^8$ is a C1-C4 alkyl group optionally substituted with a halogen atom; a group in which R$^8$ is a C1-C4 alkoxy group optionally substituted with a halogen atom; a group in which R$^8$ is a C3-C6 alkenyloxy group optionally substituted with a halogen atom; a group in which R$^8$ is a C3-C6 alkynyloxy group optionally substituted with a halogen atom; a group in which R$^8$ is an amino group, a C1-C4 alkylamino group optionally substituted with a halogen atom, or a di(C1-C4 alkyl)amino group optionally substituted with a halogen atom; a group in which R$^8$ is a C2-C5 cyclic amino group; and a group in which R$^8$ is a hydrogen atom.

In the group E2, examples of the "=NO—R$^6$" include a methoxyimino group, an ethoxyimino group, an isopropoxyimino group, a cyclopropylimino group, a 2,2,2-trifluoroethoxyimino group, an allylimino group and a 3-propynylimino group.

Examples of the "=C(R$^{11}$R$^{12}$")" in the group E2 include a methylidene group, an ethylidene group, a 1-methylethylidene group, a propylidene group and a dichloromethylidene group.

In the group E3, examples of the "C2-C6 alkylene group optionally substituted with a group selected from the group L" include an ethane-1,2-diyl group, a propane-1,2-diyl group, a propane-1,3-diyl group, a butane-1,4-diyl group, a 2,3-dichlorobutane-1,4-diyl group and a pentane-1,5-diyl group.

In the group E3 examples of the "C4-C6 alkenylene group optionally substituted with a group selected from the group L" include a 2-butene-1,4-diyl group and a 3-pentene-1,5-diyl group. Examples of a group represented by "G-T$^1$-G-" in the group E3 include —OCH$_2$O—, —SCH$_2$S—, —OCH$_2$CH$_2$O— and —SCH$_2$CH$_2$S—.

Examples of the group represented by "-G-T$^1$-G-T$^2$-" in the group E3 include —OCH$_2$OCH$_2$—, —SCH$_2$SCH$_2$—, —OCH$_2$CH$_2$OCH$_2$— and —SCH$_2$CH$_2$SCH$_2$—.

Examples of the "C1-C5 haloalkyl group containing at least one fluorine atom" include a C1-C5 alkyl group substituted with only fluorine atom(s), such as a fluoromethyl group, a difluoromethyl group, a trifluoromethyl group, a 1,1,2,2,2-pentafluoroethyl group, a 2,2,2-trifluoroethyl group, a 1,1-difluoroethyl group, a 1,1,2,2,3,3,3-heptafluoropropyl group, a 1,1-difluoropropyl group, a 2,2-difluoropropyl group, a 3,3,3-trifluoropropyl group, a 1,1,2,2,3,3,4,4,4-nonafluorobutyl group, a 1,1-difluorobutyl group, a 2,2-difluorobutyl group, a 1,1,2,2,3,3,4,4,5,5,5-undecafluoropentyl group, a 1,1-difluropentyl group, a 2,2-difluoropentyl group and the like; a C1-C5 alkyl group substituted with fluorine atom(s) and chlorine atom(s), such as a chlorodifluoromethyl group, a 1,2-dichloro-1,2,2-trifluoroethyl group, a 1,1-dichloro-2,2,2-trifluoroethyl group, a 1-chloro-1,3,3,3-tetrafluoropropyl group, a 2,3-dichloro-2,3,3-trifluoropropyl group, a 2,2-dichloro-3,3,3-trifluoropropyl group and the like; and a C1-C5 alkyl group substituted with fluorine atom(s) and bromine atom(s), such as a 2,2-dibromo-3,3,3-trifluoropropyl group, a 2-bromo-3,3,3-trifluoropropyl group, a 2,3-dibromo-3,3-difluoropropyl group, a 3-bromo-3,3-difluoropropyl group, a 1-bromo-1,3,3,3-tetrafluoropropyl group, a 1-bromo-2,2,3,3,3-pentafluoropropyl group, a 1,3-dibromo-2,2,3,3-tetrafluoropropyl group, a 3-bromo-2,3,3-trifluoropropyl group, a 3-bromo-2,2,3,3-tetrafluoropropyl group, a 2,3-dibromo-2,3,3-trifluoropropyl group, a 3-bromo-3,3-difluoropropyl group and the like.

Examples of the "C1-C3 haloalkyl group containing at least one fluorine atom" include a C1-C3 alkyl group substituted with only fluorine atom(s), such as a trifluoromethyl group, a 1,1,2,2,2-pentafluoroethyl group, a 1,1-difluoroethyl group, a 1,1,2,2,3,3,3-heptafluoropropyl group and the like; a C1-C3 alkyl group substituted with fluorine atom(s) and chlorine atom(s), such as a chlorodifluoromethyl group, a 1,2-dichloro-1,2,2-trifluoroethyl group, a 1,1-dichloro-2,2,2-trifluoroethyl group, a 1-chloro-1,3,3,3-tetrafluoropropyl group, a 2,3-dichloro-2,3,3-trifluoropropyl group, a 2,2-dichloro-3,3,3-trifluoropropyl group and the like; and a C1-C3 alkyl group substituted with fluorine atom(s) and bromine atom(s), such as a 2,2-dibromo-3,3,3-trifluoropropyl group, a 2-bromo-3,3,3-trifluoropropyl group, a 2,3-dibromo-3,3-difluoropropyl group, a 3-bromo-3,3-difluoropropyl group, a 1-bromo-1,3,3,3-tetrafluoropropyl group, a 1-bromo-2,2,3,3,3-pentafluoropropyl group, a 1,3-dibromo-2,2,3,3-tetrafluoropropyl group, a 3-bromo-2,3,3-trifluoropropyl group, a 3-bromo-2,2,3,3-tetrafluoropropyl group, a 2,3-dibromo-2,3,3-trifluoropropyl group, a 3-bromo-3,3-difluoropropyl group and the like.

Examples of the "C1-C5 fluoroalkyl group" include a fluoromethyl group, a trifluoromethyl group, a 1,1,2,2,2-pentafluoroethyl group, a 2,2,2-trifluoroethyl group, a 1,1-difluoroethyl group, a 1,1,2,2,3,3,3-heptafluoropropyl group, a 1,1-difluoropropyl group, a 2,2-difluoropropyl group, a 3,3,3-trifluoropropyl group, a 1,1,2,2,3,3,4,4,4-nonafluorobutyl group, a 1,1-difluorobutyl group, a 2,2-difluorobutyl group, a 1,1,2,2,3,3,4,4,5,5,5-undecafluoropentyl group, a 1,1-difluoropentyl group and a 2,2-difluoropentyl group.

Examples of the "C1-C3 fluoroalkyl group" include a fluoromethyl group, a trifluoromethyl group, a 1,1,2,2,2-pentafluoroethyl group, a 1,1-difluoroethyl group and a 1,1,2,2,3,3,3-heptafluoropropyl group.

Examples of the "halogen atom" include a fluorine atom, a chlorine atom and a bromine atom.

Examples of the "C1-C4 chain hydrocarbon group optionally substituted with a halogen atom" include a C1-C4 alkyl group optionally substituted with a halogen atom, a C2-C4 alkenyl group optionally substituted with a halogen atom, and a C2-C4 alkynyl group optionally substituted with a halogen atom.

Examples of the "C1-C4 alkyl group optionally substituted with a halogen atom" include a methyl group, an ethyl group, a propyl group, a 1-methylethyl group (hereinafter referred to as an i-propyl group in some cases), a 2,2-dimethylpropyl group, a chloromethyl group, a fluoromethyl group, a difluoromethyl group, a trifluoromethyl group, a 2,2,2-trifluoromethyl group, a 1,1,2,2-tetrafluoroethyl group, a 1,1,2,2,2-pentafluoroethyl group and a 1,1-dimethylethyl group (hereinafter, referred to as a t-butyl group in some cases).

Examples of the "C2-C4 alkenyl group optionally substituted with a halogen atom" include a vinyl group, a 2,2-difluorovinyl group, a 1,2,2-trifluorovinyl group, a 1-propenyl group, a 2-propenyl group, a 3,3-difluoro-2-propenyl group, a 1-methyl-2-propenyl group, a 2-methyl-2-propenyl group, a 1-butenyl group and a 2-butenyl group.

Examples of the "C2-C4 alkynyl group optionally substituted with a halogen atom" include an ethynyl group, a 1-propynyl group, a 3,3,3-trifluoro-1-propynyl group, a 2-propynyl group, a 1-methyl-2-propynyl group, a 1-butynyl group, a 2-butynyl group, and a 3-butynyl group.

Examples of the "C1-C4 alkoxy group optionally substituted with a halogen atom" include a methoxy group, an ethoxy group, a propoxy group, a trifluoromethoxy group, a bromodifluoromethoxy group, a difluoromethoxy group, a chlorodifluoromethoxy group, a pentafluoroethoxy group, a 2,2,2-trifluoroethoxy group and a 1,1,2,2-tetrafluoroethoxy group.

Examples of the "C3-C6 alkenyloxy group optionally substituted with a halogen atom" include a 1-propenyloxy group, a 2-propenyloxy group, a 1-methyl-2-propenyloxy group, a 1,1-dimethyl-2-propenyloxy group and a 2,2-difluoro-2-propenyloxy group.

Examples of the "C3-C6 alkynyloxy group optionally substituted with a halogen atom" include a 2-propynyloxy group, a 1-methyl-2-propynyloxy group, a 1,1-dimethyl-2-propynyloxy group, a 2-butynyloxy group, a 1-methyl-2-butynyloxy group, a 1,1-dimethyl-2-butynyloxy group and a 3,3,3-trifluoro-1-propynyloxy group.

Examples of the "C1-C4 alkylamino group optionally substituted with a halogen atom" include a N-methylamino group, a N-ethylamino group, a N-propylamino group, a N-(1-methylethyl)amino group and a N-(2,2,2-trifluoroethyl)amino group.

Examples of the "di(C1-C4 alkyl)amino group optionally substituted with a halogen atom" include a N,N-dimethylamino group, a N-ethyl-N-methylamino group, a N,N-diethylamino group, a N-methyl-N-propylamino group, a N-ethyl-N-propylamino group, a N,N-dipropylamino group, a N-methyl-N-(1-methylethyl)amino group, a N-ethyl-N-(1-methylethyl)amino group, a N,N-di(1-methylethyl)amino group, a N-methyl-N-(2,2,2-trifluoroethyl)amino group and a N-methyl-N-ethyl-N-(2,2,2-trifluoroethyl)amino group.

Examples of the "C2-C5 cyclic amino group" include a 1-aziridino group, a 1-azetidinyl group, a 1-pyrrolidinyl group, a piperidino group, and a morpholino group.

Examples of the "C1-C6 chain hydrocarbon group optionally substituted with a group selected from the group L" include a C1-C6 alkyl group optionally substituted with a group selected from the group L, a C2-C6 alkenyl group optionally substituted with a group selected from the group L, and a C2-C6 alkynyl group optionally substituted with a group selected from the group L.

Examples of the "C1-C6 alkyl group optionally substituted with a group selected from the group L" include a C1-C6 alkyl group optionally substituted with a halogen atom, such as a methyl group, an ethyl group, a propyl group, a 1-methylethyl group, a 2,2-dimethylpropyl group, chloromethyl group, a fluoromethyl group, a difluoromethyl group, a trifluoromethyl group, a 2,2,2-trifluoroethyl group, a 1,1,2,2-tetrafluoroethyl group, a 1,1,2,2,2-pentafluoroethyl group, a 1,1-dimethylethyl group and the like; a (C1-C4 alkoxy)C1-C4 alkyl group optionally substituted with a halogen atom, such as a methoxymethyl group, an ethoxymethyl group, a 1-methoxyethyl group, a 1-ethoxyethyl group, a trifluoromethoxymethyl group and the like; a (C3-C6 alkenyloxy)C1-C4 alkyl group optionally substituted with a halogen atom, such as a (1-propenyloxy)methyl group, a (2-propenyloxy)methyl group, a (1-methyl-2-propenyloxy)methyl group, a (1,1-dimethyl-2-propenyloxy)methyl group, a (2,2-difluoro-2-propenyloxy)methyl group, a 1-(1-propenyloxy)ethyl group, a 1-(2-propenyloxy)ethyl group, a 1-(1-methyl-2-propenyloxy)ethyl group, a 1-(1,1-dimethyl-2-propenyloxy)ethyl group, a 1-(2,2-difluoro-2-propenyloxy)ethyl group, a 2-(1-propenyloxy)ethyl group, a 2-(2-propenyloxy)ethyl group, a 2-(1-methyl-2-propenyloxy)ethyl group, a 2-(1,1-dimethyl-2-propenyloxy)ethyl group and a 2-(2,2-difluoro-2-propenyloxy)ethyl group; a (C3-C6 alkynyloxy)C1-C4 alkyl group optionally substituted with a halogen atom such as a (2-propynyloxy)methyl group, a (1-methyl-2-propynyloxy)methyl group, a (1,1-dimethyl-2-propynyloxy)methyl group, a (2-butynyloxy)methyl group, a (1-methyl-2-butynyloxy)methyl group, a (1,1-dimethyl-2-butynyloxy)methyl group, a (3,3,3-trifluoro-1-propynyloxy)methyl group, a 1-(2-propynyloxy)ethyl group, a 1-(1-methyl-2-propynyloxy)ethyl group, a 1-(1,1-dimethyl-2-propynyloxy)ethyl group, a 1-(2-butynyloxy)ethyl group, a 1-(1-methyl-2-butynyloxy)ethyl group, a 1-(1,1-dimethyl-2-butynyloxy)ethyl group, a 1-(3,3,3-trifluoro-1-propynyloxy)ethyl group, a 2-(2-propynyloxy)ethyl group, a 2-(1-methyl-2-propynyloxy)ethyl group, a 2-(1,1-dimethyl-2-propynyloxy)ethyl group, a 2-(2-butynyloxy)ethyl group, a 2-(1-methyl-2-butynyloxy)ethyl group, a 2-(1,1-dimethyl-2-butynyloxy)ethyl group, a 2-(3,3,3-trifluoro-1-propynyloxy)ethyl group and the like; and a (hydroxy)C1-C4 alkyl group optionally substituted with a halogen atom, such as a hydroxymethyl group, a 1-hydroxyethyl group, a 1-hydroxy-1-methylethyl group, a 2-hydroxyethyl group, a 2-hydroxy-1-methylethyl group and the like.

Examples of the "C2-C6 alkenyl group optionally substituted with a group selected from the group L" include a C2-C6 alkenyl group optionally substituted with a halogen atom, such as a vinyl group, a 2,2-difluorovinyl group, a 1,2,2-trifluorovinyl group, a 1-propenyl group, a 2-propenyl group, a 3,3-difluoro-2-propenyl group, a 1-methyl-2-propenyl group and the like.

Examples of the "C2-C6 alkynyl group optionally substituted with a group selected from the group L" include an ethynyl group, such as a 1-ethynyl group, a 2-bromoethynyl group, a 2-iodoethynyl group, a 2-(methoxycarbonyl)ethynyl group and the like;

a 1-propynyl group, such as a 1-propynyl group, a 3-fluoro-1-propynyl group, a 3,3-difluoro-1-propynyl group, a 3-(dimethylamino)-1-propynyl group, a 3,3,3-trifluoro-1-propynyl group, a 3-methoxy-1-propynyl group, a 3-(methoxycarbonyl)-1-propynyl group and the like;

a 2-propynyl group, such as a 2-propynyl group, a 1-fluoro-2-propynyl group and a 1,1-difluoro-2-propynyl group;

a 1-butynyl group such as a 1-butynyl group, a 4-fluoro-1-butynyl group, a 4-methoxy-1-butynyl group, a 4-(dimethylamino)-1-butynyl group, a 4-(methoxycarbonyl)-1-butynyl group and the like;

a 2-butynyl group, such as a 2-butynyl group, a 4-fluoro-2-butynyl group, a 4-methoxy-2-butynyl group, a 4-(dimethylamino)-2-butynyl group, a 4-(methoxycarbonyl)-2-butynyl group and the like;

a 3-butynyl group, such as a 3-butynyl group, a 1,1-difluoro-3-butynyl group and the like;

a 1-pentynyl group, such as a 1-pentynyl group, a 5-fluoro-1-pentynyl group, a 5-methoxy-1-pentynyl group, a 5-(dimethylamino)-1-pentynyl group, a 5-(methoxycarbonyl)-1-pentynyl group and the like; and a 2-pentynyl group, such as a 2-pentynyl group, a 5-fluoro-2-pentynyl group, a 5-methoxy-2-pentynyl group, a 5-(dimethylamino)-2-pentynyl group, a 5-(methoxycarbonyl)-2-pentynyl group and the like.

Examples of the "C3-C6 cycloalkyl group optionally substituted with a halogen atom" include a cyclopropyl group, a 1-methylcyclopropyl group, a 2,2-dichlorocyclopropyl group, a 2,2-dichloro-1-methylcyclopropyl group, a 2,2-difluorocyclopropyl group, a 2,2-difluoro-1-methylcyclopropyl group, a cyclobutyl group, a cyclopentyl group and a cyclohexyl group.

Examples of the "phenyl group optionally substituted with a halogen atom" include a phenyl group, a 2-chlorophenyl group, a 3-chlorophenyl group, a 4-chlorophenyl group, a 2,3-dichlorophenyl group, a 2,4-dichlorophenyl group, a 2,5-dichlorophenyl group, a 2,6-dichlorophenyl group, a 3,4-dichlorophenyl group, a 3,5-dichlorophenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2-bromophenyl group, a 3-bromophenyl group, a 4-bromophenyl group, a 2,3-dibromophenyl group, a 2,4-dibromophenyl group, a 2,5-dibromophenyl group, a 2,6-dibromophenyl group, a 3,4-dibromophenyl group and a 3,5-dibromophenyl group.

Specific examples of the compound of the present invention include:

a compound represented by the formula (I) wherein m is 0;
a compound represented by the formula (I) wherein m is 1;
a compound represented by the formula (I) wherein m is 2;
a compound represented by the formula (I) wherein n is 0;
a compound represented by the formula (I) wherein n is 1;
a compound represented by the formula (I) wherein n is 2;
a compound represented by the formula (I) wherein $R^1$ is a hydrogen atom;
a compound represented by the formula (I) wherein $R^1$ is a C1-C4 alkyl group optionally substituted with a halogen atom;
a compound represented by the formula (I) wherein $R^1$ is a methyl group;
a compound represented by the formula (I) wherein $R^1$ is a C2-C4 alkenyl group optionally substituted with a halogen atom;
a compound represented by the formula (I) wherein $R^1$ is a C2-C4 alkynyl group optionally substituted with a halogen atom;
a compound represented by the formula (I) wherein $R^1$ is a halogen atom;
a compound represented by the formula (I) wherein $R^1$ is a fluorine atom;
a compound represented by the formula (I) wherein $R^1$ is a chlorine atom;
a compound represented by the formula (I) wherein $R^1$ is a bromine atom;
a compound represented by the formula (I) wherein $R^2$ is a hydrogen atom;
a compound represented by the formula (I) wherein $R^2$ is a C1-C4 alkyl group optionally substituted with a halogen atom;
a compound represented by the formula (I) wherein $R^2$ is —C(=O)$R^5$ and $R^5$ is a C1-C4 alkyl group optionally substituted with a halogen atom;
a compound represented by the formula (I) wherein $R^2$ is —C(=O)$R^5$ and $R^5$ is a C1-C4 alkoxy group optionally substituted with a halogen atom;
a compound represented by the formula (I) wherein $R^2$ is a methoxycarbonyl group;
a compound represented by the formula (I) wherein $R^2$ is —C(=O)$R^5$ and $R^5$ is a C3-C6 alkenyloxy group optionally substituted with a halogen atom;
a compound represented by the formula (I) wherein $R^2$ is —C(=O)$R^5$ and $R^5$ is a C3-C6 alkynyloxy group optionally substituted with a halogen atom;
a compound represented by the formula (I) wherein $R^2$ is —C(=O)$R^5$ and $R^5$ is an amino group, a C1-C4 alkylamino group optionally substituted with a halogen atom or a di(C1-C4 alkyl)amino group optionally substituted with a halogen atom;
a compound represented by the formula (I) wherein $R^2$ is —C(=O)$R^5$ and $R^5$ is a C2-C5 cyclic amino group;
a compound represented by the formula (I) wherein $R^2$ is —C(=O)$NH_2$;
a compound represented by the formula (I) wherein $R^2$ is —C(=O)OH;
a compound represented by the formula (I) wherein $R^2$ is —C(=O)H;
a compound represented by the formula (I) wherein $R^2$ is —C(=S)$R^5$ and $R^5$ is a C1-C4 alkyl group optionally substituted with a halogen atom;
a compound represented by the formula (I) wherein $R^2$ is —C(=S)$R^5$ and $R^5$ is a C1-C4 alkoxy group optionally substituted with a halogen atom;
a compound represented by the formula (I) wherein $R^2$ is —C(=S)$R^5$ and $R^5$ is a C3-C6 alkenyloxy group optionally substituted with a halogen atom;
a compound represented by the formula (I) wherein $R^2$ is —C(=S)$R^5$ and $R^5$ is a C3-C6 alkynyloxy group optionally substituted with a halogen atom;
a compound represented by the formula (I) wherein $R^2$ is —C(=S)$R^5$ and $R^5$ is a C1-C4 alkylamino group optionally substituted with a halogen atom or a di(C1-C4 alkyl)amino group optionally substituted with a halogen atom;
a compound represented by the formula (I) wherein $R^2$ is —C(=S)$R^5$ and $R^5$ is a C2-C5 cyclic amino group;
a compound represented by the formula (I) wherein $R^2$ is —C(=S)$NH_2$;
a compound represented by the formula (I) wherein $R^2$ is —C(=S)OH and $R^5$ is a hydroxyl group;
a compound represented by the formula (I) wherein $R^2$ is —C(=S)H;
a compound represented by the formula (I) wherein $R^2$ is a cyano group;
a compound represented by the formula (I) wherein $R^2$ is a halogen atom;
a compound represented by the formula (I) wherein $R^1$ and $R^2$ are hydrogen atoms;
a compound represented by the formula (I) wherein Q is a C1-C3 haloalkyl group containing at least one fluorine atom;
a compound represented by the formula (I) wherein Q is a C1-C5 fluoroalkyl group;
a compound represented by the formula (I) wherein Q is a fluorine atom;
a compound represented by the formula (I) wherein Q is a C1-C3 fluoroalkyl group;
a compound represented by the formula (I) wherein Q is a fluoromethyl group;
a compound represented by the formula (I) wherein Q is a trifluoromethyl group;

a compound represented by the formula (I) wherein Q is a 2,2,2-trifluoroethyl group;

a compound represented by the formula (I) wherein Q is a 1,1,2,2,2-pentafluoroethyl group;

a compound represented by the formula (I) wherein A is a C3-C7 cycloalkyl group optionally substituted with a group selected from the groups E1 to E3;

a compound represented by the formula (I) wherein A is a cyclopropyl group optionally substituted with a group selected from the groups E1 to E3;

a compound represented by the formula (I) wherein A is a cyclopentyl group optionally substituted with a group selected from the groups E1 to E3;

a compound represented by the formula (I) wherein A is a cyclohexyl group optionally substituted with a group selected from the groups E1 to E3;

a compound represented by the formula (I) wherein A is a cycloheptyl group optionally substituted with a group selected from the groups E1 to E3;

a compound represented by the formula (I) wherein A is a C5-C7 cycloalkenyl group optionally substituted with a group selected from the groups E1 to E3;

a compound represented by the formula (I) wherein A is a 1-cyclopentenyl group optionally substituted with a group selected from the groups E1 to E3;

a compound represented by the formula (I) wherein A is a 2-cyclopentenyl group optionally substituted with a group selected from the groups E1 to E3;

a compound represented by the formula (I) wherein A is a 3-cyclopentenyl group optionally substituted with a group selected from the groups E1 to E3;

a compound represented by the formula (I) wherein A is a 1-cyclohexenyl group optionally substituted with a group selected from the groups E1 to E3;

a compound represented by the formula (I) wherein A is a 2-cyclohexenyl group optionally substituted with a group selected from the groups E1 to E3;

a compound represented by the formula (I) wherein A is a 3-cyclohexenyl group optionally substituted with a group selected from the groups E1 to E3;

a compound represented by the formula (I) wherein A is a 1-cycloheptenyl group optionally substituted with a group selected from the groups E1 to E3;

a compound represented by the formula (I) wherein A is a 2-cycloheptenyl group optionally substituted with a group selected from the groups E1 to E3;

a compound represented by the formula (I) wherein A is a 3-cycloheptenyl group optionally substituted with a group selected from the groups E1 to E3;

a compound represented by the formula (I) wherein A is a 4-cycloheptenyl group optionally substituted with a group selected from the groups E1 to E3;

a compound represented by the formula (I) wherein A is a cyclopentyl group optionally substituted with a group selected from the groups E1 to E3 at the 3-position;

a compound represented by the formula (I) wherein A is a cyclopentyl group optionally substituted with two groups selected from the groups E1 to E3 at the 3-position;

a compound represented by the formula (I) wherein A is a cyclopentyl group the 2-position and 3-position of which are each optionally substituted with a group selected from the groups E1 to E3;

a compound represented by the formula (I) wherein A is a cyclopentyl group the 3-position and 4-position of which are each optionally substituted with a group selected from the groups E1 to E3;

a compound represented by the formula (I) wherein A is a cyclohexyl group optionally substituted with a group selected from the groups E1 to E3 at the 3-position;

a compound represented by the formula (I) wherein A is a cyclohexyl group optionally substituted with two groups selected from the groups E1 to E3 at the 3-position;

a compound represented by the formula (I) wherein A is a cyclohexyl group optionally substituted with a group selected from the groups E1 to E3 at the 4-position;

a compound represented by the formula (I) wherein A is a cyclohexyl group optionally substituted with two groups selected from the groups E1 to E3 at the 4-position;

a compound represented by the formula (I) wherein A is a cyclohexyl group the 2-position and 3-position of which are each optionally substituted with a group selected from the groups E1 to E3;

a compound represented by the formula (I) wherein A is a cyclohexyl group the 2-position and 4-position of which are each optionally substituted with a group selected from the groups E1 to E3;

a compound represented by the formula (I) wherein A is a cyclohexyl group the 3-position and 4-position of which are each optionally substituted with a group selected from the groups E1 to E3;

a compound represented by the formula (I) wherein A is a 1-cyclopentenyl group optionally substituted with a group selected from the groups E1 to E3 at the 3-position;

a compound represented by the formula (I) wherein A is a 1-cyclopentenyl group optionally substituted with a group selected from the groups E1 to E3 at the 4-position;

a compound represented by the formula (I) wherein A is a 1-cyclopentenyl group optionally substituted with two groups selected from the groups E1 to E3 at the 3-position;

a compound represented by the formula (I) wherein A is a 1-cyclopentenyl group optionally substituted with two groups selected from the groups E1 to E3 at the 4-position;

a compound represented by the formula (I) wherein A is a 1-cyclopentenyl group the 3-position and 4-position of which are each optionally substituted with a group selected from the groups E1 to E3;

a compound represented by the formula (I) wherein A is a 2-cyclopentenyl group optionally substituted with a group selected from the groups E1 to E3 at the 3-position;

a compound represented by the formula (I) wherein A is a 2-cyclopentenyl group optionally substituted with a group selected from the groups E1 to E3 at the 4-position;

a compound represented by the formula (I) wherein A is a 2-cyclopentenyl group optionally substituted with two groups selected from the groups E1 to E3 at the 4-position;

a compound represented by the formula (I) wherein A is a 2-cyclopentenyl group the 3-position and 4-position of which are each optionally substituted with a group selected from the groups E1 to E3;

a compound represented by the formula (I) wherein A is a 3-cyclopentenyl group optionally substituted with a group selected from the groups E1 to E3 at the 3-position;

a compound represented by the formula (I) wherein A is a 3-cyclopentenyl group optionally substituted with a group selected from the groups E1 to E3 at the 4-position;

a compound represented by the formula (I) wherein A is a 3-cyclopentenyl group the 3-position and 4-position of which are each optionally substituted with a group selected from the groups E1 to E3;

a compound represented by the formula (I) wherein A is a 1-cyclohexenyl group optionally substituted with a group selected from the groups E1 to E3 at the 3-position;

a compound represented by the formula (I) wherein A is a 1-cyclohexenyl group optionally substituted with a group selected from the groups E1 to E3 at the 4-position;

a compound represented by the formula (I) wherein A is a 1-cyclohexenyl group optionally substituted with a group selected from the groups E1 to E3 at the 5-position;

a compound represented by the formula (I) wherein A is a 1-cyclohexenyl group optionally substituted with two groups selected from the groups E1 to E3 at the 3-position;

a compound represented by the formula (I) wherein A is a 1-cyclohexenyl group optionally substituted with two groups selected from the groups E1 to E3 at the 4-position;

a compound represented by the formula (I) wherein A is a 1-cyclohexenyl group optionally substituted with two groups selected from the groups E1 to E3 at the 5-position;

a compound represented by the formula (I) wherein A is a 1-cyclohexenyl group the 2-position and 3-position of which are each optionally substituted with a group selected from the groups E1 to E3;

a compound represented by the formula (I) wherein A is a 1-cyclohexenyl group the 2-position and 4-position of which are each optionally substituted with a group selected from the groups E1 to E3;

a compound represented by the formula (I) wherein A is a 1-cyclohexenyl group the 2-position and 5-position of which are each optionally substituted with a group selected from the groups E1 to E3;

a compound represented by the formula (I) wherein A is a 1-cyclohexenyl group the 3-position and 4-position of which are each optionally substituted with a group selected from the groups E1 to E3;

a compound represented by the formula (I) wherein A is a 1-cyclohexenyl group the 3-position and 5-position of which are each optionally substituted with a group selected from the groups E1 to E3;

a compound represented by the formula (I) wherein A is a 1-cyclohexenyl group the 3-position and 6-position of which are each optionally substituted with a group selected from the groups E1 to E3;

a compound represented by the formula (I) wherein A is a 1-cyclohexenyl group the 4-position and 5-position of which are each optionally substituted with a group selected from the groups E1 to E3;

a compound represented by the formula (I) wherein A is a 1-cyclohexenyl group the 4-position and 6-position of which are each optionally substituted with a group selected from the groups E1 to E3;

a compound represented by the formula (I) wherein A is a 1-cyclohexenyl group the 5-position and 6-position of which are each optionally substituted with a group selected from the groups E1 to E3;

a compound represented by the formula (I) wherein A is a 2-cyclohexenyl group optionally substituted with a group selected from the groups E1 to E3 at the 3-position;

a compound represented by the formula (I) wherein A is a 2-cyclohexenyl group optionally substituted with a group selected from the groups E1 to E3 at the 4-position;

a compound represented by the formula (I) wherein A is a 2-cyclohexenyl group optionally substituted with a group selected from the groups E1 to E3 at the 5-position;

a compound represented by the formula (I) wherein A is a 2-cyclohexenyl group optionally substituted with two groups selected from the groups E1 to E3 at the 4-position;

a compound represented by the formula (I) wherein A is a 2-cyclohexenyl group optionally substituted with two groups selected from the groups E1 to E3 at the 5-position;

a compound represented by the formula (I) wherein A is a 2-cyclohexenyl group the 2-position and 3-position of which are each optionally substituted with a group selected from the groups E1 to E3;

a compound represented by the formula (I) wherein A is a 2-cyclohexenyl group the 2-position and 4-position of which are each optionally substituted with a group selected from the groups E1 to E3;

a compound represented by the formula (I) wherein A is a 2-cyclohexenyl group the 2-position and 5-position of which are each optionally substituted with a group selected from the groups E1 to E3;

a compound represented by the formula (I) wherein A is a 2-cyclohexenyl group the 3-position and 4-position of which are each optionally substituted with a group selected from the E1 to E3;

a compound represented by the formula (I) wherein A is a 2-cyclohexenyl group the 3-position and 5-position of which are each optionally substituted with a group selected from the groups E1 to E3;

a compound represented by the formula (I) wherein A is a 2-cyclohexenyl group the 3-position and 6-position of which are each optionally substituted with a group selected from the groups E1 to E3;

a compound represented by the formula (I) wherein A is a 2-cyclohexenyl group the 4-position and 5-position of which are each optionally substituted with a group selected from the groups E1 to E3;

a compound represented by the formula (I) wherein A is a 2-cyclohexenyl group the 4-position and 6-position of which are each optionally substituted with a group selected from the groups E1 to E3;

a compound represented by the formula (I) wherein A is a 2-cyclohexenyl group the 5-position and 6-position of which are each optionally substituted with a group selected from the groups E1 to E3;

a compound represented by the formula (I) wherein A is a 3-cyclohexenyl group optionally substituted with a group selected from the groups E1 to E3 at the 3-position;

a compound represented by the formula (I) wherein A is a 3-cyclohexenyl group optionally substituted with a group selected from the groups E1 to E3 at the 4-position;

a compound represented by the formula (I) wherein A is a 3-cyclohexenyl group optionally substituted with a group selected from the groups E1 to E3 at the 5-position;

a compound represented by the formula (I) wherein A is a 3-cyclohexenyl group optionally substituted with two groups selected from the groups E1 to E3 at the 5-position;

a compound represented by the formula (I) wherein A is a 3-cyclohexenyl group the 2-position and 3-position of which are each optionally substituted with a group selected from the groups E1 to E3;

a compound represented by the formula (I) wherein A is a 3-cyclohexenyl group the 2-position and 4-position of which are each optionally substituted with a group selected from the groups E1 to E3;

a compound represented by the formula (I) wherein A is a 3-cyclohexenyl group the 2-position and 5-position of which are each optionally substituted with a group selected from the groups E1 to E3;

a compound represented by the formula (I) wherein A is a 3-cyclohexenyl group the 3-position and 4-position of which are each optionally substituted with a group selected from the groups E1 to E3;

a compound represented by the formula (I) wherein A is a 3-cyclohexenyl group the 3-position and 5-position of which are each optionally substituted with a group selected from the groups E1 to E3;
a compound represented by the formula (I) wherein A is a 3-cyclohexenyl group the 3-position and 6-position of which are each optionally substituted with a group selected from the groups E1 to E3;
a compound represented by the formula (I) wherein A is a 3-cyclohexenyl group the 4-position and 5-position of which are each optionally substituted with a group selected from the groups E1 to E3;
a compound represented by the formula (I) wherein A is a 3-cyclohexenyl group the 4-position and 6-position of which are each optionally substituted with a group selected from the groups E1 to E3;
a compound represented by the formula (I) wherein A is a 3-cyclohexenyl group the 5-position and 6-position of which are each optionally substituted with a group selected from the groups E1 to E3;
a compound represented by the formula (I) wherein m is 0 and A is a 3-cyanocyclopentyl group;
a compound represented by the formula (I) wherein m is 0 and A is a 3-fluorocyclopentyl group;
a compound represented by the formula (I) wherein m is 0 and A is a 3,3-difluorocyclopentyl group;
a compound represented by the formula (I) wherein m is 0 and A is a 3-ethynylcyclopentyl group;
a compound represented by the formula (I) wherein m is 0 and A is a 3-(1-propynyl)cyclopentyl group;
a compound represented by the formula (I) wherein m is 0 and A is a 3-(2-propynyl)cyclopentyl group;
a compound represented by the formula (I) wherein m is 0 and A is a 3-(2-butynyl)cyclopentyl group;
a compound represented by the formula (I) wherein m is 0 and A is a 3-methoxyiminocyclopentyl group;
a compound represented by the formula (I) wherein m is 0 and A is a 3-ethoxyiminocyclopentyl group;
a compound represented by the formula (I) wherein m is 0 and A is a 3-cyanocyclohexyl group;
a compound represented by the formula (I) wherein m is 0 and A is a 3-fluorocyclohexyl group;
a compound represented by the formula (I) wherein m is 0 and A is a 3,3-difluorocyclohexyl group;
a compound represented by the formula (I) wherein m is 0 and A is a 3-ethynylcyclohexyl group;
a compound represented by the formula (I) wherein m is 0 and A is a 3-(1-propynyl)cyclohexyl group;
a compound represented by the formula (I) wherein m is 0 and A is a 3-(2-propynyl)cyclohexyl group;
a compound represented by the formula (I) wherein m is 0 and A is a 3-(2-butynyl)cyclohexyl group;
a compound represented by the formula (I) wherein m is 0 and A is a 4-cyanocyclohexyl group;
a compound represented by the formula (I) wherein m is 0 and A is a 3-fluoro-4-cycanocyclohexyl group;
a compound represented by the formula (I) wherein m is 0 and A is a 4-fluoro-4-cycanocyclohexyl group;
a compound represented by the formula (I) wherein m is 0 and A is a 4-fluorocyclohexyl group;
a compound represented by the formula (I) wherein m is 0 and A is a 4,4-difluorocyclohexyl group;
a compound represented by the formula (I) wherein m is 0 and A is a 4-ethynylcyclohexyl group;
a compound represented by the formula (I) wherein m is 0 and A is a 3-fluoro-4-ethynylcyclohexyl group;
a compound represented by the formula (I) wherein m is 0 and A is a 4-fluoro-4-ethynylcyclohexyl group;
a compound represented by the formula (I) wherein m is 0 and A is a 4-(1-propynyl)cyclohexyl group;
a compound represented by the formula (I) wherein m is 0 and A is a 4-(2-propynyl)cyclohexyl group;
a compound represented by the formula (I) wherein m is 0 and A is a 4-(1-butynyl)cyclohexyl group;
a compound represented by the formula (I) wherein m is 0 and A is a 4-(2-butynyl)cyclohexyl group;
a compound represented by the formula (I) wherein m is 0 and A is a 4-(3-methoxy-1-propynyl)cyclohexyl group;
a compound represented by the formula (I) wherein m is 0 and A is a 4-(3-methoxy-1-butynyl)cyclohexyl group;
a compound represented by the formula (I) wherein m is 0 and A is a 4-(4-methoxy-1-butynyl)cyclohexyl group;
a compound represented by the formula (I) wherein m is 0 and A is a 4-(4-methoxy-2-butynyl)cyclohexyl group;
a compound represented by the formula (I) wherein m is 0 and A is a 4-(3-methoxy-1-pentynyl)cyclohexyl group;
a compound represented by the formula (I) wherein m is 0 and A is a 4-(4-methoxy-1-pentynyl)cyclohexyl group;
a compound represented by the formula (I) wherein m is 0 and A is a 4-(5-methoxy-1-pentynyl)cyclohexyl group;
a compound represented by the formula (I) wherein m is 0 and A is a 4-(4-methoxy-2-pentynyl)cyclohexyl group;
a compound represented by the formula (I) wherein m is 0 and A is a 4-(5-methoxy-2-pentynyl)cyclohexyl group;
a compound represented by the formula (I) wherein m is 0 and A is a 4-(3-dimethylamino-1-propynyl)cyclohexyl group;
a compound represented by the formula (I) wherein m is 0 and A is a 4-(3-dimethylamino-1-butynyl)cyclohexyl group;
a compound represented by the formula (I) wherein m is 0 and A is a 4-(4-dimethylamino-1-butynyl)cyclohexyl group;
a compound represented by the formula (I) wherein m is 0 and A is a 4-(4-dimethylamino-2-butynyl)cyclohexyl group;
a compound represented by the formula (I) wherein m is 0 and A is a 4-(3-dimethylamino-1-pentynyl)cyclohexyl group;
a compound represented by the formula (I) wherein m is 0 and A is a 4-(4-dimethylamino-1-pentynyl)cyclohexyl group;
a compound represented by the formula (I) wherein m is 0 and A is a 4-(5-dimethylamino-1-pentynyl)cyclohexyl group;
a compound represented by the formula (I) wherein m is 0 and A is a 4-(4-dimethylamino-2-pentynyl)cyclohexyl group;
a compound represented by the formula (I) wherein m is 0 and A is a 4-(5-dimethylamino-2-pentynyl)cyclohexyl group;
a compound represented by the formula (I) wherein m is 0 and A is a 4-(2-methoxycarbonylethynyl)cyclohexyl group;
a compound represented by the formula (I) wherein m is 0 and A is a 4-(3-methoxycarbonyl-1-propynyl)cyclohexyl group;
a compound represented by the formula (I) wherein m is 0 and A is a 4-(3-methoxycarbonyl-1-butynyl)cyclohexyl group;
a compound represented by the formula (I) wherein m is 0 and A is a 4-(4-methoxycarbonyl-1-butynyl)cyclohexyl group;
a compound represented by the formula (I) wherein m is 0 and A is a 4-(4-methoxycarbonyl-2-butynyl)cyclohexyl group;
a compound represented by the formula (I) wherein m is 0 and A is a 4-(3-methoxycarbonyl-1-pentynyl)cyclohexyl group;
a compound represented by the formula (I) wherein m is 0 and A is a 4-(4-methoxycarbonyl-1-pentynyl)cyclohexyl group;
a compound represented by the formula (I) wherein m is 0 and A is a 4-(5-methoxycarbonyl-1-pentynyl)cyclohexyl group;

a compound represented by the formula (I) wherein m is 0 and A is a 4-(4-methoxycarbonyl-2-pentynyl)cyclohexyl group;
a compound represented by the formula (I) wherein m is 0 and A is a 4-(5-methoxycarbonyl-2-pentynyl)cyclohexyl group;
a compound represented by the formula (I) wherein m is 0 and A is a 4-(2-bromoethynyl)cyclohexyl group;
a compound represented by the formula (I) wherein m is 0 and A is a 4-(2-iodoethynyl)cyclohexyl group;
a compound represented by the formula (I) wherein m is 0 and A is a 4-(3-fluoro-1-propynyl)cyclohexyl group;
a compound represented by the formula (I) wherein m is 0 and A is a 4-(3,3-difluoro-1-propynyl)cyclohexyl group;
a compound represented by the formula (I) wherein m is 0 and A is a 4-(3,3,3-trifluoro-1-propynyl)cyclohexyl group;
a compound represented by the formula (I) wherein m is 0 and A is a 4-(1-fluoro-2-propynyl)cyclohexyl group;
a compound represented by the formula (I) wherein m is 0 and A is a 4-(1,1-difluoro-2-propynyl)cyclohexyl group;
a compound represented by the formula (I) wherein m is 0 and A is a 4-(3-fluoro-1-butynyl)cyclohexyl group;
a compound represented by the formula (I) wherein m is 0 and A is a 4-(4-fluoro-1-butynyl)cyclohexyl group;
a compound represented by the formula (I) wherein m is 0 and A is a 4-(3-fluoro-1-pentynyl)cyclohexyl group;
a compound represented by the formula (I) wherein m is 0 and A is a 4-(4-fluoro-1-pentynyl)cyclohexyl group;
a compound represented by the formula (I) wherein m is 0 and A is a 4-(5-fluoro-1-pentynyl)cyclohexyl group;
a compound represented by the formula (I) wherein m is 0 and A is a 3-methoxyiminocyclohexyl group;
a compound represented by the formula (I) wherein m is 0 and A is a 3-ethoxyiminocyclohexyl group;
a compound represented by the formula (I) wherein m is 0 and A is a 4-methoxyiminocyclohexyl group;
a compound represented by the formula (I) wherein m is 0 and A is a 4-ethoxyiminocyclohexyl group;
a compound represented by the formula (I) wherein m is 0 and A is a 3-cyano-3-cyclopentenyl group;
a compound represented by the formula (I) wherein m is 0 and A is a 3-fluoro-3-cyclopentenyl group;
a compound represented by the formula (I) wherein m is 0 and A is a 3-ethynyl-3-cyclopentenyl group;
a compound represented by the formula (I) wherein m is 0 and A is a 3-(1-propynyl)-3-cyclopentenyl group;
a compound represented by the formula (I) wherein m is 0 and A is a 3-(2-propynyl)-3-cyclopentenyl group;
a compound represented by the formula (I) wherein m is 0 and A is a 3-(2-butynyl)-3-cyclopentenyl group;
a compound represented by the formula (I) wherein m is 0 and A is a 3-cyano-3-cyclohexenyl group;
a compound represented by the formula (I) wherein m is 0 and A is a 3-fluoro-3-cyclohexenyl group;
a compound represented by the formula (I) wherein m is 0 and A is a 3-ethynyl-3-cyclohexenyl group;
a compound represented by the formula (I) wherein m is 0 and A is a 3-(1-propynyl)-3-cyclohexenyl group;
a compound represented by the formula (I) wherein m is 0 and A is a 3-(2-propynyl)-3-cyclohexenyl group;
a compound represented by the formula (I) wherein m is 0 and A is a 3-(2-butynyl)-3-cyclohexenyl group;
a compound represented by the formula (I) wherein m is 0 and A is a 4-cyano-3-cyclohexenyl group;
a compound represented by the formula (I) wherein m is 0 and A is a 4-fluoro-3-cyclohexenyl group;
a compound represented by the formula (I) wherein m is 0 and A is a 4-ethynyl-3-cyclohexenyl group;
a compound represented by the formula (I) wherein m is 0 and A is a 4-(1-propynyl)-3-cyclohexenyl group;
a compound represented by the formula (I) wherein m is 0 and A is a 4-(2-propynyl)-3-cyclohexenyl group;
a compound represented by the formula (I) wherein m is 0 and A is a 4-(1-butynyl)-3-cyclohexenyl group;
a compound represented by the formula (I) wherein m is 0 and A is a 4-(2-butynyl)-3-cyclohexenyl group;
a compound represented by the formula (I) wherein m is 0 and A is a 4-(3-methoxy-1-propynyl)-3-cyclohexenyl group;
a compound represented by the formula (I) wherein m is 0 and A is a 4-(3-methoxy-1-butynyl)-3-cyclohexenyl group;
a compound represented by the formula (I) wherein m is 0 and A is a 4-(4-methoxy-1-butynyl)-3-cyclohexenyl group;
a compound represented by the formula (I) wherein m is 0 and A is a 4-(4-methoxy-2-butynyl)-3-cyclohexenyl group;
a compound represented by the formula (I) wherein m is 0 and A is a 4-(3-methoxy-1-pentynyl)-3-cyclohexenyl group;
a compound represented by the formula (I) wherein m is 0 and A is a 4-(4-methoxy-1-pentynyl)-3-cyclohexenyl group;
a compound represented by the formula (I) wherein m is 0 and A is a 4-(5-methoxy-1-pentynyl)-3-cyclohexenyl group;
a compound represented by the formula (I) wherein m is 0 and A is a 4-(4-methoxy-2-pentynyl)-3-cyclohexenyl group;
a compound represented by the formula (I) wherein m is 0 and A is a 4-(5-methoxy-2-pentynyl)-3-cyclohexenyl group;
a compound represented by the formula (I) wherein m is 0 and A is a 4-(3-dimethylamino-1-propyl)-3-cyclohexenyl group;
a compound represented by the formula (I) wherein m is 0 and A is a 4-(3-dimethylamino-1-butynyl)-3-cyclohexenyl group;
a compound represented by the formula (I) wherein m is 0 and A is a 4-(4-dimethylamino-1-butynyl)-3-cyclohexenyl group;
a compound represented by the formula (I) wherein m is 0 and A is a 4-(4-dimethylamino-2-butynyl)-3-cyclohexenyl group;
a compound represented by the formula (I) wherein m is 0 and A is a 4-(3-dimethylamino-1-pentynyl)-3-cyclohexenyl group;
a compound represented by the formula (I) wherein m is 0 and A is a 4-(4-dimethylamino-1-pentynyl)-3-cyclohexenyl group;
a compound represented by the formula (I) wherein m is 0 and A is a 4-(5-dimethylamino-1-pentynyl)-3-cyclohexenyl group;
a compound represented by the formula (I) wherein m is 0 and A is a 4-(4-dimethylamino-2-pentynyl)-3-cyclohexenyl group;
a compound represented by the formula (I) wherein m is 0 and A is a 4-(5-dimethylamino-2-pentynyl)-3-cyclohexenyl group;
a compound represented by the formula (I) wherein m is 0 and A is a 4-(3-methoxycarbonyl-1-propynyl)-3-cyclohexenyl group;
a compound represented by the formula (I) wherein m is 0 and A is a 4-(3-methoxycarbonyl-1-butynyl)-3-cyclohexenyl group;
a compound represented by the formula (I) wherein m is 0 and A is a 4-(4-methoxycarbonyl-1-butynyl)-3-cyclohexenyl group;
a compound represented by the formula (I) wherein m is 0 and A is a 4-(4-methoxycarbonyl-2-butynyl)-3-cyclohexenyl group;

a compound represented by the formula (I) wherein m is 0 and
A is a 4-(3-methoxycarbonyl-1-pentynyl)-3-cyclohexenyl group;
a compound represented by the formula (I) wherein m is 0 and
A is a 4-(4-methoxycarbonyl-1-pentynyl)-3-cyclohexenyl group;
a compound represented by the formula (I) wherein m is 0 and
A is a 4-(5-methoxycarbonyl-1-pentynyl)-3-cyclohexenyl group;
a compound represented by the formula (I) wherein m is 0 and
A is a 4-(4-methoxycarbonyl-2-pentynyl)-3-cyclohexenyl group;
a compound represented by the formula (I) wherein m is 0 and
A is a 4-(5-methoxycarbonyl-2-pentynyl)-3-cyclohexenyl group;
a compound represented by the formula (I) wherein m is 0 and
A is a 4-(2-bromoethynyl)-3-cyclohexenyl group;
a compound represented by the formula (I) wherein m is 0 and
A is a 4-(2-iodoethynyl)-3-cyclohexenyl group;
a compound represented by the formula (I) wherein m is 0 and
A is a 4-(3-fluoro-1-propynyl)-3-cyclohexenyl group;
a compound represented by the formula (I) wherein m is 0 and
A is a 4-(3,3-difluoro-1-propynyl)-3-cyclohexenyl group;
a compound represented by the formula (I) wherein m is 0 and
A is a 4-(3,3,3-trifluoro-1-propynyl)-3-cyclohexenyl group;
a compound represented by the formula (I) wherein m is 0 and
A is a 4-(1-fluoro-2-propynyl)-3-cyclohexenyl group;
a compound represented by the formula (I) wherein m is 0 and
A is a 4-(1,1-difluoro-2-propynyl)-3-cyclohexenyl group;
a compound represented by the formula (I) wherein m is 0 and
A is a 4-(3-fluoro-1-butynyl)-3-cyclohexenyl group;
a compound represented by the formula (I) wherein m is 0 and
A is a 4-(4-fluoro-1-butynyl)-3-cyclohexenyl group;
a compound represented by the formula (I) wherein m is 0 and
A is a 4-(3-fluoro-1-pentynyl)-3-cyclohexenyl group;
a compound represented by the formula (I) wherein m is 0 and
A is a 4-(4-fluoro-1-pentynyl)-3-cyclohexenyl group;
a compound represented by the formula (I) wherein m is 0 and
A is a 4-(5-fluoro-1-pentynyl)-3-cyclohexenyl group;
a compound represented by the formula (I) wherein m is 1 and
A is a 3-cyanocyclopentyl group;
a compound represented by the formula (I) wherein m is 1 and
A is a 3-fluorocyclopentyl group;
a compound represented by the formula (I) wherein m is 1 and
A is a 3,3-difluorocyclopentyl group;
a compound represented by the formula (I) wherein m is 1 and
A is a 3-ethynylcyclopentyl group;
a compound represented by the formula (I) wherein m is 1 and
A is a 3-(1-propynyl)cyclopentyl group;
a compound represented by the formula (I) wherein m is 1 and
A is a 3-(2-propynyl)cyclopentyl group;
a compound represented by the formula (I) wherein m is 1 and
A is a 3-(2-butynyl)cyclopentyl group;
a compound represented by the formula (I) wherein m is 1 and
A is a 3-cyanocyclohexyl group;
a compound represented by the formula (I) wherein m is 1 and
A is a 3-fluorocyclohexyl group;
a compound represented by the formula (I) wherein m is 1 and
A is a 3,3-difluorocyclohexyl group;
a compound represented by the formula (I) wherein m is 1 and
A is a 3-ethynylcyclohexyl group;
a compound represented by the formula (I) wherein m is 1 and
A is a 3-(1-propynyl)cyclohexyl group;
a compound represented by the formula (I) wherein m is 1 and
A is a 3-(2-propynyl)cyclohexyl group;
a compound represented by the formula (I) wherein m is 1 and
A is a 3-(2-butynyl)cyclohexyl group;
a compound represented by the formula (I) wherein m is 1 and
A is a 4-cyanocyclohexyl group;
a compound represented by the formula (I) wherein m is 1 and
A is a 3-fluoro-4-cycanocyclohexyl group;
a compound represented by the formula (I) wherein m is 1 and
A is a 4-fluoro-4-cycanocyclohexyl group;
a compound represented by the formula (I) wherein m is 1 and
A is a 4-fluorocyclohexyl group;
a compound represented by the formula (I) wherein m is 1 and
A is a 4,4-difluorocyclohexyl group;
a compound represented by the formula (I) wherein m is 1 and
A is a 4-ethynylcyclohexyl group;
a compound represented by the formula (I) wherein m is 1 and
A is a 3-fluoro-4-ethynylcyclohexyl group;
a compound represented by the formula (I) wherein m is 1 and
A is a 4-fluoro-4-ethynylcyclohexyl group;
a compound represented by the formula (I) wherein m is 1 and
A is a 4-(1-propynyl)cyclohexyl group;
a compound represented by the formula (I) wherein m is 1 and
A is a 4-(2-propynyl)cyclohexyl group;
a compound represented by the formula (I) wherein m is 1 and
A is a 4-(1-butynyl)cyclohexyl group;
a compound represented by the formula (I) wherein m is 1 and
A is a 4-(2-butynyl)cyclohexyl group;
a compound represented by the formula (I) wherein m is 1 and
A is a 4-(3-methoxy-1-propynyl)cyclohexyl group;
a compound represented by the formula (I) wherein m is 1 and
A is a 4-(3-methoxy-1-butynyl)cyclohexyl group;
a compound represented by the formula (I) wherein m is 1 and
A is a 4-(4-methoxy-1-butynyl)cyclohexyl group;
a compound represented by the formula (I) wherein m is 1 and
A is a 4-(4-methoxy-2-butynyl)cyclohexyl group;
a compound represented by the formula (I) wherein m is 1 and
A is a 4-(3-methoxy-1-pentynyl)cyclohexyl group;
a compound represented by the formula (I) wherein m is 1 and
A is a 4-(4-methoxy-1-pentynyl)cyclohexyl group;
a compound represented by the formula (I) wherein m is 1 and
A is a 4-(5-methoxy-1-pentynyl)cyclohexyl group;
a compound represented by the formula (I) wherein m is 1 and
A is a 4-(4-methoxy-2-pentynyl)cyclohexyl group;
a compound represented by the formula (I) wherein m is 1 and
A is a 4-(5-methoxy-2-pentynyl)cyclohexyl group;
a compound represented by the formula (I) wherein m is 1 and
A is a 4-(3-dimethylamino-1-propynyl)cyclohexyl group;
a compound represented by the formula (I) wherein m is 1 and
A is a 4-(3-dimethylamino-1-butynyl)cyclohexyl group;
a compound represented by the formula (I) wherein m is 1 and
A is a 4-(4-dimethylamino-1-butynyl)cyclohexyl group;
a compound represented by the formula (I) wherein m is 1 and
A is a 4-(4-dimethylamino-2-butynyl)cyclohexyl group;
a compound represented by the formula (I) wherein m is 1 and
A is a 4-(3-dimethylamino-1-pentynyl)cyclohexyl group;
a compound represented by the formula (I) wherein m is 1 and
A is a 4-(4-dimethylamino-1-pentynyl)cyclohexyl group;
a compound represented by the formula (I) wherein m is 1 and
A is a 4-(5-dimethylamino-1-pentynyl)cyclohexyl group;
a compound represented by the formula (I) wherein m is 1 and
A is a 4-(4-dimethylamino-2-pentynyl)cyclohexyl group;
a compound represented by the formula (I) wherein m is 1 and
A is a 4-(5-dimethylamino-2-pentynyl)cyclohexyl group;
a compound represented by the formula (I) wherein m is 1 and
A is a 4-(2-methoxycarbonylethynyl)cyclohexyl group;
a compound represented by the formula (I) wherein m is 1 and
A is a 4-(3-methoxycarbonyl-1-propynyl)cyclohexyl group;

a compound represented by the formula (I) wherein m is 1 and
    A is a 4-(3-methoxycarbonyl-1-butynyl)cyclohexyl group;
a compound represented by the formula (I) wherein m is 1 and
    A is a 4-(4-methoxycarbonyl-1-butynyl)cyclohexyl group;
a compound represented by the formula (I) wherein m is 1 and
    A is a 4-(4-methoxycarbonyl-2-butynyl)cyclohexyl group;
a compound represented by the formula (I) wherein m is 1 and
    A is a 4-(3-methoxycarbonyl-1-pentynyl)cyclohexyl group;
a compound represented by the formula (I) wherein m is 1 and
    A is a 4-(4-methoxycarbonyl-1-pentynyl)cyclohexyl group;
a compound represented by the formula (I) wherein m is 1 and
    A is a 4-(5-methoxycarbonyl-1-pentynyl)cyclohexyl group;
a compound represented by the formula (I) wherein m is 1 and
    A is a 4-(4-methoxycarbonyl-2-pentynyl)cyclohexyl group;
a compound represented by the formula (I) wherein m is 1 and
    A is a 4-(5-methoxycarbonyl-2-pentynyl)cyclohexyl group;
a compound represented by the formula (I) wherein m is 1 and
    A is a 4-(2-bromoethynyl)cyclohexyl group;
a compound represented by the formula (I) wherein m is 1 and
    A is a 4-(2-iodoethynyl)cyclohexyl group;
a compound represented by the formula (I) wherein m is 1 and
    A is a 4-(3-fluoro-1-propynyl)cyclohexyl group;
a compound represented by the formula (I) wherein m is 1 and
    A is a 4-(3,3-difluoro-1-propynyl)cyclohexyl group;
a compound represented by the formula (I) wherein m is 1 and
    A is a 4-(3,3,3-trifluoro-1-propynyl)cyclohexyl group;
a compound represented by the formula (I) wherein m is 1 and
    A is a 4-(1-fluoro-2-propynyl)cyclohexyl group;
a compound represented by the formula (I) wherein m is 1 and
    A is a 4-(1,1-difluoro-2-propynyl)cyclohexyl group;
a compound represented by the formula (I) wherein m is 1 and
    A is a 4-(3-fluoro-1-butynyl)cyclohexyl group;
a compound represented by the formula (I) wherein m is 1 and
    A is a 4-(4-fluoro-1-butynyl)cyclohexyl group;
a compound represented by the formula (I) wherein m is 1 and
    A is a 4-(3-fluoro-1-pentynyl)cyclohexyl group;
a compound represented by the formula (I) wherein m is 1 and
    A is a 4-(4-fluoro-1-pentynyl)cyclohexyl group;
a compound represented by the formula (I) wherein m is 1 and
    A is a 4-(5-fluoro-1-pentynyl)cyclohexyl group;
a compound represented by the formula (I) wherein m is 2 and
    A is a 3-cyanocyclopentyl group;
a compound represented by the formula (I) wherein m is 2 and
    A is a 3-fluorocyclopentyl group;
a compound represented by the formula (I) wherein m is 2 and
    A is a 3,3-difluorocyclopentyl group;
a compound represented by the formula (I) wherein m is 2 and
    A is a 3-ethynylcyclopentyl group;
a compound represented by the formula (I) wherein m is 2 and
    A is a 3-(1-propynyl)cyclopentyl group;
a compound represented by the formula (I) wherein m is 2 and
    A is a 3-(1-butynyl)cyclopentyl group;
a compound represented by the formula (I) wherein m is 2 and
    A is a 3-cyanocyclohexyl group;
a compound represented by the formula (I) wherein m is 2 and
    A is a 3-fluorocyclohexyl group;
a compound represented by the formula (I) wherein m is 2 and
    A is a 3,3-difluorocyclohexyl group;
a compound represented by the formula (I) wherein m is 2 and
    A is a 3-ethynylcyclohexyl group;
a compound represented by the formula (I) wherein m is 2 and
    A is a 3-(1-propynyl)cyclohexyl group;
a compound represented by the formula (I) wherein m is 2 and
    A is a 3-(1-butynyl)cyclohexyl group;
a compound represented by the formula (I) wherein m is 2 and
    A is a 4-cyanocyclohexyl group;
a compound represented by the formula (I) wherein m is 2 and
    A is a 4-fluorocyclohexyl group;
a compound represented by the formula (I) wherein m is 2 and
    A is a 4,4-difluorocyclohexyl group;
a compound represented by the formula (I) wherein m is 2 and
    A is a 4-ethynylcyclohexyl group;
a compound represented by the formula (I) wherein m is 2 and
    A is a 4-fluoro-4-ethynylcyclohexyl group;
a compound represented by the formula (I) wherein m is 2 and
    A is a 4-(1-propynyl)cyclohexyl group;
a compound represented by the formula (I) wherein m is 2 and
    A is a 4-(1-butynyl)cyclohexyl group;
a compound represented by the formula (I) wherein m is 1 and
    A is a 3-cyano-3-cyclopentenyl group;
a compound represented by the formula (I) wherein m is 1 and
    A is a 3-fluoro-3-cyclopentenyl group;
a compound represented by the formula (I) wherein m is 1 and
    A is a 3-ethynyl-3-cyclopentenyl group;
a compound represented by the formula (I) wherein m is 1 and
    A is a 3-(1-propynyl)-3-cyclopentenyl group;
a compound represented by the formula (I) wherein m is 1 and
    A is a 3-(2-propynyl)-3-cyclopentenyl group;
a compound represented by the formula (I) wherein m is 1 and
    A is a 3-(2-butynyl)-3-cyclopentenyl group;
a compound represented by the formula (I) wherein m is 1 and
    A is a 3-cyano-3-cyclohexenyl group;
a compound represented by the formula (I) wherein m is 1 and
    A is a 3-fluoro-3-cyclohexenyl group;
a compound represented by the formula (I) wherein m is 1 and
    A is a 3-ethynyl-3-cyclohexenyl group;
a compound represented by the formula (I) wherein m is 1 and
    A is a 3-(1-propynyl)-3-cyclohexenyl group;
a compound represented by the formula (I) wherein m is 1 and
    A is a 3-(2-propynyl)-3-cyclohexenyl group;
a compound represented by the formula (I) wherein m is 1 and
    A is a 3-(2-butynyl)-3-cyclohexenyl group;
a compound represented by the formula (I) wherein m is 1 and
    A is a 4-cyano-3-cyclohexenyl group;
a compound represented by the formula (I) wherein m is 1 and
    A is a 4-fluoro-3-cyclohexenyl group;
a compound represented by the formula (I) wherein m is 1 and
    A is a 4-ethynyl-3-cyclohexenyl group;
a compound represented by the formula (I) wherein m is 1 and
    A is a 4-(1-propynyl)-3-cyclohexenyl group;
a compound represented by the formula (I) wherein m is 1 and
    A is a 4-(2-propynyl)-3-cyclohexenyl group;
a compound represented by the formula (I) wherein m is 1 and
    A is a 4-(1-butynyl)-3-cyclohexenyl group;
a compound represented by the formula (I) wherein m is 1 and
    A is a 4-(2-butynyl)-3-cyclohexenyl group;
a compound represented by the formula (I) wherein m is 1 and
    A is a 4-(3-methoxy-1-propynyl)-3-cyclohexenyl group;
a compound represented by the formula (I) wherein m is 1 and
    A is a 4-(3-methoxy-1-butynyl)-3-cyclohexenyl group;
a compound represented by the formula (I) wherein m is 1 and
    A is a 4-(4-methoxy-1-butynyl)-3-cyclohexenyl group;
a compound represented by the formula (I) wherein in is 1 and
    A is a 4-(4-methoxy-2-butynyl)-3-cyclohexenyl group;
a compound represented by the formula (I) wherein m is 1 and
    A is a 4-(3-methoxy-1-pentynyl)-3-cyclohexenyl group;
a compound represented by the formula (I) wherein m is 1 and
    A is a 4-(4-methoxy-1-pentynyl)-3-cyclohexenyl group;

a compound represented by the formula (I) wherein m is 1 and
   A is a 4-(5-methoxy-1-pentynyl)-3-cyclohexenyl group;
a compound represented by the formula (I) wherein m is 1 and
   A is a 4-(4-methoxy-2-pentynyl)-3-cyclohexenyl group;
a compound represented by the formula (I) wherein m is 1 and
   A is a 4-(5-methoxy-2-pentynyl)-3-cyclohexenyl group;
a compound represented by the formula (I) wherein m is 1 and
   A is a 4-(3-dimethylamino-1-propynyl)-3-cyclohexenyl group;
a compound represented by the formula (I) wherein m is 1 and
   A is a 4-(3-dimethylamino-1-butynyl)-3-cyclohexenyl group;
a compound represented by the formula (I) wherein m is 1 and
   A is a 4-(4-dimethylamino-1-butynyl)-3-cyclohexenyl group;
a compound represented by the formula (I) wherein m is 1 and
   A is a 4-(4-dimethylamino-2-butynyl)-3-cyclohexenyl group;
a compound represented by the formula (I) wherein m is 1 and
   A is a 4-(3-dimethylamino-1-pentynyl)-3-cyclohexenyl group;
a compound represented by the formula (I) wherein m is 1 and
   A is a 4-(4-dimethylamino-1-pentynyl)-3-cyclohexenyl group;
a compound represented by the formula (I) wherein m is 1 and
   A is a 4-(5-dimethylamino-1-pentynyl)-3-cyclohexenyl group;
a compound represented by the formula (I) wherein m is 1 and
   A is a 4-(4-dimethylamino-2-pentynyl)-3-cyclohexenyl group;
a compound represented by the formula (I) wherein m is 1 and
   A is a 4-(5-dimethylamino-2-pentynyl)-3-cyclohexenyl group;
a compound represented by the formula (I) wherein m is 1 and
   A is a 4-(3-methoxycarbonyl-1-propynyl)-3-cyclohexenyl group;
a compound represented by the formula (I) wherein m is 1 and
   A is a 4-(3-methoxycarbonyl-1-butynyl)-3-cyclohexenyl group;
a compound represented by the formula (I) wherein m is 1 and
   A is a 4-(4-methoxycarbonyl-1-butynyl)-3-cyclohexenyl group;
a compound represented by the formula (I) wherein m is 1 and
   A is a 4-(4-methoxycarbonyl-2-butynyl)-3-cyclohexenyl group;
a compound represented by the formula (I) wherein m is 1 and
   A is a 4-(3-methoxycarbonyl-1-pentynyl)-3-cyclohexenyl group;
a compound represented by the formula (I) wherein m is 1 and
   A is a 4-(4-methoxycarbonyl-1-pentynyl)-3-cyclohexenyl group;
a compound represented by the formula (I) wherein m is 1 and
   A is a 4-(5-methoxycarbonyl-1-pentynyl)-3-cyclohexenyl group;
a compound represented by the formula (I) wherein m is 1 and
   A is a 4-(4-methoxycarbonyl-2-pentynyl)-3-cyclohexenyl group;
a compound represented by the formula (I) wherein m is 1 and
   A is a 4-(5-methoxycarbonyl-2-pentynyl)-3-cyclohexenyl group;
a compound represented by the formula (I) wherein m is 1 and
   A is a 4-(2-bromoethynyl-3-cyclohexenyl group;
a compound represented by the formula (I) wherein m is 1 and
   A is a 4-(2-iodoethynyl)-3-cyclohexenyl group;
a compound represented by the formula (I) wherein m is 1 and
   A is a 4-(3-fluoro-1-propynyl)-3-cyclohexenyl group;
a compound represented by the formula (I) wherein m is 1 and
   A is a 4-(3,3-difluoro-1-propynyl)-3-cyclohexenyl group;
a compound represented by the formula (I) wherein m is 1 and
   A is a 4-(3,3,3-trifluoro-1-propynyl)-3-cyclohexenyl group;
a compound represented by the formula (I) wherein m is 1 and
   A is a 4-(1-fluoro-2-propynyl)-3-cyclohexenyl group;
a compound represented by the formula (I) wherein m is 1 and
   A is a 4-(1,1-difluoro-2-propynyl)-3-cyclohexenyl group;
a compound represented by the formula (I) wherein m is 1 and
   A is a 4-(3-fluoro-1-butynyl)-3-cyclohexenyl group;
a compound represented by the formula (I) wherein m is 1 and
   A is a 4-(4-fluoro-1-butynyl)-3-cyclohexenyl group;
a compound represented by the formula (I) wherein m is 1 and
   A is a 4-(3-fluoro-1-pentynyl)-3-cyclohexenyl group;
a compound represented by the formula (I) wherein m is 1 and
   A is a 4-(4-fluoro-1-pentynyl)-3-cyclohexenyl group;
a compound represented by the formula (I) wherein m is 1 and
   A is a 4-(5-fluoro-1-pentynyl)-3-cyclohexenyl group;
a compound represented by the formula (I) wherein m is 2 and
   A is a 3-cyclopentenyl group;
a compound represented by the formula (I) wherein m is 2 and
   A is a 3-cyano-3-cyclopentenyl group;
a compound represented by the formula (I) wherein m is 2 and
   A is a 3-fluoro-3-cyclopentenyl group;
a compound represented by the formula (I) wherein m is 2 and
   A is a 3-ethynyl-3-cyclopentenyl group;
a compound represented by the formula (I) wherein m is 2 and
   A is a 3-(1-propynyl)-3-cyclopentenyl group;
a compound represented by the formula (I) wherein m is 2 and
   A is a 3-(1-butynyl)-3-cyclopentenyl group;
a compound represented by the formula (I) wherein m is 2 and
   A is a 3-cyclohexenyl group;
a compound represented by the formula (I) wherein m is 2 and
   A is a 3-cyano-3-cyclohexenyl group;
a compound represented by the formula (I) wherein m is 2 and
   A is a 3-fluoro-3-cyclohexenyl group;
a compound represented by the formula (I) wherein m is 2 and
   A is a 3-ethenyl-3-cyclohexenyl group;
a compound represented by the formula (I) wherein m is 2 and
   A is a 3-(1-propynyl)-3-cyclohexenyl group;
a compound represented by the formula (I) wherein m is 2 and
   A is a 3-(1-butynyl)-3-cyclohexenyl group;
a compound represented by the formula (I) wherein m is 1 and
   A is a 3-methoxyiminocyclopentyl group;
a compound represented by the formula (I) wherein m is 1 and
   A is a 3-ethoxyiminocyclopentyl group;
a compound represented by the formula (I) wherein m is 1 and
   A is a 3-methoxyiminocyclohexyl group;
a compound represented by the formula (I) wherein m is 1 and
   A is a 3-ethoxyiminocyclohexyl group;
a compound represented by the formula (I) wherein m is 1 and
   A is a 4-methoxyiminocyclohexyl group;
a compound represented by the formula (I) wherein m is 1 and
   A is a 4-ethoxyiminocyclohexyl group;
a compound represented by the formula (I) wherein m is 2 and
   A is a 3-methoxyiminocyclopentyl group;
a compound represented by the formula (I) wherein m is 2 and
   A is a 3-ethoxyiminocyclopentyl group;
a compound represented by the formula (I) wherein m is 2 and
   A is a 3-methoxyiminocyclohexyl group;
a compound represented by the formula (I) wherein m is 2 and
   A is a 3-ethoxyiminocyclohexyl group;
a compound represented by the formula (I) wherein m is 2 and
   A is a 4-methoxyiminocyclohexyl group;
a compound represented by the formula (I) wherein m is 2 and
   A is a 4-ethoxyiminocyclohexyl group;

a compound represented by the formula (I) wherein m is 1, $R^3$ and $R^4$ are hydrogen atoms, and A is a 3-cyanocyclopentyl group;
a compound represented by the formula (I) wherein m is 1, $R^3$ and $R^4$ are hydrogen atoms, and A is a 3-fluorocyclopentyl group;
a compound represented by the formula (I) wherein m is 1, $R^3$ and $R^9$ are hydrogen atoms, and A is a 3,3-difluorocyclopentyl group;
a compound represented by the formula (I) wherein m is 1, $R^3$ and $R^4$ are hydrogen atoms, and A is a 3-ethynylcyclopentyl group;
a compound represented by the formula (I) wherein m is 1, $R^3$ and $R^4$ are hydrogen atoms, and A is a 3-(1-propyl)cyclopentyl group;
a compound represented by the formula (I) wherein m is 1, $R^3$ and $R^4$ are hydrogen atoms, and A is a 3-(2-propyl)cyclopentyl group;
a compound represented by the formula (I) wherein m is 1, $R^3$ and $R^4$ are hydrogen atoms, and A is a 3-(2-butynyl)cyclopentyl group;
a compound represented by the formula (I) wherein m is 1, $R^3$ and $R^4$ are hydrogen atoms, and A is a 3-cyanocyclohexyl group;
a compound represented by the formula (I) wherein m is 1, $R^3$ and $R^4$ are hydrogen atoms, and A is a 3-fluorocyclohexyl group;
a compound represented by the formula (I) wherein m is 1, $R^3$ and $R^4$ are hydrogen atoms, and A is a 3,3-difluorocyclohexyl group;
a compound represented by the formula (I) wherein m is 1, $R^3$ and $R^4$ are hydrogen atoms, and A is a 3-ethynylcyclohexyl group;
a compound represented by the formula (I) wherein m is 1, $R^3$ and $R^4$ are hydrogen atoms, and A is a 3-(1-propynyl)cyclohexyl group;
a compound represented by the formula (I) wherein m is 1, $R^3$ and $R^4$ are hydrogen atoms, and A is a 3-(2-propynyl)cyclohexyl group;
a compound represented by the formula (I) wherein m is 1, $R^3$ and $R^4$ are hydrogen atoms, and A is a 3-(2-butynyl)cyclohexyl group;
a compound represented by the formula (I) wherein m is 1, $R^3$ and $R^4$ are hydrogen atoms, and A is a 4-cyanocyclohexyl group;
a compound represented by the formula (I) wherein m is 1, $R^3$ and $R^4$ are hydrogen atoms, and A is a 3-fluoro-4-cyanocyclohexyl group;
a compound represented by the formula (I) wherein m is 1, $R^3$ and $R^4$ are hydrogen atoms, and A is a 4-fluoro-4-cyanocyclohexyl group;
a compound represented by the formula (I) wherein m is 1, $R^3$ and $R^4$ are hydrogen atoms, and A is a 4-fluorocyclohexyl group;
a compound represented by the formula (I) wherein m is 1, $R^3$ and $R^4$ are hydrogen atoms, and A is a 4,4-difluorocyclohexyl group;
a compound represented by the formula (I) wherein m is 1, $R^3$ and $R^4$ are hydrogen atoms, and A is a 4-ethynylcyclohexyl group;
a compound represented by the formula (I) wherein m is 1, $R^3$ and $R^4$ are hydrogen atoms, and A is a 3-fluoro-4-ethynylcyclohexyl group;
a compound represented by the formula (I) wherein m is 1, $R^3$ and $R^4$ are hydrogen atoms, and A is a 4-fluoro-4-ethynylcyclohexyl group;
a compound represented by the formula (I) wherein m is 1, $R^3$ and $R^4$ are hydrogen atoms, and A is a 4-(1-propynyl)cyclohexyl group;
a compound represented by the formula (I) wherein m is 1, $R^3$ and $R^4$ are hydrogen atoms, and A is a 4-(2-propynyl)cyclohexyl group;
a compound represented by the formula (I) wherein m is 1, $R^3$ and $R^4$ are hydrogen atoms, and A is a 4-(1-butynyl)cyclohexyl group;
a compound represented by the formula (I) wherein m is 1, $R^3$ and $R^4$ are hydrogen atoms, and A is a 4-(2-butynyl)cyclohexyl group;
a compound represented by the formula (I) wherein m is 1, $R^3$ and $R^4$ are hydrogen atoms, and A is a 4-(3-methoxy-1-propynyl)cyclohexyl group;
a compound represented by the formula (I) wherein m is 1, $R^3$ and $R^4$ are hydrogen atoms, and A is a 4-(3-methoxy-1-butynyl)cyclohexyl group;
a compound represented by the formula (I) wherein m is 1, $R^3$ and $R^4$ are hydrogen atoms, and A is a 4-(4-methoxy-1-butynyl)cyclohexyl group;
a compound represented by the formula (I) wherein m is 1, $R^3$ and $R^4$ are hydrogen atoms, and A is a 4-(4-methoxy-2-butynyl)cyclohexyl group;
a compound represented by the formula (I) wherein m is 1, $R^3$ and $R^4$ are hydrogen atoms, and A is a 4-(3-methoxy-1-pentynyl)cyclohexyl group;
a compound represented by the formula (I) wherein m is 1, $R^3$ and $R^4$ are hydrogen atoms, and A is a 4-(4-methoxy-1-pentynyl)cyclohexyl group;
a compound represented by the formula (I) wherein m is 1, $R^3$ and $R^4$ are hydrogen atoms, and A is a 4-(5-methoxy-1-pentynyl)cyclohexyl group;
a compound represented by the formula (I) wherein m is 1, $R^3$ and $R^4$ are hydrogen atoms, and A is a 4-(4-methoxy-2-pentynyl)cyclohexyl group;
a compound represented by the formula (I) wherein m is 1, $R^3$ and $R^4$ are hydrogen atoms, and A is a 4-(5-methoxy-2-pentynyl)cyclohexyl group;
a compound represented by the formula (I) wherein m is 1, $R^3$ and $R^4$ are hydrogen atoms, and A is a 4-(3-dimethylamino-1-propynyl)cyclohexyl group;
a compound represented by the formula (I) wherein m is 1, $R^3$ and $R^4$ are hydrogen atoms, and A is a 4-(3-dimethylamino-1-butynyl)cyclohexyl group;
a compound represented by the formula (I) wherein m is 1, $R^3$ and $R^4$ are hydrogen atoms, and A is a 4-(4-dimethylamino-1-butynyl)cyclohexyl group;
a compound represented by the formula (I) wherein m is 1, $R^3$ and $R^4$ are hydrogen atoms, and A is a 4-(4-dimethylamino-2-butynyl)cyclohexyl group;
a compound represented by the formula (I) wherein m is 1, $R^3$ and $R^4$ are hydrogen atoms, and A is a 4-(3-dimethylamino-1-pentynyl)cyclohexyl group;
a compound represented by the formula (I) wherein m is 1, $R^3$ and $R^4$ are hydrogen atoms, and A is a 4-(4-dimethylamino-1-pentynyl)cyclohexyl group;
a compound represented by the formula (I) wherein m is 1, $R^3$ and $R^4$ are hydrogen atoms, and A is a 4-(5-dimethylamino-1-pentynyl)cyclohexyl group;
a compound represented by the formula (I) wherein m is 1, $R^3$ and $R^4$ are hydrogen atoms, and A is a 4-(4-dimethylamino-2-pentynyl)cyclohexyl group;
a compound represented by the formula (I) wherein m is 1, $R^3$ and $R^4$ are hydrogen atoms, and A is a 4-(5-dimethylamino-2-pentynyl)cyclohexyl group;

a compound represented by the formula (I) wherein m is 1, $R^3$ and $R^4$ are hydrogen atoms, and A is a 4-(2-methoxycarbonylethynyl)cyclohexyl group;

a compound represented by the formula (I) wherein m is 1, $R^3$ and $R^4$ are hydrogen atoms, and A is a 4-(3-methoxycarbonyl-1-propynyl)cyclohexyl group;

a compound represented by the formula (I) wherein m is 1, $R^3$ and $R^4$ are hydrogen atoms, and A is a 4-(3-methoxycarbonyl-1-butynyl)cyclohexyl group;

a compound represented by the formula (I) wherein m is 1, $R^3$ and $R^4$ are hydrogen atoms, and A is a 4-(4-methoxycarbonyl-1-butynyl)cyclohexyl group;

a compound represented by the formula (I) wherein m is 1, $R^3$ and $R^4$ are hydrogen atoms, and A is a 4-(4-methoxycarbonyl-2-butynyl)cyclohexyl group;

a compound represented by the formula (I) wherein m is 1, $R^3$ and $R^4$ are hydrogen atoms, and A is a 4-(3-methoxycarbonyl-1-pentynyl)cyclohexyl group;

a compound represented by the formula (I) wherein m is 1, $R^3$ and $R^4$ are hydrogen atoms, and A is a 4-(4-methoxycarbonyl-1-pentynyl)cyclohexyl group;

a compound represented by the formula (I) wherein m is 1, $R^3$ and $R^4$ are hydrogen atoms, and A is a 4-(5-methoxycarbonyl-1-pentynyl)cyclohexyl group;

a compound represented by the formula (I) wherein m is 1, $R^3$ and $R^4$ are hydrogen atoms, and A is a 4-(4-methoxycarbonyl-2-pentynyl)cyclohexyl group;

a compound represented by the formula (I) wherein m is 1, $R^3$ and $R^4$ are hydrogen atoms, and A is a 4-(5-methoxycarbonyl-2-pentynyl)cyclohexyl group;

a compound represented by the formula (I) wherein m is 1, $R^3$ and $R^4$ are hydrogen atoms, and A is a 4-(2-bromoethynyl)cyclohexyl group;

a compound represented by the formula (I) wherein m is 1, $R^3$ and $R^4$ are hydrogen atoms, and A is a 4-(2-iodoethynyl)cyclohexyl group;

a compound represented by the formula (I) wherein m is 1, $R^3$ and $R^4$ are hydrogen atoms, and A is a 4-(3-fluoro-1-propynyl)cyclohexyl group;

a compound represented by the formula (I) wherein m is 1, $R^3$ and $R^4$ are hydrogen atoms, and A is a 4-(3,3-difluoro-1-propynyl)cyclohexyl group;

a compound represented by the formula (I) wherein m is 1, $R^3$ and $R^4$ are hydrogen atoms, and A is a 4-(3,3,3-trifluoro-1-propynyl)cyclohexyl group;

a compound represented by the formula (I) wherein m is 1, $R^3$ and $R^4$ are hydrogen atoms, and A is a 4-(1-fluoro-2-propynyl)cyclohexyl group;

a compound represented by the formula (I) wherein m is 1, $R^3$ and $R^4$ are hydrogen atoms, and A is a 4-(1,1-difluoro-2-propynyl)cyclohexyl group;

a compound represented by the formula (I) wherein m is 1, $R^3$ and $R^4$ are hydrogen atoms, and A is a 4-(3-fluoro-1-butynyl)cyclohexyl group;

a compound represented by the formula (I) wherein m is 1, $R^3$ and $R^4$ are hydrogen atoms, and A is a 4-(4-fluoro-1-butynyl)cyclohexyl group;

a compound represented by the formula (I) wherein m is 1, $R^3$ and $R^4$ are hydrogen atoms, and A is a 4-(3-fluoro-1-pentynyl)cyclohexyl group;

a compound represented by the formula (I) wherein m is 1, $R^3$ and $R^4$ are hydrogen atoms, and A is a 4-(4-fluoro-1-pentynyl)cyclohexyl group;

a compound represented by the formula (I) wherein m is 1, $R^3$ and $R^4$ are hydrogen atoms, and A is a 4-(5-fluoro-1-pentynyl)cyclohexyl group;

a compound represented by the formula (I) wherein m is 2, $R^3$ and $R^4$ are hydrogen atoms, and A is a 3-cyanocyclopentyl group;

a compound represented by the formula (I) wherein m is 2, $R^3$ and $R^4$ are hydrogen atoms, and A is a 3-fluorocyclopentyl group;

a compound represented by the formula (I) wherein m is 2, $R^3$ and $R^4$ are hydrogen atoms, and A is a 3,3-difluorocyclopentyl group;

a compound represented by the formula (I) wherein m is 2, $R^3$ and $R^4$ are hydrogen atoms, and A is a 3-ethynylcyclopentyl group;

a compound represented by the formula (I) wherein m is 2, $R^3$ and $R^4$ are hydrogen atoms, and A is a 3-(1-propyl)cyclopentyl group;

a compound represented by the formula (I) wherein m is 2, $R^3$ and $R^4$ are hydrogen atoms, and A is a 3-(1-butynyl)cyclopentyl group;

a compound represented by the formula (I) wherein m is 2, $R^3$ and $R^4$ are hydrogen atoms, and A is a 3-cyanocyclohexyl group;

a compound represented by the formula (I) wherein m is 2, $R^3$ and $R^4$ are hydrogen atoms, and A is a 3-fluorocyclohexyl group;

a compound represented by the formula (I) wherein m is 2, $R^3$ and $R^4$ are hydrogen atoms, and A is a 3,3-difluorocyclohexyl group;

a compound represented by the formula (I) wherein m is 2, $R^3$ and $R^4$ are hydrogen atoms, and A is a 3-ethynylcyclohexyl group;

a compound represented by the formula (I) wherein m is 2, $R^3$ and $R^4$ are hydrogen atoms, and A is a 3-(1-propynyl)cyclohexyl group;

a compound represented by the formula (I) wherein m is 2, $R^3$ and $R^4$ are hydrogen atoms, and A is a 3-(1-butynyl)cyclohexyl group;

a compound represented by the formula (I) wherein m is 2, $R^3$ and $R^4$ are hydrogen atoms, and A is a 4-cyanocyclohexyl group;

a compound represented by the formula (I) wherein m is 2, $R^3$ and $R^4$ are hydrogen atoms, and A is a 4-fluorocyclohexyl group;

a compound represented by the formula (I) wherein m is 2, $R^3$ and $R^4$ are hydrogen atoms, and A is a 4,4-difluorocyclohexyl group;

a compound represented by the formula (I) wherein m is 2, $R^3$ and $R^4$ are hydrogen atoms, and A is a 4-ethynylcyclohexyl group;

a compound represented by the formula (I) wherein m is 2, $R^3$ and $R^4$ are hydrogen atoms, and A is a 4-fluoro-4-ethynylcyclohexyl group;

a compound represented by the formula (I) wherein m is 2, $R^3$ and $R^4$ are hydrogen atoms, and A is a 4-(1-propynyl)cyclohexyl group;

a compound represented by the formula (I) wherein m is 2, $R^3$ and $R^4$ are hydrogen atoms, and A is a 4-(1-butynyl)cyclohexyl group;

a compound represented by the formula (I) wherein m is 1, $R^3$ and $R^4$ are hydrogen atoms, and A is a 3-cyano-3-cyclopentenyl group;

a compound represented by the formula (I) wherein m is 1, $R^3$ and $R^4$ are hydrogen atoms, and A is a 3-fluoro-3-cyclopentenyl group;

a compound represented by the formula (I) wherein m is 1, $R^3$ and $R^4$ are hydrogen atoms, and A is a 3-ethynyl-3-cyclopentenyl group;

a compound represented by the formula (I) wherein m is 1, $R^3$ and $R^4$ are hydrogen atoms, and A is a 3-(1-propynyl)-3-cyclopentenyl group;

a compound represented by the formula (I) wherein m is 1, $R^3$ and $R^4$ are hydrogen atoms, and A is a 3-(2-propynyl)-3-cyclopentenyl group;

a compound represented by the formula (I) wherein m is 1, $R^3$ and $R^4$ are hydrogen atoms, and A is a 3-(2-butynyl)-3-cyclopentenyl group;

a compound represented by the formula (I) wherein m is 1, $R^3$ and $R^4$ are hydrogen atoms, and A is a 3-cyano-3-cyclohexenyl group;

a compound represented by the formula (I) wherein m is 1, $R^3$ and $R^4$ are hydrogen atoms, and A is a 3-fluoro-3-cyclohexenyl group;

a compound represented by the formula (I) wherein m is 1, $R^3$ and $R^4$ are hydrogen atoms, and A is a 3-ethynyl-3-cyclohexenyl group;

a compound represented by the formula (I) wherein m is 1, $R^3$ and $R^4$ are hydrogen atoms, and A is a 3-(1-propynyl)-3-cyclohexenyl group;

a compound represented by the formula (I) wherein m is 1, $R^3$ and $R^4$ are hydrogen atoms, and A is a 3-(2-propynyl)-3-cyclohexenyl group;

a compound represented by the formula (I) wherein m is 1, $R^3$ and $R^4$ are hydrogen atoms, and A is a 3-(2-butynyl)-3-cyclohexenyl group;

a compound represented by the formula (I) wherein m is 1, $R^3$ and $R^4$ are hydrogen atoms, and A is a 4-cyano-3-cyclohexenyl group;

a compound represented by the formula (I) wherein m is 1, $R^3$ and $R^4$ are hydrogen atoms, and A is a 4-fluoro-3-cyclohexenyl group;

a compound represented by the formula (I) wherein m is 1, $R^3$ and $R^4$ are hydrogen atoms, and A is a 4-ethynyl-3-cyclohexenyl group;

a compound represented by the formula (I) wherein m is 1, $R^3$ and $R^4$ are hydrogen atoms, and A is a 4-(1-propynyl)-3-cyclohexenyl group;

a compound represented by the formula (I) wherein m is 1, $R^3$ and $R^4$ are hydrogen atoms, and A is a 4-(2-propynyl)-3-cyclohexenyl group;

a compound represented by the formula (I) wherein m is 1, $R^3$ and $R^4$ are hydrogen atoms, and A is a 4-(1-butynyl)-3-cyclohexenyl group;

a compound represented by the formula (I) wherein m is 1, $R^3$ and $R^4$ are hydrogen atoms, and A is a 4-(2-butynyl)-3-cyclohexenyl group;

a compound represented by the formula (I) wherein m is 1, $R^3$ and $R^4$ are hydrogen atoms, and A is a 4-(3-methoxy-1-propynyl)-3-cyclohexenyl group;

a compound represented by the formula (I) wherein m is 1, $R^3$ and $R^4$ are hydrogen atoms, and A is a 4-(3-methoxy-1-butynyl)-3-cyclohexenyl group;

a compound represented by the formula (I) wherein m is 1, $R^3$ and $R^4$ are hydrogen atoms, and A is a 4-(4-methoxy-1-butynyl)-3-cyclohexenyl group;

a compound represented by the formula (I) wherein m is 1, $R^3$ and $R^4$ are hydrogen atoms, and A is a 4-(4-methoxy-2-butynyl)-3-cyclohexenyl group;

a compound represented by the formula (I) wherein m is 1, $R^3$ and $R^4$ are hydrogen atoms, and A is a 4-(3-methoxy-1-pentynyl)-3-cyclohexenyl group;

a compound represented by the formula (I) wherein m is 1, $R^3$ and $R^4$ are hydrogen atoms, and A is a 4-(4-methoxy-1-pentynyl)-3-cyclohexenyl group;

a compound represented by the formula (I) wherein m is 1, $R^3$ and $R^4$ are hydrogen atoms, and A is a 4-(5-methoxy-1-pentynyl)-3-cyclohexenyl group;

a compound represented by the formula (I) wherein m is 1, $R^3$ and $R^4$ are hydrogen atoms, and A is a 4-(4-methoxy-2-pentynyl)-3-cyclohexenyl group;

a compound represented by the formula (I) wherein m is 1, $R^3$ and $R^4$ are hydrogen atoms, and A is a 4-(5-methoxy-2-pentynyl)-3-cyclohexenyl group;

a compound represented by the formula (I) wherein m is 1, $R^3$ and $R^4$ are hydrogen atoms, and A is a 4-(3-dimethylamino-1-propynyl)-3-cyclohexenyl group;

a compound represented by the formula (I) wherein m is 1, $R^3$ and $R^4$ are hydrogen atoms, and A is a 4-(3-dimethylamino-1-butynyl)-3-cyclohexenyl group;

a compound represented by the formula (I) wherein m is 1, $R^3$ and $R^4$ are hydrogen atoms, and A is a 4-(4-dimethylamino-1-butynyl)-3-cyclohexenyl group;

a compound represented by the formula (I) wherein m is 1, $R^3$ and $R^4$ are hydrogen atoms, and A is a 4-(4-dimethylamino-2-butynyl)-3-cyclohexenyl group;

a compound represented by the formula (I) wherein m is 1, $R^3$ and $R^4$ are hydrogen atoms, and A is a 4-(3-dimethylamino-1-pentynyl)-3-cyclohexenyl group;

a compound represented by the formula (I) wherein m is 1, $R^3$ and $R^4$ are hydrogen atoms, and A is a 4-(4-dimethylamino-1-pentynyl)-3-cyclohexenyl group;

a compound represented by the formula (I) wherein m is 1, $R^3$ and $R^4$ are hydrogen atoms, and A is a 4-(5-dimethylamino-1-pentynyl)-3-cyclohexenyl group;

a compound represented by the formula (I) wherein m is 1, $R^3$ and $R^4$ are hydrogen atoms, and A is a 4-(4-dimethylamino-2-pentynyl)-3-cyclohexenyl group;

a compound represented by the formula (I) wherein m is 1, $R^3$ and $R^4$ are hydrogen atoms, and A is a 4-(5-dimethylamino-2-pentynyl)-3-cyclohexenyl group;

a compound represented by the formula (I) wherein m is 1, $R^3$ and $R^4$ are hydrogen atoms, and A is a 4-(3-methoxycarbonyl-1-propynyl)-3-cyclohexenyl group;

a compound represented by the formula (I) wherein m is 1, $R^3$ and $R^4$ are hydrogen atoms, and A is a 4-(3-methoxycarbonyl-1-butynyl)-3-cyclohexenyl group;

a compound represented by the formula (I) wherein m is 1, $R^3$ and $R^4$ are hydrogen atoms, and A is a 4-(4-methoxycarbonyl-1-butynyl)-3-cyclohexenyl group;

a compound represented by the formula (I) wherein m is 1, $R^3$ and $R^4$ are hydrogen atoms, and A is a 4-(4-methoxycarbonyl-2-butynyl)-3-cyclohexenyl group; a compound represented by the formula (I) wherein m is 1, $R^3$ and $R^4$ are hydrogen atoms, and A is a 4-(3-methoxycarbonyl-1-pentynyl)-3-cyclohexenyl group;

a compound represented by the formula (I) wherein m is 1, $R^3$ and $R^4$ are hydrogen atoms, and A is a 4-(4-methoxycarbonyl-1-pentynyl)-3-cyclohexenyl group;

a compound represented by the formula (I) wherein m is 1, $R^3$ and $R^4$ are hydrogen atoms, and A is a 4-(5-methoxycarbonyl-1-pentynyl)-3-cyclohexenyl group;

a compound represented by the formula (I) wherein m is 1, $R^3$ and $R^4$ are hydrogen atoms, and A is a 4-(4-methoxycarbonyl-2-pentynyl)-3-cyclohexenyl group;

a compound represented by the formula (I) wherein m is 1, $R^3$ and $R^4$ are hydrogen atoms, and A is a 4-(5-methoxycarbonyl-2-pentynyl)-3-cyclohexenyl group;

a compound represented by the formula (I) wherein m is 1, $R^3$ and $R^4$ are hydrogen atoms, and A is a 4-(2-bromoethynynl)-3-cyclohexenyl group;

a compound represented by the formula (I) wherein m is 1, $R^3$ and $R^4$ are hydrogen atoms, and A is a 4-(2-iodoethynynl)-3-cyclohexenyl group;

a compound represented by the formula (I) wherein m is 1, $R^3$ and $R^4$ are hydrogen atoms, and A is a 4-(3-fluoro-1-propynyl)-3-cyclohexenyl group;

a compound represented by the formula (I) wherein m is 1, $R^3$ and $R^4$ are hydrogen atoms, and A is a 4-(3,3-difluoro-1-propynyl)-3-cyclohexenyl group;

a compound represented by the formula (I) wherein m is 1, $R^3$ and $R^4$ are hydrogen atoms, and A is a 4-(3,3,3-trifluoro-1-propynyl)-3-cyclohexenyl group;

a compound represented by the formula (I) wherein m is 1, $R^3$ and $R^4$ are hydrogen atoms, and A is a 4-(1-fluoro-2-propynyl)-3-cyclohexenyl group;

a compound represented by the formula (I) wherein m is 1, $R^3$ and $R^4$ are hydrogen atoms, and A is a 4-(1,1-difluoro-2-propynyl)-3-cyclohexenyl group;

a compound represented by the formula (I) wherein m is 1, $R^3$ and $R^4$ are hydrogen atoms, and A is a 4-(3-fluoro-1-butynyl)-3-cyclohexenyl group;

a compound represented by the formula (I) wherein m is 1, $R^3$ and $R^4$ are hydrogen atoms, and A is a 4-(4-fluoro-1-butynyl)-3-cyclohexenyl group;

a compound represented by the formula (I) wherein m is 1, $R^3$ and $R^4$ are hydrogen atoms, and A is a 4-(3-fluoro-1-pentynyl)-3-cyclohexenyl group;

a compound represented by the formula (I) wherein m is 1, $R^3$ and $R^4$ are hydrogen atoms, and A is a 4-(4-fluoro-1-pentynyl)-3-cyclohexenyl group;

a compound represented by the formula (I) wherein m is 1, $R^3$ and $R^4$ are hydrogen atoms, and A is a 4-(5-fluoro-1-pentynyl)-3-cyclohexenyl group;

a compound represented by the formula (I) wherein m is 2, $R^3$ and $R^4$ are hydrogen atoms, and A is a 3-cyclopentenyl group;

a compound represented by the formula (I) wherein m is 2, $R^3$ and $R^4$ are hydrogen atoms, and A is a 3-cyano-3-cyclopentenyl group;

a compound represented by the formula (I) wherein m is 2, $R^3$ and $R^4$ are hydrogen atoms, and A is a 3-fluoro-3-cyclopentenyl group;

a compound represented by the formula (I) wherein m is 2, $R^3$ and $R^4$ are hydrogen atoms, and A is a 3-ethynyl-3-cyclopentenyl group;

a compound represented by the formula (I) wherein m is 2, $R^3$ and $R^4$ are hydrogen atoms, and A is a 3-(1-propynyl)-3-cyclopentenyl group;

a compound represented by the formula (I) wherein m is 2, $R^3$ and $R^4$ are hydrogen atoms, and A is a 3-(1-butynyl)-3-cyclopentenyl group;

a compound represented by the formula (I) wherein m is 2, $R^3$ and $R^4$ are hydrogen atoms, and A is a 3-cyclohexenyl group;

a compound represented by the formula (I) wherein m is 2, $R^3$ and $R^4$ are hydrogen atoms, and A is a 3-cyano-3-cyclohexenyl group;

a compound represented by the formula (I) wherein m is 2, $R^3$ and $R^4$ are hydrogen atoms, and A is a 3-fluoro-3-cyclohexenyl group;

a compound represented by the formula (I) wherein m is 2, $R^3$ and $R^4$ are hydrogen atoms, and A is a 3-ethynyl-3-cyclohexenyl group;

a compound represented by the formula (I) wherein m is 2, $R^3$ and $R^4$ are hydrogen atoms, and A is a 3-(1-propynyl)-3-cyclohexenyl group;

a compound represented by the formula (I) wherein m is 2, $R^3$ and $R^4$ are hydrogen atoms, and A is a 3-(1-butynyl)-3-cyclohexenyl group;

a compound represented by the formula (I) wherein m is 1, $R^3$ and $R^4$ are hydrogen atoms, and A is a 3-methoxyiminocyclopentyl group;

a compound represented by the formula (I) wherein m is 1, $R^3$ and $R^4$ are hydrogen atoms, and A is a 3-ethoxyiminocyclopentyl group;

a compound represented by the formula (I) wherein m is 1, $R^3$ and $R^4$ are hydrogen atoms, and A is a 3-methoxyiminocyclohexyl group;

a compound represented by the formula (I) wherein m is 1, $R^3$ and $R^4$ are hydrogen atoms, and A is a 3-ethoxyiminocyclohexyl group;

a compound represented by the formula (I) wherein m is 1, $R^3$ and $R^4$ are hydrogen atoms, and A is a 4-methoxyiminocyclohexyl group;

a compound represented by the formula (I) wherein m is 1, $R^3$ and $R^4$ are hydrogen atoms, and A is a 4-ethoxyiminocyclohexyl group;

a compound represented by the formula (I) wherein m is 2, $R^3$ and $R^4$ are hydrogen atoms, and A is a 3-methoxyiminocyclopentyl group;

a compound represented by the formula (I) wherein m is 2, $R^3$ and $R^4$ are hydrogen atoms, and A is a 3-ethoxyiminocyclopentyl group;

a compound represented by the formula (I) wherein m is 2, $R^3$ and $R^4$ are hydrogen atoms, and A is a 3-methoxyiminocyclohexyl group;

a compound represented by the formula (I) wherein m is 2, $R^3$ and $R^4$ are hydrogen atoms, and A is a 3-ethoxyiminocyclohexyl group;

a compound represented by the formula (I) wherein m is 2, $R^3$ and $R^4$ are hydrogen atoms, and A is a 4-methoxyiminocyclohexyl group; and a compound represented by the formula (I) wherein m is 2, $R^3$ and $R^4$ are hydrogen atoms, and A is a 4-ethoxyiminocyclohexyl group.

Then, a process for producing the compound of the present compound is explained.

A compound represented by the formula (I-a), which is a compound of the present invention represented by the formula (I) wherein n is 0, can be produced, for example, by the following Production Process 1 to Production Process 4.

Production Process 1

A compound represented by the formula (I-a) can be produced, for example, by reacting the following compound (a) and the following compound (b):

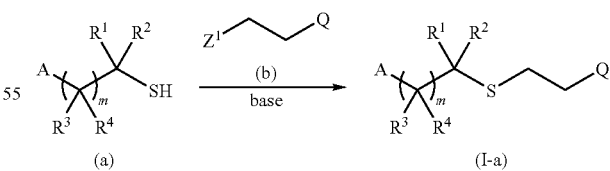

wherein A, Q, $R^1$, $R^2$, $R^3$, $R^4$ and m are as defined above, and $Z^1$ represents a leaving group such as a chlorine atom, a bromine atom, an iodine atom, or a methanesulfonyl group.

The reaction is performed in a conventional solvent in the presence of a conventional base.

Examples of the solvent used in the reaction include ethers such as diethyl ether, tetrahydrofuran and dimethoxymethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, water, and a mixture thereof.

Examples of the base used in the reaction include inorganic bases such as sodium hydride, sodium hydroxide, potassium hydroxide and potassium carbonate, alkali metal alkoxides such as sodium methoxide and potassium tert-butoxide, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (a).

The amount of the compound (b) used in the reaction is usually 1 to 10 mol per 1 mol of the compound (a).

The reaction temperature is usually in a range of −50 to 100° C., and the reaction time is usually 1 to 24 hours.

After completion of the reaction, the compound (I-a) can be isolated, for example, by pouring a reaction mixture into water and extracting the resulting mixture with an organic solvent followed by concentration. The isolated compound (I-a) can be further purified by chromatography, recrystallization or the like, if necessary.

Production Process 2

A compound represented by the formula (I-a) can be also produced, for example, by reacting the following compound (c) and compound (d):

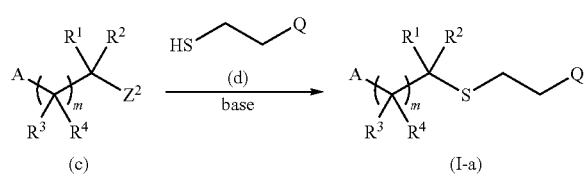

wherein A, Q, $R^1$, $R^2$, $R^3$, $R^4$ and m are as defined above, and $Z^2$ represents a leaving group such as a chlorine atom, a bromine atom, an iodine atom or a methanesulfonyl group.

The reaction is performed in a conventional solvent in the presence of a conventional base.

Examples of the solvent used in the reaction include ethers such as diethyl ether, tetrahydrofuran and dimethoxymethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, water, and a mixture thereof.

Examples of the base used in the reaction include inorganic bases such as sodium hydride, sodium hydroxide, potassium hydroxide and potassium carbonate, alkali metal alkoxides such as sodium methoxide and potassium tert-butoxide, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (d).

The amount of the compound (c) used in the reaction is usually 1 to 10 mol per 1 mol of the compound (d).

The reaction temperature is usually in a range of −50 to 100° C., and the reaction time is usually 1 to 24 hours.

After completion of the reaction, the compound (I-a) can be isolated, for example, by pouring a reaction mixture into water and extracting the resulting mixture with an organic solvent followed by concentration. The isolated compound (I-a) can be further purified by chromatography, recrystallization or the like, if necessary.

Production Process 3

A compound represented by the formula (I-a) can be also produced by from the compound (c) according to the following method:

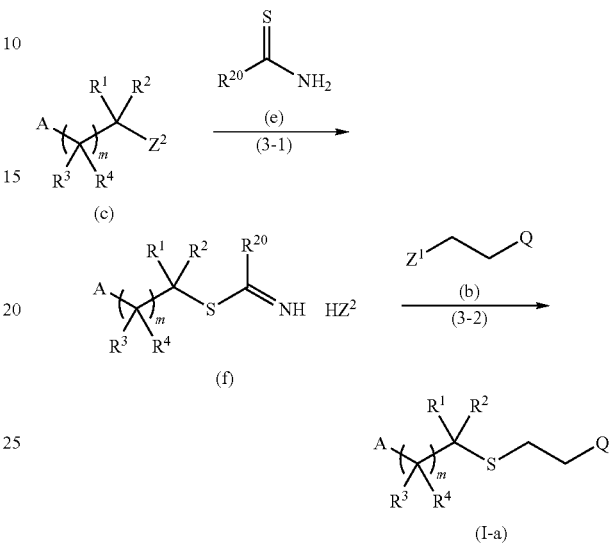

wherein A, Q, $R^1$, $R^2$, $R^3$, $R^4$, m, $Z^1$ and $Z^2$ are as defined above, and $R^{20}$ represents a methyl group or an amino group.

Step (3-1):

The compound (f) can be produced by reacting the compound (c) with the compound (e).

The reaction is performed in a conventional solvent.

Examples of the solvent used in the reaction include halogenated hydrocarbons such as dichloromethane and chloroform, alcohols such as methanol and ethanol, and a mixture thereof.

The amount of the compound (e) used in the reaction is usually 1 to 3 mol per 1 mol of the compound (c).

The reaction temperature is usually in a range of 20 to 200° C., and the reaction time is usually 0.5 to 240 hours.

After completion of the reaction, the compound (f) can be isolated, for example, by concentrating a reaction mixture. The isolated compound (f) can be used as it is in the step (3-2) or, if necessary, can be further purified by recrystallization or the like.

Step (3-2):

A compound represented by the formula (I-a) can be produced by reacting the compound (f) and the compound (b) in the presence of a base.

The reaction is performed in a conventional solvent in the presence of a conventional base.

Examples of the solvent used in the reaction include ethers such as diethyl ether, tetrahydrofuran and dimethoxyethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, water, and a mixture thereof.

Examples of the base used in the reaction include inorganic bases such as sodium hydroxide and potassium hydroxide, and alkali metal alcoxides such as sodium methoxide, and potassium tert-butoxide.

The amount of the base used in the reaction is usually 1 to 50 mol per 1 mol of the compound (f).

The amount of the compound (b) used in the reaction is usually 1 to 10 mol per 1 mol of the compound (f).

The reaction can be performed using a phase transfer catalyst such as tetra n-butylammonium bromide, if necessary.

The amount of the phase transfer catalyst used is usually 0.05 to 1.0 mol per 1 mol of the compound (f).

The reaction temperature is usually in a range of −50 to 100° C., and the reaction time is usually 1 to 24 hours.

After completion of the reaction, the compound (I-a) can be isolated, for example, by pouring a reaction mixture into water and extracting the resulting mixture with an organic solvent followed by concentration. The isolated compound (I-a) can be further purified by chromatography, recrystallization or the like, if necessary.

Production Process 4

A compound represented by the formula (I-a) can be also produced from the compound (c) according to the following method:

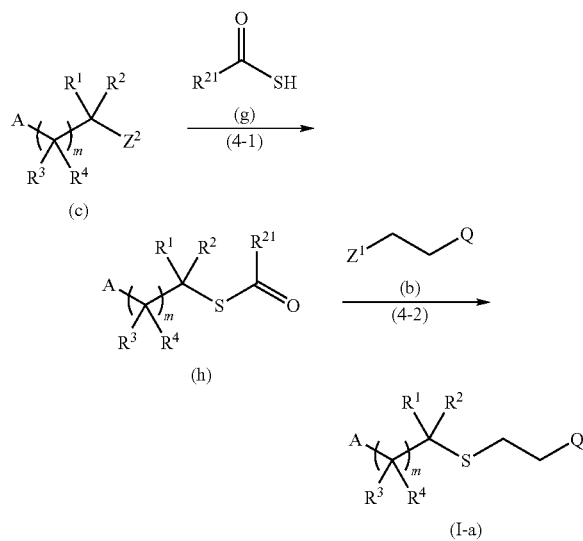

wherein A, Q, $R^1$, $R^2$, $R^3$, $R^4$, m, $Z^1$ and $Z^2$ are as defined above, and $R^{21}$ represents a methyl group or a phenyl group.

Step (4-1):

The compound (h) can be produced by reacting the compound (b) with the compound (g) in the presence of a base.

The reaction is performed in a conventional solvent in the presence of a conventional base.

Examples of the solvent used in the reaction include ethers such as diethyl ether, tetrahydrofuran and dimethoxyethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, and a mixture thereof.

Examples of the base used in the reaction include inorganic bases such as sodium hydride and potassium carbonate, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (c).

The amount of the compound (g) used in the reaction is usually 1 to 5 mol per 1 mol of the compound (b).

The reaction temperature is usually in a range of −20 to 80° C., and the reaction time is usually 1 to 24 hours.

After completion of the reaction, the compound (h) can be isolated, for example, by pouring a reaction mixture into acidic water (e.g. diluted hydrochloric acid etc.) and extracting the resulting mixture with an organic solvent followed by concentration. The isolated compound (h) can be further purified by chromatography, recrystallization or the like, if necessary.

Step (4-2):

A compound represented by the formula (I-a) can be produced by reacting the compound (c) and the compound (h) in the presence of a base.

The reaction is performed in a conventional solvent in the presence of a conventional base.

Examples of the solvent used in the reaction include ethers such as diethyl ether, tetrahydrofuran and dimethoxyethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, water, and a mixture thereof.

Examples of the base used in the reaction include inorganic bases such as sodium hydroxide and potassium hydroxide, and alkali methal alkoxides such as sodium methoxide, sodium ethoxide and potassium tert-butoxide.

The amount of the base used in the reaction is usually 1 to 10 mol per 1 mol of the compound (h).

The amount of the compound (c) used in the reaction is usually 1 to 10 mol per 1 mol of the compound (h).

The reaction temperature is usually in a range of −50 to 100° C., and the reaction time is usually 1 to 24 hours.

After completion of the reaction, the compound (I-a) can be isolated, for example, by pouring a reaction mixture into water and extracting the resulting mixture with an organic solvent followed by concentration. The isolated compound (I-a) can be further purified by chromatography, recrystallization or the like, if necessary.

Production Process 5

A compound represented by the formula (I-a) can be also produced from the compound (b) according to the following method:

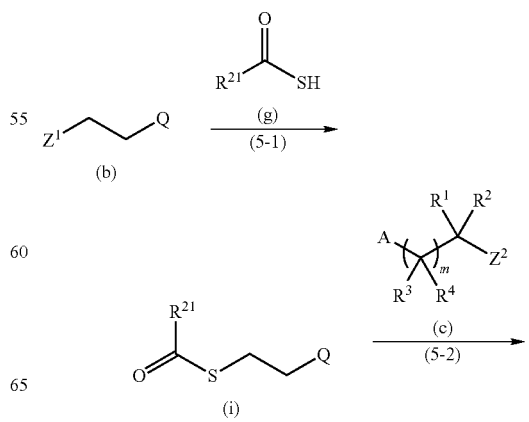

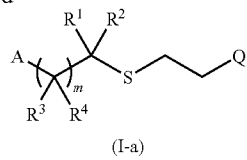

(I-a)

wherein A, Q, $R^1$, $R^2$, $R^3$, $R^4$, $R^5$, $R^{21}$, m, $Z^1$ and $Z^2$ are as defined above.

Step (5-1):

The compound (i) can be produced by reacting the compound (b) with the compound (g) in the presence of a base.

The reaction is performed in a conventional solvent in the presence of a conventional base.

Examples of the solvent used in the reaction include ethers such as diethyl ether, tetrahydrofuran and dimethoxyethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, and a mixture thereof.

Examples of the base used in the reaction include inorganic bases such as sodium hydride and potassium carbonate, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (b).

The amount of the compound (g) used in the reaction is usually 1 to 5 mol per 1 mol of the compound (b).

The reaction temperature is usually in a range of −20 to 80° C., and the reaction time is usually 1 to 24 hours.

After completion of the reaction, the compound (h) can be isolated, for example, by pouring a reaction mixture into acidic water (e.g. diluted hydrochloric acid etc.) and extracting the resulting mixture with an organic solvent followed by concentration. The isolated compound (h) can be further purified by chromatography, recrystallization or the like, if necessary.

Step (5-2):

A compound represented by the formula (I-a) can be produced by reacting the compound (c) with the compound (i) in the presence of a base.

The reaction is performed in a conventional solvent in the presence of a conventional base.

Examples of the solvent used in the reaction include ethers such as diethyl ether, tetrahydrofuran and dimethoxyethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, water, and a mixture thereof.

Examples of the base used in the reaction include inorganic bases such as sodium hydroxide and potassium hydroxide, and alkali metal alkoxides such as sodium methoxide, sodium ethoxide and potassium tert-butoxide.

The amount of the base used in the reaction is usually 1 to 10 mol per 1 mol of the compound (i).

The amount of the compound (c) used in the reaction is usually 1 to 10 mol per 1 mol of the compound (i).

The reaction temperature is usually in a range of −50 to 100° C., and the reaction time is usually 1 to 24 hours.

After completion of the reaction, the compound (I-a) can be isolated, for example, by pouring a reaction mixture into water and extracting the resulting mixture with an organic solvent followed by concentration. The isolated compound (I-a) can be further purified by chromatography, recrystallization or the like, if necessary.

Production Process 6

A compound represented by the formula (I-b) or (I-c), which is a compound of the present invention represented by the formula (I) wherein $R^1$ is a C1-C4 chain hydrocarbon group optionally substituted with a halogen atom or a hydrogen atom and $R^2$ is —C(=O) $R^5$ or a cyano group, can be produced from the compound (j) according to the following method:

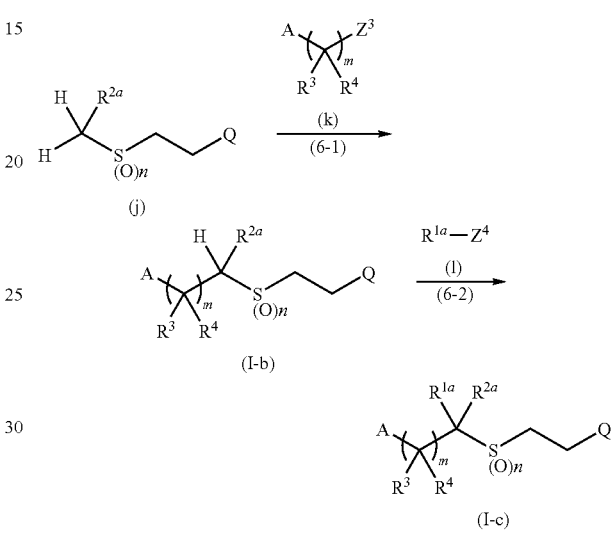

wherein A, Q, $R^3$, $R^4$, n and m are as defined above, $Z^3$ and $Z^4$ represent a leaving group such as a chlorine atom, a bromine atom, an iodine atom or a methanesulfonyl group, $R^{1a}$ represents a C1-C4 chain hydrocarbon group optionally substituted with a halogen atom, and $R^{2a}$ represents —C(=O)$R^5$ or a cyano group.

Step (6-1):

A compound represented by the formula (I-b) can be produced by reacting the compound (k) with the compound (j) in the presence of a base.

The reaction is performed in a conventional solvent in the presence of a base.

Examples of the solvent used in the reaction include ethers such as diethyl ether, tetrahydrofuran and diethoxyethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, water, and a mixture thereof.

Examples of the base used in the reaction include inorganic bases such as sodium hydride, sodium hydroxide, potassium hydroxide and potassium carbonate, alkali metal alkoxides such as sodium methoxide and potassium tert-butoxide, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (j).

The amount of the compound (k) used in the reaction is usually 1 to 10 mol per 1 mol of the compound (j).

The reaction temperature is usually in a range of −50 to 100° C., and the reaction time is usually 1 to 24 hours.

After completion of the reaction, the compound (I-b) can be isolated, for example, by pouring a reaction mixture into water and extracting the resulting mixture with an organic solvent followed by concentration. The isolated compound (I-b) can be further purified by chromatography, recrystallization or the like, if necessary.

Step (6-2):

A compound represented by the formula (I-c) can be produced by reacting the compound (1) with the compound (I-b) in the presence of a base.

The reaction is performed in a conventional solvent in the presence of a conventional base.

Examples of the solvent used in the reaction include ethers such as diethyl ether, tetrahydrofuran and dimethoxyethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, water, and a mixture thereof.

Examples of the base used in the reaction include inorganic bases such as sodium hydride, sodium hydroxide, potassium hydroxide and potassium carbonate, alkali metal alkoxides such as sodium methoxide and potassium tert-butoxide, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (I-b).

The amount of the compound (1) used in the reaction is usually 1 to 10 mol per 1 mol of the compound (I-b).

The reaction temperature is usually in a range of −50 to 100° C., and the reaction time is usually 1 to 24 hours.

After completion of the reaction, the compound (I-c) can be isolated, for example, by pouring a reaction mixture into water and extracting the resulting mixture with an organic solvent followed by concentration. The isolated compound (I-c) can be further purified by chromatography, recrystallization or the like, if necessary.

Production Process 7

A compound (I-c), which is a compound of the present invention represented by the formula (I) wherein $R^1$ is a C1-C4 chain hydrocarbon group optionally substituted with a halogen atom or a hydrogen atom and $R^2$ is $-C(=O)R^5$ or a cyano group, can be also produced from the compound (j) according to the following method:

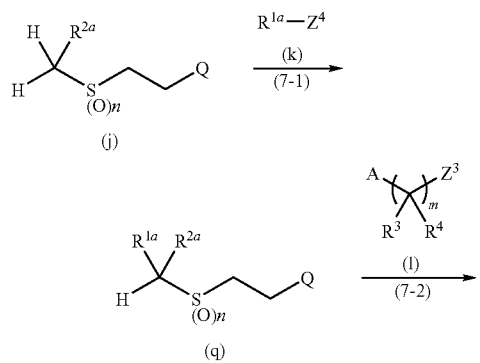

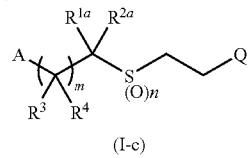

wherein A, Q, $R^{1a}$, $R^{2a}$, $R^3$, $R^4$, n, m, $Z^3$ and $Z^4$ are as defined above.

Step (7-1):

The compound (q) can be produced by reacting the compound (k) with the compound (j) in the presence of a base.

The reaction is performed in a conventional solvent in the presence of a conventional base.

Examples of the solvent used in the reaction include ethers such as diethyl ether, tetrahydrofuran and dimethoxyethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, water, and a mixture thereof.

Examples of the base used in the reaction include inorganic bases such as sodium hydride, sodium hydroxide, potassium hydroxide and potassium carbonate, alkali metal alkoxides such as sodium methoxide, and potassium tert-butoxide, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (j).

The amount of the compound (k) used in the reaction is usually 1 to 10 mol per 1 mol of the compound (j).

The reaction temperature is usually in a range of −50 to 100° C., and the reaction time is usually 1 to 24 hours.

After completion of the reaction, the compound (q) can be isolated, for example, by pouring a reaction mixture into water and extracting the resulting mixture with an organic solvent followed by concentration. The isolated compound (q) can be further purified by chromatography, recrystallization or the like, if necessary.

Step (7-2):

A compound represented by the formula (I-c) can be produced by reacting the compound (1) with the compound (q) in the presence of a base.

The reaction is performed in a conventional solvent in the presence of a conventional base.

Examples of the solvent used in the reaction include ethers such as diethyl ether, tetrahydrofuran and dimethoxymethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, and halogenated hydrocarbons such as 1,2-dichloroethane and chlorobenzene, water, and a mixture thereof.

Examples of the base used in the reaction include inorganic bases such as sodium hydride, sodium hydroxide, potassium hydroxide and potassium carbonate, alkali metal alkoxides such as sodium methoxide and potassium tert-butoxide, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (I-b).

The amount of the compound (1) used in the reaction is usually 1 to 10 mol per 1 mol of the compound (q).

The reaction temperature is usually in a range of −50 to 100° C., and the reaction time is usually 1 to 24 hours.

After completion of the reaction, the compound (I-c) can be isolated, for example, by pouring a reaction mixture into water and extracting the resulting mixture with an organic solvent followed by concentration. The isolated compound (I-c) can be further purified by chromatography, recrystallization or the like, if necessary.

Production Process 8

A compound represented by the formula (I-d), which is a compound of the present invention represented by the formula (I) wherein $R^1$ is a halogen atom and $R^2$ is —$C(=O)R^5$ or a cyano group, can be produced from the compound (I-b) according to the following method:

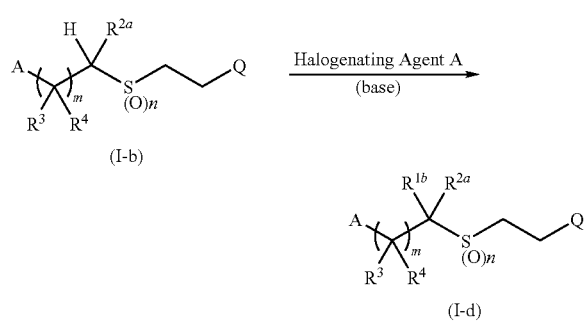

wherein, A, Q, $R^{2a}$, $R^3$, $R^4$, n and m are as defined above, and $R^{1b}$ represents a halogen atom.

The reaction is performed in a conventional solvent in the presence of a conventional base.

Examples of the solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, carbon tetrachloride, 1,2-dichloroethane, dichloromethane and dichlorobenzene, aliphatic nitriles such as acetonitrile and propionitrile, aromatic hydrocarbons such as toluene and xylene, water, and a mixture thereof.

Examples of the base used in the reaction include inorganic bases such as sodium hydride, sodium hydroxide, potassium hydroxide and potassium carbonate, alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (I-b).

Examples of the halogenating agent A used in the reaction include halogenated hydrocarbons such as carbon tetrachloride and hexachloroethane, halogens such as fluorine, chlorine, bromine and iodine, N-halogenated succinimide such as N-chlorosuccinimide, N-bromosuccinimide and N-iodosuccinimide, N-fluoropyrridinium salts such as 1-fluoro-2,4,6-trimethylpyrridinium trifluoromethane sulfonate and 1,1'-difluoro-2,2'-bipyridinium bistetrafluoroborate, and inorganic salts such as copper (II) chloride and copper (II) bromide.

The amount of the halogenating agent used in the reaction is usually 1 to 10 mol per 1 mol of the compound (I-b).

The reaction temperature is usually in a range of −100 to 100° C., and the reaction time is usually 1 to 24 hours.

After completion of the reaction, the compound (I-d) can be isolated, for example, by pouring a reaction mixture into water and extracting the resulting mixture with an organic solvent followed by concentration. The isolated compound (I-d) can be further purified by chromatography, recrystallization or the like, if necessary.

Production Process 9

A compound represented by the formula (I-d), which is a compound of the present invention represented by the formula (I) wherein $R^1$ is a halogen atom and $R^2$ is —$C(=O)R^5$ or a cyano group, can be produced from the compound (I-b) according to the following method:

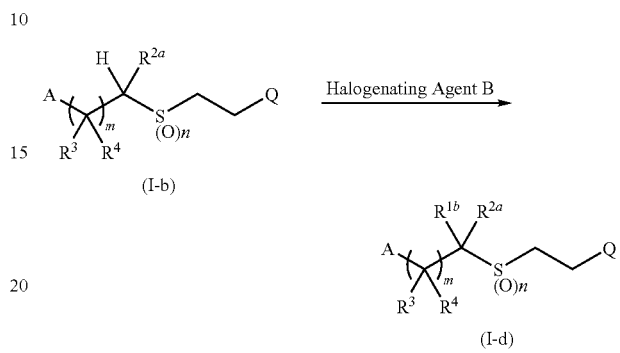

wherein A, Q, $R^{1b}$, $R^{2a}$, $R^3$, $R^4$, n and m are as defined above.

The reaction is performed in a conventional solvent.

Examples of the solvent used in the reaction include halogenated hydrocarbons such as chloroform, carbon tetrachloride, 1,2-dichloroethane, dichloromethane and dichlorobenzene, aliphatic nitriles such as acetonitrile, and propionitrile, aromatic hydrocarbons such as toluene and xylene, aliphatic carboxylic acids such as acetic acid, carbon disulfide, water, and a mixture thereof.

Examples of the halogenating agent B used in the reaction include halogens such as fluorine, chlorine, bromine and iodine, hydrogen halide such as hydrogen fluoride, hydrogen chloride, hydrogen bromide and hydrogen iodide, sulfur halide compounds such as thionyl chloride, thionyl bromide and sulfuryl chloride, and phosphorus halide compounds such as phosphorus trichloride, phosphorus tribromide, phosphorus pentachloride and phosphorus oxychloride.

The amount of the halogenating agent used in the reaction is usually 1 to 10 mol per 1 mol of the compound (I-b).

The reaction temperature is usually in a range of −100 to 200° C., and the reaction time is usually 1 to 24 hours.

After completion of the reaction, the compound (I-d) can be isolated, for example, by pouring a reaction mixture into water and extracting the resulting mixture with an organic solvent followed by concentration. The isolated compound (I-d) can be further purified by chromatography, recrystallization or the like, if necessary.

Production Process 10

A compound represented by the formula (I-e), which is a compound of the present invention represented by the formula (I) wherein n is 1 or 2, can be produced by oxidizing a compound represented by the formula (I-a):

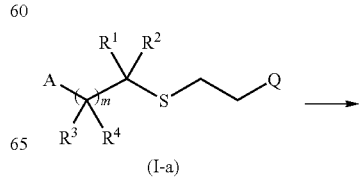

-continued

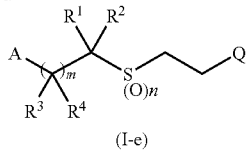

wherein A, Q, R$^1$, R$^2$, R$^3$, R$^4$ and m are as defined above, and n' represents 1 or 2.

The reaction is performed in a conventional solvent.

Examples of the solvent used in the reaction include alcohols such as methanol and ethanol, halogenated hydrocarbons such as dichloromethane and chloroform, aromatic hydrocarbons such as toluene and xylene, aliphatic carboxylic acids such as acetic acid and trifluoroacetic acid, water, and a mixture thereof.

Examples of the oxidizing agent used in the reaction include organic peroxides such as peracetic acid, trifluoroperacetic acid and m-chloroperbenzoic acid, halogen molecules such as chlorine and bromine, halogen-containing imides such as N-chlorosuccinimide, halogenated compounds of perchloric acid (or a salt thereof), periodic acid (or a salt thereof) and the like, permanganates such as potassium permanganate, chromates such as potassium chromate, peroxysulfates such as potassium persulfate, and hydrogen peroxide.

The amount of the oxidizing agent used in the reaction is usually 1 to 10 mol per 1 mol of the compound (I-a).

The reaction temperature is usually in a range of −50 to 200° C., and the reaction time is usually 1 to 72 hours.

After completion of the reaction, the compound (I-e) can be isolated as a sulfide derivative, for example, by pouring a reaction mixture into water and extracting the resulting mixture with an organic solvent followed by concentration. The isolated sulfide derivative (I-e) can be further purified by chromatography, recrystallization or the like, if necessary.

The compound (I-a) can be produced according to a known production method.

Examples of arthropod pests on which the compound of the present invention exhibits a controlling effect include harmful insects and harmful mites, and more specifically, the following arthropods.

Hemiptera:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), green rice leafhopper (*Nephotettix virescens*), and tea green leafhopper (*Empoasca onukii*); aphids (Aphididae) such as cotton aphid (*Aphis gossypii*), green peach aphid (*Myzus persicae*), cabbage aphid (*Brevicoryne brassicae*), piraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), and stink bug (*Halyomorpha mista*); whiteflies (Aleyrodidae) such as greenhouse whitefly (*Trialeurodes vaporariorum*), sweetpotato whitefly (*Bemisia tabaci*), citrus whitefly (*Dialeurodes citri*), and citrus spiny white fly (*Aleurocanthus spiniferus*); scales (Coccidae) such as California red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*), Japanese mealybug (*Planococcus kraunhiae*), Cosmstock mealybug (*Pseudococcus longispinis*), and white peach scale (*Pseudaulacaspis pentagona*); lace bugs (Tingidae); cimices such as *Cimex lectularius*; psyllids (Psyllidae); etc.

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes honmai.*), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); Carposinidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback (*Plutella xylostella*); gelechiid moths (Gelechiidae) such as pink bollworm (*Pectinophora gossypiella*), and potato tubeworm (*Phthorimaea operculella*); tiger moths and allies (Arctiidae) such as fall webworm (*Hyphantria cunea*); tineid moths (Tineidae) such as casemaking clothes moth (*Tinea translucens*), and webbing clothes moth (*Tineola bisselliella*); etc.

Thysanoptera:

Thrips (Thripidae) such as yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), etc.

Diptera:

Culices such as common mosquito (*Culex pipiens pallens*), *Cluex tritaeniorhynchus*, and *Cluex quinquefasciatus; Aedes* spp. such as yellow fever mosquito (*Aedes aegypti*), and Asian tiger mosquito (*Aedes albopictus*); *Anopheles* spp. such as *Anopheles sinensis*; chironomids (Chironomidae); house flies (Muscidae) such as *Musca domestica*, and *Muscina stabulans*; blow flies (Calliphoridae); flesh flies (Sarcophagidae); little house flies. (Fanniidae); anthomyiid flies (Anthomyiidae) such as seedcorn fly (*Delia platura*), and onion fly (*Delia antiqua*); leafminer flies (Agromyzidae) such as rice leafminer (*Agromyza oryzae*), little rice leafminer (*Hydrellia griseola*), tomato leafminer (*Liriomyza sativae*), legume leafminer (*Liriomyza trifolii*), and garden pea leafminer (*Chromatomyia horticola*); gout flies (Chloropidae) such as rice stem maggot (*Chlorops oryzae*); fruit flies (Tephritidae) such as melon fly (*Dacus cucurbitae*), and Mediterranean fruit fly (*Ceratitis capitata*); Drosophilidae; humpbacked flies (Phoridae) such as *Megaselia spiracularis*; moth flies (Psychodidae) such as *Clogmia albipunctata*; Simuliidae; Tabanidae such as horsefly (*Tabanus trigonus*); stable flies, etc.

Coleoptera:

Corn root worms (*Diabrotica* spp.) such as Western corn root worm (*Diabrotica virgifera virgifera*), and Southern corn root worm (*Diabrotica undecimpunctata howardi*); scarabs (Scarabaeidae) such as cupreous chafer (*Anomala cuprea*), soybean beetle (*Anomala rufocuprea*), and Japanese beetle (*Popillia japonica*); weevils such as maize weevil (*Sitophilus zeamais*), rice water weevil (*Lissorhoptrus oryzophilus*), azuki bean weevil (*Callosobruchus chinensis*), rice curculio (*Echinocnemus squameus*), boll weevil (*Anthonomus grandis*), and hunting billbug (*Sphenophorus venatus*); darkling beetles (Tenebrionidae) such as yellow mealworm (*Tenebrio molitor*), and red flour beetle (*Tribolium castaneum*); leaf beetles (Chrysomelidae) such as rice leaf beetle (*Oulema oryzae*), cucurbit leaf beetle (*Aulacophora femoralis*), striped flea beetle (*Phyllotreta striolata*), and Colorado potato beetle (*Leptinotarsa decemlineata*); dermestid beetles (Dermestidae) such as varied carper beetle (*Anthrenus verbasci*), and hide beetle (*Dermestes maculates*); deathwatch beetles (Anobiidae) such as cigarette beetle (*Lasioderma serricorne*); *Epilachna* such as Twenty-eight-spotted ladybird (*Epilachna vigintioctopunctata*); bark beetles (Scolytidae) such as powder-post beetle (*Lyctus brunneus*), and pine shoot beetle (*Tomicus piniperda*); false powder-post beetles (Bostrychidae); spider beetles (Ptinidae); longhorn beetles (Cerambycidae) such as white-spotted longicorn beetle (*Anoplophora malasiaca*); click beetles (*Agriotes* spp.); *Paederus fuscipens*, etc.

Orthoptera:

Asiatic locust (*Locusta migratoria*), African mole cricket (*Gryllotalpa africana*), rice grasshopper (*Oxya yezoensis*), rice grasshopper (*Oxya japonica*), Gryllidae, etc.

Shiphonaptera:

Cat flea (*Ctenocephalides felis*), dog flea (*Ctenocephalides canis*), human flea (*Pulex irritans*), oriental rat flea (*Xenopsylla cheopis*), etc.

Anoplura:

Human body louse (*Pediculus humanus corporis*), crab louse (*Phthirus pubis*), short-nosed cattle louse (*Haematopinus eurysternus*), sheep louse (*Dalmalinia ovis*), hog louse (*Haematopinus suis*), etc.

Hymenoptera:

Ants (Formicidae) such as pharaoh ant (*Monomorium pharaosis*), negro ant (*Formica fusca japonica*), black house ant (*Ochetellus glaber*), *Pristomyrmex pungens*, *Pheidole noda*, leaf-cutting ant (*Acromyrmex* spp.), and fire ant (*Solenopsis* spp.); hornets (Vespidae); bethylid wasps (Betylidae); sawflies (Tenthredinidae) such as cabbage sawfly (*Athalia rosae*), and *Athalia japonica*, etc.

Blattodea:

German cockroach (*Blattella germanica*), smokybrown cockroach (*Periplaneta fuliginosa*), American cockroach (*Periplaneta americana*), *Periplaneta brunnea*, oriental cockroach (*Blatta orientalis*);

Isoptera:

Termites such as Japanese subterranean termite (*Reticulitermes speratus*), Formosan subterranean termite (*Coptotermes formosanus*), western drywood termite (*Incisitermes minor*), Daikoku drywood termite (*Cryptotermes domesticus*), *Odontotermes formosanus*, *Neotermes koshunensis*, *Glyptotermes satsumesis*, *Glyptotermes nakajimai*, *Glyptotermes fuscus*, *Glyptotermes kodamai*, *Glyptotermes kushimensis*, Japanese dampwood termite (*Hodotermopsis japonica*), *Coptotermes guangzhoensis*, *Reticulitermes miyatakei*, eastern subterranean termite (*Reticulitermes flavipes amamianus*), *Reticulitermes* sp., *Nasutitermes takasagoesis*, *Pericapritermes nitobei*, and *Sinocapritermes mushae*, etc.

Acarina:

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as pink citrus rust mite (*Aculops pelekassi*), *Phyllocoptruta citri*, tomato rust mite (*Aculops lycopersici*), purple tea mite (*Calacarus carinatus*), pink tea rust mite (*Acaphylla theavagran*), *Eriophyes chibaensis*, and apple rust mite (*Aculus schlechtendali*); tarosonemid mites (Tarsonemidae) such as broad mite (*Polyphagotarsonemus latus*); false spider mites (Tenuipalpidae) such as *Brevipalpus phoenicis*; Tuckerellidae; ticks (Ixodidae) such as *Haemaphysalis longicornis*, *Haemaphysalis flava*, *Dermacentor taiwanicus*, American dog tick (*Dermacentor variabilis*), *Ixodes ovatus*, *Ixodes persulcatus*, black leg tick (*Ixodes scapularis*), lone star tick (*Amblyomma americanum*), *Boophilus microplus*, and *Rhipicephalus sanguineus*; Psoroptidae such as ear mite (*Otodectes cynotis*); itch mites (Sarcoptidae) such as *Sarcoptes scabiei*; folicle mites (Demodicidae) such as dog folicle mite (*Demodex canis*); acarid mites (Acaridae) such as mold mite (*Tyrophagus putrescentiae*), and *Tyrophagus similis*; house dust mites (Pyroglyphidae) such as *Dermatophagoides farinae*, and *Dermatophagoides ptrenyssnus*; cheyletide mites (Cheyletidae) such as *Cheyletus eruditus*, *Cheyletus malaccensis*, and *Cheyletus moorei*; parasitoid mites (Dermanyssidae) such as tropical rat mite (*Ornithonyssus bacoti*), northern fowl mite (*Ornithonyssus sylviarum*), and poultry red mite (*Dermanyssus gallinae*); chiggers (Trombiculidae) such as *Leptotrombidium akamushi*; spiders (Araneae) such as Japanese foliage spider (*Chiracanthium japonicum*), redback spider (*Latrodectus hasseltii*), etc.

Chilopoda: house centipede (*Thereuonema hilgendorfi*), *Scolopendra subspinipes*, etc.;

Diplopoda: garden millipede (*Oxidus gracilis*), *Nedyopus tambanus*, etc.;

Isopoda: common pill bug (*Armadillidium vulgare*), etc.;

Gastropoda: *Limax marginatus*, *Limax flavus*, etc.

Although the pesticidal composition of the present invention may be the compound of the present invention itself, the pesticidal composition of the present invention usually comprises the compound of the present invention in combination with a solid carrier, a liquid carrier and/or a gaseous carrier, and if necessary, a surfactant or other pharmaceutical additives and takes the form of an emulsifiable concentrate, an oil solution, a shampoo formulation, a flowable formulation, a dust, a wettable powder, a granule, a paste formulation, a microcapsule formulation, a foam formulation, an aerosol formulation, a carbon dioxide gas formulation, a tablet, a resin formulation or the like. The pesticidal composition of the present invention may be processed into a poison bait, a mosquito coil, an electric mosquito mat, a smoking pesticide, a fumigant or a sheet, and then be used.

The pesticidal composition of the present invention usually contains 0.1 to 95% by weight of the compound of the present invention.

Examples of the solid carrier include finely-divided powder or granules of clay (e.g., kaolin clay, diatomaceous earth, bentonite, Fubasami clay, acid clay, etc.), synthetic hydrated silicon oxide, talc, ceramics, other inorganic minerals (e.g., sericite, quartz, sulfur, activated carbon, calcium carbonate, hydrated silica, etc.), chemical fertilizers (e.g., ammonium sulfate, ammonium phosphate, ammonium nitrate, ammonium chloride, urea, etc.) and the like.

Examples of the liquid carrier include aromatic or aliphatic hydrocarbons (e.g., xylene, toluene, alkylnaphthalene, phenylxylylethane, kerosene, light oil, hexane, cyclohexane, etc.), halogenated hydrocarbons (e.g., chlorobenzene, dichloromethane, dichloroethane, trichloroethane, etc.), alcohols (e.g., methanol, ethanol, isopropyl alcohol, butanol, hexanol, ethylene glycol, etc.), ethers (e.g., diethyl ether, ethylene glycol dimethyl ether, diethylene glycol monomethyl ether, diethylene glycol monoethyl ether, propylene glycol monomethyl ether, tetrahydrofuran, dioxane, etc.), esters (e.g., ethyl acetate, butyl acetate, etc.), ketones (e.g., acetone, methyl ethyl ketone, methyl isobutyl ketone, cyclohexanone etc.), nitriles (e.g., acetonitrile, isobutyronitrile etc.), sulfoxides (e.g.; dimethyl sulfoxide etc.), acid amides (e.g., N,N-dimethylformamide, N,N-dimethylacetamide etc.), vegetable oils (e.g., soybean oil, cottonseed oil etc.), vegetable essential oils (e.g., orange oil, hyssop oil, lemon oil, etc.), water and the like.

Examples of the gaseous carrier include butane gas, chlorofluorocarbon, LPG (liquefied petroleum gas), dimethyl ether, carbon dioxide gas and the like.

Examples of the surfactant include alkyl sulfate salts, alkyl sulfonate salts, alkylaryl sulfonate salts, alkyl aryl ethers and their polyoxyethylated derivatives, polyethylene glycol ethers, polyhydric alcohol esters, and sugar alcohol derivatives.

Examples of other pharmaceutical additives include a binder, a dispersant, a stabilizer and the like, and specific examples thereof include casein, gelatin, polysaccharides (e.g., starch, gum arabic, cellulose derivatives, alginic acid, etc.), lignin derivatives, bentonite, saccharides, synthetic water-soluble polymers (e.g., polyvinyl alcohol, polyvinylpyrrolidone, polyacrylic acid, etc.), PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids, and fatty acid esters.

Examples of a base material for a resin formulation include vinyl chloride polymers, polyurethane and the like. To the base material, if necessary, a plasticizer such as phthalate (e.g., dimethyl phthalate, dioctyl phthalate, etc.), adipate, stearic acid or the like may be added. The resin formulation is obtained by kneading the compound of the present invention into the base material using a conventional kneading apparatus, followed by molding such as injection molding, extrusion molding, press molding or the like. The resulting resin formulation may be formed into the shape of a plate, a film, a tape, a net, a string or the like via a further step of molding, cutting, or the like, if necessary. These resin formulations may be used, for example, in the form of an animal collar, an animal ear tag, a sheet formulation, a lead, or a horticultural post.

Examples of a base material of a poison bait includes cereal powder, vegetable oil, sugar, crystalline cellulose and the like. To the base material, if necessary, an antioxidant such as dibutylhydroxytoluene or nordihydroguaiaretic acid, a preservative such as dehydroacetic acid, an agent for preventing children or pets from erroneously eating such as hot pepper powder, a pest-attractive perfume such as cheese perfume, onion perfume or peanut oil or the like may be added.

The pesticidal composition of the present invention can be applied, for example, to arthropod pests directly and/or a place where arthropod pests inhabit (e.g., plants, animals, soil, etc.).

When the pesticidal composition of the present invention is used for controlling pests in agriculture and forestry, the application amount is usually 1 to 10,000 g/ha, preferably 10 to 500 g/ha of the active ingredient. When the pesticidal composition of the present invention is the form of an emulsifiable concentrate, a wettable powder, a flowable formulation or a microcapsule formulation, it is usually used after dilution with water so as to have an active ingredient concentration of 0.01 to 1,000 ppm. When the pesticidal composition of the present invention is the form of a dust or a granule, it is usually used as it is. The pesticidal composition of the present invention may be sprayed directly to plants to be protected from arthropod pests. Alternatively, soil can be treated with the pesticidal composition of the present invention to control arthropod pests living in the soil. Seedbeds before planting or planting holes or plant feet in planting can be also treated with the pesticidal composition of the present invention. Further, a sheet formulation of the pesticidal composition of the present invention may be applied by winding around plants, disposing in the vicinity of plants, laying on the soil surface at the plant feet, or the like.

The pesticidal composition of the present invention can be used at crop lands such as cultivated lands, paddy fields, lawns and orchards. The pesticidal composition of the present invention can control arthropod pests at crop lands without causing drug damage to crop plants which are cultivated at the crop lands, in some cases.

Examples of such crop plants are listed below.

Agricultural crops: corn, rice, wheat, barley, rye, oat, sorghum, cotton, soybean, peanut, sarrazin, sugar beet, rapeseed, sunflower, sugar cane, tobacco etc.;

Vegetables: Solanaceae vegetables (eggplant, tomato, green pepper, hot pepper, potato etc.), Cucurbitaceae vegetables (cucumber, pumpkin, zucchini, watermelon, melon etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce etc.), Liliaceae vegetables (Welsh onion, onion, garlic, asparagus etc.), Umbelliferae vegetables (carrot, parsley, celery, parsnip etc.), Chenopodiaceae vegetables (spinach, Swiss chard etc.), Labiatae vegetables (Japanese basil, mint, basil etc.), strawberry, sweat potato, yam, aroid etc.;

Flowers and ornamental plants;

Foliage plant;

Fruit trees: pomaceous fruits (apple, common pear, Japanese pear, Chinese quince, quince etc.), stone fleshy fruits (peach, plum, nectarine, Japanese plum, cherry, apricot, prune etc.), citrus plants (Satsuma mandarin, orange, lemon, lime, grapefruit etc.), nuts (chestnut, walnut, hazel nut, almond, pistachio, cashew nut, macadamia nut etc.), berry fruits (blueberry, cranberry, blackberry, raspberry etc.), grape, persimmon, olive, loquat, banana, coffee, date, coconut etc.;

Trees other than fruit trees: tea, mulberry, flowering trees and shrubs, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew) etc.

The aforementioned crop plants include those to which resistance to an HPPD inhibitor such as isoxaflutole, an ALS inhibitor such as imazethapyr or thifensulfuron-methyl, an EPSP synthesizing enzyme inhibitor, a glutamine synthesizing enzyme inhibitor, an acetyl CoA carboxylase inhibitor, or an herbicide such as bromoxynil has been imparted by a classical breeding method or a genetic engineering technique.

Examples of the crop plant to which the resistance has been imparted by a classical breeding method include Clearfield (registered trademark) canola which is resistant to an imidazolinone herbicide such as imazethapyr, and STS soybean which is resistant to a sulfonylurea ALS inhibitor herbicide such as thifensulfuron-methyl, as well as SR corn which is resistant to an acetyl CoA carboxylase inhibitor such as trione oxime hebicides or aryloxyphenoxypropionic acid herbicides. For example, a crop plant to which the resistance to an acetyl CoA carboxylase inhibitor has been imparted is found in Proc. Natl. Acad. Sci. USA, 1990, vol. 87, p. 7175-7179. In addition, a mutant acetyl CoA carboxylase which is resistant to an acetyl CoA carboxylase inhibitor is described in Weed Science, vol. 53, p. 728-746, 2005. When a gene encoding the mutant acetyl CoA carboxylase is introduced into a crop plant by a genetic engineering technique or when a mutation related to impartation of the acetyl CoA carboxylase resistance is introduced into a gene encoding acetyl CoA carboxylase of a crop plant, a crop plant resistant to an acetyl CoA carboxylase inhibitor can be produced. Further, nucleic acids for introduction of a base substitution mutation can be introduced into the cells of a crop plant by chimeraplasty (see, Gura T. 1999, Repairing the Genome's Spelling Mistakes, Science 285: 316-318) to induce a site-directed amino acid substitution mutation in the gene which is targeted by an acetyl CoA carboxylase inhibitor or herbicide of the crop plant, and thereby a crop plant resistant to an acetyl CoA carboxylase inhibitor or herbicide can be produced.

Examples of the crop plant to which the resistance has been imparted by a genetic engineering technique include corn cultivars which are resistant to glyphosate and glufosinate. Some of such corn cultivars are sold under the trade name of RoundupReady (registered trademark) and LibertyLink (registered trademark).

The aforementioned crop plants include those to which ability to produce an insecticidal toxin, for example a selective toxin which is known to be produced by Bacillus, has been imparted by a genetic engineering technique.

Examples of the insecticidal toxin which is produced by such a genetically engineered plant include insecticidal proteins derived from Bacillus cereus and Bacillus popilliae; δ-endotoxins derived from Bacillus thuringiensis, such as Cry1Ab, Cry1Ac, Cry1F, Cry1Fa2, Cry2Ab, Cry3A, Cry3Bb1 and Cry9C; insecticidal proteins derived from Bacillus thuringiensis, such as VIP 1, VIP 2, VIP 3 and VIP 3A; insecticidal proteins derived from nematodes; toxins produced by animals such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, saporin, and briodin; steroid metabolizing enzymes such as 3-hydroxysteroid oxidase, ecdysteroid-UDP-glucosyltransferase, and cholesterol oxidase; ecdysone inhibitors; HMG-COA reductase; ion channel inhibitors such as sodium channel inhibitors and calcium channel inhibitors; juvenile hormone esterase; diuretic hormone receptors; stilbene synthase; bibenzyl synthase; chitinase; and glucanase.

The insecticidal toxin which is produced by such a genetically engineered plant also includes hybrid toxins of different insecticidal proteins, for example, δ-endotoxins such as Cry1Ab, Cry1Ac, Cry1F, Cry1Fa2, Cry2Ab, Cry3A, Cry3Bb1 and Cry9C and insecticidal proteins such as VIP 1, VIP 2, VIP 3 and VIP 3A, and toxins in which a part of amino acids constituting an insecticidal protein is deleted or modified. The hybrid toxin is made by combining different domains of the insecticidal proteins by a genetic engineering technique. An example of the toxin in which a part of amino acids constituting an insecticidal protein is deleted includes Cry1Ab in which a part of amino acids is deleted. An example of the toxin in which a part of amino acids constituting an insecticidal protein is modified includes a toxin in which one or more of amino acids of a naturally occurring toxin are substituted.

The insecticidal toxin and the genetically engineered crop plant having the ability to produce the insecticidal toxin are described, for example, in EP-A-0 374 753, WO 93/07278, WO 95/34656, EP-A-0 427 529, EP-A-451878, WO 03/052073, and the like.

The genetically engineered crop plant having the ability to produce the insecticidal toxin particularly has resistance to attack by a coleopteran pest, dipteran pest or a lepidopteran pest.

Genetically engineered plants which have one or more pest-resistance genes and thereby produce one or more insecticidal toxins are also known, and some of them are commercially available. Examples of such genetically engineered plants include YieldGard (registered trademark) (a corn cultivar expressing Cry1Ab toxin), YieldGard Rootworm (registered trademark) (a corn cultivar expressing Cry3Bb1 toxin), YieldGard Plus (registered trademark) (a corn cultivar expressing Cry1Ab and Cry3Bb1 toxins), Herculex I (registered trademark) (a corn cultivar expressing Cry1Fa2 toxin and phosphinothricin N-acetyltransferase (PAT) for imparting resistance to gluphosinate), NuCOTN33B (registered trademark) (a cotton cultivar expressing Cry1Ac toxin), Bollgard I (registered trademark) (a cotton cultivar expressing Cry1A c toxin), Bollgard II (registered trademark) (a cotton cultivar expressing Cry1A c and Cry2Ab toxins), VIPCOT (registered trademark) (a cotton cultivar expressing VIP toxin), NewLeaf (registered trademark) (a potato cultivar expressing Cry3A toxin), NatureGard Agrisure GT Advantage (registered trademark) (GA21 glyphosate-resistance character), Agrisure CB Advantage (registered trademark) (Bt11 corn borer (CB) character), Protecta (registered trademark), and the like.

The aforementioned crop plants include those to which ability to produce an anti-pathogen substance has been imparted by a genetic engineering technique.

Examples of the anti-pathogen substance includes PR proteins (PRPs described in EP-A-0 392 225); ion channel inhibitors such as sodium channel inhibitors, and calcium channel inhibitors (e.g. KP1, KP4, KP6 toxins etc. produced by viruses); stilbene synthase; bibenzyl synthase; chitinase; glucanase; substances produced by microorganisms such as peptide antibiotics, heterocycle-containing antibiotics, and protein factors involved in plant disease-resistance (referred to as plant disease resistance genes and described in WO 03/000906); and the like. Such anti-pathogen substances and genetically engineered plants which produce the anti-pathogen substances are described in EP-A-0 392 225, WO 05/33818, EP-A-0 353 191, and the like.

When the pesticidal composition of the present invention is used for control of epidemic, the application amount is usually 0.001 to 10 mg/m$^3$ of the active ingredient for application to space, and 0.001 to 100 mg/m$^2$ of the active ingredient for application to a plane. The pesticidal composition in the form of an emulsifiable concentrate, a wettable powder or a flowable formulation is usually applied after dilution with water so as to contain usually 0.001 to 10,000 ppm of the active ingredient. The pesticidal composition in the form of an oil solution, an aerosol formulation, a smoking pesticide or a poison bait is usually applied as it is.

When the pesticidal composition of the present invention is used for controlling external parasites of livestock such as a cow, a horse, a pig, a sheep, a goat and a chicken, or small animals such as a dog, a cat, a rat and a mouse, it can be applied to said animals by a known method in the veterinary filed. Specifically, when systemic control is intended, the pesticidal composition of the present invention is administered, for example, as a tablet, a mixture with feed, a suppository or an injection (e.g., intramuscularly, subcutaneously, intravenously, intraperitoneally, etc.). When non-systemic control is intended, a method of using the pesticidal composition of the present invention includes spraying, pour-on treatment or a spot-on treatment with the pesticidal composition in the form of an oil solution or an aqueous liquid, washing an animal with the pesticidal composition in the form of a shampoo formulation, and attachment of a collar or a ear tag made of the pesticidal composition in the form of a resin formulation to an animal. When administered to an animal, the amount of the compound of the present invention is usually in the range of 0.1 to 1,000 mg per 1 kg body weight of the animal.

The pesticidal composition of the present invention may be used in admixture or combination with other insecticides, nematocides, acaricides, fungicides, herbicides, plant growth regulators, synergists, fertilizers, soil conditioners, animal feed, and the like.

Examples of an active ingredient of such insecticide include (1) Organic Phosphorus Compounds:

acephate, aluminum phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos, and the like;

(2) Carbamate Compounds:

alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb, and the like;

(3) Synthetic Pyrethroid Compounds:

acrinathrin, allethrin, benfluthrin, beta-cyfluthrin, bifenthrin, cycloprothrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, 2,3,5,6-tetrafluoro-4-methylbenzyl 2,2-dimethyl-3-(1-propenyl)cyclopropanecarboxylate, 2,3,5,6-tetrafluoro-4-(methoxymethyl)benzyl 2,2-dimethyl-3-(2-methyl-1-propenyl) cyclopropanecarboxylate, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl 2,2,3,3-tetramethylcyclopropanecarboxylate, and the like;

(4) Nereistoxin Compounds:

cartap, bensultap, thiocyclam, monosultap, bisultap, and the like;

(5) Neonicotinoid Compounds:

imidacloprid, nitenpyram, acetamiprid, thiamethoxam, thiacloprid, dinotefuran, clothianidin, and the like;

(6) Benzoylurea Compounds:

chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, triazuron, and the like;

(7) Phenylpyrazole Compounds:

acetoprole, ethiprole, fipronil, vaniliprole, pyriprole, pyrafluprole, and the like;

(8) Bt Toxin Insecticides:

live spores derived from and crystal toxins produced from *Bacillus thuringiesis* and a mixture thereof;

(9) Hydrazine Compounds:

chromafenozide, halofenozide, methoxyfenozide, tebufenozide, and the like;

(10) Organic Chlorine Compounds:

aldrin, dieldrin, dienochlor, endosulfan, methoxychlor, and the like;

(11) Natural Insecticides:

machine oil, nicotine sulfate, and the like;

(12) Other Insecticides:

avermectin-B, bromopropylate, buprofezin, chlorphenapyr, cyromazine, D-D (1,3-dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, protrifenbute, spiromesifen, sulfur, metaflumizone, spirotetramat, pyrifluquinazone, spinetoram, chlorantraniliprole, tralopyril, a compound represented by the following formula (A):

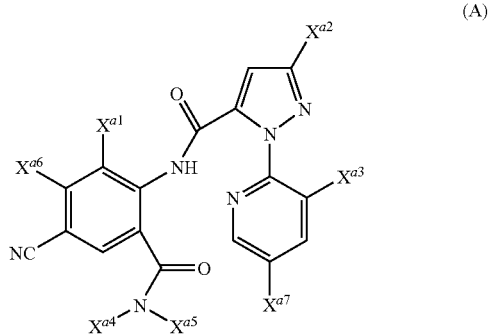

(A)

wherein $X^{a1}$ represents methyl, chlorine, bromine or fluorine, $X^{a2}$ represents fluorine, chlorine, bromine, C1-C4 haloalkyl or C1-C4 haloalkoxy, $X^{a3}$ represents fluorine, chlorine or bromine, $X^{a4}$ represents optionally substituted C1-C4 alkyl, optionally substituted C3-C4 alkenyl, optionally substituted C3-C4 alkynyl, optionally substituted C3-C5 cycloalkyl or hydrogen, $X^{a5}$ represents hydrogen or methyl, $X^{a6}$ represents hydrogen, fluorine or chlorine, and $X^{a7}$ represents hydrogen, fluorine or chlorine;

a compound represented by the following formula (B):

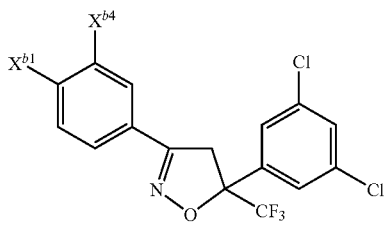

wherein $X^{b1}$ represents $X^{b2}$—NH—C(=O), $X^{b2}$—C(=O)—NH—CH$_2$, $X^{b3}$—S(O), optionally substituted pyrrol-1-yl, optionally substituted imidazol-1-yl, optionally substituted pyrazol-1-yl, or optionally substituted 1,2,4-triazol-1-yl, $X^{b2}$ represents optionally substituted C1-C4 haloalkyl such as 2,2,2-trifluoroethyl or optionally substituted C3-C6 cycloalkyl such as cyclopropyl, $X^{b3}$ represents optionally substituted C1-C4 alkyl such as methyl, and $X^{b4}$ represents hydrogen, chroline, cyano or methyl;

a compound represented by the following formula (C):

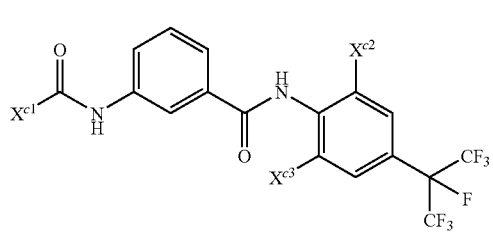

wherein $X^{c1}$ represents optionally substituted C1-C4 alkyl such as 3,3,3-trifluoropropyl, optionally substituted. C1-C4 alkoxy such as 2,2,2-trichloroethoxy or optionally substituted phenyl such as 4-cyanophenyl or optionally substituted pyridyl such as 2-chloro-3-pyridyl, $X^{c2}$ represents methyl or trifluoromethylthio, and $X^{c3}$ represents methyl or halogen; and the like.

Examples of an active ingredient of the acaricide include acequinocyl, amitraz, benzoximate, bifenazate, bromopropylate, chinomethionate, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite (BPPS), polynactins, pyridaben, pyrimidifen, tebufenpyrad, tetradifon, spirodiclofen, spiromesifen, spirotetramat, amidoflumet, cyenopyrafen, and the like.

Examples of the nematicide include DCIP, fosthiazate, levamisol hydrochloride, methylisothiocyanate, morantel tartarate, imicyafos, and the like.

Examples of an active ingredient of such fungicide include strobilurin compounds such as azoxystrobin; organophosphate compounds such as tolclofos-methyl; azole compounds such as triflumizole, pefurazoate and difenoconazole; fthalide, flutolanil, validamycin, probenazole, diclomezine, pencycuron, dazomet, kasugamycin, IBP, pyroquilon, oxolinic acid, tricyclazole, ferimzone, mepronil, EDDP, isoprothiolane, carpropamid, diclocymet, furametpyr, fludioxonil, procymidone and diethofencarb.

EXAMPLES

Hereinafter, the present invention will be explained in more detail by reference to Production Examples, Formulation Examples and Test Examples, but the present invention is not limited to them.

Abbreviations used herein have the following meanings. Me: methyl group, Et: ethyl group, Bn: benzyl group, Ph: phenyl group, Ts: p-toluenesulfonnyl group, Ac: acetyl group.

First, Production Examples of the compound of the present invention is shown.

Production Example 1

Step 1-1

To a solution of 5.45 g of 1,4-dioxaspiro[4.5]decane-8-methanol in 30 ml of pyridine was added 6.64 g of p-toluenesulfonyl chloride, and the mixture was stirred at room temperature for 6 hours. To a reaction mixture was added 100 ml of water, and then extracted with ethyl acetate twice. An organic layer was washed successively with 100 ml of an aqueous 1N hydrochloric acid solution twice, 100 ml of an aqueous saturated sodium hydrogen carbonate solution once, and 100 ml of an aqueous saturated sodium chloride solution once. The organic layer was dried over sodium sulfate, filtered, and then concentrated under reduced pressure. The residue was subjected to silica gel column chromatography to obtain 9.86 g of 1,4-dioxaspiro[4.5]deca-8-ylmethyl p-toluenesulfonate represented by the formula:

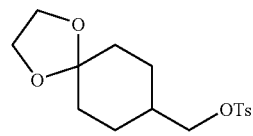

$^1$H-NMR(CDCl$_3$, TMS, δ(ppm)): 1.17-1.28 (2H, m), 1.43-1.57 (3H, m), 1.71-1.73 (4H, m), 2.45 (3H, S), 3.83 (2H, d), 3.88-3.95 (4H, m), 7.33 (2H, d), 7.77 (2H, d).

Step 1-2

To a solution of 9.86 g of 1,4-dioxaspiro[4.5]deca-8-ylmethyl p-toluenesulfonate in 40 ml of dimethyl sulfoxide was added 4.00 g of potassium thioacetate, and the mixture was stirred at 70° C. for 8 hours. The reaction mixture was cooled to room temperature, and 100 ml of water was added thereto. The reaction mixture was extracted with 100 ml of ethyl acetate twice. An organic layer was washed with 100 ml of an aqueous saturated sodium chloride solution, dried over sodium sulfate, filtered, and then concentrated under reduced pressure. The residue was subjected to silica gel column chromatography to obtain 5.41 g of 1,4-dioxaspiro[4.5]deca-8-ylmethyl thioacetate represented by the formula:

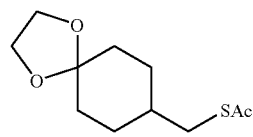

$^1$H-NMR (CDCl$_3$, TMS, δ(ppm)): 1.29-1.36 (2H, m), 1.49-1.52 (3H, m), 1.73-1.80 (4H, m), 2.33 (3H, s), 2.82 (2H, d), 3.93 (4H, s).

Step 1-3

To a solution of 5.41 g of 1,4-dioxaspiro[4.5]deca-8-ylmethyl thioacetate in 20 ml of methanol was added 6.75 g of a 28% solution of sodium methoxide in methanol at 0° C. under a nitrogen atmosphere. To the mixture was added 7.81 g of 3,3,3-trifluoro-1-iodopropane, and the mixture was stirred at room temperature for 1 hour and then at 70° C. for 1 hour. After the reaction mixture was cooled to room temperature, 100 ml of water was added and the mixture was concentrated under reduced pressure. An aqueous layer was extracted with 100 ml of ethyl acetate twice. An organic layer was washed with 100 ml of an aqueous saturated sodium chloride solution, dried over sodium sulfate, filtered, and then concentrated under reduced pressure. The residue was subjected to silica gel column chromatography to obtain 3.69 g of 8-(3,3,3-trifluoropropylmethyl)-1,4-dioxaspiro[4.5]decane (hereinafter, referred to as the present compound (1)) represented by the formula:

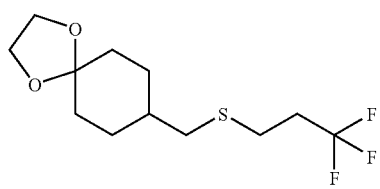

(1)

$^1$H-NMR (CDCl$_3$, TMS, δ(ppm)): 1.25-1.35 (2H, m), 1.48-1.58 (3H, m), 1.73-1.79 (2H, m), 1.84-1.88 (2H, m), 2.33-2.43 (2H, m), 2.46 (2H, d), 2.65-2.69 (2H, m), 3.94 (4H, s).

Production Example 2

To a solution of 3.69 g of the present compound (1) in 60 ml of chloroform was added 6.56 g of m-chloroperbenzoic acid at 0° C., and the mixture was stirred at room temperature for 1 hour and then at 50° C. for 3 hours. The reaction mixture was cooled to 0° C., and 50 ml of a 5% aqueous sodium sulfite solution was added. After the mixture was stirred for 1 hour, an organic layer was then separated. An aqueous layer was extracted with 50 ml of chloroform. Organic layers were combined, and washed with 50 ml of an aqueous saturated sodium hydrogen carbonate solution twice and then with 100 ml of an aqueous saturated sodium chloride solution. The resulting organic layer was dried over sodium sulfate, filtered, and then concentrated under reduced pressure. The residue was subjected to silica gel column chromatography to obtain 4.10 g of 8-(3,3,3-trifluoropropylsulfonylmethyl)-1,4-dioxaspiro[4.5]decane (hereinafter, referred to as the present compound (2)) represented by the formula:

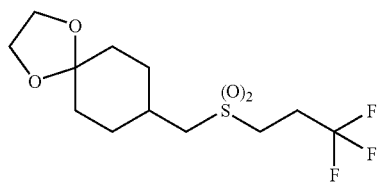

(2)

$^1$H-NMR (CDCl$_3$, TMS, δ(ppm)): 1.43-1.53 (2H, m), 1.58-1.66 (2H, m), 1.73-1.79 (2H, m), 1.97-2.01 (2H, m), 2.15-2.17 (1H, m), 2.64-2.74 (2H, m), 2.95 (2H, d), 3.16-3.20 (2H, m), 3.92-3.97 (4H, m).

Production Example 3

To a solution of 4.00 g of the present compound (2) in 30 ml of acetone was added 0.43 g of toluenesulfonic acid, and the mixture was stirred at 50° C. for 8 hours under a nitrogen atmosphere. The reaction solution was concentrated under reduced pressure, and the residue was subjected to silica gel column chromatography to obtain 3.35 g of 4-(3,3,3-trifluoropropylsulfonylmethyl)cyclohexanone (hereinafter, referred to as the present compound (3)) represented by the formula:

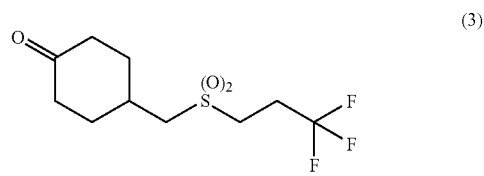

(3)

$^1$H-NMR (CDCl$_3$, TMS, δ(ppm)): 1.59-1.70 (2H, m), 2.33-2.36 (2H, m), 2.43-2.46 (4H, m), 2.58-2.67 (1H, m), 2.69-2.73 (2H, m), 3.03 (2H, d), 3.20-3.25 (2H, m).

Production Example 4

To a solution of 0.82 g of the present compound (3) in 6 ml of chloroform was added 1.06 g of diethylaminosulfur trifluoride at 0° C. under a nitrogen atmosphere, and the mixture was stirred at room temperature for 5 hours. The reaction solution was diluted with 30 ml of chloroform. Thereto 30 ml of water was added, and an organic layer was separated. An aqueous layer was extracted with 30 ml of chloroform twice, and organic layers were combined and washed with 50 ml of an aqueous saturated sodium chloride solution. The resulting organic layer was dried over sodium sulfate, filtered, and then concentrated under reduced pressure. The residue was subjected to silica gel column chromatography to obtain 0.30 g of 1,1-difluoro-4-(3,3,3,-trifluoropropylsulfonylmethyl)cyclohexanone (hereinafter, referred to as the present compound (4)) and 0.27 g of 1-fluoro-4-(3,3,3,-trifluoropropylsulfonylmethyl)cyclohexanone (hereinafter, referred to as the present compound(5)), which compounds are represented by the formulas:

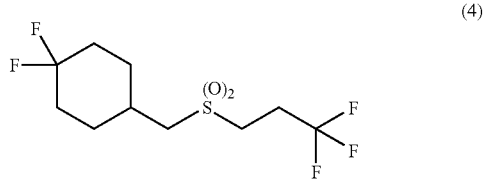

(4)

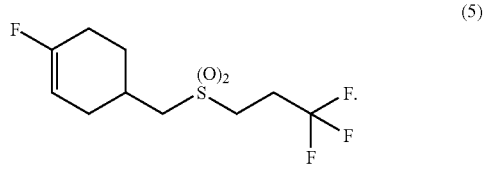

(5)

The present compound (4)

$^1$H-NMR (CDCl$_3$, TMS, δ(ppm)): 1.45-1.56 (2H, m), 1.72-1.88 (2H, m), 2.05-2.23 (5H, m), 2.63-2.75 (2H, m), 2.97 (2H, d), 3.02-3.22 (2H, m).

Present Compound (5)

$^1$H-NMR (CDCl$_3$, TMS, δ(ppm)): 1.65-1.73 (1H, m), 1.99-2.10 (2H, m), 2.19-2.25 (1H, m), 2.33-2.43 (3H, m), 2.63-2.75 (2H, m), 3.02 (2H, d), 3.18-3.22 (2H, m), 5.11-5.19 (1H, m).

Production Example 5

To a solution of 0.83 g of the present compound (3) in 10 ml of tetrahydrofuran was added 7.2 ml of a 0.5M solution of ethynylmagnesium bromide in tetrahydrofuran at 0° C. under a nitrogen atmosphere, and the mixture was stirred at 0° C. for 5 hours. To the reaction solution was added 30 ml of an aqueous 1N hydrochloric acid solution, and the mixture was extracted with 30 ml of ethyl acetate twice. Organic layers were combined, and washed with 30 ml of an aqueous saturated sodium hydrogen carbonate solution, and 30 ml of an aqueous saturated sodium chloride solution. The resulting organic layer was dried over sodium sulfate, filtered, and then concentrated under reduced pressure. The residue was subjected to silica gel column chromatography to obtain 0.43 g of 1-ethynyl-4-(3,3,3-trifluoropropylsulfonylmethyl)cyclohexanol (hereinafter, referred to as the present compound (6)) represented by the formula:

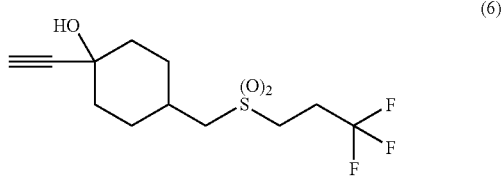

(6)

$^1$H-NMR (CDCl$_3$, TMS, δ(ppm)): 1.50-1.59 (4H, m), 2.03-2.11 (6H, m), 2.53 (1H, s), 2.63-2.74 (2H, m), 2.97 (2H, d), 3.16-3.20 (2H, m).

Production Example 6

To a solution of 0.29 g of the present compound (6) in 2 ml of chloroform was added 0.32 g of diethylaminosulfur trifluoride at 0° C. under a nitrogen atmosphere, and the mixture was stirred at room temperature for 5 hours. The reaction solution was diluted with 20 ml of chloroform, and 20 ml of water was added thereto. Then an organic layer was separated. An aqueous layer was extracted with 20 ml of chloroform twice. Organic layers were combined, and washed with 50 ml of an aqueous saturated sodium chloride solution. The resulting organic layer was dried over sodium sulfate, filtered, and concentrated under reduced pressure. The residue was subjected to silica gel column chromatography to obtain 0.14 g of 1-ethenyl-1-fluoro-4-(3,3,3-trifluoropropylsulfonylmethyl)cyclohexane (hereinafter, referred to as the present compound (7)) represented by the formula:

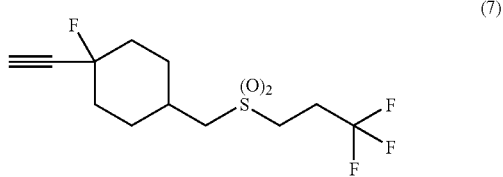

(7)

$^1$H-NMR(CDCl$_3$, TMS, δ(ppm)): 1.52-1.59 (2H, m), 1.72-1.94 (4H, m), 2.17-2.28 (3H, m), 2.62-2.72 (3H, m), 2.95 (2H, d), 3.17-3.22. (2H, m).

Production Example 7

Step 7-1

A solution of 4.86 g of diisopropylamine in 50 ml of tetrahydrofuran was cooled to −50° C. under a nitrogen atmosphere. To the solution was added 30 ml of a 1.6M n-butyllithium/n-hexane solution, and stirred at −50° C. for 30 minutes. To the solution, a solution of 9.28 g of methyl 2-(1,4-dioxaspiro[4.5]dec-8-yl)acetate in 40 ml of tetrahydrofuran was added dropwise over 15 minutes. The mixture was stirred at 0° C. for 30 minutes, and then cooled to −50° C. Thereto a solution of 8.54 g of N-bromosuccinimide in 30 ml of tetrahydrofuran was added, and the mixture was stirred at 0° C. for 2 hours and then at room temperature for 5 hours. To the reaction mixture was added 100 ml of water, and an organic layer was separated. An aqueous layer was extracted with 100 ml of ethyl acetate twice. Organic layers were combined, and washed with 100 ml of an aqueous 1N hydrochloric acid solution twice, with 100 ml of an aqueous saturated sodium hydrogen carbonate solution, and 100 ml of an aqueous saturated sodium chloride solution. The organic layer was dried over sodium sulfate, filtered, and concentrated under reduced pressure. The residue was dissolved in 50 ml of dimethyl sulfoxide. Thereto 5.04 g of potassium thioacetate was added, and the mixture was stirred at 50° C. for 4 hours. After cooling to room temperature, 100 ml of water was added to the reaction mixture, followed by extraction with 100 ml of ethyl acetate twice. Organic layers were combined, washed with 100 ml of an aqueous 1N hydrochloric acid solution, 100 ml of an aqueous saturated sodium hydrogen carbonate solution and 100 ml of an aqueous saturated sodium chloride solution, dried over sodium sulfate, filtered, and then concentrated under reduced pressure. The residue was subjected to silica gel column chromatography to obtain 4.27 g of methyl 2-(acetylthio)-2-(1,4-dioxaspiro[4.5]dec-8-yl)acetate represented by the formula:

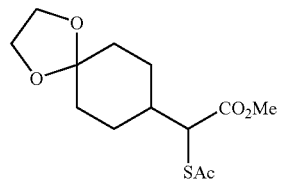

$^1$H-NMR (CDCl$_3$, TMS, δ(ppm)): 1.36-1.59 (4H, m), 1.65-1.81 (4H, m), 1.83-1.93 (1H, m), 2.33 (3H, s), 3.73 (3H, s), 3.93 (4H, s), 4.17 (1H, d).

Step-7-2

To a solution of 4.27 g of methyl 2-(acetylthio)-2-(1,4-dioxaspiro[4.5]dec-8-yl)acetate in 30 ml of methanol was added 3.14 g of a 28% solution of sodium methoxide in methanol at 0° C. under a nitrogen atmosphere. To the mixture was added 4.31 g of 3,3,3-trifluoro-1-iodopropane, and the mixture was stirred at room temperature for 1 hour and then at 70° C. for 1 hours. The reaction mixture was cooled to room temperature, and 100 ml of water was added thereto. The mixture was concentrated to a total amount of about 100 ml under reduced pressure, followed by extraction with 100 ml of ethyl acetate twice. Organic layers were combined, washed with 100 ml of an aqueous saturated sodium chloride solution, dried over sodium sulfate, filtered, and then concentrated under reduced pressure. The residue was subjected to silica gel column chromatography to obtain 3.60 g of methyl 2-(1,4-dioxaspiro[4.5]dec-8-yl)-2-(3,3,3-trifluoropropylthio)acetate (hereinafter, referred to as the present compound (8)) represented by the formula:

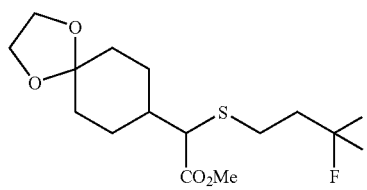

(8)

¹H-NMR (CDCl₃, TMS, δ(ppm)): 1.31-1.81 (8H, m), 2.11-2.16 (1H, m), 2.34-2.41 (2H, m), 2.71-2.78 (2H, m), 3.04 (1H, d), 3.75 (3H, s), 4.91-4.96 (4H, m).

Production Example 8

To a solution of 3.60 g of the present compound (8) in 20 ml of chloroform was added 4.75 g of m-chloroperbenzoic acid at 0° C. under a nitrogen atmosphere. The mixture was stirred at room temperature for 1 hour and then at 50° C. for 3 hours. The reaction mixture was cooled to 0° C., and 50 ml of a 5% aqueous sodium sulfite solution was added. The mixture was stirred for 1 hour, and an organic layer was then separated. An aqueous layer was extracted with 50 ml of chloroform, and organic layers were combined and washed with 50 ml of an aqueous saturated sodium hydrogen carbonate solution twice and 100 ml of an aqueous saturated sodium chloride solution. The resulting organic layer was dried over sodium sulfate, filtered, and concentrated under reduced pressure. The residue was subjected to silica gel column chromatography to obtain 2.41 g of methyl 2-(1,4-dioxaspiro[4.5]dec-8-yl)-2-(3,3,3-trifluoropropylsulfonyl)acetate (hereinafter, referred to as the present compound (9)) represented by the formula:

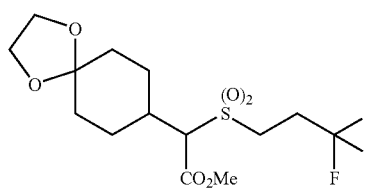

(9)

¹H-NMR (CDCl₃, TMS, δ(ppm)): 1.50-1.83 (7H, m), 2.14-2.17 (1H, m), 2.26-2.29 (1H, m), 2.66-2.74 (2H, m), 3.19-3.27 (1H, m), 3.48-3.53 (1H, m), 3.75 (1H, d), 3.84 (3H, s), 3.91-3.96 (4H, m).

Production Example 9

To a solution of 2.41 g of the present compound (9) in 25 ml of acetone was added 0.11 g of toluenesulfonic acid, and the mixture was stirred at 50° C. for 8 hours under a nitrogen atmosphere. The reaction mixture was concentrated under reduced pressure. The residue was subjected to silica gel column chromatography to obtain 1.24 g of methyl 2-(4-oxocyclohexyl)-2-(3,3,3-trifluoropropylsulfonyl)acetate (hereinafter referred to as the present compound (10)) represented by the formula:

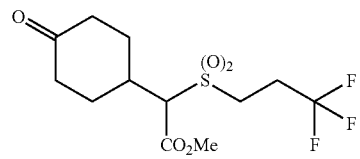

(10)

¹H-NMR (CDCl₃, TMS, δ(ppm)): 1.73-1.86 (2H, m), 2.10-2.13 (1H, m), 2.40-2.49 (5H, m), 2.68-2.77 (3H, m), 3.28-3.35 (1H, m), 3.47-3.53 (1H, m), 3.85 (2H, d), 3.87 (3H, s).

Production Example 10

To a solution of 1.24 g of the present compound (9) in 17 ml of chloroform was added 1.37 g of diethylaminosulfur fluoride at 0° C. under a nitrogen atmosphere, and the mixture was stirred at room temperature for 5 hours. The reaction solution was diluted with 40 ml of chloroform, and 30 ml of water was added thereto. An organic layer was then separated. An aqueous layer was extracted with 30 ml of chloroform twice. Organic layers were combined, and washed with 50 ml of an aqueous saturated sodium chloride solution. The resulting organic layer was dried over sodium sulfate, filtered, and then concentrated under reduced pressure. The residue was subjected to silica gel column chromatography to obtain 0.87 g of methyl 2-(4,4-difluorocyclohexyl)-2-(3,3,3-trifluoropropylsulfonyl)acetate (hereinafter, referred to as the present compound (11)) represented by the formula:

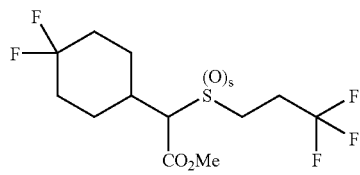

(11)

¹H-NMR (CDCl₃, TMS, δ(ppm)): 1.67-1.83 (6H, m), 2.14-2.37 (3H, m), 2.66-2.74 (2H, m), 3.22-3.29 (1H, m), 3.45-3.52 (1H, m), 3.77 (1H, d), 3.86 (3H, s).

Production Example 11

To a solution of 0.50 g of the present compound (11) in 5 ml of tetrahydrofuran was added 0.07 g of 60% sodium hydride at 0° C. under a nitrogen atmosphere. Thereto 0.50 g of N-fluorobenzenesulfonimide was further added, and the mixture was stirred at room temperature for 5 hours. To the reaction solution was added 30 ml of water, and an organic layer was separated. An aqueous layer was extracted with 30 ml of ethyl acetate twice. Organic layers were combined, and washed with 50 ml of an aqueous saturated sodium chloride solution. The resulting organic layer was dried over sodium sulfate, filtered, and then concentrated under reduced pressure. The residue was subjected to silica gel column chromatography to obtain 0.43 g of methyl 2-(4,4-difluorocyclohexyl)-2-fluoro-2-(3,3,3-trifluoropropylsulfonyl)acetate (hereinafter referred to as the present compound (12)) represented by the formula:

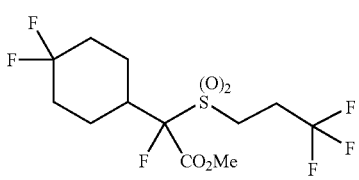

(12)

¹H-NMR (CDCl₃, TMS, δ(ppm)): 1.67-1.89 (5H, m), 2.12-2.43 (3H, m), 2.55-2.74 (3H, m), 3.21-3.40 (2H, m), 3.98 (3H, s).

Production Example 12

To a solution of 0.33 g of the present compound (12) in 3 ml of methanol was added 3 ml of a 2.0M solution of ammonia in methanol at 0° C., and the mixture was then stirred at room temperature for 18 hours. To the reaction solution was added 30 ml of water, and then extracted with 30 ml of ethyl acetate twice. An organic layers were combined, and washed with 50 ml of an aqueous saturated sodium chloride solution. The resulting organic layer was dried over sodium sulfate, filtered, and then concentrated under reduced pressure. The residue was subjected to silica gel column chromatography to obtain 0.43 g of 2-(4,4-difluorocyclohexyl)-2-fluoro-2-(3,3,3-trifluoropropylsulfonyl)acetamide (hereinafter, referred to as the present compound (13)) represented by the formula:

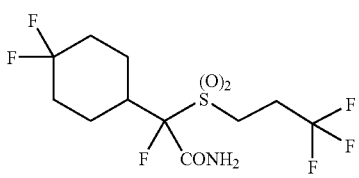

(13)

¹H-NMR (CDCl₃, TMS, δ(ppm)): 1.73-1.88 (4H, m), 2.21-2.61 (4H, m), 2.61-2.77 (3H, m), 3.28-3.35 (1H, m), 3.40-3.48 (1H, m), 5.90 (1H, s), 6.53 (1H, s).

Production Example 13

To a mixture of 22.8 g of cyclohexane-1,4-dimethanol monotosylate (trans/cis=6/4) and 100 ml of dimethyl sulfoxide was added 8.68 g of potassium thioacetate, and the mixture was stirred at room temperature for 1 hour and then at 60° C. for 6 hours. After the mixture was cooled to room temperature, thereto 100 ml of an aqueous saturated sodium chloride solution was added and then extracted with 200 ml of t-butyl methyl ether twice. Organic layers were combined, washed with 100 ml of an aqueous saturated sodium chloride solution and 100 ml of water, dried over sodium sulfate, filtered, and then concentrated under reduced pressure. To the residue was added 100 ml of methanol. Under cooling with an ice bath, to the mixture was added dropwise a 28% dilution of 15.43 g of sodium methoxide with 50 ml of methanol over 30 minutes. The mixture was stirred for 30 minutes. To the mixture was added 17.92 g of 3,3,3-trifluoro-1-iodopropane, and then stirred at 60° C. for 6 hours. After the reaction mixture was cooled to room temperature, 150 ml of an aqueous saturated sodium chloride solution was added. Methanol was distilled off under reduced pressure. The resulting concentrate was extracted with 200 ml of t-butyl methyl ether twice, and subjected to silica gel column chromatography to obtain 8.46 g of 4-(3,3,3-trifluoropropylthiomethyl)cyclohexanemethanol (hereinafter referred to as the present compound (14)) represented by the formula:

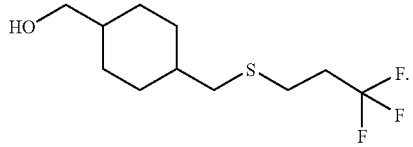

(14)

The resulting present compound (14) was a mixture of trans form/cis form=6/4.

Trans-4-(3,3,3-trifluoropropylthiomethyl)cyclohexanemethanol

¹H-NMR(CDCl₃, TMS, δ(ppm)): 0.96-1.01 (4H, m), 1.40-1.47 (4H, m), 1.58-1.83 (1H, m), 1.92-1.94 (1H, m), 2.34-2.40 (2H, m), 2.43 (2H, d), 2.64-2.68 (2H, m), 3.45 (2H, dd).

Cis-4-(3,3,3-trifluoropropylthiomethyl)cyclohexanemethanol

¹H-NMR (CDCl₃, TMS, δ(ppm)): 1.22-1.27 (4H, m), 1.40-1.62 (6H, m), 2.34-2.40 (2H, m), 2.52 (2H, d), 2.64-2.68 (2H, m), 3.53 (2H, dd).

Production Example 14

To a solution of 7.4 g of the present compound (14) (trans form/cis form=6/4) in 60 ml of chloroform was added 10.85 g of m-chloroperbenzoic acid at 0° C. under a nitrogen atmosphere, and the mixture was stirred at room temperature for 1 hour and then at 50° C. for 3 hours. The reaction mixture was cooled to 0° C., and 50 ml of a 5% aqueous sodium sulfite solution was added. The mixture was stirred for 1 hour. An organic layer was separated, and an aqueous layer was extracted with 50 ml of chloroform twice. Organic layers were combined, and washed with 50 ml of an aqueous saturated sodium hydrogen carbonate solution twice, and 100 ml of an aqueous saturated sodium chloride solution. The resulting organic layer was dried over sodium sulfate, filtered, and then concentrated under reduced pressure. The residue was subjected to silica gel column chromatography, and then crystallized from t-butyl methyl ether to obtain 4.13 g of a trans form (hereinafter referred to as the present compound (15t)) and 3.83 g of a cis form (hereinafter, referred to as the present compound (15c)) of 4-(3,3,3-trifluoropropylsulfonylmethyl)cyclohexanemethanol (hereinafter, referred to as the present compound (15)) (trans form/cis form=1/9), represented by the formula:

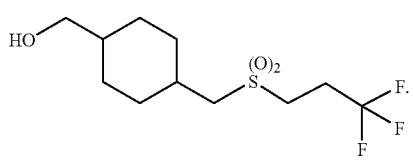

(15)

The Present Compound (15t)

¹H-NMR (CDCl₃, TMS, δ(ppm)): 1.04-1.19 (4H, m), 1.30 (1H, t), 1.45-1.49 (1H, m), 1.84-1.89 (2H, m), 2.04-2.10 (3H, m), 2.62-2.74 (2H, m), 2.93 (2H, d), 3.15-3.19 (2H, m), 3.45 (2H, dd).

The Present Compound (15c)

¹H-NMR (CDCl₃, TMS, δ(ppm)): 1.04-1.19 (4H, m), 1.30 (1H, t), 1.45-1.49 (1H, m), 1.84-1.89 (2H, m), 2.04-2.10 (3H, m), 2.62-2.74 (2H, m), 2.93 (2H, d), 3.15-3.19 (2H, m), 3.45 (2H, dd).

Production Example 15

A solution of 7.46 g of oxalyl chloride in 50 ml of dichloromethane was cooled to −78° C. under a nitrogen atmosphere. To the solution was added dropwise a solution of 9.53 g of dimethyl sulfoxide in 50 ml of dichloromethane over 20 minutes, and the mixture was stirred at −50° C. for 30 minutes. To the reaction mixture was added dropwise a solution of 13.51 g of the present compound (15t) in 150 ml of dichloromethane over 30 minutes, and then stirred at −50° C. for 40 minutes. To the mixture was added dropwise 15.70 g of triethylamine over 40 minutes. The reaction mixture was stirred at room temperature for 18 hours. To the reaction mixture was added 100 ml of water, and an organic layer was separated, followed by extraction with 100 ml of chloroform twice. Organic layers were combined, washed successively with 150 ml of an aqueous 1N hydrochloric acid solution, 150 ml of an aqueous saturated sodium hydrogen carbonate solution, and 150 ml of water, dried over sodium sulfate, filtered and then concentrated under reduced pressure. The residue was subjected to silica gel column chromatography to obtain 10.04 g of a trans form (hereinafter referred to as the present compound (16t)) of 4-(3,3,3-trifluoropropanesulfonylmethyl)cyclohexane carbaldehyde (hereinafter referred to as the present compound (16)) represented by the formula:

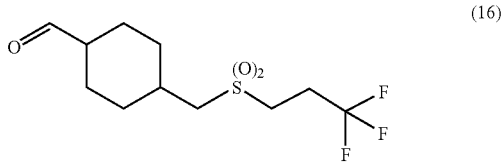

(16)

¹H-NMR (CDCl₃, TMS, δ(ppm)): 1.18-1.27 (2H, m), 1.33-1.43 (2H, m), 2.06-2.24 (6H, m), 2.63-2.74 (2H, m), 2.95 (2H, d), 3.16-3.21 (2H, m), 9.62 (1H, s).

Production Example 16

A solution of 23.21 g of carbon tetrabromide in 100 ml of dichloromethane was cooled to 0° C. under a nitrogen atmosphere, and 36.72 g of triphenylphosphine was added thereto over 30 minutes. The mixture was stirred for 30 minutes. To the solution was added dropwise a solution of 10.4 g of the present compound (16t) in 50 ml of dichloromethane over 30 minutes, and then stirred at room temperature for 6 hours. To the reaction mixture was added 150 ml of t-butyl methyl ether. A solid was filtered, and the filtrate was concentrated under reduced pressure. The residue was subjected to silica gel column chromatography to obtain 12.9 g of a trans form (hereinafter, referred to as the present compound (17t)) of 1-(2,2-dibromovinyl)-4-(3,3,3-trifluoropropylsulfonylmethyl)cyclohexane (hereinafter, referred to as the present compound (17)) represented by the formula:

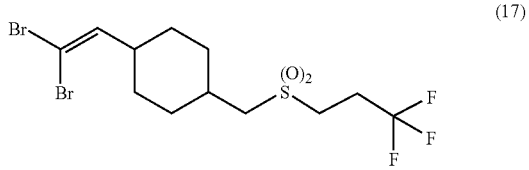

(17)

¹H-NMR (CDCl₃, TMS, δ(ppm)): 1.16-1.29 (4H, m), 1.84-1.86 (2H, m), 2.04-2.08 (2H, m), 2.21-2.26 (1H, m), 2.62-2.74 (2H, s), 2.92 (2H, d), 3.15-3.22 (2H, m), 6.19 (2H, d).

Production Example 17

A solution of 12.90 g of the present compound (17t) in 60 ml of tetrahydrofuran was cooled to −78° C. under a nitrogen atmosphere. To the solution was added dropwise a 1.6M n-butyllithium/n-hexane solution over 30 minutes, and the mixture was stirred at −50° C. for 1 hour and then at 0° C. for 2 hours. The reaction mixture was poured into 100 ml of an aqueous 1N hydrochloric acid solution which had been cooled with an ice bath, followed by extraction with 200 ml of t-butyl methyl ether twice. Organic layers were combined, washed with 100 ml of an aqueous saturated sodium hydrogen carbonate solution and 100 ml of an aqueous saturated sodium chloride solution, filtered, and then concentrated under reduced pressure. The residue was subjected to silica gel column chromatography to obtain 5.59 g of a trans form (hereinafter, referred to as the present compound (18t)) of 1-ethynyl-4-(3,3,3-trifluoropropylsulfonylmethyl)cyclohexane (hereinafter, referred to as the present compound (18)) represented by the formula:

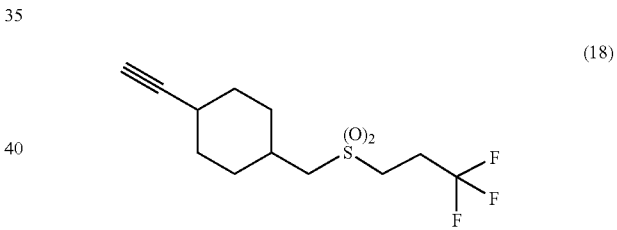

(18)

¹H-NMR (CDCl₃, TMS, δ(ppm)): 1.11-1.20 (2H, m), 1.43-1.53 (2H, m), 2.02-2.13 (6H, m), 2.19-2.23 (1H, m), 2.62-2.73 (2H, m), 2.91 (2H, d), 3.15-3.19 (2H, m).

Production Example 17

Step 17-1

A solution of 7.87 g of oxalyl chloride in 50 ml of dichloromethane was cooled to −78° C. under a nitrogen atmosphere. To the solution was added dropwise a solution of 4.85 g of dimethyl sulfoxide in 50 ml of dichloromethane over 20 minutes, and the mixture was stirred at −50° C. for 30 minutes. To the reaction mixture was added dropwise a solution of 9.28 g of the present compound (15) (trans form/cis form=6/4) in 150 ml of dichloromethane over 30 minutes, and then stirred at −50° C. for 40 minutes. Thereto 18.22 g of triethylamine was added dropwise over 40 minutes. The reaction mixture was stirred at room temperature for 18 hours. To the reaction mixture was added 100 ml of water, and an organic layer was separated, followed by extraction with 100 ml of chloroform twice. Organic layers were combined, washed successively with 150 ml of an aqueous 1N hydrochloric acid solution, 150 ml of an aqueous saturated sodium hydrogen carbonate solution and 150 ml of water, dried over sodium sulfate, filtered, and then concentrated under reduced pressure. The residue was subjected to silica gel column chromatography to obtain 8.41 g of the present compound (16). The resulting present compound (16) was a mixture of trans form/cis form=6/4.

Step 17-2

A solution of 19.90 g of carbon tetrabromide in 100 ml of dichloromethane was cooled to 0° C. under a nitrogen atmosphere. Thereto 31.48 g of triphenylphosphine was added over 30 minutes, and the mixture was stirred for 30 minutes. To the solution was added dropwise a solution of 8.41 g of the present compound (16) (trans form/cis form=6/4) in 50 ml of dichloromethane over 30 minutes, and the mixture was stirred at room temperature for 6 hours. To the reaction mixture was added 150 ml of t-butyl methyl ether. A solid was filtered and the filtrate was concentrated under reduced pressure. The residue was subjected to silica gel column chromatography to obtain 12.7 g of the present compound (17). The resulting present compound (17) was a mixture of trans form/cis form=6/4.

Step 17-3

A solution of 12.7 g of the present compound (17) (trans/cis=6/4) in 60 ml of tetrahydrofuran was cooled to −78° C. under a nitrogen atmosphere. To the solution was added dropwise 40 ml of a 1.6M solution of n-butyllithium in n-hexane over 30 minutes. The mixture was stirred at −50° C. for 1 hour and then at 0° C. for 2 hours. The reaction mixture was poured into 100 ml of an aqueous 1N hydrochloric acid solution which had been cooled with an ice bath, followed by extraction with 200 ml of n-butyl methyl ether twice. Organic layers were combined, washed with 100 ml of an aqueous saturated sodium hydrogen carbonate solution and 100 ml of an aqueous saturated sodium chloride solution, dried over sodium sulfate, filtered and then concentrated under reduced pressure. The residue was subjected to silica gel column chromatography to obtain 1.68 g of a cis form (hereinafter, referred to as the present compound (18c)) of the present compound (18).

$^1$H-NMR (CDCl$_3$, TMS, δ(ppm)): 1.58-1.67 (2H, m), 1.82-1.84 (3H, m), 2.01-2.17 (5H, m), 2.62-2.74 (2H, m), 2.78 (1H, br.s), 2.97 (2H, d), 3.15-3.19 (2H, m).

Production Example 18

A solution of 1.88 g of the present compound (17) in 10 ml of tetrahydrofuran was cooled to −78° C. under a nitrogen atmosphere. To the solution was added dropwise 2.8 ml of a 1.6M solution of n-butyllithium in n-hexane over 10 minutes, and the mixture was stirred at −50° C. for 1 hour. Thereto 0.37 g of methyl acrylate was added, and the mixture was stirred at 0° C. for 2 hours. The reaction mixture was poured into 30 ml of an aqueous 1N hydrochloric acid solution which had been cooled with an ice bath, followed by extraction with 30 ml of t-butyl methyl ether twice. Organic layers were combined, washed with 30 ml of an aqueous saturated sodium hydrogen carbonate solution and 30 ml of an aqueous saturated sodium chloride solution, dried over sodium sulfate, filtered and then concentrated under reduced pressure. The residue was subjected to silica gel column chromatography to obtain 0.70 g of 5-[4-(3,3,3-trifluoropropylsulfonylmethyl) cycohexanyl]-4-pentynic acid methyl ester (hereinafter, referred to as the present compound (19)) represented by the formula:

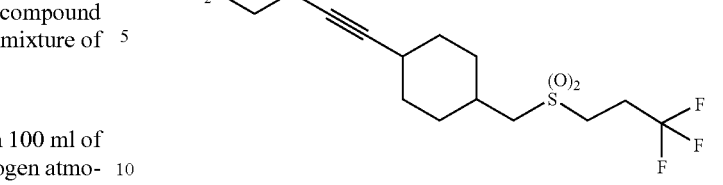

$^1$H-NMR (CDCl$_3$, TMS, δ(ppm)): 1.14-1.20 (2H, m), 1.43-1.56 (2H, m), 2.02-2.22 (8H, m), 2.31-2.40 (2H, m), 2.54-2.60 (1H, m), 2.60-2.71 (1H, m), 2.89-2.96 (3H, m), 3.24-3.26 (1H, m), 3.70 (3H, s).

Production Example 19

To 0.57 g of the present compound (16) were added 0.32 g of pyridine and 0.14 g of hydroxylamine hydrochloride, and the mixture was stirred for 1 hour. To the mixture was added 1 ml of acetic anhydride, and then stirred at 100° C. for 2 hours. To the reaction mixture was added 30 ml of an aqueous saturated sodium hydrogen carbonate solution, followed by extraction with 30 ml of ethyl acetate twice. Organic layers were combined, washed with 30 ml of an aqueous saturated sodium chloride solution, dried over sodium sulfate, filtered, and then concentrated under reduced pressure. The residue was subjected to silica gel column chromatography to obtain 0.32 g of 1-cyano-4-(3,3,3-trifluoropropylsulfonylmethyl) cyclohexane (hereinafter, referred to as the present compound (20)) represented by the formula:

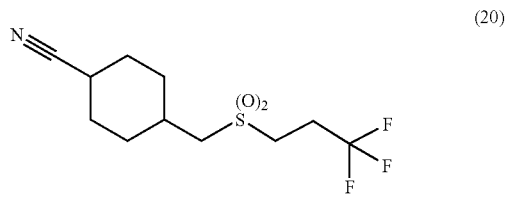

$^1$H-NMR (CDCl$_3$, TMS, δ(ppm)): 1.14-1.26 (2H, m), 1.63-1.73 (1H, m), 2.03-2.43 (7H, m), 2.64-2.74 (2H, m), 2.92 (2H, d), 3.16-3.20 (2H, m).

Production Example 20

To a solution of 0.19 g of the present compound (3) in 1 ml of pyridine was added 0.08 g of 0-methylhydroxylamine hydrochloride, and the mixture was stirred at room temperature for 5 hours. To the reaction solution was added 30 ml of water, followed by extraction with 30 ml of ethyl acetate twice. Organic layers were combined, and washed with 50 ml of an aqueous saturated sodium chloride solution. The resulting organic layer was dried over sodium sulfate, filtered, and then concentrated under reduced pressure. The residue was subjected to silica gel column chromatography to obtain 0.19 g of 4-(3,3,3-trifluoropropylsulfonylmethyl)-cyclohexanone O-methyloxime (hereinafter, referred to as the present compound (21)) represented by the formula:

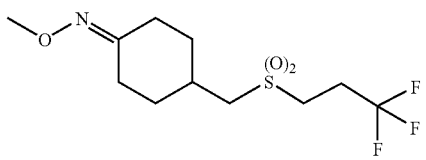

(21)

¹H-NMR (CDCl₃, TMS, δ(ppm)): 1.30-1.39 (2H, m), 1.84-1.92 (1H, m), 2.12-2.23 (3H, m), 2.37-2.46 (2H, m), 2.65-2.72 (2H, m), 2.96 (2H, d), 3.17-3.24 (2H, m).

Production Example 21

To a solution of 0.58 g of the present compound (7) in 4 ml of tetrahydrofuran was added 2.2 ml of a 0.9M solution of methylmagnesium bromide in tetrahydrofuran at 0° C. under a nitrogen atmosphere, and the mixture was stirred at room temperature for 5 hours. To the reaction solution was added 20 ml of water, followed by extraction with 20 ml of ethyl acetate. Organic layers were combined, and washed with 50 ml of an aqueous saturated sodium chloride solution. The resulting organic layer was dried over sodium sulfate, filtered, and then concentrated under reduced pressure.

The residue was subjected to silica gel column chromatography to obtain 0.21 g of 1-ethynyl-4-(3,3,3-trifluoropropyl-1-sulfonylmethyl)cyclohexene (hereinafter referred to as the present compound (22)) represented by the formula:

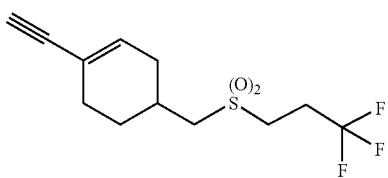

(22)

¹H-NMR (CDCl₃, TMS, δ(ppm)): 1.47-1.61 (1H, m), 1.97-2.06 (2H, m), 2.24-2.30 (2H, m), 2.42-2.47 (2H, m), 2.65-2.75 (2H, m), 2.84 (1H, s), 3.00-3.03 (2H, m), 3.17-3.21 (2H, m), 6.14 (1H, br.s).

Production Example 22

A solution of 62.83 g of oxalyl chloride in 250 ml of dichloromethane was cooled to –78° C. under a nitrogen atmosphere. To the solution was added dropwise a solution of 77.35 g of dimethyl sulfoxide in 250 ml of dichloromethane over 60 minutes, and the mixture was stirred at –50° C. for 60 minutes. To the reaction mixture was added dropwise a solution of 84.54 g of the present compound (14) (a mixture of trans form/cis form=6/4) in 250 ml of dichloromethane, and then stirred at –50° C. for 90 minutes. Thereto 100.18 g of triethylamine was added dropwise over 90 minutes. The reaction mixture was stirred at room temperature for 18 hours. To the reaction mixture was added 300 ml of water, and an organic layer was separated. An aqueous layer was then extracted with 200 ml of chloroform twice. Organic layers were combined, washed successively with 300 ml of an aqueous 1N hydrochloric acid solution, 300 ml of an aqueous saturated sodium hydrogen carbonate solution and 300 ml of water, dried over sodium sulfate, filtered, and then concentrated under reduced pressure. The residue was subjected to silica gel column chromatography to obtain 23.03 g of a cis form (hereinafter, referred to as the present compound (23c)) and 38.51 g of a trans form (hereinafter, referred to as the present compound (23t)) of 4-(3,3,3-trifluoropropylthiomethyl)cyclohexanecarbaldehyde (hereafter, referred to as the present compound (23)) represented by the formula:

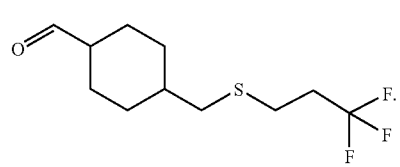

(23)

The Present Compound (23c)
¹H-NMR (CDCl₃, TMS, δ(ppm)): 1.05-1.16 (2H, m), 1.49-1.66 (3H, m), 1.72-1.80 (2H, m), 2.07-2.16 (2H, m), 2.30-2.47 (5H, m), 2.63-2.67 (2H, m), 9.62 (1H, d).

The Present Compound (23t)
¹H-NMR (CDCl₃, TMS, δ(ppm)): 0.99-1.10 (2H, m), 1.24-1.34 (2H, m), 1.40-1.53 (1H, m), 1.97-2.08 (4H, m), 2.13-2.25 (1H, m), 2.31-2.43 (2H, m), 2.46 (2H, m), 2.65-2.69 (2H, m), 9.69 (1H, d).

Production Example 23

A solution of 100.48 g of carbon tetrabromide in 300 ml of dichloromethane was cooled to 0° C. under a nitrogen atmosphere. Thereto 158.86 g of triphenylphosphine was added over 90 minutes. The mixture was stirred for 30 minutes. To the solution was added dropwise a solution of 38.51 g of the present compound (23t) in 100 ml of dichloromethane over 30 minutes, and the mixture was stirred at room temperature for 6 hours. To the reaction mixture was added 500 ml of t-butyl methyl ether. A solid was filtered, and the filtrate was concentrated under reduced pressure. The residue was subjected to silica gel column chromatography to obtain 66.56 g of a trans form (hereinafter refereed to as the present compound (24t)) of 1-(2,2-dibromovinyl)-4-(3,3,3-trifluoropropylthiomethyl)cyclohexane (hereinafter, referred to as the present compound (24)) represented by the formula:

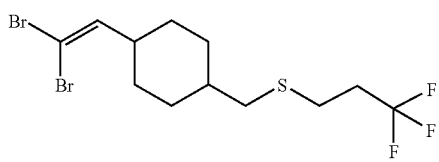

(24)

¹H-NMR (CDCl₃, TMS, δ(ppm)): 0.98-1.08 (2H, m), 1.10-1.20 (2H, m), 1.37-1.49 (1H, m), 1.78-1.85 (2H, m), 1.88-1.95 (2H, m), 2.17-2.29 (1H, m), 2.31-2.41 (2H, m), 2.43 (2H, m), 2.64-2.68 (2H, m), 6.19 (1H, d).

Production Example 2.4

A solution of 53.78 g of the present compound (24t) in 300 ml of tetrahydrofuran was cooled to –78° C. under a nitrogen atmosphere. To the solution was added dropwise 180 ml of a 1.6M solution of n-butyllithium in hexane over 60 minutes, and the mixture was stirred at –50° C. for 1 hour and then at 0° C. for 2 hours. The reaction mixture was poured into 300 ml of an aqueous 1N hydrochloric acid solution which had been cooled with an ice bath, followed by extraction with 300 ml of t-butyl methyl ether twice. Organic layers were combined, washed with 300 ml of an aqueous saturated sodium hydrogen carbonate solution and 300 ml of an aqueous saturated sodium chloride solution, dried over sodium sulfate, filtered, and then concentrated under reduced pressure. The residue was subjected to silica gel column chromatography to obtain 31.54 g of a trans form (hereinafter, referred to as the present compound (25t)) of 1-ethynyl-4-(3,3,3-trifluoropropyl-1-sulfonylmethyl)cyclohexane (hereinafter, referred to as the present compound (25)) represented by the formula:

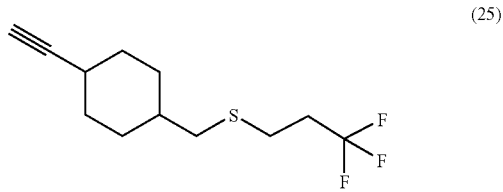

(25)

$^1$H-NMR (CDCl$_3$, TMS, δ(ppm)): 0.92-1.03 (2H, m), 1.34-1.53 (3H, m), 1.86-1.94 (2H, m), 1.98-2.06 (3H, m), 2.15-2.24 (1H, m), 2.30-2.41 (2H, m), 2.42 (2H, d), 2.64-2.68 (2H, m).

Production Example 25

A cis form of the present compound (25) (hereinafter, referred to as the present compound (25c)) was produced in the same manner as Production Example 23 and Production Example 24 except that the present compound (23c) was used in place of the present compound (23t).

$^1$H-NMR (CDCl$_3$, TMS, δ(ppm)): 1.38-1.53 (5H, m), 1.67-1.75 (2H, m), 1.78-1.86 (2H, m), 2.05 (1H, d), 2.31-2.4.4 (2H, m), 2.47 (2H, d), 2.65-2.69 (2H, m), 2.74-2.79 (1H, m).

Production Example 26

To a suspension of 20.30 g of a double salt of 2KHSO$_5$.KHSO$_4$.K$_2$SO$_4$ (Oxone, registered trade mark) in 60 ml of water was added dropwise a solution of 7.51 g of the present compound (24t) in 60 ml of methanol over 60 minutes at −20° C. under a nitrogen atmosphere. The mixture was stirred for 2 hours. To the reaction mixture was added 50 ml of a 10% aqueous sodium sulfite solution, followed by extraction with 100 ml of ethyl acetate twice. Organic layers were combined, washed with 50 ml of a 10% aqueous sodium sulfite solution and 50 ml of an aqueous saturated sodium chloride solution, dried over sodium sulfate, filtered, and then concentrated under reduced pressure. The residue was subjected to silica gel column chromatography to obtain 4.88 g of a trans form (hereinafter, referred to as the present compound (26t)) of 1-ethynyl-4-(3,3,3-trifluoropropylsulfinylmethyl)cyclohexane (hereinafter, referred to as the present compound (26)) represented by the formula:

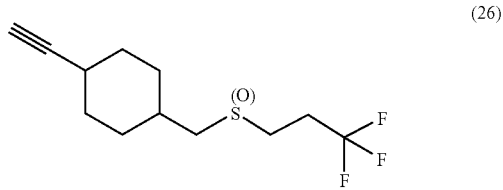

(26)

$^1$H-NMR (CDCl$_3$, TMS, δ(ppm)): 1.02-1.21 (2H, m), 1.41-1.53 (2H, m), 1.82-2.00 (2H, m), 2.00-2.09 (4H, m), 2.20-2.27 (1H, m), 2.40-2.46 (1H, m), 2.57-2.68 (2H, m), 2.71-2.92 (3H, m).

Production Example 27

Step 27-1

To a suspension of 7.35 g of potassium thioacetate in 30 ml of N-methyl-2-pyrrolidone was added dropwise 11.39 g of 3-bromo-1,1,1-trifluoropropane over 15 minutes at 0° C. under a nitrogen atmosphere, and the mixture was stirred at room temperature for 1 hour. The reaction mixture was heated to 80° C., followed by distillation under reduced pressure to obtain 9.99 g of 3,3,3-trifluoropropyl thioacetate represented by the formula:

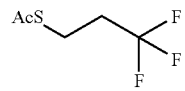

$^1$H-NMR (CDCl$_3$, TMS, δ(ppm)): 2.35-2.43 (2H, m), 2.36 (3H, s), 3.01-3.06 (2H, m).

When 3-iodo-1,1,1-trifluoropropane is used in place of 3-bromo-1,1,1-trifluoropropane, 3,3,3-trifluoropropyl thioacetate is obtained in the same manner.

Step 27-2

A solution of 9.99 g of 3,3,3-trifluoropropyl thioacetate in 60 ml of tetrahydrofuran was cooled to 0° C. Thereto 11.2 g of a 28% solution of sodium methoxide in methanol was added dropwise over 15 minutes, and then stirred at room temperature for 1 hour. To the mixture was added 4.38 g of chloroacetonitrile at 0° C., and then stirred at room temperature for 3 hours. A reaction vessel was cooled in an ice bath. To the reaction mixture was added an aqueous saturated sodium chloride solution, and the mixture was extracted with 100 ml of t-butyl methyl ether twice. Organic layers were combined, washed with an aqueous saturated sodium chloride solution, dried over sodium sulfate, filtered, and then concentrated under reduced pressure. The residue was subjected to silica gel column chromatography to obtain 7.56 g of (3,3,3-trifluoropropylthio)acetonitrile represented by the formula:

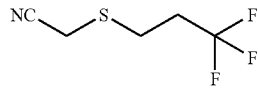

$^1$H-NMR (CDCl$_3$, TMS, δ(ppm)): 2.44-2.55 (2H, m), 2.92-2.98 (2H, m), 3.36 (2H, s).

Step 27-3

To a suspension of 4.97 g of (3,3,3-trifluoropropylthio)acetonitrile and 0.07 g of sodium tungstate dihydrate in 7 ml of water was added 2.3 ml of 31% aqueous hydrogen peroxide while the suspension was stirred. In the middle of the reaction, a part of solids formed in the reaction solution were taken out, purified by thin layer chromatography and then subjected to $^1$H-NMR to confirm the formation of (3,3,3-trifluoropropylsulfinyl)acetonitrile. The reaction mixture was heated to 65° C., and 2.3 ml of 31% aqueous hydrogen peroxide was added thereto. The mixture was stirred at 70° C. for 1 hour, and then cooled to room temperature. To the mixture was added 5 ml of a 10% aqueous sodium sulfite solution, followed by extraction with 30 ml of ethyl acetate three times.

Organic layers were combined, washed with an aqueous saturated sodium chloride solution, dried over sodium sulfate, filtered, and then concentrated under reduced pressure. The residue was crystallized from chloroform: hexane=1:2 to obtain 5.44 g of (3,3,3-trifluoropropylsulfonyl)acetonitrile represented by the formula:

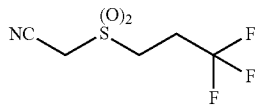

$^1$H-NMR (CDCl$_3$, TMS, δ(ppm)): 2.73-2.85 (2H, m), 3.50-3.56 (2H, m), 4.07 (2H, s).

(3,3,3-Trifluoropropylsulfinyl)acetonitrile

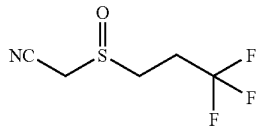

1H-NMR (CDCl$_3$, TMS, δ(ppm)): 2.66-2.73 (2H, m), 3.15-3.23 (2H, m), 3.67-3.81 (2H, m).

Step 27-4

A mixture of 4.02 g of (3,3,3-trifluoropropylsulfonyl)acetonitrile, 100 ml of toluene, 0.23 g of DL-proline and 3.32 g of 1,4-cyclohexanedione monoethylene ketal was heated and stirred for 3 hours under the reflux condition. After 20 ml of toluene was distilled off, the reaction mixture was cooled to room temperature. To the reaction mixture was added 100 ml of tetrahydrofuran. The mixture was cooled to 0° C. and then 1.01 g of sodium borohydride was added thereto. The mixture was stirred at room temperature for 6 hours and then cooled to 0° C. Thereto 100 ml of water and 100 ml of ethyl acetate were added. While the reaction mixture was stirred, 100 ml of an aqueous 1N hydrochloric acid solution was added dropwise, followed by extraction with 100 ml of ethyl acetate twice. An organic layer was washed with 100 ml of an aqueous saturated sodium hydrogen carbonate solution, 100 ml of an aqueous saturated sodium chloride solution and 100 ml of water, dried over sodium sulfate, filtered, and concentrated under reduced pressure. The residue was subjected to silica gel column chromatography to obtain 5.45 g of 2-(1,4-dioxaspiro[4.5]dec-8-yl)-2-(3,3,3-trifluoropropylsulfonyl)acetonitrile (hereinafter referred to as the present compound (27)) represented by the following formula (27).

(27)

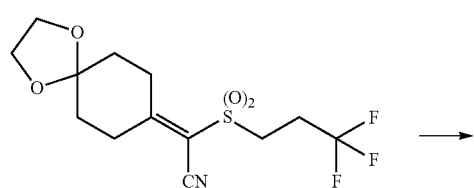

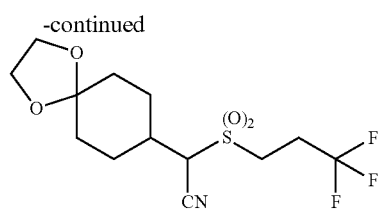

$^1$H-NMR (CDCl$_3$, TMS, δ(ppm)): 1.61-1.90 (7H, m), 2.13-2.23 (1H, m), 2.39-2.51 (1H, m), 2.67-2.86 (2H, m), 3.39-3.47 (1H, m), 3.51-3.60 (1H, m), 3.85 (1H, d), 3.92-3.99 (4H, m).

Production Example 28

A mixture of 3.20 g of the present compound (27), 7 ml of acetic acid and 3 ml of water was heated to 70° C. and stirred for 10 hours. After the reaction mixture was cooled to room temperature, 100 ml of ethyl acetate was added thereto. The mixture was added slowly into 100 ml of an aqueous saturated sodium hydrogen carbonate solution. The solution was stirred for 1 hour, followed by extraction with 100 ml of ethyl acetate twice. Organic layers were combined, washed with 100 ml of an aqueous saturated sodium hydrogen carbonate solution and 100 ml of an aqueous saturated sodium chloride solution, dried over sodium sulfate, filtered, and concentrated under reduced pressure. The residue was subjected to silica gel column chromatography to obtain 2.59 g of 2-(4-oxocyclohexyl)-2-(3,3,3-trifluoropropylsulfonyl)acetonitrile (hereinafter, referred to as the present compound (28)) represented by the formula:

(28)

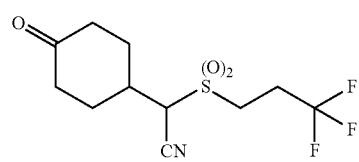

$^1$H-NMR (CDCl$_3$, TMS, δ(ppm)): 1.87-1.97 (2H, m), 2.18-2.25 (1H, m), 2.42-2.60 (5H, m), 2.73-2.95 (3H, m), 3.41-3.51 (1H, m), 3.55-3.66 (1H, m), 3.97 (1H, d).

Production Example 29

To a solution of 0.15 g of the present compound (28) in 5 ml of dichloromethane was added 0.21 g of diethylaminosulfur trifluoride at −20° C. under a nitrogen atmosphere. The mixture was stirred at room temperature for 5 hours. The reaction solution was diluted with 30 ml of chloroform. Thereto 30 ml of water was added, and an organic layer was separated. An aqueous layer was extracted with 30 ml of chloroform twice, and organic layers were combined and washed with 50 ml of an aqueous saturated sodium chloride solution. The resulting organic layer was dried over sodium sulfate, filtered, and then concentrated under reduced pressure. The residue was subjected to silica gel column chromatography to obtain 0.16 g of 2-(4,4-difluorocyclohexyl)-2-(3,3,3-trifluoropropylsulfonyl)acetonitrile (hereinafter, referred to as the present compound (29)) represented by the formula:

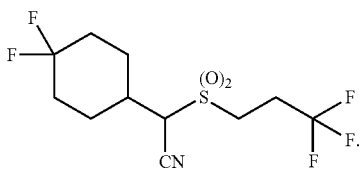

(29)

¹H-NMR (CDCl₃, TMS, δ(ppm)): 1.41-1.99 (5H, m), 2.16-2.32 (3H, m), 2.42-2.58 (1H, m), 2.70-2.86 (2H, m), 3.38-3.49 (1H, m), 3.54-3.68 (1H, m), 3.87 (1H, d)

Production Example 30

To a solution of 1.49 g of the present compound (28) in 20 ml of tetrahydrofuran was added 30 ml of a 0.5M solution of ethynylmagnesium bromide in tetrahydrofuran at 0° C. under a nitrogen atmosphere, and the mixture was stirred at 0° C. for 5 hours. To the reaction solution was added 50 ml of an aqueous 1N hydrochloric acid solution, followed by extraction with 50 ml of ethyl acetate twice. Organic layers were combined, and washed with 50 ml of an aqueous saturated sodium hydrogen carbonate solution and 50 ml of an aqueous saturated sodium chloride solution. The resulting organic layer was dried over sodium sulfate, filtered, and then concentrated under reduced pressure. The residue was subjected to silica gel column chromatography to obtain 1.69 g of 2-(4-ethynyl-4-hydroxycyclohexyl)-2-(3,3,3-trifluoropropylsulfonyl)acetonitrile (hereinafter, referred to as the present compound (30)) represented by the formula:

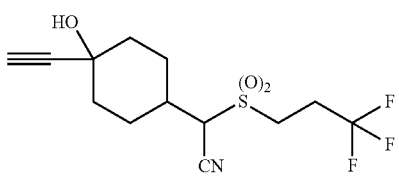

(30)

¹H-NMR (CDCl₃, TMS, δ(ppm)): 1.59-2.28 (9H, m), 2.28-2.47 (1H, m), 2.61 (1H, s), 2.71-2.84 (2H, m), 3.40-3.48 (1H, m), 3.52-3.60 (1H, m), 3.87 (1H, d).

Production Example 31

To a solution of 0.65 g of the present compound (30) in 6 ml of dichloromethane was added 0.48 g of diethylaminosulfur trifluoride at 0° C. under a nitrogen atmosphere, and the mixture was stirred at room temperature for 5 hours. The reaction solution was diluted with 20 ml of chloroform. Thereto 20 ml of water was added, and an organic layer was separated. An aqueous layer was extracted with 20 ml of chloroform twice. Organic layers were combined, and washed with 50 ml of an aqueous saturated sodium chloride solution. The resulting organic layer was dried over sodium sulfate, filtered, and then concentrated under reduced pressure. The residue was subjected to silica gel column chromatography to obtain 0.31 g of 2-(4-ethynyl-4-fluorocyclohexyl)-2-(3,3,3-trifluoropropylsulfonyl)acetonitrile (hereinafter, referred to as the present compound (31)) and 0.23 g of 2-(4-ethynyl-cyclohexen-3-yl)-2-(3,3,3-trifluoropropylsulfonyl)acetonitrile (hereinafter, referred to as the present compound (32)), which are represented by the formulas:

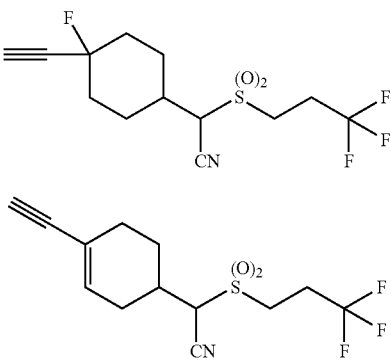

The resulting present compound (32) was a 1:1 isomer mixture.

The Present Compound (31)
¹H-NMR (CDCl₃, TMS, δ(ppm)): 1.73-2.15 (6H, m), 2.25-2.39 (2H, m), 2.44-2.54 (1H, m), 2.66 (1H, d), 2.71-2.84 (2H, m), 3.40-3.48 (1H, m), 3.53-3.61 (1H, m), 3.87 (1H, d).

The Present Compound (32)
¹H-NMR (CDCl₃, TMS, δ(ppm)): 1.68-2.84 (9H, m), 2.84 (1H, d), 3.39-3.49 (1H, m), 3.51-3.66 (1H, m), 3.89 (1H, d), 6.10-6.18 (2H, m).

Production Example 32

To a solution of 2.81 g of the present compound (28) in 10 ml of tetrahydrofuran were added 0.75 g of pyridine and 0.79 g of methoxyamine hydrochloride, and the mixture was stirred at room temperature for 3 hours. To the reaction solution was added 30 ml of an aqueous 1N hydrochloric acid solution, followed by extraction with 50 ml of ethyl acetate twice. Organic layers were combined, washed with 50 ml of an aqueous saturated sodium hydrogen carbonate solution and 50 ml of an aqueous saturated sodium chloride solution. The resulting organic layer was dried over sodium sulfate, filtered, and then concentrated under reduced pressure. The residue was subjected to silica gel column chromatography to obtain 2.86 g of 2-[4-(methoxyimino)cyclohexyl]-2-(3,3,3-trifluoropropylsulfonyl)acetonitrile (hereinafter, referred to as the present compound (33)) represented by the formula:

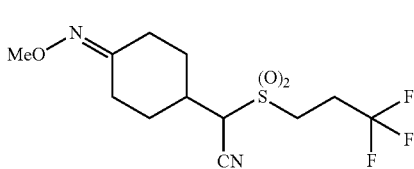

(33)

¹H-NMR (CDCl₃, TMS, δ(ppm)): 1.50-1.71 (2H, m), 1.80-1.91 (1H, m), 1.95-2.08 (1H, m), 2.16-2.27 (1H, m), 2.30-2.44 (1H, m), 2.49-2.57 (1H, m), 2.62-2.71 (1H, m), 2.72-2.86 (2H, m), 3.32-3.48 (2H, m), 3.52-3.61 (1H, m), 3.83 (3H, s), 3.87 (1H, d).

Production Example 33

To a solution of 0.20 g of the present compound (28) in 2 ml of pyridine was added 0.06 g of hydroxylamine hydrochloride, and the mixture was stirred at room temperature for 3 hours. To the reaction solution was added 50 ml of hexane, followed by concentration under reduced pressure. The residue was subjected to silica gel column chromatography to obtain 0.093 g of 2-[4-(hydroxyimino)cyclohexyl]-2-(3,3,3-trifluoropropylsulfonyl)acetonitrile (hereinafter, referred to as the present compound (34)) represented by the formula:

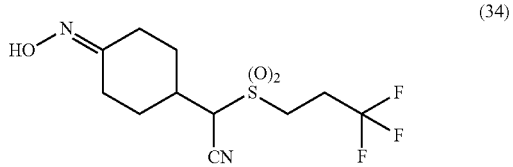

(34)

¹H-NMR (CD₃OD, TMS, δ(ppm)): 1.29-1.48 (2H, m), 1.69-1.85 (1H, m), 1.87-2.01 (1H, m), 2.07-2.27 (2H, m), 2.29-2.38 (1H, m), 2.51-2.59 (1H, m), 2.67-2.81 (2H, m), 3.18-3.22 (1H, m), 3.26-3.34 (2H, m), 4.47 (1H, br.s).

Production Example 34

According to Production Example 33 except that 0.008 g of ethoxyamine hydrochloride was used in place of hydroxylamine hydrochloride, 0.095 g of 2-[4-(ethoxyimino)cyclohexyl]-2-(3,3,3-trifluoropropylsufonyl)acetonitrile (hereinafter, referred to as the present compound (35)) represented by the formula:

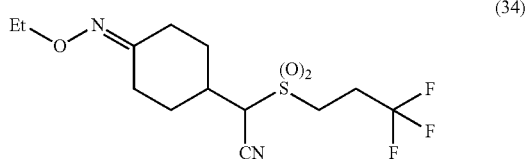

(34)

was obtained.
¹H-NMR (CDCl₃, TMS, δ(ppm)): 1.25 (3H, t), 1.51-1.72 (2H, m), 1.79-1.92 (1H, m), 1.95-2.07 (1H, m), 2.17-2.27 (1H, m), 2.31-2.43 (1H, m), 2.49-2.59 (1H, m), 2.61-2.71 (1H, m), 2.72-2.86 (2H, m), 3.35-3.49 (2H, m), 3.51-3.61 (1H, m), 3.85 (1H, d), 4.05 (2H, q).

Production Example 35

According to Production Example 33 except that 0.01 g of t-butoxyamine hydrochloride was used in place of hydroxylamine hydrochloride, 0.19 g of 2-[4-(t-butoxyimino)cyclohexyl]-2-(3,3,3-trifluoropropylsulfonyl)acetonitrile (hereinafter, referred to as the present compound (36)) represented by the formula:

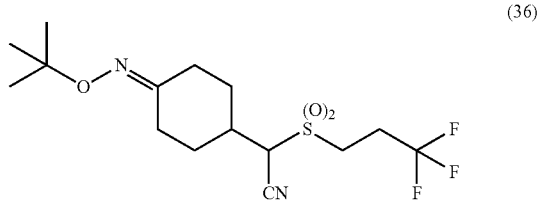

(36)

was obtained.
¹H-NMR (CDCl₃, TMS, δ(ppm)): 1.26 (9H, s), 1.49-1.70 (2H, m), 1.75-1.88 (1H, m), 1.91-2.06 (1H, m), 2.14-2.25 (1H, m), 2.27-2.42 (1H, m), 2.51-2.59 (1H, m), 2.59-2.70 (1H, m), 2.71-2.88 (2H, m), 3.35-3.48 (2H, m), 3.52-3.68 (1H, m), 3.86-3.88 (1H, m).

Production Example 36

According to Production Example 33 except that 0.009 g of O-allylhydroxylamine hydrochloride was used in place of hydroxylamine hydrochloride, 0.061 g of 2-[4-(O-allylhydroxylimino)cyclohexyl]-2-(3,3,3-trifluoropropylsulfonyl)acetonitrile (hereinafter, referred to as the present compound (37)) represented by the formula:

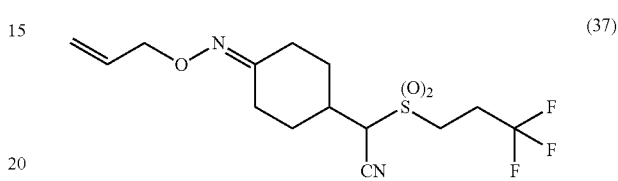

(37)

was obtained.
¹H-NMR (CDCl₃, TMS, δ(ppm)): 1.52-1.72 (2H, m), 1.79-1.94 (1H, m), 1.96-2.09 (1H, m), 2.16-2.28 (1H, m), 2.31-2.42 (1H, m), 2.50-2.59 (1H, m), 2.61-2.72 (1H, m), 2.72-2.86 (2H, m), 3.38-3.48 (2H, m), 3.52-3.61 (1H, m), 3.85-3.88 (1H, m), 4.52-4.55 (2H, m), 5.19-5.33 (2H, m), 5.92-6.04 (2H, m).

Production Example 37

According to Production Example 33 except that 0.009 g of O-benzylhyroxylamine hydrochloride was used in place of hydroxylaminde hydrochloride, 0.10 g of 2-[4-(O-benzylhydroxylimino)cyclohexyl]-2-(3,3,3-trifluoropropylsulfonyl)acetonitrile (hereinafter, referred to as the present compound (38)) represented by the formula:

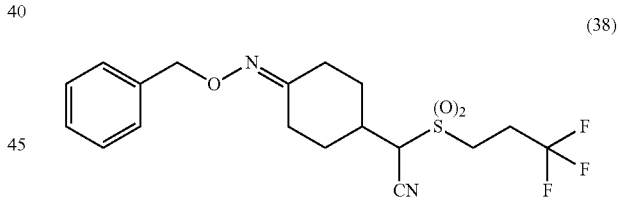

(38)

was obtained.
¹H-NMR (CDCl₃, TMS, δ(ppm)): 1.49-1.72 (2H, m), 1.81-2.08 (2H, m), 2.16-2.27 (1H, m), 2.30-2.43 (1H, m), 2.50-2.58 (1H, m), 2.61-2.70 (1H, m), 2.72-2.83 (2H, m), 3.38-3.48 (2H, m), 3.51-3.61 (1H, m), 3.84-3.87 (1H, m), 5.07 (2H, s), 7.28-7.34 (1H, m), 7.35-7.36 (4H, m).

Production Example 38

To a solution of 0.20 g of the present compound (28) in 2 ml of pyridine was added 0.06 g of O-carboxymethylhydroxylamine hydrochloride, and the mixture was stirred at room temperature for 3 hours. To the reaction solution was added 30 ml of an aqueous 1N hydrochloric acid solution, followed by extraction with 30 ml of ethyl acetate twice. The resulting organic layer was dried over sodium chloride, filtered, and then concentrated under reduced pressure. The residue was subjected to silica gel column chromatography to obtain 0.094 g of 2-[4-(O-carboxymethylhydroxylimine)cyclohexyl]-2-(3,3,3-trifluoropropylsulfonyl)acetonitrile (hereinafter, referred to as the present compound (39)) represented by the formla:

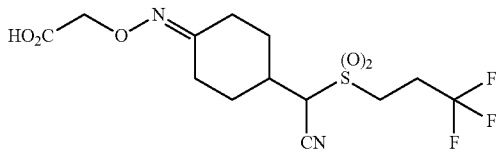

¹H-NMR (CDCl₃, TMS, δ(ppm)): 1.56-1.72 (2H, m), 1.88-2.11 (2H, m), 2.17-2.29 (1H, m), 2.31-2.43 (1H, m), 2.47-2.56 (1H, m), 2.60-2.70 (1H, m), 2.73-2.84 (2H, m), 3.38-3.43 (4H, m), 4.57 (2H, s).

Production Example 39

A solution of 0.16 g of the present compound (33) in 3 ml of dimethyl sulfoxide was cooled to 0° C. under a nitrogen atmosphere. To the mixture was added 0.05 g of 60% sodium hydride dispersion in paraffin liquid, and the mixture was stirred for 30 minutes. Thereto was added 0.11 g of methyl iodide, and the mixture was stirred at room temperature overnight. To the reaction solution was added 10 ml of an aqueous 1N hydrochloric acid solution, followed by extraction with 30 ml of ethyl acetate twice. Organic layers were combined, and washed with 10 ml of an aqueous saturated sodium hydrogen carbonate solution and 10 ml of an aqueous saturated sodium chloride solution. The resulting organic layer was dried over sodium sulfate, filtered, and then concentrated under reduced pressure. The residue was subjected to silica gel column chromatography to obtain 0.13 g of 2-[4-(methoxyimino)cyclohexyl]-2-(3,3,3-trifluoropropylsulfonyl)propionitrile (hereinafter, referred to as the present compound (40)) represented by the formula:

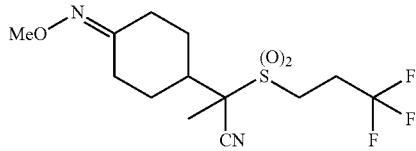

¹H-NMR (CDCl₃, TMS, δ(ppm)): 1.31-1.64 (2H, m), 1.75 (3H, s), 1.76-1.91 (1H, m), 2.13-2.32 (3H, m), 2.48-2.62 (2H, m), 2.69-2.87 (2H, m), 3.32-3.47 (2H, m), 3.55-3.64 (1H, m), 3.83 (3H, s).

Production Example 40

According to Production Example 39 except that 0.13 g of ethyl iodide was used in place of methyl iodide, 0.13 g of 2-[4-(methoxyimino)cyclohexyl]-2-(3,3,3-trifluoropropylsulfonyl)butyronitrile (hereinafter, referred to as the present compound (41)) represented by the formula:

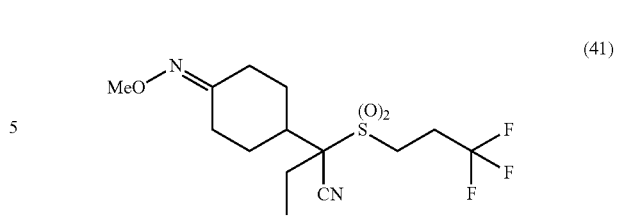

was obtained.

¹H-NMR (CDCl₃, TMS, δ(ppm)): 1.27 (3H, t), 1.43-1.69 (2H, m), 1.73-1.87 (1H, m), 2.10-2.31 (5H, m), 2.49-2.61 (2H, m), 2.71-2.87 (2H, m), 3.33-3.47 (2H, m), 3.55-3.66 (1H, m), 3.83 (3H, s).

Production Example 41

According to Production Example 39 except that 0.14 g of 1-iodopropane was used in place of methyl iodide, 0.055 g of 2-[4-(methoxyimino)cyclohexyl]-2-(3,3,3-trifluoropropylsulfonyl)pentanenitrile (hereinafter, referred to as the present compound (42)) represented by the formula:

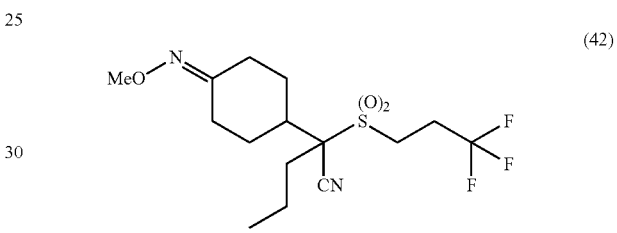

was obtained.

¹H-NMR (CDCl₃, TMS, δ(ppm)): 1.06 (3H, t), 1.44-1.71 (4H, m), 1.73-1.86 (1H, m), 1.94-2.13 (2H, m), 2.15-2.31 (3H, m), 2.48-2.61 (2H, m), 2.73-2.83 (2H, m), 3.32-3.46 (2H, m), 3.55-3.65 (1H, m), 3.83 (3H, s).

Production Example 42

According to Production Example 39 except that 0.10 g of 3-bromopropane was used in place of methyl iodide, 0.14 g of 2-[4-(methoxyimino)cyclohexyl]-3-methyl-2-(3,3,3-trifluoropropylsufonyl)-4-pentenenitrile (hereinafter, referred to as the present compound (43)) represented by the formula:

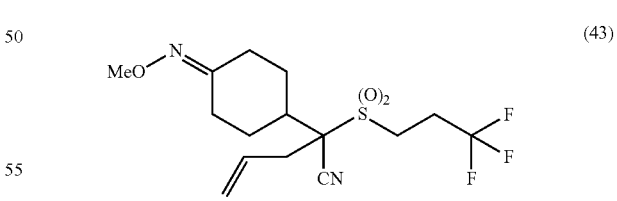

was obtained.

¹H-NMR (CDCl₃, TMS, δ(ppm)): 1.41-1.68 (2H, m), 1.73-1.87 (1H, m), 2.12-2.33 (3H, m), 2.47-2.82 (5H, m), 2.86-2.91 (1H, m), 3.31-3.48 (2H, m), 3.61-3.68 (1H, m), 3.83 (3H, s), 5.40-5.49 (2H, m), 5.87-6.02 (1H, m).

Production Example 43

According to Production Example 39 except that 0.10 g of 3-bromopropane was used in place of methyl iodide, 0.14 g of 2-[4-(methoxyimino)cyclohexyl]-3-methyl-2-(3,3,3-trifluoropropylsulfonyl)-4-pentynenitrile (hereinafter, referred to as the present compound (44)) represented by the formula:

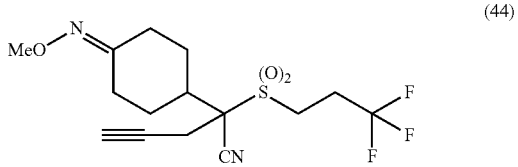

(44)

was obtained.

¹H-NMR (CDCl₃, TMS, δ(ppm)): 1.29-1.47 (1H, m), 1.50-1.68 (1H, m), 1.74-1.91 (1H, m), 2.13-2.35 (3H, m), 2.43-2.45 (1H, m), 2.49-2.61 (1H, m), 2.73-2.86 (3H, m), 2.91-3.11 (2H, m), 3.32-3.47 (1H, m), 3.73-3.89 (2H, m), 3.83 (3H, s).

Production Example 44

A solution of 0.45 g of the present compound (33) in 5 ml of tetrahydrofuran was cooled to 0° C. under a nitrogen atmosphere. Thereto 0.10 g of 60% sodium hydride dispersion in paraffin liquid was added, and the mixture was stirred for 30 minutes. Then 0.20 g of N-chlorosuccinimide was added, and the mixture was stirred at room temperature overnight. To the reaction solution was added 10 ml of an aqueous 1N hydrochloric acid solution, followed by extraction with 30 ml of ethyl acetate twice. Organic layers were combined, washed with 10 ml of an aqueous saturated sodium hydrogen carbonate solution and 10 ml of an aqueous saturated sodium chloride solution. The resulting organic layer was dried over sodium sulfate, filtered, and then concentrated under reduced pressure. The residue was subjected to silica gel column chromatography to obtain 0.39 g of 2-chloro-2-[4-(methoxyimino)-cyclohexyl]-2-(3,3,3-trifluoropropylsulfonyl)acetonitrile (hereinafter, referred to as the present compound (45)) represented by the formula:

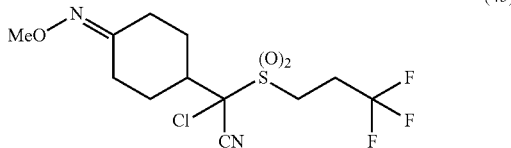

(45)

¹H-NMR (CDCl₃, TMS, δ(ppm)): 1.52-1.91 (3H, m), 2.16-2.29 (1H, m), 2.34-2.48 (2H, m), 2.52-2.63 (1H, m), 2.74-2.89 (3H, m), 3.36-3.46 (1H, m), 3.64-3.82 (2H, m), 3.84 (3H, s).

Production Example 45

A mixture of 1.00 g of (3,3,3-trifluoropropylsulfonyl)acetonitrile, 30 ml of tetrahydrofuran, 0.12 g of DL-proline and 1.01 g of cyclopentanone was heated and stirred for 6 hours under the reflux condition. The reaction mixture was cooled to 0° C., and 0.42 g of sodium borohydride was added thereto. The mixture was stirred at room temperature for 6 hours. After the reaction mixture was cooled to 0° C., 10 ml of water and 30 ml of ethyl acetate were added. While the mixture was stirred, 50 ml of 1N hydrochloric acid was added dropwise thereto, followed by extraction with 30 ml of ethyl acetate twice. Organic layers were combined, washed successively with 30 ml of an aqueous saturated sodium hydrogen carbonate solution and 30 ml of an aqueous saturated sodium chloride solution, dried over sodium sulfate, filtered, and then concentrated under reduced pressure. The residue was subjected to silica gel column chromatography to obtain 1.01 g of 2-cyclopentyl-2-(3,3,3-trifluoropropylsulfonyl)acetonitrile (referred to as the present compound (46)) represented by the following formula (46).

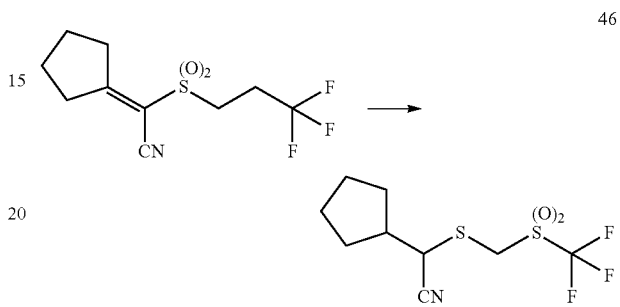

46

¹H-NMR (CDCl₃, TMS, δ(ppm)): 1.46-1.56 (1H, m), 1.59-1.71 (3H, m), 1.73-1.85 (2H, m), 2.02-2.17 (2H, m), 2.66-2.86 (3H, m), 3.38-3.56 (2H, m), 4.03 (1H, d).

Production Example 46

According to Production Example 45 except that 1.14 g of cyclohexanone was used in place of cyclopentanone, 1.01 g of 2-cyclohexyl-2-(3,3,3-trifluoropropylsulfonyl)acetonitrile (hereinafter, referred to as the present compounds (47)) represented by the following formula (47) was obtained.

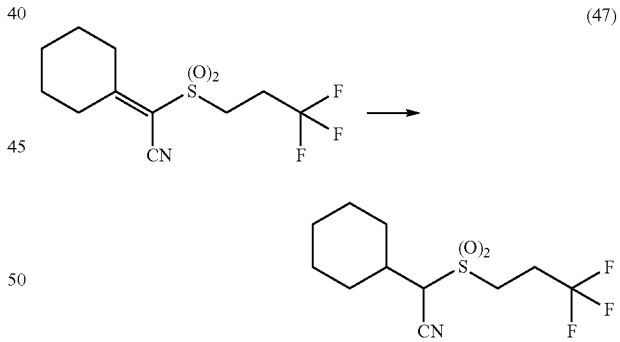

(47)

¹H-NMR (CDCl₃, TMS, δ(ppm)): 1.16-1.28 (1H, m), 1.30-1.47 (4H, m), 1.69-1.77 (1H, m), 1.79-1.88 (3H, m), 2.15-2.22 (1H, m), 2.39-2.49 (1H, m), 2.70-2.84 (2H, m), 3.37-3.46 (1H, m), 3.48-3.56 (1H, m), 3.80 (1H, d).

Production Example 47

According to Production Example 45 except that 1.23 g of cycloheptanone was used in place of cyclopentanone, 1.24 g of 2-cyclohexyl-2-(3,3,3-trifluoropropylsulfonyl)acetonitrile (hereinafter, referred to as the present compound (48)) represented by the following formula (48) was obtained.

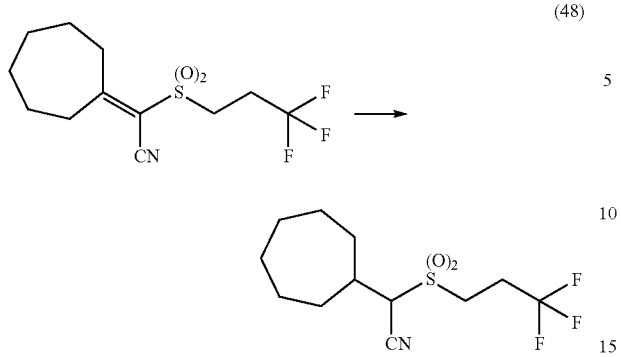

$^1$H-NMR (CDCl$_3$, TMS, δ(ppm)): 1.50-1.86 (11H, m), 2.14-2.22 (1H, m), 2.56-2.62 (1H, m), 2.70-2.83 (2H, m), 3.36-3.44 (1H, m), 3.48-3.56 (1H, m), 3.84 (1H, d).

Production Example 48

According of Production Example 45 except that 1.34 g of 4-methylcyclohexanone was used in place of cyclopentanone, 1.12 g of 2-(4-methylcyclohexyl)-2-(3,3,3-trifluoropropylsulfonyl)acetonitrile (hereinafter, referred to as the present compound (49)) represented by the following formula (49) was obtained. The resulting present compound (49) was a 6/4 isomer mixture.

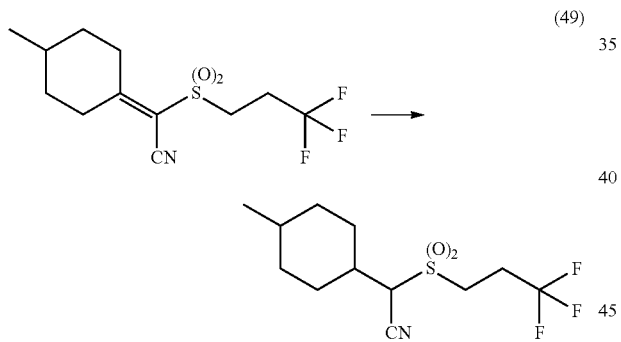

The Main Isomer of the Present Compound (49):

$^1$H-NMR (CDCl$_3$, TMS, δ(ppm)): 0.98 (3H, d), 1.00-1.12 (1H, m), 1.32-1.97 (8H, m), 2.45-2.54 (1H, m), 2.71-2.87 (2H, m), 3.37-3.59 (2H, m), 3.92 (1H, d).

Minor Isomer of the Present Compound (49):

$^1$H-NMR (CDCl$_3$, TMS, δ(ppm)): 0.91 (3H, d), 1.32-1.97 (8H, m), 2.14-2.23 (1H, m), 2.33-2.43 (1H, m), 2.71-2.87 (2H, m), 3.37-3.59 (2H, m), 3.82 (1H, d).

Production Example 49

According to Production Example 45 except that 1.24 g of 4,4-dimetylcyclohexanone was used in place of cyclopentanone, 0.98 g of 2-(4,4-dimethylcyclohexyl)-2-(3,3,3-trifluoropropylsulfonyl)acetonitrile (hereinafter, referred to as the present compound (50)) represented by the following formula (50) was obtained.

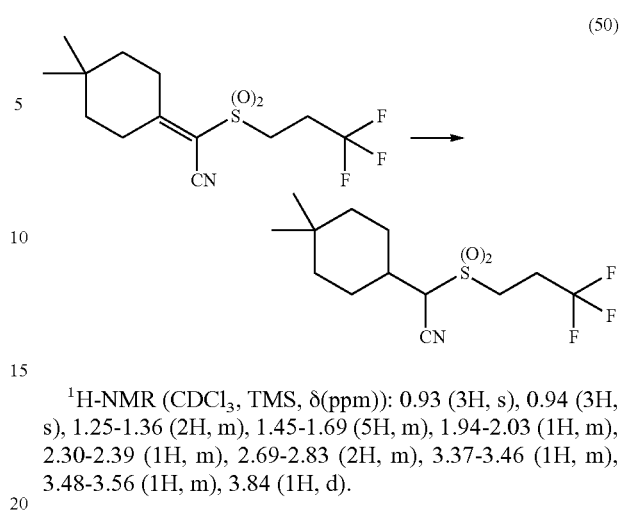

$^1$H-NMR (CDCl$_3$, TMS, δ(ppm)): 0.93 (3H, s), 0.94 (3H, s), 1.25-1.36 (2H, m), 1.45-1.69 (5H, m), 1.94-2.03 (1H, m), 2.30-2.39 (1H, m), 2.69-2.83 (2H, m), 3.37-3.46 (1H, m), 3.48-3.56 (1H, m), 3.84 (1H, d).

Production Example 50

A mixture of 3.31 g of (3,3,3-trifluoropropylsulfonyl)acetonitrile, 60 ml of tetrahydrofuran, 0.19 g of DL-proline and 2.03 g of 4-cyanocyclohexanone was heated and stirred for 6 hours under the reflux condition. After the reaction mixture was cooled to 0° C., 0.62 g of sodium borohydride was added thereto. The mixture was stirred at room temperature for 6 hours. After the reaction mixture was cooled to 0° C., 30 ml of water and 50 ml of ethyl acetate were added thereto. While the mixture was stirred, 90 ml of 1N hydrochloric acid was added dropwise, followed by extraction with 50 ml of ethyl acetate three times. An organic layer was washed with 50 ml of an aqueous saturated sodium hydrogen carbonate solution and 50 ml of an aqueous saturated sodium chloride solution, dried over sodium sulfate, filtered, and then concentrated under reduced pressure. The residue was subjected to silica gel column chromatography to obtain 0.51 g of a trans form (hereinafter, referred to as the present compound (51t)) and 0.59 g of a cis form (hereinafter, referred to as the present compound (51c)) of 2-(4-cyanocyclohexyl)-2-(3,3,3-trifluoropropylsulfonyl)acetnitrile represented by the following formula(51).

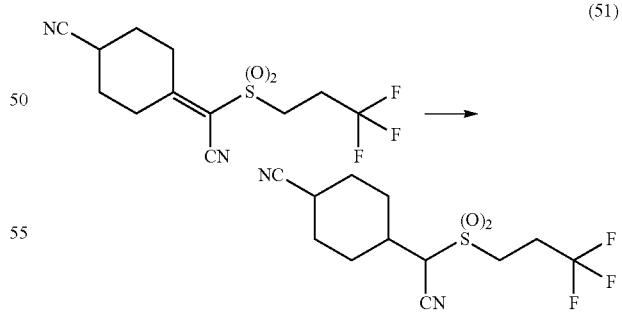

The Present Compound (51c):

$^1$H-NMR (CDCl$_3$, TMS, δ(ppm)): 1.40-1.54 (2H, m), 1.64-1.79 (2H, m), 1.89-1.99 (1H, m), 2.21-2.30 (2H, m), 2.30-2.38 (1H, m), 2.41-2.54 (2H, m), 2.69-2.84 (2H, m), 3.37-3.47 (1H, m), 3.51-3.59 (1H, m), 3.83 (1H, d).

The Present Compound (51t):

$^1$H-NMR (CDCl$_3$, TMS, δ(ppm)): 1.64-1.88 (4H, m), 1.95-2.02 (1H, m), 2.09-2.19 (2H, m), 2.19-2.29 (1H, m), 2.41-

2.51 (1H, m), 2.51-2.69 (2H, m), 3.00-3.05 (1H, m), 3.41-3.50 (1H, m), 3.54-3.63 (1H, m), 3.83 (1H, d).

Production Example 51

To a solution of 0.34 g of the present compound (27) in 10 ml of acetonitrile were added 0.21 g of 1,2-ethanedithiol and 0.05 g of tetrabutylammonium tribromide, and the mixture was stirred at room temperature for 1 hour. To the reaction mixture were added 100 ml of ethyl acetate and then 50 ml of an aqueous saturate sodium hydrogen carbonate solution. The solution was stirred for 1 hour and then extracted with 50 ml of ethyl acetate twice. Organic layers were combined, washed with 50 ml of an aqueous saturated sodium hydrogen carbonate solution and 50 ml of an aqueous saturated sodium chloride solution, dried over sodium sulfate, filtered, and then concentrated under reduced pressure. The residue was subjected to silica gel column chromatography to obtain 0.36 g of 2-(1,4-dithiaspiro[4.5]dec-8-yl)-2-(3,3,3-trifluoropropylsulfonyl)acetonitrile (hereinafter, referred to as the present compound (52)) represented by the formula:

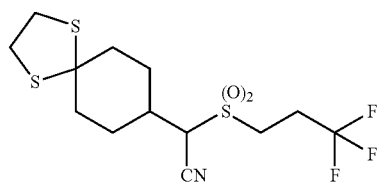

(52)

$^1$H-NMR (CDCl$_3$, TMS, δ(ppm)): 1.67-1.83 (2H, m), 1.88-1.97 (1H, m), 1.98-2.09 (2H, m), 2.17-2.30 (3H, m), 2.36-2.48 (1H, m), 2.67-2.85 (2H, m), 3.24-3.36 (4H, m), 3.48-3.50 (1H, m), 3.60-3.83 (1H, m), 3.86 (1H, d).

Production Example 52

Step 52-1

To a suspension of 22.85 g of potassium thioacetate in 200 ml of methanol was added dropwise 54.79 g of 1-iodo-3,3,4,4,4-pentafluorobutane at 0° C. over 30 minutes under a nitrogen atmosphere, and the mixture was stirred at room temperature for 1 hour. At this time, the reaction mixture was analyzed by thin layer chromatography (TLC), and thereby the formation of 3,3,4,4,4-pentafluorobutyl thioacetate was confirmed. After the mixture was cooled to 0° C., 40.52 g of a 28% solution of sodium methoxide in methanol was added dropwise over 15 minutes thereto. The mixture was stirred at room temperature for 1 hour. To the mixture was added 16.61 g of chloroacetonitrile at 0° C., and the mixture was stirred at room temperature for 3 hours. A reaction vessel was cooled in an ice bath, and an aqueous 1N hydrochloric acid solution was added to the reaction mixture. Methanol was distilled off under reduced pressure. The residual reaction mixture was extracted with 200 ml of t-butyl methyl ether twice. Organic layers were combined, washed with an aqueous saturated sodium chloride solution, dried over sodium sulfate, filtered, and then subjected to reduced pressure to distill off the solvent. The residue was subjected to silica gel column chromatography to obtain 17.81 g of (3,3,4,4,4-pentafluorobutylthio)acetonitrile.

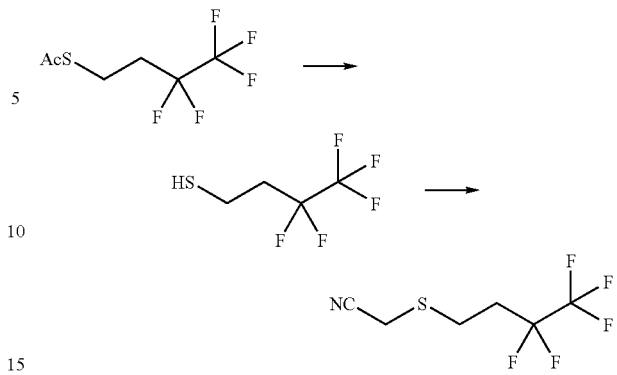

$^1$H-NMR (CDCl$_3$, TMS, δ(ppm)): 2.35-2.52 (2H, m), 2.94-3.03 (2H, m), 3.36 (2H, s).

Alternatively, 3,3,4,4,4-pentafluorobutyl thioacetate was synthesized according to Step 27-1 of Production Example 27 except that 1.22 g of 1-iodo-3,3,4,4,4-pentafluorobutane was used in place of 1-iodo-3,3,3-trifluoropropane.

Step 52-2

To a suspension of 17.81 g of (3,3,4,4,4-pentafluorobutylthio)acetonitrile and 0.28 g of sodium tungstate dihydrate in 30 ml of water was added 8.94 ml of 31% aqueous hydrogen peroxide while the suspension was stirred. The temperature of the mixture was raised to 65° C., and 8.94 ml of 31% aqueous hydrogen peroxide was added thereto. The mixture was stirred at 70° C. for 1 hour. In the middle of the reaction, the formation of a deduced sulfoxide compound was confirmed by thin layer chromatography (TLC) analysis. The reaction mixture was cooled to room temperature, and 30 ml of an aqueous sodium sulfite solution was added thereto, followed by extraction with 150 ml of ethyl acetate three times. Organic layers were combined, washed with an aqueous saturated sodium chloride solution, dried over sodium sulfate, filtered, and then concentrated under reduced pressure. The residue was crystallized from chloroform:hexane=1:2 to obtain 17.84 g of (3,3,4,4,4-pentafluorobutylsulfonyl)acetonitrile represented by the formula:

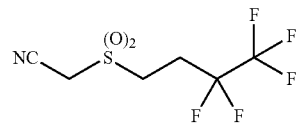

$^1$H-NMR (CDCl$_3$, TMS, δ(ppm)): 2.66-2.80 (2H, m), 3.53-3.58 (2H, m), 4.09 (2H, s).

Step 52-3

A mixture of 7.74 g of (3,3,4,4,4-pentafluorobutylsulfonyl)acetonitrile, 100 ml of toluene, 0.23 g of DL-proline and 4.81 g of 1,4-cyclohexanedionemonoethylene ketal was heated and stirred for 3 hours under the reflux condition. After 20 ml of toluene was distilled off, the reaction mixture was cooled to room temperature. To the reaction mixture was added 100 ml of tetrahydrofuran. After cooled to 0° C., to the reaction mixture was added 1.17 g of sodium borohydride. The mixture was stirred at room temperature for 6 hours and then cooled to 0° C., and 100 ml of water and 100 ml of ethyl acetate were added thereto. To the mixture was added dropwise 100 ml of 1N hydrochloric acid while the mixture was stirred, followed by, extraction with 100 ml of ethyl acetate twice. An organic layer was washed with 100 ml of an aqueous saturated sodium hydrogen carbonate solution, 100 ml of an aqueous saturated sodium chloride solution and then 100 ml of water, dried over sodium sulfate, filtered, and then concentrated under reduced pressure. The residue was subjected to silica gel column chromatography to obtain 5.00 g of 2-(1,4-dioxaspiro[4.5]dec-8-yl)-2-(3,3,4,4,4-pentafluorobutylsulfonyl)acetonitrile (hereinafter, referred to as the present compound (53)) represented by the following formula (53).

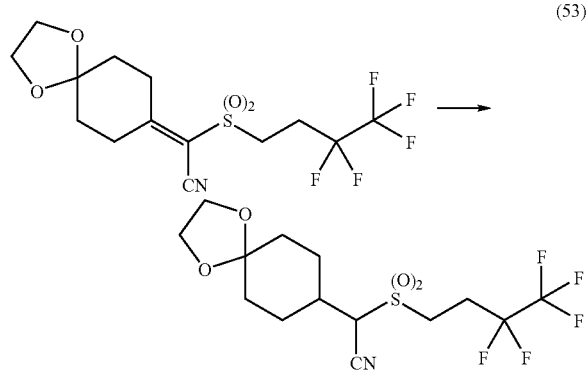

$^1$H-NMR (CDCl$_3$, TMS, δ(ppm)): 1.58-1.91 (7H, m), 2.13-2.22 (1H, m), 2.39-2.51 (1H, m), 2.58-2.82 (2H, m), 3.40-3.50 (1H, m), 3.53-3.63 (1H, m), 3.87 (1H, d), 3.93-3.98 (4H, m).

Production Example 53

A mixture of 5.00 g of the present compound (53), 14 ml of acetic acid and 6 ml of water was heated to 70° C. and stirred for 10 hours. After the reaction mixture was cooled to room temperature, 100 ml of ethyl acetate was added. The mixture was slowly added to 100 ml of an aqueous saturated sodium hydrogen carbonate solution. The solution was stirred for 1 hour, followed by extraction with 100 ml of ethyl acetate twice. Organic layers were combined, washed with 100 ml of an aqueous saturated sodium hydrogen carbonate solution and 100 ml of an aqueous saturated sodium chloride solution, dried over sodium sulfate, filtered, and then concentrated under reduced pressure. The residue was subjected to silica gel column chromatography to obtain 3.56 g of 2-(4-oxocyclohexyl)-2-(3,3,4,4,4-pentafluorobutylsulfonyl)acetonitrile (hereinafter, referred to as the present compound (54)) represented by the formula:

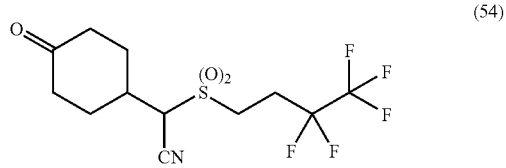

$^1$H-NMR (CDCl$_3$, TMS, δ(ppm)): 1.84-1.97 (2H, m), 2.17-2.26 (1H, m), 2.40-2.61 (5H, m), 2.81-2.85 (2H, m), 3.44-3.54 (1H, m), 3.59-3.70 (1H, m), 3.99 (1H, d).

Production Example 54

To a solution of 0.35 g of the present compound (54) in 10 ml of tetrahydrofuran were added 0.75 g of pyridine and 0.79 g of methoxyamine hydrochloride, and the mixture was stirred at room temperature for 3 hours. To the reaction mixture was added 30 ml of an aqueous 1N hydrochloric acid solution, followed by extraction with 50 ml of ethyl acetate twice. Organic layers were combined, and washed with 50 ml of an aqueous saturated sodium hydrogen carbonate solution and 50 ml of an aqueous saturated sodium chloride solution. The resulting organic layer was dried over sodium sulfate, filtered, and then concentrated under reduced pressure. The residue was subjected to silica gel column chromatography to obtain 0.34 g of 2-[4-(methoxyimino)cyclohexyl]-2-(3,3,4,4,4-pentafluorobutylsulfonyl)acetonitrile (hereinafter, referred to as the present compound (55)) represented by the formula:

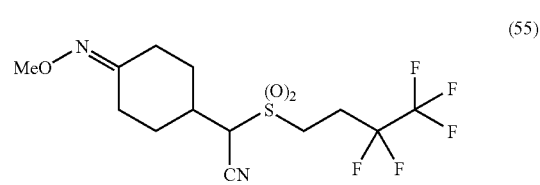

$^1$H-NMR (CDCl$_3$, TMS, δ(ppm)): 1.55-1.72 (2H, m), 1.80-1.92 (1H, m), 1.95-2.11 (1H, m), 2.17-2.28 (1H, m), 2.31-2.45 (1H, m), 2.48-2.58 (1H, m), 2.61-2.80 (3H, m), 3.33-3.40 (1H, m), 3.42-3.50 (1H, m), 3.55-3.65 (1H, m), 3.83 (3H, s), 3.89 (1H, d).

Production Example 55

To a solution of 2.88 g of the present compound (15) in 10 ml of pyridine was added 1.91 g of p-toluenesulfonyl chloride, and the mixture was stirred at room temperature for 3 hours. To the reaction solution was added 30 ml of an aqueous 1N hydrochloric acid solution, followed by extraction with 50 ml of ethyl acetate twice. Organic layers were combined, washed with 50 ml of an aqueous saturated sodium hydrogen carbonate solution and 50 ml of an aqueous saturated sodium chloride solution. The resulting organic layer was dried over sodium sulfate, filtered, and then concentrated under reduced pressure. The residue was dissolved in 20 ml of toluene. To the solution were added 1.50 g of sodium iodide and 1.52 g of 1,8-diazabicyclo[5.4.0]undec-7-ene, and the mixture was heated to 110° C. and stirred for 10 hours. To the reaction solution was added 30 ml of an aqueous 1N hydrochloric acid solution, followed by extraction with 50 ml of ethyl acetate twice. Organic layers were combined, and washed successively with 50 ml of an aqueous saturated sodium hydrogen carbonate solution and 50 ml of an aqueous saturated sodium chloride solution. The resulting organic layer was dried over sodium sulfate, filtered, and then concentrated under reduced pressure. The residue was subjected to silica gel column chromatography to obtain 1.01 g of 1-methylene-4-(3,3,3-trifluoropropylsulfonylmethyl)-cyclohexanone (hereinafter, referred to as the present compound (56)) represented by the formula:

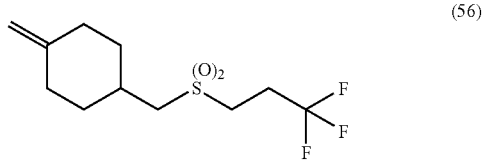

¹H-NMR (CDCl₃, TMS, δ(ppm)): 1.20-1.31 (2H, m), 2.03-2.17 (4H, m), 2.22-2.36 (3H, m), 2.62-2.74 (2H, m), 2.95 (2H, d), 3.16-3.21 (2H, m), 4.66 (2H, s).

Production Example 56

To a solution of 0.60 g of the present compound (56) in 4 ml of dichloromethane were added 0.86 g of bromoform, 0.44 g of sodium hydroxide and 0.02 g of benzyltriethylammonium chloride, and the mixture was stirred at 30° C. for 4 hours under an ultrasound irradiation condition. To the reaction mixture was added 20 ml of an aqueous 2N hydrochloric acid solution, followed by extraction with 30 ml of ethyl acetate twice. Organic layers were combined, washed successively with 30 ml of an aqueous saturated sodium hydrogen carbonate solution and 30 ml of an aqueous saturated sodium chloride solution, dried over sodium sulfate, filtered, and then concentrated under reduced pressure. The residue was subjected to silica gel column chromatography to obtain 0.31 g of 1,1-dibromo-6-(3,3,3-trifluoropropylsulfonylmethyl)spiro[2.5]octane (hereinafter, referred to as the present compound (57)) represented by the formula:

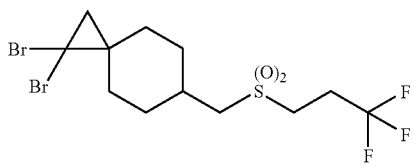

(57)

¹H-NMR (CDCl₃, TMS, δ(ppm)): 1.23-1.34 (2H, m), 1.39 (2H, s), 1.59-1.67 (2H, m), 1.85-1.95 (2H, m), 2.07-2.15 (2H, m), 2.16-2.25 (1H, m), 2.63-2.75 (2H, m), 2.99 (2H, d), 3.17-3.21 (2H, m).

Production Example 57

According to Production Example 56 except that 0.71 g of chloroform was used in place of bromoform, 0.41 g of 1,1-dichloro-6-(3,3,3-trifluoropropylsulfonylmethyl)-spiro[2.5]octane (hereinafter, referred to as the present compound (58)) represented by the formula:

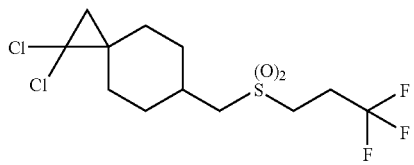

(58)

was obtained.

¹H-NMR (CDCl₃, TMS, δ(ppm)): 1.24-1.35 (2H, m), 1.53-1.62 (4H, m), 1.84-1.93 (2H, m), 2.08-2.15 (2H, m), 2.16-2.26 (1H, m), 2.63-2.75 (2H, m), 2.99 (2H, d), 3.18-3.22 (2H, m).

Production Example 58

To a solution of 0.46 g of the present compound (54) in 10 ml of tetrahydrofuran were added 0.86 g of pyridine and 0.86 g of an aqueous 30% ethoxyamine hydrochloride solution, and the mixture was stirred at room temperature for 3 hours. To the reaction mixture was added 30 ml of an aqueous 1N hydrochloric acid solution, followed by extraction with 50 ml of ethyl acetate twice. Organic layers were combined, and washed with 50 ml of an aqueous saturated sodium hydrogen carbonate solution and 50 ml of an aqueous saturated sodium chloride solution. The resulting organic layer was dried over sodium sulfate, filtered, and then concentrated under reduced pressure. The residue was subjected to silica gel column chromatography to obtain 0.34 g of 2-[4-(methoxyimino)cyclohexyl]-2-(3,3,4,4,4-pentafluorobutylsulfonyl)acetonitrile (hereinafter, referred to as the present compound (59)) represented by the formula:

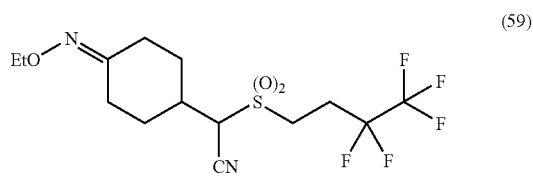

(59)

¹H-NMR (CDCl₃, TMS, δ(ppm)): 1.25 (3H, t), 1.55-1.73 (2H, m), 1.76-1.92 (1H, m), 1.94-2.09 (1H, m), 2.16-2.29 (1H, m), 2.31-2.44 (1H, m), 2.48-2.57 (1H, m), 2.62-2.79 (3H, m), 3.36-3.51 (2H, m), 3.54-3.65 (1H, m), 3.88 (1H, d), 4.08 (2H, q).

Production Example 59

Step 59-1

According to Production Example 53 except that 4.19 g of 1-iodo-3-(trifluoromethyl)-3,4,4,4-tetrafluorobutane was used in place of 1-iodo-3,3,4,4,4-pentafluorobutane, 4.77 g of (3-(trifluoromethyl)-3,4,4,4-tetrafluorobutylthio)acetonitrile was obtained.

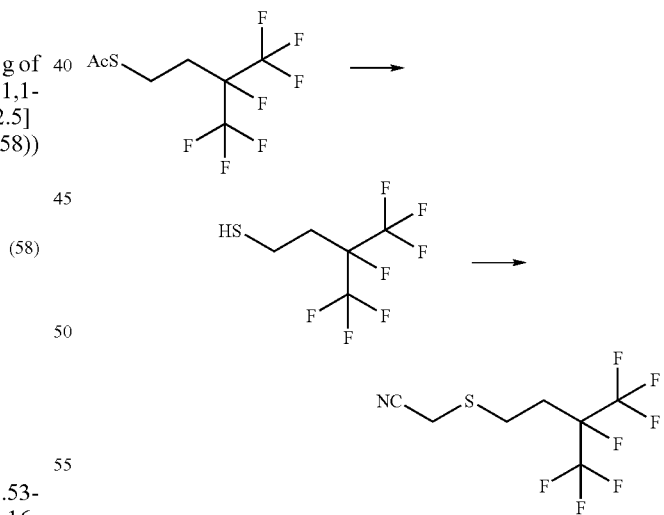

Step 59-2

To a suspension of 16.14 g of a double salt of 2 KHSO₅·KHSO₄·K₂SO₄ (Oxone, registered trade mark) in 50 ml of water was added dropwise a solution of 4.77 g of (3-(trifluoromethyl)-3,4,4,4-tetrafluorobutylthio)acetonitrile in 50 ml of methanol at room temperature over 60 minutes under a nitrogen atmosphere, and the mixture was stirred for 2 hours. To the reaction mixture was added 50 ml of an aqueous 10% sodium sulfite solution, followed by extraction with 100 ml of ethyl acetate twice. Organic layers were combined, washed with 50 ml of an aqueous 10% sodium sulfite solution and 50 ml of an aqueous saturated sodium chloride solution, dried over sodium sulfate, filtered, and then concentrated under rescued pressure. The residue was subjected to silica gel column chromatography to obtain 4.00 g of (3-(trifluoromethyl)-3,4,4,4-tetrafluorobutylsulfonyl)acetonitrile represented by the formula:

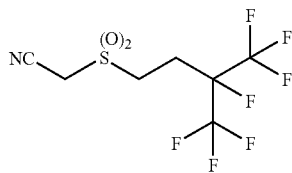

¹H-NMR (CDCl₃, TMS, δ(ppm)): 2.70-2.81 (2H, m), 3.50-3.55 (2H, m), 4.08 (2H, s).

Step 59-3

A mixture of 4.00 g of (3-(trifluoromethyl)-3,4,4,4-tetrafluorobutylsulfonyl)acetonitrile, 50 ml of toluene, 0.15 g of DL-proline and 2.28 g of 1,4-cyclohexanedionemonoethylene ketal was heated and stirred for 3 hours under the reflux condition. After 30 ml of the toluene was distilled off, the reaction mixture was cooled to 0° C. To the reaction mixture were added 0.25 g of sodium borohydride and 2 ml of N,N-dimethylformamide. The mixture was stirred at room temperature for 6 hours, and then cooled to 0° C., and 50 ml of water and 50 ml of ethyl acetate were added thereto. To the mixture was added dropwise 20 ml of 1N hydrochloric acid while the mixture was stirred, followed by extraction with 100 ml of ethyl acetate twice. An organic layer was washed with 100 ml of an aqueous saturated sodium hydrogen carbonate solution and 100 ml of an aqueous saturated sodium chloride solution, dried over sodium sulfate, filtered, and then concentrated under reduced pressure. The residue was subjected to silica gel column chromatography to obtain 4.41 g of 2 (1,4-dioxaspiro[4,5]dec-8-yl)-2-(3-(trifluoromethyl)-3,4,4,4-tetrafluorobutylsulfonyl)acetonitrile (hereinafter, referred to as the present compound (60)) represented by the following formula (60).

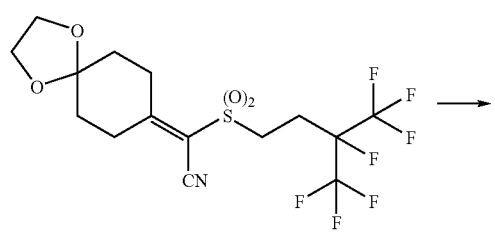

¹H-NMR (CDCl₃, TMS, δ(ppm)): 1.51-2.22 (8H, m), 2.40-2.51 (1H, m), 2.64-2.83 (2H, m), 3.37-3.48 (1H, m), 3.49-3.61 (1H, m), 3.86-3.89 (1H, m), 3.90-3.99 (4H, m).

Production Example 60

A mixture of 4.41 g of the present compound (60), 14 ml of acetic acid, 6 ml of water, 1.50 g of methoxyamine hydrochloride and 1.47 g of sodium acetate was heated to 100° C. and stirred for 10 hours. The reaction mixture was cooled to room temperature, and 100 ml of ethyl acetate was added thereto. The mixture was slowly added to 100 ml of an aqueous saturated sodium hydrogen carbonate solution. The mixture was stirred for 1 hour, followed by extraction with 100 ml of ethyl acetate twice. Organic layers were combined, washed with 100 ml of an aqueous saturated sodium hydrogen carbonate solution and 100 ml of an aqueous saturated sodium chloride solution, dried over sodium sulfate, filtered, and then concentrated under reduced pressure. The residue was subjected to silica gel column chromatography to obtain 3.61 g of 2-(4-methoxyiminocyclohexyl)-2-(3-(trifluoromethyl)-3,4,4,4-tetrafluorobutylsulfonyl)acetonitrile (hereinafter, referred to as the present compound (61)) represented by the following formula (61).

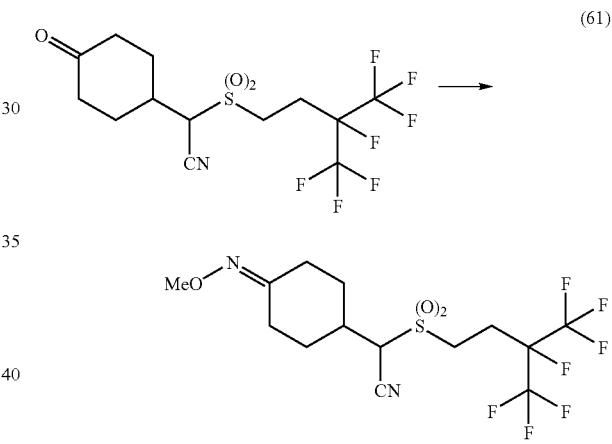

¹H-NMR (CDCl₃, TMS, δ(ppm)): 1.52-1.72 (2H, m), 1.81-1.91 (1H, m), 1.96-2.08 (1H, m), 2.16-2.28 (1H, m), 2.31-2.44 (1H, m), 2.50-2.57 (1H, m), 2.62-2.82 (3H, m), 3.33-3.48 (2H, m), 3.53-3.63 (1H, m), 3.83 (3H, s), 3.89 (1H, d).

Production Example 61

Step 61-1

A mixture of 42.65 g of 3,3,4,4,5,5,6,6,6-nonafluorohexyl p-toluenesulfonate, 100 ml of N,N-dimethylformamide and 11.65 g of potassium thioacetate was heated and stirred at 80° C. for 4 hours under a nitrogen atmosphere. A reaction vessel was cooled in an ice bath. To the reaction mixture was added an aqueous 1N hydrochloric acid solution, and the mixture was extracted with 200 ml of ethylacetate twice. Organic layers were combined, washed with an aqueous saturated sodium chloride solution, dried over sodium sulfate, filtered, and then concentrated under reduced pressure. The residue was subjected to silica gel column chromatography to obtain 18.91 g of 3,3,4,4,5,5,6,6,6-nonafluorohexyl thioacetate represented by the formula:

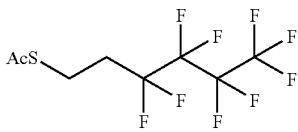

¹H-NMR (CDCl₃, TMS, δ(ppm)): 2.28-2.45 (5H, m), 3.04-3.13 (2H, m)

Step 61-2

A solution of 18.91 g of 3,3,4,4,5,5,6,6,6-nonafluorohexyl thioacetate in 60 ml of tetrahydrofuran was cooled to 0° C. Thereto 11.32 g of a 28% solution of sodium methoxide in methanol was added dropwise over 15 minutes, and then stirred at room temperature for 1 hour. To the mixture was added 4.40 g of chloroacetonitrile at 0° C., and then stirred at room temperature for 3 hours. A reaction vessel was cooled in an ice bath. To the reaction mixture was added an aqueous saturated sodium chloride solution, and the mixture was extracted with 100 ml of t-butyl methyl ether twice. Organic layers were combined, washed with an aqueous saturated sodium chloride solution, dried over sodium sulfate, filtered, and then concentrated under reduced pressure. The residue was subjected to silica gel column chromatography to obtain 15.70 g of (3,3,4,4,5,5,6,6,6-nonafluorohexylthio)acetonitrile.

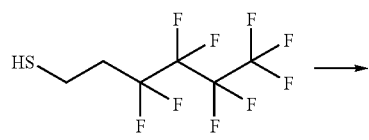

¹H-NMR (CDCl₃, TMS, δ(ppm)): 2.40-2.59 (2H, m), 2.93-3.06 (2H, m), 3.38 (2H, s)

Step 61-3

To a suspension of 15.10 g of a double salt of 2KHSO₅.KHSO₄.K₂SO₄ (Oxone, registered trade mark) in 100 ml of water was added dropwise a solution of 4.77 g of (3,3,4,4,5,5,6,6,6-nonafluorohexylthio)acetonitrile in 100 ml of methanol at −20° C. over 60 minutes under a nitrogen atmosphere, and the mixture was stirred for 2 hours. To the reaction mixture was added 50 ml of an aqueous 10% sodium sulfite solution, followed by extraction with 100 ml of ethyl acetate twice. Organic layers were combined, washed with 50 ml of an aqueous 10% sodium sulfite solution and 50 ml of an aqueous saturated sodium chloride solution, dried over sodium sulfate, filtered, and then concentrated under rescued pressure. The residue was subjected to silica gel column chromatography to obtain 12.56 g of (3,3,4,4,5,5,6,6,6-nonafluorohexylsulfinyl)acetonitrile represented by the formula:

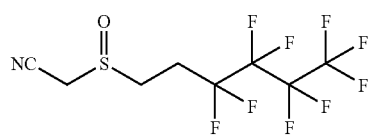

¹H-NMR (CDCl₃, TMS, δ(ppm)): 2.56-2.79 (2H, m), 3.10-3.29 (2H, m), 3.63-3.84 (2H, m).

Step 61-4

To a suspension of 9.21 g of a double salt of 2KHSO₅.KHSO₄.K₂SO₄ (Oxone, registered trade mark) in 50 ml of water was added dropwise a solution of 6.80 g of (3,3,4,4,5,5,6,6,6-nonafluorohexylsulfinyl)acetonitrile in 50 ml of methanol at room temperature over 60 minutes under a nitrogen atmosphere, and the mixture was stirred overnight. To the reaction mixture was added 25 ml of an aqueous 10% sodium sulfite solution, followed by extraction with 100 ml of ethyl acetate twice. Organic layers were combined, washed with 25 ml of an aqueous 10% sodium sulfite solution and 50 ml of an aqueous saturated sodium chloride solution, dried over sodium sulfate, filtered, and then concentrated under rescued pressure. The residue was subjected to silica gel column chromatography to obtain 5.4 g of (3,3,4,4,5,5,6,6,6-nonafluorohexylsulfonyl)acetonitrile represented by the formula:

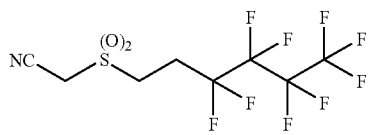

¹H-NMR (CDCl₃, TMS, δ(ppm)): 2.69-2.83 (2H, m), 3.54-3.60 (2H, m), 4.09 (2H, s).

Step 61-5

A mixture of 5.40 g of (3,3,4,4,5,5,6,6,6-nonafluorohexylsulfonyl)acetonitrile, 60 ml of toluene, 0.18 g of DL-proline and 2.77 g of 1,4-cyclohexanedione monoethylene ketal was heated and stirred for 3 hours under the reflux condition. After 40 ml of toluene was distilled off, the reaction mixture was cooled to room temperature. The mixture was cooled to 0° C. and then 0.61 g of sodium borohydride was added thereto. To the reaction mixture was added 3 ml of N,N-dimethylformamide. The mixture was stirred at room temperature for 6 hours and then cooled to 0° C. Thereto 50 ml of water and 50 ml of ethyl acetate were added. While the reaction mixture was stirred, 20 ml of an aqueous 1N hydrochloric acid solution was added dropwise, followed by extraction with 100 ml of ethyl acetate twice. An organic layer was washed with 100 ml of an aqueous saturated sodium hydrogen carbonate solution, 100 ml of an aqueous saturated sodium chloride solution and 100 ml of water, dried over sodium sulfate, filtered, and concentrated under reduced pressure. The residue was dissolve to 14 ml of acetic acid and 6 ml of water. The mixture was heated to 100° C. and stirred for 8 hours. After the reaction mixture was cooled to room temperature, 100 ml of ethyl acetate was added thereto. The mixture was added slowly into 100 ml of an aqueous saturated sodium hydrogen carbonate solution. The solution was stirred for 1 hour, followed by extraction with 100 ml of ethyl acetate twice. Organic layers were combined, washed with 100 ml of an aqueous saturated sodium hydrogen carbonate solution and 100 ml of an aqueous saturated sodium chloride solution, dried over sodium sulfate, filtered, and concentrated under reduced pressure. The residue was subjected to silica gel column chromatography to obtain 2.94 g of 2-(4-oxocyclohexyl)-2-(3,3,4,4,5,5,6,6,6-nonafluorohexylsulfonyl)acetonitrile (hereinafter, referred to as the present compound (62)) represented by the formula:

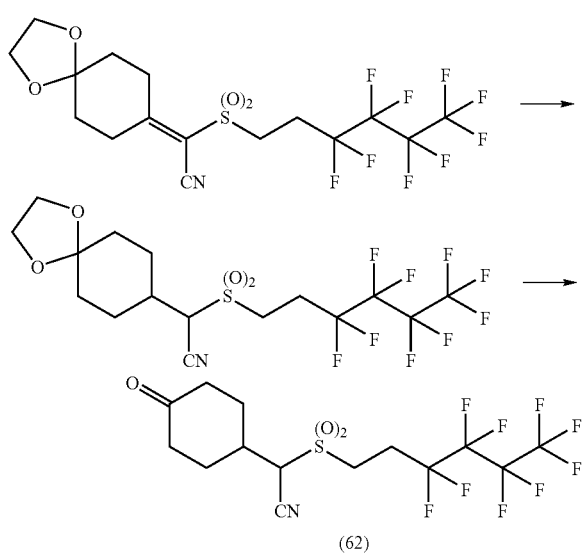

¹H-NMR (CDCl₃, TMS, δ(ppm)): 1.83-1.98 (2H, m), 2.17-2.26 (1H, m), 2.38-2.59 (5H, m), 2.67-2.97 (3H, m), 3.44-3.54 (1H, m), 3.60-3.70 (1H, m), 4.00 (1H, d).

Production Example 62

To a solution of 2.69 g of the present compound (62) in 12 ml of tetrahydrofuran were added 0.52 g of pyridine and 0.55 g of methoxyamine hydrochloride, and the mixture was stirred at room temperature for 3 hours. To the reaction solution was added 30 ml of an aqueous 1N hydrochloric acid solution, followed by extraction with 50 ml of ethyl acetate twice. Organic layers were combined, washed with 50 ml of an aqueous saturated sodium hydrogen carbonate solution and 50 ml of an aqueous saturated sodium chloride solution. The resulting organic layer was dried over sodium sulfate, filtered, and then concentrated under reduced pressure. The residue was subjected to silica gel column chromatography to obtain 2.86 g of 2-[4-(methoxyimino)cyclohexyl]-2-(3,3,4,4,5,5,6,6,6-nonafluorohexylsulfonyl)acetonitrile (hereinafter, referred to as the present compound (63)) represented by the formula:

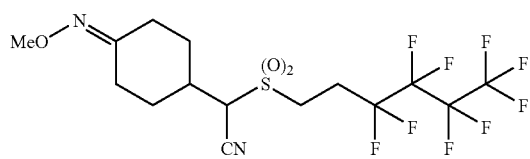

¹H-NMR (CDCl₃, TMS, δ(ppm)): 1.49-1.73 (2H, m), 1.77-1.91 (1H, m), 1.95-2.09 (1H, m), 2.17-2.27 (1H, m), 2.31-2.43 (1H, m), 2.49-2.57 (1H, m), 2.62-2.86 (3H, m), 3.32-3.39 (1H, m), 3.42-3.53 (1H, m), 3.55-3.66 (1H, m), 3.84 (3H, s), 3.90 (1H, d)

Production Example 63

Step 63-1

A mixture of 23.80 g of 1-iodo-4,4,4-trifluorobutane, 100 ml of N,N-dimethylformamide and 11.42 g of potassium thioacetate was heated and stirred at 80° C. for 4 hours under a nitrogen atmosphere. A reaction vessel was cooled in an ice bath. To the reaction mixture was added an aqueous 1N hydrochloric acid solution, and the mixture was extracted with 100 ml of t-butyl methyl ether twice. Organic layers were combined, washed with an aqueous saturated sodium chloride solution, dried over sodium sulfate, filtered, and then concentrated under reduced pressure. The residue was subjected to silica gel column chromatography to obtain 18.20 g of 4,4,4-trifluorobutyl thioacetate represented by the formula:

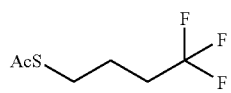

¹H-NMR (CDCl₃, TMS, δ(ppm)): 1.82-1.92 (2H, m), 2.08-2.23 (2H, m), 2.35 (3H, s), 2.88-2.99 (2H, m)

Step 63-2

A solution of 18.91 g of 4,4,4-trifluorobutyl thioacetate in 60 ml of tetrahydrofuran was cooled to 0° C. Thereto 19.29 g of a 28% solution of sodium methoxide in methanol was added dropwise over 15 minutes, and then stirred at room temperature for 1 hour. To the mixture was added 7.50 g of chloroacetonitrile at 0° C., and then stirred at room temperature for 3 hours. A reaction vessel was cooled in an ice bath. To the reaction mixture was added an aqueous saturated sodium chloride solution, and the mixture was extracted with 200 ml of t-butyl methyl ether twice. Organic layers were combined, washed with an aqueous saturated sodium chloride solution, dried over sodium sulfate, filtered, and then concentrated under reduced pressure. The residue was subjected to silica gel column chromatography to obtain 17.82 g of (4,4,4-trifluorobutylthio)acetonitrile.

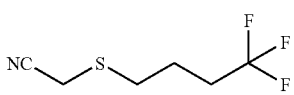

¹H-NMR (CDCl₃, TMS, δ(ppm)): 1.91-1.99 (2H, m), 2.17-2.32 (2H, m), 2.80-2.87 (2H, m).

Step 63-3

To a suspension of 67.50 g of a double salt 2KHSO₅·KHSO₄·K₂SO₄ (Oxone, registered trade mark) in 100 ml of water was added dropwise a solution of 17.82 g of (4,4,4-trifluorobutylthio)acetonitrile in 100 ml of methanol at room temperature over 60 minutes under a nitrogen atmosphere, and the mixture was stirred overnight. To the reaction mixture was added 50 ml of an aqueous 10% sodium sulfite solution, followed by extraction with 200 ml of ethyl acetate twice. Organic layers were combined, washed with 50 ml of an aqueous 10% sodium sulfite solution and 50 ml of an aqueous saturated sodium chloride solution, dried over sodium sulfate, filtered, and then concentrated under rescued pressure. The residue was subjected to silica gel column chromatography to obtain 22.34 g of (4,4,4-trifluorobutyl sulfonyl)acetonitrile represented by the formula:

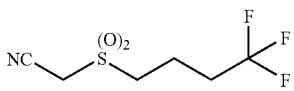

¹H-NMR (CDCl₃, TMS, δ(ppm)): 2.11-2.28 (2H, m), 2.32-2.46 (2H, m), 3.31-3.43 (2H, m), 4.03 (2H, s)

Step 63-4

A mixture of 20.76 g of (4,4,4-trifluorobutyl sulfonyl)acetonitrile, 200 ml of toluene, 1.11 g of DL-proline and 16.58 g of 1,4-cyclohexanedionemonoethylene ketal was heated and stirred for 5 hours under the reflux condition. After 100 ml of the toluene was distilled off, the reaction mixture was cooled to 0° C. To the reaction mixture were added 1.89 g of sodium borohydride and 5 ml of N,N-dimethylformamide. The mixture was stirred at room temperature for 12 hours, and then cooled to 0° C., and 200 ml of water and 200 ml of ethyl acetate were, added thereto. To the mixture was added dropwise 100 ml of 1N hydrochloric acid while the mixture was stirred, followed by extraction with 200 ml of ethyl acetate twice. An organic layer was washed with 100 ml of an aqueous saturated sodium hydrogen carbonate solution and 100 ml of an aqueous saturated sodium chloride solution, dried over sodium sulfate, filtered, and then concentrated under reduced pressure. The residue was subjected to silica gel column chromatography to obtain 22.03 g of 2-(1,4-dioxaspiro[4,5]dec-8-yl)-2-(4,4,4-trifluorobutylsulfonyl)acetonitrile (hereinafter, referred to as the present compound (64)) represented by the following formula (64).

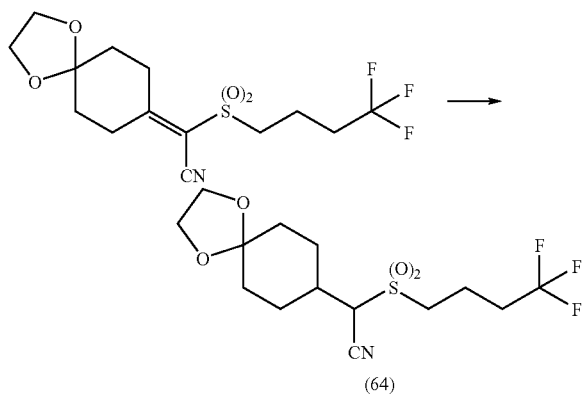

(64)

¹H-NMR (CDCl₃, TMS, δ(ppm)): 1.56-2.49 (13H, m), 3.27-3.43 (2H, m), 3.81 (1H, d), 3.90-4.00 (4H, m)

Production Example 64

A mixture of 22.03 g of the present compound (64), 70 ml of acetic acid and 30 ml of water was heated to 100° C. and stirred for 8 hours. After the reaction mixture was cooled to room temperature, 300 ml of ethyl acetate was added thereto. The mixture was added slowly into 300 ml of an aqueous saturated sodium hydrogen carbonate solution. The solution was stirred for 1 hour, followed by extraction with 200 ml of ethyl acetate twice. Organic layers were combined, washed with 300 ml of an aqueous saturated sodium hydrogen carbonate solution and 300 ml of an aqueous saturated sodium chloride solution, dried over sodium sulfate, filtered, and concentrated under reduced pressure. The residue was subjected to silica gel column chromatography to obtain 15.82 g of 2-(4-oxocyclohexyl)-2-(4,4,4-trifluorobutylsulfonyl)acetonitrile (hereinafter, referred to as the present compound (65)) represented by the formula:

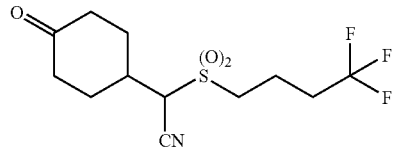

(65)

¹H-NMR (CDCl₃, TMS, δ(ppm)): 1.81-1.99 (2H, m), 2.17-2.64 (10H, m), 2.82-2.95 (1H, m), 3.30-3.89 (2H, m), 3.93 (1H, d)

Production Example 65

To a solution of 3.11 g of the present compound (65) in 10 ml of tetrahydrofuran were added 0.87 g of pyridine and 0.92 g of methoxyamine hydrochloride, and the mixture was stirred at room temperature for 3 hours. To the reaction solution was added 30 ml of an aqueous 1N hydrochloric acid solution, followed by extraction with 50 ml of ethyl acetate twice. Organic layers were combined, washed with 50 ml of an aqueous saturated sodium hydrogen carbonate solution and 50 ml of an aqueous saturated sodium chloride solution. The resulting organic layer was dried over sodium sulfate, filtered, and then concentrated under reduced pressure. The residue was subjected to silica gel column chromatography to obtain 3.26 g of 2-[4-(methoxyimino)cyclohexyl]-2-(4,4,4-trifluorobutylsulfonyl)acetonitrile (hereinafter, referred to as the present compound (66)) represented by the formula:

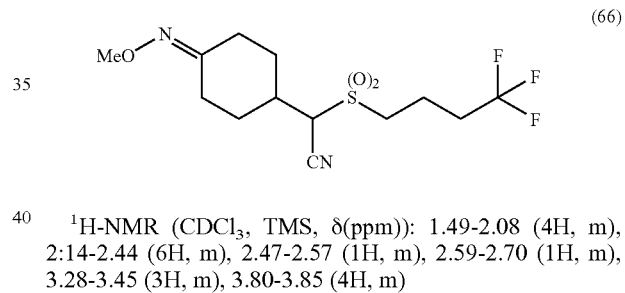

(66)

¹H-NMR (CDCl₃, TMS, δ(ppm)): 1.49-2.08 (4H, m), 2:14-2.44 (6H, m), 2.47-2.57 (1H, m), 2.59-2.70 (1H, m), 3.28-3.45 (3H, m), 3.80-3.85 (4H, m)

Production Example 66

According to Production Example 65 except that 1.72 g of ethoxyamine hydrochloride was used in place of hydroxylamine hydrochloride, 2.87 g of 2-[4-(ethoxyimino)cyclohexyl]-2-(4,4,4-trifluorobutylsulfonyl)acetonitrile (hereinafter, referred to as the present compound (67)) represented by the formula:

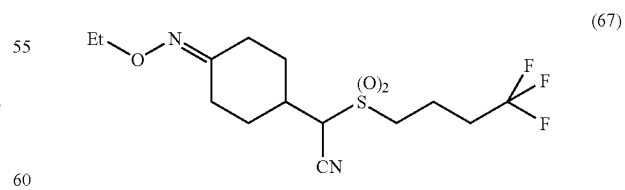

(67)

was obtained.

¹H-NMR (CDCl₃, TMS, δ(ppm)): 1.25 (3H, t), 1.46-2.07 (4H, m), 2.14-2.43 (6H, m), 2.48-2.56 (1H, m), 2.59-2.70 (1H, m), 3.28-3.44 (3H, m), 3.83 (1H, d), 4.05 (2H, q)

Then, specific examples of the compound of the present invention are shown.

A compound represented by the formula (I-1):

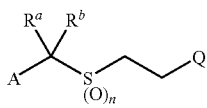

wherein A, $R^a$, $R^b$, n and Q represent any one of combinations shown below.

A compound represented by the formula (I-2):

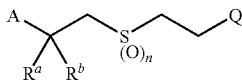

wherein A, $R^a$, $R^b$, n and Q represent any one of combinations shown below.

A compound represented by the formula (I-3):

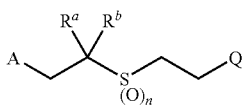

wherein A, $R^a$, $R^b$, n and Q represent any one of combinations shown below.

A compound represented by the formula (I-4):

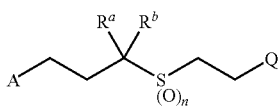

wherein A, $R^a$, $R^b$, n and Q represent any one of combinations shown below.

Combinations of A, $R^a$, $R^b$, n and Q for the compounds represented by the formulas (I-1) to (I-4) are as follows.
[A;$R^a$;$R^b$;n;Q]=
[{3-(fluoromethyl)cyclopentyl};H;H;0;$CF_3$];
[{3-(difluoromethyl)cyclopentyl};H;H;0;$CF_3$];
[{3-(trifluoromethyl)cyclopentyl};H;H;0;$CF_3$];
[{3-ethynylcyclopentyl};H;H;0;$CF_3$];
[{3-(prop-1-ynyl)cyclopentyl};H;H;0;$CF_3$];
[{3-(prop-2-ynyl)cyclopentyl};H;H;0;$CF_3$];
[{3-(prop-2-ynyloxy)cyclopentyl};H;H;0;$CF_3$];
[{3-ethynylcyclohexyl};H;H;0;$CF_3$];
[{3-(prop-1-ynyl)cyclohexyl};H;H;0;$CF_3$];
[{3-(prop-2-ynyl)cyclohexyl};H;H;0;$CF_3$];
[{3-(prop-2-ynyloxy)cyclohexyl};H;H;0;$CF_3$];
[{4-fluorocyclohexyl};H;H;0;$CF_3$];
[{4,4-difluorocyclohexyl};H;H;0;$CF_3$];
[{4-ethynylcyclohexyl};H;H;0;$CF_3$];
[{4-(prop-1-ynyl)cyclohexyl};H;H;0;$CF_3$];
[{4-(prop-2-ynyl)cyclohexyl};H;H;0;$CF_3$];
[{4-(3-methoxyprop-1-ynyl)cyclohexyl};H;H;0;$CF_3$];
[{4-(3-dimethylaminoprop-1-ynyl)cyclohexyl};H;H;0;$CF_3$];
[{4-(4-methoxycarbonylbut-1-ynyl)cyclohexyl};H;H;0;$CF_3$];
[{cyclopent-1-enyl};H;H;0;$CF_3$];
[{3-(prop-1-ynyl)cyclopent-1-enyl};H;H;0;$CF_3$];
[{3-(prop-2-ynyl)cyclopent-1-enyl};H;H;0;$CF_3$];
[{cyclopent-2-enyl};H;H;0;$CF_3$];
[{3-(prop-1-ynyl)cyclopent-2-enyl};H;H;0;$CF_3$];
[{3-(prop-2-ynyl)cyclopent-2-enyl};H;H;0;$CF_3$];
[{cyclopent-3-enyl};H;H;0;$CF_3$];
[{3-(prop-1-ynyl)cyclopent-3-enyl};H;H;0;$CF_3$];
[{3-(prop-2-ynyl)cyclopent-3-enyl};H;H;0;$CF_3$];
[{3-ethynylcyclohex-1-enyl};H;H;0;$CF_3$];
[{3-(prop-1-ynyl)cyclohex-1-enyl};H;H;0;$CF_3$];
[{3-(prop-2-ynyl)cyclohex-1-enyl};H;H;0;$CF_3$];
[{4-fluorocyclohex-1-enyl};H;H;0;$CF_3$];
[{4-(prop-2-enyl)cyclohex-1-enyl};H;H;0;$CF_3$];
[{4-ethynylcyclohex-1-enyl};H;H;0;$CF_3$];
[{4-(prop-1-ynyl)cyclohex-1-enyl};H;H;0;$CF_3$];
[{4-(prop-2-ynyl)cyclohex-1-enyl};H;H;0;$CF_3$];
[{3-(prop-1-ynyl)cyclohex-2-enyl};H;H;0;$CF_3$];
[{3-(prop-2-ynyl)cyclohex-2-enyl};H;H;0;$CF_3$];
[{4-(prop-2-enyl)cyclohex-2-enyl};H;H;0;$CF_3$];
[{4-ethynylcyclohex-2-enyl};H;H;0;$CF_3$];
[{4-(prop-1-ynyl)cyclohex-2-enyl};H;H;0;$CF_3$];
[{4-(prop-2-ynyl)cyclohex-2-enyl};H;H;0;$CF_3$];
[{3-(prop-1-ynyl)cyclohex-3-enyl};H;H;0;$CF_3$];
[{3-(prop-2-ynyl)cyclohex-3-enyl};H;H;0;$CF_3$];
[{4-fluorocyclohex-3-enyl};H;H;0;$CF_3$];
[{4-(prop-2-enyl)cyclohex-3-enyl};H;H;0;$CF_3$];
[{4-ethynylcyclohex-3-enyl};H;H;0;$CF_3$];
[{4-(prop-1-ynyl)cyclohex-3-enyl};H;H;0;$CF_3$];
[{4-(prop-2-ynyl)cyclohex-3-enyl};H;H;0;$CF_3$];
[{2,2-dichlorocyclopropyl};H;H;2;$CF_3$];
[{2,2-difluorocyclopropyl};H;H;2;$CF_3$];
[{2,2-dimethylcyclopropyl};H;H;2;$CF_3$];
[{3-cyanocyclopentyl};H;H;2;$CF_3$];
[{3,3-fluorocyclopentyl};H;H;2;$CF_3$];
[{3,3-difluorocyclopentyl};H;H;2;$CF_3$];
[{3-(fluoromethyl)cyclopentyl};H;H;2;$CF_3$];
[{3-(difluoromethyl)cyclopentyl};H;H;2;$CF_3$];
[{3-(trifluoromethyl)cyclopentyl};H;H;2;$CF_3$];
[{3-vinylcyclopentyl};H;H;2;$CF_3$];
[{3-(2,2-difluorovinyl)cyclopentyl};H;H;2;$CF_3$];
[{3-ethynylcyclopentyl};H;H;2;$CF_3$];
[{3-(prop-1-ynyl)cyclopentyl};H;H;2;$CF_3$];
[{3-(prop-2-ynyl)cyclopentyl};H;H;2;$CF_3$];
[{3-(1-fluoroprop-2-ynyl)cyclopentyl};H;H;2;$CF_3$];
[{3-(but-1-ynyl)cyclopentyl};H;H;2;$CF_3$];
[{3-(but-2-ynyl)cyclopentyl};H;H;2;$CF_3$];
[{3-(but-3-ynyl)cyclopentyl};H;H;2;$CF_3$];
[{3-(prop-2-ynyloxy)cyclopentyl};H;H;2;$CF_3$];
[{3,3-difluorocyclohexyl};H;H;2;$CF_3$];
[{3-ethynylcyclohexyl};H;H;2;$CF_3$];
[{3-(prop-1-ynyl)cyclohexyl};H;H;2;$CF_3$];
[{3-(prop-2-ynyl)cyclohexyl};H;H;2;$CF_3$];
[{3-(but-2-ynyl)cyclohexyl};H;H;2;$CF_3$];
[{3-(but-3-ynyl)cyclohexyl};H;H;2;$CF_3$];
[{3-(prop-2-ynyloxy)cyclohexyl};H;H;2;$CF_3$];
[{4,4-difluorocyclohexyl};H;H;2;$CF_3$];
[{4-vinylcyclohexyl};H;H;2;$CF_3$];
[{4-(2,2-difluorovinyl)cyclohexyl};H;H;2;$CF_3$];
[{4-(prop-2-enyl)cyclohexyl};H;H;2;$CF_3$];
[{4-ethynylcyclohexyl};H;H;2;$CF_3$];
[{4-(2-bromoethynyl)cyclohexyl};H;H;2;$CF_3$];
[{4-(2-iodoethynyl)cyclohexyl};H;H;2;$CF_3$];
[{4-ethynyl-4-fluorocyclohexyl};H;H;2;$CF_3$];
[{4-(prop-1-ynyl)cyclohexyl};H;H;2;$CF_3$];
[{4-(prop-2-ynyl)cyclohexyl};H;H;2;$CF_3$];
[{4-(but-2-ynyl)cyclohexyl};H;H;2;$CF_3$];

[{4-(but-3-ynyl)cyclohexyl};H;H;2;CF₃];
[{4-(pent-1-ynyl)cyclohexyl};H;H;2;CF₃];
[{4-(pent-2-ynyl)cyclohexyl};H;H;2;CF₃];
[{4-(pent-3-ynyl)cyclohexyl};H;H;2;CF₃];
[{4-(3-methoxyprop-1-ynyl)cyclohexyl};H;H;2;CF₃];
[{4-(4-methoxybut-1-ynyl)cyclohexyl};H;H;2;CF₃];
[{4-(4-methoxybut-2-ynyl)cyclohexyl};H;H;2;CF₃];
[{4-(5-methoxypent-1-ynyl)cyclohexyl};H;H;2;CF₃];
[{4-(5-methoxypent-2-ynyl)cyclohexyl};H;H;2;CF₃];
[{4-(3-dimethylaminoprop-1-ynyl)cyclohexyl};H;H;2; CF₃];
[{4-(4-dimethylaminobut-1-ynyl)cyclohexyl};H;H;2;CF₃];
[{4-(4-dimethylaminobut-2-ynyl)cyclohexyl};H;H;2;CF₃];
[{4-(5-dimethylaminopent-1-ynyl)cyclohexyl};H;H;2;CF₃];
[{4-(5-dimethylaminopent-2-ynyl)cyclohexyl};H;H;2;CF₃];
[{4-(2-methoxycarbonylethynyl)cyclohexyl};H;H;2;CF₃];
[{4-(3-methoxycarbonylprop-1-ynyl)cyclohexyl};H;H;2; CF₃];
[{4-(4-methoxycarbonylbut-1-ynyl)cyclohexyl};H;H;2; CF₃];
[{4-(4-methoxycarbonylbut-2-ynyl)cyclohexyl};H;H;2; CF₃];
[{4-(5-methoxycarbonylpent-1-ynyl)cyclohexyl};H;H;2; CF₃];
[{4-(5-methoxycarbonylpent-2-ynyl)cyclohexyl};H;H;2; CF₃];
[{4-(1-fluoroprop-2-ynyl)cyclohexyl};H;H;2;CF₃];
[{4-(1,1-difluoroprop-2-ynyl)cyclohexyl};H;H;2;CF₃];
[{4-(3-fluoroprop-1-ynyl)cyclohexyl};H;H;2;CF₃];
[{4-(3,3-difluoroprop-1-ynyl)cyclohexyl};H;H;2;CF₃];
[{4-(3,3,3-trifluoroprop-1-ynyl)cyclohexyl};H;H;2;CF₃];
[{4-(4-fluorobut-1-ynyl)cyclohexyl};H;H;2;CF₃];
[{4-(4-fluorobut-2-ynyl)cyclohexyl};H;H;2;CF₃];
[{4-(5-fluoropent-1-ynyl)cyclohexyl};H;H;2;CF₃];
[{4-(5-fluoropent-2-ynyl)cyclohexyl};H;H;2;CF₃];
[{cyclopent-1-enyl};H;H;2;CF₃];
[{3-cyanocyclopent-1-enyl};H;H;2;CF₃];
[{3,3-difluorocyclopent-1-enyl};H;H;2;CF₃];
[{3-(fluoromethyl)cyclopent-1-enyl};H;H;2;CF₃];
[{3-(difluoromethyl)cyclopent-1-enyl};H;H;2;CF₃];
[{3-(trifluoromethyl)cyclopent-1-enyl};H;H;2;CF₃];
[{3-(prop-1-ynyl)cyclopent-1-enyl};H;H;2;CF₃];
[{3-(prop-2-ynyl)cyclopent-1-enyl};H;H;2;CF₃];
[{3-(1-fluoroprop-2-ynyl)cyclopent-1-enyl};H;H;2;CF₃];
[{3-(but-2-ynyl)cyclopent-1-enyl};H;H;2;CF₃];
[{3-(but-3-ynyl)cyclopent-1-enyl};H;H;2;CF₃];
[{cyclopent-2-enyl};H;H;2;CF₃];
[{3-cyanocyclopent-2-enyl};H;H;2;CF₃];
[{3-fluorocyclopent-2-enyl};H;H;2;CF₃];
[{3-(fluoromethyl)cyclopent-2-enyl};H;H;2;CF₃];
[{3-(difluoromethyl)cyclopent-2-enyl};H;H;2;CF₃];
[{3-(trifluoromethyl)cyclopent-2-enyl};H;H;2;CF₃];
[{3-(prop-1-ynyl)cyclopent-2-enyl};H;H;2;CF₃];
[{3-(prop-2-ynyl)cyclopent-2-enyl};H;H;2;CF₃];
[{3-(1-fluoroprop-2-ynyl)cyclopent-2-enyl};H;H;2;CF₃];
[{3-(but-2-ynyl)cyclopent-2-enyl};H;H;2;CF₃];
[{3-(but-3-ynyl)cyclopent-2-enyl};H;H;2;CF₃];
[{cyclopent-3-enyl};H;H;2;CF₃];
[{3-cyanocyclopent-3-enyl};H;H;2;CF₃];
[{3-fluorocyclopent-3-enyl};H;H;2;CF₃];
[{3-(fluoromethyl)cyclopent-3-enyl};H;H;2;CF₃];
[{3-(difluoromethyl)cyclopent-3-enyl};H;H;2;CF₃];
[{3-(trifluoromethyl)cyclopent-3-enyl};H;H;2;CF₃];
[{3-(prop-1-ynyl)cyclopent-3-enyl};H;H;2;CF₃];
[{3-(prop-2-ynyl)cyclopent-3-enyl};H;H;2;CF₃];
[{3-(1-fluoroprop-2-ynyl)cyclopent-3-enyl};H;H;2;CF₃];
[{3-(but-2-ynyl)cyclopent-3-enyl};H;H;2;CF₃];
[{3-(but-3-ynyl)cyclopent-3-enyl};H;H;2;CF₃];
[{3-ethynylcyclohex-1-enyl};H;H;2;CF₃];
[{3-(prop-1-ynyl)cyclohex-1-enyl};H;H;2;CF₃];
[{3-(prop-2-ynyl)cyclohex-1-enyl};H;H;2;CF₃];
[{3-(prop-2-ynyloxy)cyclohex-1-enyl};H;H;2;CF₃];
[{4-fluorocyclohex-1-enyl};H;H;2;CF₃];
[{4-(prop-2-enyl)cyclohex-1-enyl};H;H;2;CF₃];
[{4-ethynylcyclohex-1-enyl};H;H;2;CF₃];
[{4-(prop-1-ynyl)cyclohex-1-enyl};H;H;2;CF₃];
[{4-(prop-2-ynyl)cyclohex-1-enyl};H;H;2;CF₃];
[{3-ethynylcyclohex-2-enyl};H;H;2;CF₃];
[{3-(prop-1-ynyl)cyclohex-2-enyl};H;H;2;CF₃];
[{3-(prop-2-ynyl)cyclohex-2-enyl};H;H;2;CF₃];
[{3-(prop-2-ynyloxy)cyclohex-2-enyl};H;H;2;CF₃];
[{4-fluorocyclohex-2-enyl};H;H;2;CF₃];
[{4-(prop-2-enyl)cyclohex-2-enyl};H;H;2;CF₃];
[{4-ethynylcyclohex-2-enyl};H;H;2;CF₃];
[{4-(prop-1-ynyl)cyclohex-2-enyl};H;H;2;CF₃];
[{4-(prop-2-ynyl)cyclohex-2-enyl};H;H;2;CF₃];
[{3-ethynylcyclohex-3-enyl};H;H;2;CF₃];
[{3-(prop-1-ynyl)cyclohex-3-enyl};H;H;2;CF₃];
[{3-(prop-2-ynyl)cyclohex-3-enyl};H;H;2;CF₃];
[{3-(prop-2-ynyloxy)cyclohex-3-enyl};H;H;2;CF₃];
[{4-fluorocyclohex-3-enyl};H;H;2;CF₃];
[{4-(prop-2-enyl)cyclohex-3-enyl};H;H;2;CF₃];
[{4-ethynylcyclohex-3-enyl};H;H;2;CF₃];
[{4-(prop-1-ynyl)cyclohex-3-enyl};H;H;2;CF₃];
[{4-(prop-2-ynyl)cyclohex-3-enyl};H;H;2;CF₃];
[{3-(fluoromethyl)cyclopentyl};H;H;0;C₂F₅];
[{3-(difluoromethyl)cyclopentyl};H;H;0;C₂F₅];
[{3-(trifluoromethyl)cyclopentyl};H;H;0;C₂F₅];
[{3-ethynylcyclopentyl};H;H;0;C₂F₅];
[{3-(prop-1-ynyl)cyclopentyl};H;H;0;C₂F₅];
[{3-(prop-2-ynyl)cyclopentyl};H;H;0;C₂F₅];
[{3-(prop-2-ynyloxy)cyclopentyl};H;H;0;C₂F₅];
[{3-ethynylcyclohexyl};H;H;0;C₂F₅];
[{3-(prop-1-ynyl)cyclohexyl};H;H;0;C₂F₅];
[{3-(prop-2-ynyl)cyclohexyl};H;H;0;O₂F₅];
[{3-(prop-2-ynyloxy)cyclohexyl};H;H;0;C₂F₅];
[{4-fluorocyclohexyl};H;H;0;C₂F₅];
[{4,4-difluorocyclohexyl};H;H;0;C₂F₅];
[{4-ethynylcyclohexyl};H;H;0;C₂F₅];
[{4-(prop-1-ynyl)cyclohexyl};H;H;0;C₂F₅];
[{4-(prop-2-ynyl)cyclohexyl};H;H;0;C₂F₅];
[{4-(3-methoxyprop-1-ynyl)cyclohexyl};H;H;0;C₂F₅];
[{4-(3-dimethylaminoprop-1-ynyl)cyclohexyl};H;H;0; C₂F₅];
[{4-(4-methoxycarbonylbut-1-ynyl)cyclohexyl};H;H;0; C₂F₅];
[{cyclopent-1-enyl};H;H;0;C₂F₅];
[{3-(prop-1-ynyl)cyclopent-1-enyl};H;H;0;C₂F₅];
[{3-(prop-2-ynyl)cyclopent-1-enyl};H;H;0;C₂F₅];
[{cyclopent-2-enyl};H;H;0;C₂F₅];
[{3-(prop-1-ynyl)cyclopent-2-enyl};H;H;0;C₂F₅];
[{3-(prop-2-ynyl)cyclopent-2-enyl};H;H;0;C₂F₅];
[{cyclopent-3-enyl};H;H;0;C₂F₅];
[{3-(prop-1-ynyl)cyclopent-3-enyl};H;H;0;C₂F₅];
[{3-(prop-2-ynyl)cyclopent-3-enyl};H;H;0;C₂F₅];
[{3-ethynylcyclohex-1-enyl};H;H;0;C₂F₅];
[{3-(prop-1-ynyl)cyclohex-1-enyl};H;H;0;C₂F₅];
[{3-(prop-2-ynyl)cyclohex-1-enyl};H;H;0;C₂F₅];
[{4-fluorocyclohex-1-enyl};H;H;0;C₂F₅];
[{4-(prop-2-enyl)cyclohex-1-enyl};H;H;0;C₂F₅];
[{4-ethynylcyclohex-1-enyl};H;H;0;C₂F₅];
[{4-(prop-1-ynyl)cyclohex-1-enyl};H;H;0;C₂F₅];
[{4-(prop-2-ynyl)cyclohex-1-enyl};H;H;0;C₂F₅];
[{3-(prop-1-ynyl)cyclohex-2-enyl};H;H;0;C₂F₅];

[{3-(prop-2-ynyl)cyclohex-2-enyl};H;H;0;C$_2$F$_5$];
[{4-(prop-2-enyl)cyclohex-2-enyl};H;H;0;C$_2$F$_5$];
[{4-ethynylcyclohex-2-enyl};H;H;0;C$_2$F$_5$];
[{4-(prop-1-enyl)cyclohex-2-enyl};H;H;0;C$_2$F$_5$];
[{4-(prop-2-ynyl)cyclohex-2-enyl};H;H;0;C$_2$F$_5$];
[{3-(prop-1-ynyl)cyclohex-3-enyl};H;H;0;C$_2$F$_5$];
[{3-(prop-2-ynyl)cyclohex-3-enyl};H;H;0;C$_2$F$_5$];
[{4-fluorocyclohex-3-enyl};H;H;0;C$_2$F$_5$];
[{4-(prop-2-enyl)cyclohex-3-enyl};H;H;0;C$_2$F$_5$];
[{4-ethynylcyclohex-3-enyl};H;H;0;C$_2$F$_5$];
[{4-(prop-1-ynyl)cyclohex-3-enyl};H;H;0;C$_2$F$_5$];
[{4-(prop-2-ynyl)cyclohex-3-enyl};H;H;0;C$_2$F$_5$];
[{3-(fluoromethyl)cyclopentyl};H;H;2;C$_2$F$_5$];
[{3-(difluoromethyl)cyclopentyl};H;H;2;C$_2$F$_5$];
[{3-(trifluoromethyl)cyclopentyl};H;H;2;C$_2$F$_5$];
[{3-ethynylcyclopentyl};H;H;2;C$_2$F$_5$];
[{3-(prop-1-ynyl)cyclopentyl};H;H;2;C$_2$F$_5$];
[{3-(prop-2-ynyl)cyclopentyl};H;H;2;C$_2$F$_5$];
[{3-(prop-2-ynyloxy)cyclopentyl};H;H;2;C$_2$F$_5$];
[{3-ethynylcyclohexyl};H;H;2;C$_2$F$_5$];
[{3-(prop-1-ynyl)cyclohexyl};2;C$_2$F$_5$];
[{3-(prop-2-ynyl)cyclohexyl};H;H;2;C$_2$F$_5$];
[{3-(prop-2-ynyloxy)cyclohexyl};H;H;2;C$_2$F$_5$];
[{4-fluorocyclohexyl};H;H;2;C$_2$F$_5$];
[{4,4-difluorocyclohexyl};H;H;2;C$_2$F$_5$];
[{4-ethynylcyclohexyl};H;H;2;C$_2$F$_5$];
[{4-(prop-1-ynyl)cyclohexyl};H;H;2;C$_2$F$_5$];
[{4-(prop-2-ynyl)cyclohexyl};H;H;2;C$_2$F$_5$];
[{4-(3-methoxyprop-1-ynyl)cyclohexyl};H;H;2;C$_2$F$_5$];
[{4-(3-dimethylaminoprop-1-ynyl)cyclohexyl};H;H;2;C$_2$F$_5$];
[{4-(4-methoxycarbonylbut-1-ynyl)cyclohexyl};H;H;2;C$_2$F$_5$];
[{cyclopent-1-enyl};H;H;2;C$_2$F$_5$];
[{3-(prop-1-ynyl)cyclopent-1-enyl};H;H;2;C$_2$F$_5$];
[{3-(prop-2-ynyl)cyclopent-1-enyl};H;H;2;C$_2$F$_5$];
[{cyclopent-2-enyl};H;H;2;C$_2$F$_5$];
[{3-(prop-1-ynyl)cyclopent-2-enyl};H;H;2;C$_2$F$_5$];
[{3-(prop-2-ynyl)cyclopent-2-enyl};H;H;2;C$_2$F$_5$];
[{cyclopent-3-enyl};H;H;2;C$_2$F$_5$];
[{3-(prop-1-ynyl)cyclopent-3-enyl};H;H;2;C$_2$F$_5$];
[{3-(prop-2-ynyl)cyclopent-3-enyl};H;H;2;C$_2$F$_5$];
[{3-ethynylcyclohex-1-enyl};H;H;2;C$_2$F$_5$];
[{3-(prop-1-ynyl)cyclohex-1-enyl};H;H;2;C$_2$F$_5$];
[{3-(prop-2-ynyl)cyclohex-1-enyl};H;H;2;C$_2$F$_5$];
[{4-fluorocyclohex-1-enyl};H;H;2;C$_2$F$_5$];
[{4-(prop-2-enyl)cyclohex-1-enyl};H;H;2;C$_2$F$_5$];
[{4-ethynylcyclohex-1-enyl};H;H;2;C$_2$F$_5$];
[{4-(prop-1-ynyl)cyclohex-1-enyl};H;H;2;C$_2$F$_5$];
[{4-(prop-2-ynyl)cyclohex-1-enyl};H;H;2;C$_2$F$_5$];
[{3-(prop-1-ynyl)cyclohex-2-enyl};H;H;2;C$_2$F$_5$];
[{3-(prop-2-ynyl)cyclohex-2-enyl};H;H;2;C$_2$F$_5$];
[{4-(prop-2-enyl)cyclohex-2-enyl};H;H;2;C$_2$F$_5$];
[{4-ethynylcyclohex-2-enyl};H;H;2;C$_2$F$_5$];
[{4-(prop-1-enyl)cyclohex-2-enyl};H;H;2;C$_2$F$_5$];
[{4-(prop-2-ynyl)cyclohex-2-enyl};H;H;2;C$_2$F$_5$];
[{3-(prop-1-ynyl)cyclohex-3-enyl};H;H;2;C$_2$F$_5$];
[{3-(prop-2-ynyl)cyclohex-3-enyl};H;H;2;C$_2$F$_5$];
[{4-fluorocyclohex-3-enyl};H;H;2;C$_2$F$_5$];
[{4-(prop-2-enyl)cyclohex-3-enyl};H;H;2;C$_2$F$_5$];
[{4-ethynylcyclohex-3-enyl};H;H;2;C$_2$F$_5$];
[{4-(prop-1-ynyl)cyclohex-3-enyl};H;H;2;C$_2$F$_5$];
[{4-(prop-2-ynyl)cyclohex-3-enyl};H;H;2;C$_2$F$_5$];
[{3-(fluoromethyl)cyclopentyl};H;CO$_2$CH$_3$;2;CF$_3$];
[{3-(difluoromethyl)cyclopentyl};H;CO$_2$CH$_3$;2;CF$_3$];
[{3-(trifluoromethyl)cyclopentyl};H;CO$_2$CH$_3$;2;CF$_3$];
[{3-ethynylcyclopentyl};H;CO$_2$CH$_3$;2;CF$_3$];
[{3-(prop-1-ynyl)cyclopentyl};H;CO$_2$CH$_3$;2;CF$_3$];
[{3-(prop-2-ynyl)cyclopentyl};H;CO$_2$CH$_3$;2;CF$_3$];
[{3-(prop-2-ynyloxy)cyclopentyl};H;CO$_2$CH$_3$;2;CF$_3$];
[{3-ethynylcyclohexyl};H;CO$_2$CH$_3$;2;CF$_3$];
[{3-(prop-1-ynyl)cyclohexyl};H;CO$_2$CH$_3$;2;CF$_3$];
[{3-(prop-2-ynyl)cyclohexyl};H;CO$_2$CH$_3$;2;CF$_3$];
[{3-(prop-2-ynyloxy)cyclohexyl};H;CO$_2$CH$_3$;2;CF$_3$];
[{4-fluorocyclohexyl};H;CO$_2$CH$_3$;2;CF$_3$];
[{4,4-difluorocyclohexyl};H;CO$_2$CH$_3$;2;CF$_3$];
[{4-ethynylcyclohexyl};H;CO$_2$CH$_3$;2;CF$_3$];
[{4-(prop-1-ynyl)cyclohexyl};H;CO$_2$CH$_3$;2;CF$_3$];
[{4-(prop-2-ynyl)cyclohexyl};H;CO$_2$CH$_3$;2;CF$_3$];
[{4-(3-methoxyprop-1-ynyl)cyclohexyl};H;CO$_2$CH$_3$;2;CF$_3$];
[{4-(3-dimethylaminoprop-1-ynyl)cyclohexyl};H;CO$_2$CH$_3$;2;CF$_3$];
[{4-(4-methoxycarbonylbut-1-ynyl)cyclohexyl};H;CO$_2$CH$_3$;2;CF$_3$];
[{cyclopent-1-enyl};H;CO$_2$CH$_3$;2;CF$_3$];
[{3-(prop-1-ynyl)cyclopent-1-enyl};H;CO$_2$CH$_3$;2;CF$_3$];
[{3-(prop-2-ynyl)cyclopent-1-enyl};H;CO$_2$CH$_3$;2;CF$_3$];
[{cyclopent-2-enyl};H;CO$_2$CH$_3$;2;CF$_3$];
[{3-(prop-1-ynyl)cyclopent-2-enyl};H;CO$_2$CH$_3$;2;CF$_3$];
[{3-(prop-2-ynyl)cyclopent-2-enyl};H;CO$_2$CH$_3$;2;CF$_3$];
[{cyclopent-3-enyl};H;CO$_2$CH$_3$;2;CF$_3$];
[{3-(prop-1-ynyl)cyclopent-3-enyl};H;CO$_2$CH$_3$;2;CF$_3$];
[{3-(prop-2-ynyl)cyclopent-3-enyl};H;CO$_2$CH$_3$;2;CF$_3$];
[{3-ethynylcyclohex-1-enyl};H;CO$_2$CH$_3$;2;CF$_3$];
[{3-(prop-1-ynyl)cyclohex-1-enyl};H;CO$_2$CH$_3$;2;CF$_3$];
[{3-(prop-2-ynyl)cyclohex-1-enyl};H;CO$_2$CH$_3$;2;CF$_3$];
[{4-fluorocyclohex-1-enyl};H;CO$_2$CH$_3$;2;CF$_3$];
[{4-(prop-2-enyl)cyclohex-1-enyl};H;CO$_2$CH$_3$;2;CF$_3$];
[{4-ethynylcyclohex-1-enyl};H;CO$_2$CH$_3$;2;CF$_3$];
[{4-(prop-1-ynyl)cyclohex-1-enyl};H;CO$_2$CH$_3$;2;CF$_3$];
[{3-(prop-1-ynyl)cyclohex-2-enyl};H;CO$_2$CH$_3$;2;CF$_3$];
[{3-(prop-2-ynyl)cyclohex-2-enyl};H;CO$_2$CH$_3$;2;CF$_3$];
[{4-(prop-2-enyl)cyclohex-2-enyl};H;CO$_2$CH$_3$;2;CF$_3$];
[{4-ethynylcyclohex-2-enyl};H;CO$_2$CH$_3$;2;CF$_3$];
[{4-(prop-1-ynyl)cyclohex-2-enyl};H;CO$_2$CH$_3$;2;CF$_3$];
[{4-(prop-2-ynyl)cyclohex-2-enyl};H;CO$_2$CH$_3$;2;CF$_3$];
[{3-(prop-1-ynyl)cyclohex-3-enyl};H;CO$_2$CH$_3$;2;CF$_3$];
[{3-(prop-2-ynyl)cyclohex-3-enyl};H;CO$_2$CH$_3$;2;C$_3$];
[{4-fluorocyclohex-3-enyl};H;CO$_2$CH$_3$;2;CF$_3$];
[{4-(prop-2-enyl)cyclohex-3-enyl};H;CO$_2$CH$_3$;2;CF$_3$];
[{4-ethynylcyclohex-3-enyl};H;CO$_2$CH$_3$;2;CF$_3$];
[{4-(prop-1-ynyl)cyclohex-3-enyl};H;CO$_2$CH$_3$;2;CF$_3$];
[{4-(prop-2-ynyl)cyclohex-3-enyl};H;CO$_2$CH$_3$;2;CF$_3$];
[{3-(fluoromethyl)cyclopentyl};F;CO$_2$CH$_3$;2;CF$_3$];
[{3-(difluoromethyl)cyclopentyl};F;CO$_2$CH$_3$;2;CF$_3$];
[{3-(trifluoromethyl)cyclopentyl};F;CO$_2$CH$_3$;2;CF$_3$];
[{3-ethynylcyclopentyl};F;CO$_2$CH$_3$;2;CF$_3$];
[{3-(prop-1-ynyl)cyclopentyl};F;CO$_2$CH$_3$;2;CF$_3$];
[{3-(prop-2-ynyl)cyclopentyl};F;CO$_2$CH$_3$;2;CF$_3$];
[{3-(prop-2-ynyloxy)cyclopentyl};F;CO$_2$CH$_3$;2;CF$_3$];
[{3-ethynylcyclohexyl};F;CO$_2$CH$_3$;2;CF$_3$];
[{3-(prop-1-ynyl)cyclohexyl};F;CO$_2$CH$_3$;2;CF$_3$];
[{3-(prop-2-ynyl)cyclohexyl};F;CO$_2$CH$_3$;2;CF$_3$];
[{3-(prop-2-ynyloxy)cyclohexyl};F;CO$_2$CH$_3$;2;CF$_3$];
[{4-fluorocyclohexyl};F;CO$_2$CH$_3$;2;CF$_3$];
[{4,4-difluorocyclohexyl};F;CO$_2$CH$_3$;2;CF$_3$];
[{4-ethynylcyclohexyl};F;CO$_2$CH$_3$;2;CF$_3$];
[{4-(prop-1-ynyl)cyclohexyl};F;CO$_2$CH$_3$;2;CF$_3$];
[{4-(prop-2-ynyl)cyclohexyl};F;CO$_2$CH$_3$;2;CF$_3$];
[{4-(3-methoxyprop-1-ynyl)cyclohexyl};F;CO$_2$CH$_3$;2;CF$_3$];

[{4-(3-dimethylaminoprop-1-ynyl)cyclohexyl};F;CO$_2$CH$_3$; 2;CF$_3$];
[{4-(4-methoxycarbonylbut-1-ynyl)cyclohexyl};F; CO$_2$CH$_3$;2;CF$_3$];
[{cyclopent-1-enyl};F;CO$_2$CH$_3$;2;CF$_3$];
[{3-(prop-1-ynyl)cyclopent-1-enyl};F;CO$_2$CH$_3$;2;CF$_3$];
[{3-(prop-2-ynyl)cyclopent-1-enyl};F;CO$_2$CH$_3$;2;CF$_3$];
[{cyclopent-2-enyl};F;CO$_2$CH$_3$;2;CF$_3$];
[{3-(prop-1-ynyl)cyclopent-2-enyl};F;CO$_2$CH$_3$;2;CF$_3$];
[{3-(prop-2-ynyl)cyclopent-2-enyl};F;CO$_2$CH$_3$;2;CF$_3$];
[{cyclopent-3-enyl};F;CO$_2$CH$_3$;2;CF$_3$];
[{3-(prop-1-ynyl)cyclopent-3-enyl};F;CO$_2$CH$_3$;2;CF$_3$];
[{3-(prop-2-ynyl)cyclopent-3-enyl};F;CO$_2$CH$_3$;2;CF$_3$];
[{3-ethynylcyclohex-1-enyl};F;CO$_2$CH$_3$;2;CF$_3$];
[{3-(prop-1-ynyl)cyclohex-1-enyl};F;CO$_2$CH$_3$;2;CF$_3$];
[{3-(prop-2-ynyl)cyclohex-1-enyl};F;CO$_2$CH$_3$;2;CF$_3$];
[{4-fluorocyclohex-1-enyl};F;CO$_2$CH$_3$;2;CF$_3$];
[{4-(prop-2-enyl)cyclohex-1-enyl};F;CO$_2$CH$_3$;2;CF$_3$];
[{4-ethynylcyclohex-1-enyl};F;CO$_2$CH$_3$;2;CF$_3$];
[{4-(prop-1-ynyl)cyclohex-1-enyl};F;CO$_2$CH$_3$;2;CF$_3$];
[{4-(prop-2-ynyl)cyclohex-1-enyl};F;CO$_2$CH$_3$;2;CF$_3$];
[{3-(prop-1-ynyl)cyclohex-2-enyl};F;CO$_2$CH$_3$;2;CF$_3$];
[{3-(prop-2-ynyl)cyclohex-2-enyl};F;CO$_2$CH$_3$;2;CF$_3$];
[{4-(prop-2-enyl)cyclohex-2-enyl};F;CO$_2$CH$_3$;2;CF$_3$];
[{4-ethynylcyclohex-2-enyl};F;CO$_2$CH$_3$;2;CF$_3$];
[{4-(prop-1-ynyl)cyclohex-2-enyl};F;CO$_2$CH$_3$;2;CF$_3$];
[{4-(prop-2-ynyl)cyclohex-2-enyl};F;CO$_2$CH$_3$;2;CF$_3$];
[{3-(prop-1-ynyl)cyclohex-3-enyl};F;CO$_2$CH$_3$;2;CF$_3$];
[{3-(prop-2-ynyl)cyclohex-3-enyl};F;CO$_2$CH$_3$;2;CF$_3$];
[{4-fluorocyclohex-3-enyl};F;CO$_2$CH$_3$;2;CF$_3$];
[{4-(prop-2-enyl)cyclohex-3-enyl};F;CO$_2$CH$_3$;2;CF$_3$];
[{4-ethynylcyclohex-3-enyl};F;CO$_2$CH$_3$;2;CF$_3$];
[{4-(prop-1-ynyl)cyclohex-3-enyl};F;CO$_2$CH$_3$;2;CF$_3$];
[{4-(prop-2-ynyl)cyclohex-3-enyl};F;CO$_2$CH$_3$;2;CF$_3$];
[{3-(fluoromethyl)cyclopentyl};Cl;CO$_2$CH$_3$;2;CF$_3$];
[{3-(difluoromethyl)cyclopentyl};Cl;CO$_2$CH$_3$;2;CF$_3$];
[{3-(trifluoromethyl)cyclopentyl};Cl;CO$_2$CH$_3$;2;CF$_3$];
[{3-ethynylcyclopentyl};Cl;CO$_2$CH$_3$;2;CF$_3$];
[{3-(prop-1-ynyl)cyclopentyl};Cl;CO$_2$CH$_3$;2;CF$_3$];
[{3-(prop-2-ynyl)cyclopentyl};Cl;CO$_2$CH$_3$;2;CF$_3$];
[{3-(prop-2-ynyloxy)cyclopentyl};Cl;CO$_2$CH$_3$;2;CF$_3$];
[{3-ethynylcyclohexyl};Cl;CO$_2$CH$_3$;2;CF$_3$];
[{3-(prop-1-ynyl)cyclohexyl};Cl;CO$_2$CH$_3$;2;CF$_3$];
[{3-(prop-2-ynyl)cyclohexyl};Cl;CO$_2$CH$_3$;2;CF$_3$];
[{3-(prop-2-ynyloxy)cyclohexyl};Cl;CO$_2$CH$_3$;2;CF$_3$];
[{4-fluorocyclohexyl};Cl;CO$_2$CH$_3$;2;CF$_3$];
[{4,4-difluorocyclohexyl};Cl;CO$_2$CH$_3$;2;CF$_3$];
[{4-ethynylcyclohexyl};Cl;CO$_2$CH$_3$;2;CF$_3$];
[{4-(prop-1-ynyl)cyclohexyl};Cl;CO$_2$CH$_3$;2;CF$_3$];
[{4-(prop-2-ynyl)cyclohexyl};Cl;CO$_2$CH$_3$;2;CF$_3$];
[{4-(3-methoxyprop-1-ynyl)cyclohexyl};Cl;CO$_2$CH$_3$;2; CF$_3$];
[{4-(3-dimethylaminoprop-1-ynyl)cyclohexyl};Cl; CO$_2$CH$_3$;2;CF$_3$];
[{4-(4-methoxycarbonylbut-1-ynyl)cyclohexyl};Cl; CO$_2$CH$_3$;2;CF$_3$];
[{cyclopent-1-enyl};Cl;CO$_2$CH$_3$;2;CF$_3$];
[{3-(prop-1-ynyl)cyclopent-1-enyl};Cl;CO$_2$CH$_3$;2;CF$_3$];
[{3-(prop-2-ynyl)cyclopent-1-enyl};Cl;CO$_2$CH$_3$;2;CF$_3$];
[{cyclopent-2-enyl};Cl;CO$_2$CH$_3$;2;CF$_3$];
[{3-(prop-1-ynyl)cyclopent-2-enyl};Cl;CO$_2$CH$_3$;2;CF$_3$];
[{3-(prop-2-ynyl)cyclopent-2-enyl};Cl;CO$_2$CH$_3$;2;CF$_3$];
[{cyclopent-3-enyl};Cl;CO$_2$CH$_3$;2;CF$_3$];
[{3-(prop-1-ynyl)cyclopent-3-enyl};Cl;CO$_2$CH$_3$;2;CF$_3$];
[{3-(prop-2-ynyl)cyclopent-3-enyl};Cl;CO$_2$CH$_3$;2;CF$_3$];
[{3-ethynylcyclohex-1-enyl};Cl;CO$_2$CH$_3$;2;CF$_3$];
[{3-(prop-1-ynyl)cyclohex-1-enyl};Cl;CO$_2$CH$_3$;2;CF$_3$];
[{3-(prop-2-ynyl)cyclohex-1-enyl};Cl;CO$_2$CH$_3$;2;CF$_3$];
[{4-fluorocyclohex-1-enyl};Cl;CO$_2$CH$_3$;2;CF$_3$];
[{4-(prop-2-enyl)cyclohex-1-enyl};Cl;CO$_2$CH$_3$;2;CF$_3$];
[{4-ethynylcyclohex-1-enyl};Cl;CO$_2$CH$_3$;2;CF$_3$];
[{4-(prop-1-ynyl)cyclohex-1-enyl};Cl;CO$_2$CH$_3$;2;CF$_3$];
[{4-(prop-2-ynyl)cyclohex-1-enyl};Cl;CO$_2$CH$_3$;2;CF$_3$];
[{3-(prop-1-ynyl)cyclohex-2-enyl};Cl;CO$_2$CH$_3$;2;CF$_3$];
[{3-(prop-2-ynyl)cyclohex-2-enyl};Cl;CO$_2$CH$_3$;2;CF$_3$];
[{4-(prop-2-enyl)cyclohex-2-enyl};Cl;CO$_2$CH$_3$;2;CF$_3$];
[{4-ethynylcyclohex-2-enyl};Cl;CO$_2$CH$_3$;2;CF$_3$];
[{4-(prop-1-ynyl)cyclohex-2-enyl};Cl;CO$_2$CH$_3$;2;CF$_3$];
[{4-(prop-2-ynyl)cyclohex-2-enyl};Cl;CO$_2$CH$_3$;2;CF$_3$];
[{3-(prop-1-ynyl)cyclohex-3-enyl};Cl;CO$_2$CH$_3$;2;CF$_3$];
[{3-(prop-2-ynyl)cyclohex-3-enyl};Cl;CO$_2$CH$_3$;2;CF$_3$];
[{4-fluorocyclohex-3-enyl};Cl;CO$_2$CH$_3$;2;CF$_3$];
[{4-(prop-2-enyl)cyclohex-3-enyl};Cl;CO$_2$CH$_3$;2;CF$_3$];
[{4-ethynylcyclohex-3-enyl};Cl;CO$_2$CH$_3$;2;CF$_3$];
[{4-(prop-1-ynyl)cyclohex-3-enyl};Cl;CO$_2$CH$_3$;2;CF$_3$];
[{4-(prop-2-ynyl)cyclohex-3-enyl};Cl;CO$_2$CH$_3$;2;CF$_3$];
[{3-(fluoromethyl)cyclopentyl};CH$_3$;CO$_2$CH$_3$;2;CF$_3$];
[{3-(difluoromethyl)cyclopentyl};CH$_3$;CO$_2$CH$_3$;2;CF$_3$];
[{3-(trifluoromethyl)cyclopentyl};CH$_3$;CO$_2$CH$_3$;2;CF$_3$];
[{3-ethynylcyclopentyl};CH$_3$;CO$_2$CH$_3$;2;CF$_3$];
[{3-(prop-1-ynyl)cyclopentyl};CH$_3$;CO$_2$CH$_3$;2;CF$_3$];
[{3-(prop-2-ynyl)cyclopentyl};CH$_3$;CO$_2$CH$_3$;2;CF$_3$];
[{3-(prop-2-ynyloxy)cyclopentyl};CH$_3$;CO$_2$CH$_3$;2;CF$_3$];
[{3-ethynylcyclohexyl};CH$_3$;CO$_2$CH$_3$;2;CF$_3$];
[{3-(prop-1-ynyl)cyclohexyl};CH$_3$;CO$_2$CH$_3$;2;CF$_3$];
[{3-(prop-2-ynyl)cyclohexyl};CH$_3$;CO$_2$CH$_3$;2;CF$_3$];
[{3-(prop-2-ynyloxy)cyclohexyl};CH$_3$;CO$_2$CH$_3$;2;CF$_3$];
[{4-fluorocyclohexyl};CH$_3$;CO$_2$CH$_3$;2;CF$_3$];
[{4,4-difluorocyclohexyl};CH$_3$;CO$_2$CH$_3$;2;CF$_3$];
[{4-ethynylcyclohexyl};CH$_3$;CO$_2$CH$_3$;2;CF$_3$];
[{4-(prop-1-ynyl)cyclohexyl};CH$_3$;CO$_2$CH$_3$;2;CF$_3$];
[{4-(prop-2-ynyl)cyclohexyl};CH$_3$;CO$_2$CH$_3$;2;CF$_3$];
[{4-(3-methoxyprop-1-ynyl)cyclohexyl};CH$_3$;CO$_2$CH$_3$;2; CF$_3$];
[{4-(3-dimethylaminoprop-1-ynyl)cyclohexyl};CH$_3$; CO$_2$CH$_3$;2;CF$_3$];
[{4-(4-methoxycarbonylbut-1-ynyl)cyclohexyl};CH$_3$; CO$_2$CH$_3$;2;CF$_3$];
[{cyclopent-1-enyl};CH$_3$;CO$_2$CH$_3$;2;CF$_3$];
[{3-(prop-1-ynyl)cyclopent-1-enyl};CH$_3$;CO$_2$CH$_3$;2;CF$_3$];
[{3-(prop-2-ynyl)cyclopent-1-enyl};CH$_3$;CO$_2$CH$_3$;2;CF$_3$];
[{cyclopent-2-enyl};CH$_3$;CO$_2$CH$_3$;2;CF$_3$];
[{3-(prop-1-ynyl)cyclopent-2-enyl};CH$_3$;CO$_2$CH$_3$;2;CF$_3$];
[{3-(prop-2-ynyl)cyclopent-2-enyl};CH$_3$;CO$_2$CH$_3$;2;CF$_3$];
[{cyclopent-3-enyl};CH$_3$;CO$_2$CH$_3$;2;CF$_3$];
[{3-(prop-1-ynyl)cyclopent-3-enyl};CH$_3$;CO$_2$CH$_3$;2;CF$_3$];
[{3-(prop-2-ynyl)cyclopent-3-enyl};CH$_3$;CO$_2$CH$_3$;2;CF$_3$];
[{3-ethynylcyclohex-1-enyl};CH$_3$;CO$_2$CH$_3$;2;CF$_3$];
[{3-(prop-1-ynyl)cyclohex-1-enyl};CH$_3$;CO$_2$CH$_3$;2;CF$_3$];
[{3-(prop-2-ynyl)cyclohex-1-enyl};CH$_3$;CO$_2$CH$_3$;2;CF$_3$];
[{4-fluorocyclohex-1-enyl};CH$_3$;CO$_2$CH$_3$;2;CF$_3$];
[{4-(prop-2-enyl)cyclohex-1-enyl};CH$_3$;CO$_2$CH$_3$;2;CF$_3$];
[{4-ethynylcyclohex-1-enyl};CH$_3$;CO$_2$CH$_3$;2;CF$_3$];
[{4-(prop-1-ynyl)cyclohex-1-enyl};CH$_3$;CO$_2$CH$_3$;2;CF$_3$];
[{4-(prop-2-ynyl)cyclohex-1-enyl};CH$_3$;CO$_2$CH$_3$;2;CF$_3$];
[{3-(prop-1-ynyl)cyclohex-2-enyl};CH$_3$;CO$_2$CH$_3$;2;CF$_3$];
[{3-(prop-2-ynyl)cyclohex-2-enyl};CH$_3$;CO$_2$CH$_3$;2;CF$_3$];
[{4-(prop-2-enyl)cyclohex-2-enyl};CH$_3$;CO$_2$CH$_3$;2;CF$_3$];
[{4-ethynylcyclohex-2-enyl};CH$_3$;CO$_2$CH$_3$;2;CF$_3$];
[{4-(prop-1-ynyl)cyclohex-2-enyl};CH$_3$;CO$_2$CH$_3$;2;CF$_3$];
[{4-(prop-2-ynyl)cyclohex-2-enyl};CH$_3$;CO$_2$CH$_3$;2;CF$_3$];
[{3-(prop-1-ynyl)cyclohex-3-enyl};CH$_3$;CO$_2$CH$_3$;2;CF$_3$];
[{3-(prop-2-ynyl)cyclohex-3-enyl};CH$_3$;CO$_2$CH$_3$;2;CF$_3$];
[{4-fluorocyclohex-3-enyl};CH$_3$;CO$_2$CH$_3$;2;CF$_3$];

[{4-(prop-2-enyl)cyclohex-3-enyl};CH$_3$;CO$_2$CH$_3$;2;CF$_3$];
[{4-ethynylcyclohex-3-enyl};CH$_3$;CO$_2$CH$_3$;2;CF$_3$];
[{4-(prop-1-ynyl)cyclohex-3-enyl};CH$_3$;CO$_2$CH$_3$;2;CF$_3$];
[{4-(prop-2-ynyl)cyclohex-3-enyl};CH$_3$;CO$_2$CH$_3$;2;CF$_3$];
[{3-(fluoromethyl)cyclopentyl};CH$_3$;CO$_2$CH$_3$;2;CF$_3$];
[{3-(difluoromethyl)cyclopentyl};CH$_3$;CO$_2$CH$_3$;2;CF$_3$];
[{3-(trifluoromethyl)cyclopentyl};CH$_3$;CO$_2$CH$_3$;2;CF$_3$];
[{3-ethynylcyclopentyl};CH$_3$;CO$_2$CH$_3$;2;CF$_3$];
[{3-(prop-1-ynyl)cyclopentyl};CH$_3$;CO$_2$CH$_3$;2;CF$_3$];
[{3-(prop-2-ynyl)cyclopentyl};CH$_3$;CO$_2$CH$_3$;2;CF$_3$];
[{3-(prop-2-ynyloxy)cyclopentyl};CH$_3$;CO$_2$CH$_3$;2;CF$_3$];
[{3-ethynylcyclohexyl};CH$_3$;CO$_2$CH$_3$;2;CF$_3$];
[{3-(prop-1-ynyl)cyclohexyl};CH$_3$;CO$_2$CH$_3$;2;CF$_3$];
[{3-(prop-2-ynyl)cyclohexyl};CH$_3$;CO$_2$CH$_3$;2;CF$_3$];
[{3-(prop-2-ynyloxy)cyclohexyl};CH$_3$;CO$_2$CH$_3$;2;CF$_3$];
[{4-fluorocyclohexyl};CH$_3$;CO$_2$CH$_3$;2;CF$_3$];
[{4,4-difluorocyclohexyl};CH$_3$;CO$_2$CH$_3$;2;CF$_3$];
[{4-ethynylcyclohexyl};CH$_3$;CO$_2$CH$_3$;2;CF$_3$];
[{4-(prop-1-ynyl)cyclohexyl};CH$_3$;CO$_2$CH$_3$;2;CF$_3$];
[{4-(prop-2-ynyl)cyclohexyl};CH$_3$;CO$_2$CH$_3$;2;CF$_3$];
[{4-(3-methoxyprop-1-ynyl)cyclohexyl};CH$_3$;CO$_2$CH$_3$;2;CF$_3$];
[{4-(3-dimethylaminoprop-1-ynyl)cyclohexyl};CH$_3$;CO$_2$CH$_3$;2;CF$_3$];
[{4-(4-methoxycarbonylbut-1-ynyl)cyclohexyl};CH$_3$;CO$_2$CH$_3$;2;CF$_3$];
[{cyclopent-1-enyl};CH$_3$;CO$_2$CH$_3$;2;CF$_3$];
[{3-(prop-1-ynyl)cyclopent-1-enyl};CH$_3$;CO$_2$CH$_3$;2;CF$_3$];
[{3-(prop-2-ynyl)cyclopent-1-enyl};CH$_3$;CO$_2$CH$_3$;2;CF$_3$];
[{cyclopent-2-enyl};CH$_3$;CO$_2$CH$_3$;2;CF$_3$];
[{3-(prop-1-ynyl)cyclopent-2-enyl};CH$_3$;CO$_2$CH$_3$;2;CF$_3$];
[{3-(prop-2-ynyl)cyclopent-2-enyl};CH$_3$;CO$_2$CH$_3$;2;CF$_3$];
[{cyclopent-3-enyl};CH$_3$;CO$_2$CH$_3$;2;CF$_3$];
[{3-(prop-1-ynyl)cyclopent-3-enyl};CH$_3$;CO$_2$CH$_3$;2;CF$_3$];
[{3-(prop-2-ynyl)cyclopent-3-enyl};CH$_3$;CO$_2$CH$_3$;2;CF$_3$];
[{3-ethynylcyclohex-1-enyl};CH$_3$;CO$_2$CH$_3$;2;CF$_3$];
[{3-(prop-1-ynyl)cyclohex-1-enyl};CH$_3$;CO$_2$CH$_3$;2;CF$_3$];
[{3-(prop-2-ynyl)cyclohex-1-enyl};CH$_3$;CO$_2$CH$_3$;2;C$_3$];
[{4-fluorocyclohex-1-enyl};CH$_3$;CO$_2$CH$_3$;2;CF$_3$];
[{4-(prop-2-enyl)cyclohex-1-enyl};CH$_3$;CO$_2$CH$_3$;2;CF$_3$];
[{4-ethynylcyclohex-1-enyl};CH$_3$;CO$_2$CH$_3$;2;CF$_3$];
[{4-(prop-1-ynyl)cyclohex-1-enyl};CH$_3$;CO$_2$CH$_3$;2;CF$_3$];
[{4-(prop-2-ynyl)cyclohex-1-enyl};CH$_3$;CO$_2$CH$_3$;2;CF$_3$];
[{3-(prop-1-ynyl)cyclohex-2-enyl};CH$_3$;CO$_2$CH$_3$;2;CF$_3$];
[{3-(prop-2-ynyl)cyclohex-2-enyl};CH$_3$;CO$_2$CH$_3$;2;CF$_3$];
[{4-(prop-2-enyl)cyclohex-2-enyl};CH$_3$;CO$_2$CH$_3$;2;CF$_3$];
[{4-ethynylcyclohex-2-enyl};CH$_3$;CO$_2$CH$_3$;2;CF$_3$];
[{4-(prop-1-ynyl)cyclohex-2-enyl};CH$_3$;CO$_2$CH$_3$;2;CF$_3$];
[{4-(prop-2-ynyl)cyclohex-2-enyl};CH$_3$;CO$_2$CH$_3$;2;CF$_3$];
[{3-(prop-1-ynyl)cyclohex-3-enyl};CH$_3$;CO$_2$CH$_3$;2;CF$_3$];
[{3-(prop-2-ynyl)cyclohex-3-enyl};CH$_3$;CO$_2$CH$_3$;2;CF$_3$];
[{4-fluorocyclohex-3-enyl};CH$_3$;CO$_2$CH$_3$;2;CF$_3$];
[{4-(prop-2-enyl)cyclohex-3-enyl};CH$_3$;CO$_2$CH$_3$;2;CF$_3$];
[{4-ethynylcyclohex-3-enyl};CH$_3$;CO$_2$CH$_3$;2;CF$_3$];
[{4-(prop-1-ynyl)cyclohex-3-enyl};CH$_3$;CO$_2$CH$_3$;2;CF$_3$];
[{4-(prop-2-ynyl)cyclohex-3-enyl};CH$_3$;CO$_2$CH$_3$;2;CF$_3$];
[{3-(fluoromethyl)cyclopentyl};H;CN;2;CF$_3$];
[{3-(difluoromethyl)cyclopentyl};H;CN;2;CF$_3$];
[{3-(trifluoromethyl)cyclopentyl};H;CN;2;CF$_3$];
[{3-ethynylcyclopentyl};H;CN;2;CF$_3$];
[{3-(prop-1-ynyl)cyclopentyl};H;CN;2;CF$_3$];
[{3-(prop-2-ynyl)cyclopentyl};H;CN;2;CF$_3$];
[{3-(prop-2-ynyloxy)cyclopentyl};H;CN;2;CF$_3$];
[{3-ethynylcyclohexyl};H;CN;2;CF$_3$];
[{3-(prop-1-ynyl)cyclohexyl};H;CN;2;CF$_3$];
[{3-(prop-2-ynyl)cyclohexyl};H;CN;2;CF$_3$];
[{3-(prop-2-ynyloxy)cyclohexyl};H;CN;2;CF$_3$];
[{4-fluorocyclohexyl};H;CN;2;CF$_3$];
[{4,4-difluorocyclohexyl};H;CN;2;CF$_3$];
[{4-ethynylcyclohexyl};H;CN;2;CF$_3$];
[{4-(prop-1-ynyl)cyclohexyl};H;CN;2;CF$_3$];
[{4-(prop-2-ynyl)cyclohexyl};H;CN;2;CF$_3$];
[{4-(3-methoxyprop-1-ynyl)cyclohexyl};H;CN;2;CF$_3$];
[{4-(3-dimethylaminoprop-1-ynyl)cyclohexyl};H;CN;2;CF$_3$];
[{4-(4-methoxycarbonylbut-1-ynyl)cyclohexyl};H;CN;2;CF$_3$];
[{cyclopent-1-enyl};H;CN;2;CF$_3$];
[{3-(prop-1-ynyl)cyclopent-1-enyl};H;CN;2;CF$_3$];
[{3-(prop-2-ynyl)cyclopent-1-enyl};H;CN;2;CF$_3$];
[{cyclopent-2-enyl};H;CN;2;CF$_3$];
[{3-(prop-1-ynyl)cyclopent-2-enyl};H;CN;2;CF$_3$];
[{3-(prop-2-ynyl)cyclopent-2-enyl};H;CN;2;CF$_3$];
[{cyclopent-3-enyl};H;CN;2;CF$_3$];
[{3-(prop-1-ynyl)cyclopent-3-enyl};H;CN;2;CF$_3$];
[{3-(prop-2-ynyl)cyclopent-3-enyl};H;CN;2;CF$_3$];
[{3-ethynylcyclohex-1-enyl};H;CN;2;CF$_3$];
[{3-(prop-1-ynyl)cyclohex-1-enyl};H;CN;2;CF$_3$];
[{3-(prop-2-ynyl)cyclohex-1-enyl};H;CN;2;CF$_3$];
[{4-fluorocyclohex-1-enyl};H;CN;2;CF$_3$];
[{4-(prop-2-enyl)cyclohex-1-enyl};H;CN;2;CF$_3$];
[{4-ethynylcyclohex-1-enyl};H;CN;2;CF$_3$];
[{4-(prop-1-ynyl)cyclohex-1-enyl};H;CN;2;CF$_3$];
[{4-(prop-2-ynyl)cyclohex-1-enyl};H;CN;2;CF$_3$];
[{3-(prop-1-ynyl)cyclohex-2-enyl};H;CN;2;CF$_3$];
[{3-(prop-2-ynyl)cyclohex-2-enyl};H;CN;2;CF$_3$];
[{4-(prop-2-enyl)cyclohex-2-enyl};H;CN;2;CF$_3$];
[{4-ethynylcyclohex-2-enyl};H;CN;2;CF$_3$];
[{4-(prop-1-ynyl)cyclohex-2-enyl};H;CN;2;CF$_3$];
[{4-(prop-2-ynyl)cyclohex-2-enyl};H;CN;2;CF$_3$];
[{3-(prop-1-ynyl)cyclohex-3-enyl};H;CN;2;CF$_3$];
[{3-(prop-2-ynyl)cyclohex-3-enyl};H;CN;2;CF$_3$];
[{4-fluorocyclohex-3-enyl};H;CN;2;CF$_3$];
[{4-(prop-2-enyl)cyclohex-3-enyl};H;CN;2;CF$_3$];
[{4-ethynylcyclohex-3-enyl};H;CN;2;CF$_3$];
[{4-(prop-1-ynyl)cyclohex-3-enyl};H;CN;2;CF$_3$];
[{4-(prop-2-ynyl)cyclohex-3-enyl};H;CN;2;CF$_3$];
[{3-(fluoromethyl)cyclopentyl};F;CN;2;CF$_3$];
[{3-(difluoromethyl)cyclopentyl};F;CN;2;CF$_3$];
[{3-(trifluoromethyl)cyclopentyl};F;CN;2;CF$_3$];
[{3-ethynylcyclopentyl};F;CN;2;CF$_3$];
[{3-(prop-1-ynyl)cyclopentyl};F;CN;2;CF$_3$];
[{3-(prop-2-ynyl)cyclopentyl};F;CN;2;CF$_3$];
[{3-(prop-2-ynyloxy)cyclopentyl};F;CN;2;CF$_3$];
[{3-ethynylcyclohexyl};F;CN;2;CF$_3$];
[{3-(prop-1-ynyl)cyclohexyl};F;CN;2;CF$_3$];
[{3-(prop-2-ynyl)cyclohexyl};F;CN;2;CF$_3$];
[{3-(prop-2-ynyloxy)cyclohexyl};F;CN;2;CF$_3$];
[{4-fluorocyclohexyl};F;CN;2;CF$_3$];
[{4,4-difluorocyclohexyl};F;CN;2;CF$_3$];
[{4-ethynylcyclohexyl};F;CN;2;CF$_3$];
[{4-(prop-1-ynyl)cyclohexyl};F;CN;2;CF$_3$];
[{4-(prop-2-ynyl)cyclohexyl};F;CN;2;CF$_3$];
[{4-(3-methoxyprop-1-ynyl)cyclohexyl};F;CN;2;CF$_3$];
[{4-(3-dimethylaminoprop-1-ynyl)cyclohexyl};F;CN;2;CF$_3$];
[{4-(4-methoxycarbonylbut-1-ynyl)cyclohexyl};F;CN;2;CF$_3$];
[{cyclopent-1-enyl};F;CN;2;CF$_3$];
[{3-(prop-1-ynyl)cyclopent-1-enyl};F;CN;2;CF$_3$];
[{3-(prop-2-ynyl)cyclopent-1-enyl};F;CN;2;CF$_3$];
[{cyclopent-2-enyl};F;CN;2;CF$_3$];
[{3-(prop-1-ynyl)cyclopent-2-enyl};F;CN;2;CF$_3$];
[{3-(prop-2-ynyl)cyclopent-2-enyl};F;CN;2;CF$_3$];

[{cyclopent-3-enyl};F;CN;2;CF$_3$];
[{3-(prop-1-ynyl)cyclopent-3-enyl};F;CN;2;CF$_3$];
[{3-(prop-2-ynyl)cyclopent-3-enyl};F;CN;2;CF$_3$];
[{3-ethynylcyclohex-1-enyl};F;CN;2;CF$_3$];
[{3-(prop-1-ynyl)cyclohex-1-enyl};F;CN;2;CF$_3$];
[{3-(prop-2-ynyl)cyclohex-1-enyl};F;CN;2;CF$_3$];
[{4-fluorocyclohex-1-enyl};F;CN;2;CF$_3$];
[{4-(prop-2-enyl)cyclohex-1-enyl};F;CN;2;CF$_3$];
[{4-ethynylcyclohex-1-enyl};F;CN;2;CF$_3$];
[{4-(prop-1-ynyl)cyclohex-1-enyl};F;CN;2;CF$_3$];
[{4-(prop-2-ynyl)cyclohex-1-enyl};F;CN;2;CF$_3$];
[{3-(prop-1-ynyl)cyclohex-2-enyl};F;CN;2;CF$_3$];
[{3-(prop-2-ynyl)cyclohex-2-enyl};F;CN;2;CF$_3$];
[{4-(prop-2-enyl)cyclohex-2-enyl};F;CN;2;CF$_3$];
[{4-ethynylcyclohex-2-enyl};F;CN;2;CF$_3$];
[{4-(prop-1-ynyl)cyclohex-2-enyl};F;CN;2;CF$_3$];
[{4-(prop-2-ynyl)cyclohex-2-enyl};F;CN;2;CF$_3$];
[{3-(prop-1-ynyl)cyclohex-3-enyl};F;CN;2;CF$_3$];
[{3-(prop-2-ynyl)cyclohex-3-enyl};F;CN;2;CF$_3$];
[{4-fluorocyclohex-3-enyl};F;CN;2;CF$_3$];
[{4-(prop-2-enyl)cyclohex-3-enyl};F;CN;2;CF$_3$];
[{4-ethynylcyclohex-3-enyl};F;CN;2;CF$_3$];
[{4-(prop-1-ynyl)cyclohex-3-enyl};F;CN;2;CF$_3$];
[{4-(prop-2-ynyl)cyclohex-3-enyl};F;CN;2;CF$_3$];
[{3-(fluoromethyl)cyclopentyl};Cl;CN;2;CF$_3$];
[{3-(difluoromethyl)cyclopentyl};Cl;CN;2;CF$_3$];
[{3-(trifluoromethyl)cyclopentyl};Cl;CN;2;CF$_3$];
[{3-ethynylcyclopentyl};Cl;CN;2;CF$_3$];
[{3-(prop-1-ynyl)cyclopentyl};Cl;CN;2;CF$_3$];
[{3-(prop-2-ynyl)cyclopentyl};Cl;CN;2;CF$_3$];
[{3-(prop-2-ynyloxy)cyclopentyl};Cl;CN;2;CF$_3$];
[{3-ethynylcyclohexyl};Cl;CN;2;CF$_3$];
[{3-(prop-1-ynyl)cyclohexyl};Cl;CN;2;CF$_3$];
[{3-(prop-2-ynyl)cyclohexyl};Cl;CN;2;CF$_3$];
[{3-(prop-2-ynyloxy)cyclohexyl};Cl;CN;2;CF$_3$];
[{4-fluorocyclohexyl};Cl;CN;2;CF$_3$];
[{4,4-difluorocyclohexyl};Cl;CN;2;CF$_3$];
[{4-ethynylcyclohexyl};Cl;CN;2;CF$_3$];
[{4-(prop-1-ynyl)cyclohexyl};Cl;CN;2;CF$_3$];
[{4-(prop-2-ynyl)cyclohexyl};Cl;CN;2;CF$_3$];
[{4-(3-methoxyprop-1-ynyl)cyclohexyl};Cl;CN;2;CF$_3$];
[{4-(3-dimethylaminoprop-1-ynyl)cyclohexyl};Cl;CN;2; CF$_3$];
[{4-(4-methoxycarbonylbut-1-ynyl)cyclohexyl};Cl;CN;2; CF$_3$];
[{cyclopent-1-enyl};Cl;CN;2;CF$_3$];
[{3-(prop-1-ynyl)cyclopent-1-enyl};Cl;CN;2;CF$_3$];
[{3-(prop-2-ynyl)cyclopent-1-enyl};Cl;CN;2;CF$_3$];
[{cyclopent-2-enyl};Cl;CN;2;CF$_3$];
[{3-(prop-1-ynyl)cyclopent-2-enyl};Cl;CN;2;CF$_3$];
[{3-(prop-2-ynyl)cyclopent-2-enyl};Cl;CN;2;CF$_3$];
[{cyclopent-3-enyl};Cl;CN;2;CF$_3$];
[{3-(prop-1-ynyl)cyclopent-3-enyl};Cl;CN;2;CF$_3$];
[{3-(prop-2-ynyl)cyclopent-3-enyl};Cl;CN;2;CF$_3$];
[{3-ethynylcyclohex-1-enyl};Cl;CN;2;CF$_3$];
[{3-(prop-1-ynyl)cyclohex-1-enyl};Cl;CN;2;CF$_3$];
[{3-(prop-2-ynyl)cyclohex-1-enyl};Cl;CN;2;CF$_3$];
[{4-fluorocyclohex-1-enyl};Cl;CN;2;CF$_3$];
[{4-(prop-2-enyl)cyclohex-1-enyl};Cl;CN;2;CF$_3$];
[{4-ethynylcyclohex-1-enyl};Cl;CN;2;CF$_3$];
[{4-(prop-1-ynyl)cyclohex-1-enyl};Cl;CN;2;CF$_3$];
[{4-(prop-2-ynyl)cyclohex-1-enyl};Cl;CN;2;CF$_3$];
[{3-(prop-1-ynyl)cyclohex-2-enyl};Cl;CN;2;CF$_3$];
[{3-(prop-2-ynyl)cyclohex-2-enyl};Cl;CN;2;CF$_3$];
[{4-(prop-2-enyl)cyclohex-2-enyl};Cl;CN;2;CF$_3$];
[{4-ethynylcyclohex-2-enyl};Cl;CN;2;CF$_3$];
[{4-(prop-1-ynyl)cyclohex-2-enyl};Cl;CN;2;CF$_3$];
[{4-(prop-2-ynyl)cyclohex-2-enyl};Cl;CN;2;CF$_3$];
[{3-(prop-1-ynyl)cyclohex-3-enyl};Cl;CN;2;CF$_3$];
[{3-(prop-2-ynyl)cyclohex-3-enyl};Cl;CN;2;CF$_3$];
[{4-fluorocyclohex-3-enyl};Cl;CN;2;CF$_3$];
[{4-(prop-2-enyl)cyclohex-3-enyl};Cl;CN;2;CF$_3$];
[{4-ethynylcyclohex-3-enyl};Cl;CN;2;CF$_3$];
[{4-(prop-1-ynyl)cyclohex-3-enyl};Cl;CN;2;CF$_3$];
[{4-(prop-2-ynyl)cyclohex-3-enyl};Cl;CN;2;CF$_3$];
[{3-(fluoromethyl)cyclopentyl};CH$_3$;CN;2;CF$_3$];
[{3-(difluoromethyl)cyclopentyl};CH$_3$;CN;2;CF$_3$];
[{3-(trifluoromethyl)cyclopentyl};CH$_3$;CN;2;CF$_3$];
[{3-ethynylcyclopentyl};CH$_3$;CN;2;CF$_3$];
[{3-(prop-1-ynyl)cyclopentyl};CH$_3$;CN;2;CF$_3$];
[{3-(prop-2-ynyl)cyclopentyl};CH$_3$;CN;2;CF$_3$];
[{3-(prop-2-ynyloxy)cyclopentyl};CH$_3$;CN;2;CF$_3$];
[{3-ethynylcyclohexyl};CH$_3$;CN;2;CF$_3$];
[{3-(prop-1-ynyl)cyclohexyl};CH$_3$;CN;2;CF$_3$];
[{3-(prop-2-ynyl)cyclohexyl};CH$_3$;CN;2;CF$_3$];
[{3-(prop-2-ynyloxy)cyclohexyl};CH$_3$;CN;2;CF$_3$];
[{4-fluorocyclohexyl};CH$_3$;CN;2;CF$_3$];
[{4,4-difluorocyclohexyl};CH$_3$;CN;2;CF$_3$];
[{4-ethynylcyclohexyl};CH$_3$;CN;2;CF$_3$];
[{4-(prop-1-ynyl)cyclohexyl};CH$_3$;CN;2;CF$_3$];
[{4-(prop-2-ynyl)cyclohexyl};CH$_3$;CN;2;CF$_3$];
[{4-(3-methoxyprop-1-ynyl)cyclohexyl};CH$_3$;CN;2;CF$_3$];
[{4-(3-dimethylaminoprop-1-ynyl)cyclohexyl};CH$_3$;CN;2; CF$_3$];
[{4-(4-methoxycarbonylbut-1-ynyl)cyclohexyl};CH$_3$;CN;2; CF$_3$];
[{cyclopent-1-enyl};CH$_3$;CN;2;CF$_3$];
[{3-(prop-1-ynyl)cyclopent-1-enyl};CH$_3$;CN;2;CF$_3$];
[{3-(prop-2-ynyl)cyclopent-1-enyl};CH$_3$;CN;2;CF$_3$];
[{cyclopent-2-enyl};CH$_3$;CN;2;CF$_3$];
[{3-(prop-1-ynyl)cyclopent-2-enyl};CH$_3$;CN;2;CF$_3$];
[{3-(prop-2-ynyl)cyclopent-2-enyl};CH$_3$;CN;2;CF$_3$];
[{cyclopent-3-enyl};CH$_3$;CN;2;CF$_3$];
[{3-(prop-1-ynyl)cyclopent-3-enyl};CH$_3$;CN;2;CF$_3$];
[{3-(prop-2-ynyl)cyclopent-3-enyl};CH$_3$;CN;2;CF$_3$];
[{3-ethynylcyclohex-1-enyl};CH$_3$;CN;2;CF$_3$];
[{3-(prop-1-ynyl)cyclohex-1-enyl};CH$_3$;CN;2;CF$_3$];
[{3-(prop-2-ynyl)cyclohex-1-enyl};CH$_3$;CN;2;CF$_3$];
[{4-fluorocyclohex-1-enyl};CH$_3$;CN;2;CF$_3$];
[{4-(prop-2-enyl)cyclohex-1-enyl};CH$_3$;CN;2;CF$_3$];
[{4-ethynylcyclohex-1-enyl};CH$_3$;CN;2;CF$_3$];
[{4-(prop-1-ynyl)cyclohex-1-enyl};CH$_3$;CN;2;CF$_3$];
[{4-(prop-2-ynyl)cyclohex-1-enyl};CH$_3$;CN;2;CF$_3$];
[{3-(prop-1-ynyl)cyclohex-2-enyl};CH$_3$;CN;2;CF$_3$];
[{3-(prop-2-ynyl)cyclohex-2-enyl};CH$_3$;CN;2;CF$_3$];
[{4-(prop-2-enyl)cyclohex-2-enyl};CH$_3$;CN;2;CF$_3$];
[{4-ethynylcyclohex-2-enyl};CH$_3$;CN;2;CF$_3$];
[{4-(prop-1-ynyl)cyclohex-2-enyl};CH$_3$;CN;2;CF$_3$];
[{4-(prop-2-ynyl)cyclohex-2-enyl};CH$_3$;CN;2;CF$_3$];
[{3-(prop-1-ynyl)cyclohex-3-enyl};CH$_3$;CN;2;CF$_3$];
[{3-(prop-2-ynyl)cyclohex-3-enyl};CH$_3$;CN;2;CF$_3$];
[{4-fluorocyclohex-3-enyl};CH$_3$;CN;2;CF$_3$];
[{4-(prop-2-enyl)cyclohex-3-enyl};CH$_3$;CN;2;CF$_3$];
[{4-ethynylcyclohex-3-enyl};CH$_3$;CN;2;CF$_3$];
[{4-(prop-1-ynyl)cyclohex-3-enyl};CH$_3$;CN;2;CF$_3$];
[{4-(prop-2-ynyl)cyclohex-3-enyl};CH$_3$;CN;2;CF$_3$];
[{3-(fluoromethyl)cyclopentyl};H;CONH$_2$;2;CF$_3$];
[{3-(difluoromethyl)cyclopentyl};H;CONH$_2$;2;CF$_3$];
[{3-(trifluoromethyl)cyclopentyl};H;CONH$_2$;2;CF$_3$];
[{3-ethynylcyclopentyl};H;CONH$_2$;2;CF$_3$];
[{3-(prop-1-ynyl)cyclopentyl};H;CONH$_2$;2;CF$_3$];
[{3-(prop-2-ynyl)cyclopentyl};H;CONH$_2$;2;CF$_3$];
[{3-(prop-2-ynyloxy)cyclopentyl};H;CONH$_2$;2;CF$_3$];
[{3-ethynylcyclohexyl};H;CONH$_2$;2;CF$_3$];

[{3-(prop-1-ynyl)cyclohexyl};H;CONH$_2$;2;CF$_3$];
[{3-(prop-2-ynyl)cyclohexyl};H;CONH$_2$;2;CF$_3$];
[{3-(prop-2-ynyloxy)cyclohexyl};H;CONH$_2$;2;CF$_3$];
[{4-fluorocyclohexyl};H;CONH$_2$;2;CF$_3$];
[{4,4-difluorocyclohexyl};H;CONH$_2$;2;CF$_3$];
[{4-ethynylcyclohexyl};H;CONH$_2$;2;CF$_3$];
[{4-(prop-1-ynyl)cyclohexyl};H;CONH$_2$;2;CF$_3$];
[{4-(prop-2-ynyl)cyclohexyl};H;CONH$_2$;2;CF$_3$];
[{4-(3-methoxyprop-1-ynyl)cyclohexyl};H;CONH$_2$;2;CF$_3$];
[{4-(3-dimethylaminoprop-1-ynyl)cyclohexyl};H;CONH$_2$;2;CF$_3$];
[{4-(4-methoxycarbonylbut-1-ynyl)cyclohexyl};H;CONH$_2$;2;CF$_3$];
[{cyclopent-1-enyl};H;CONH$_2$;2;CF$_3$];
[{3-(prop-1-ynyl)cyclopent-1-enyl};H;CONH$_2$;2;CF$_3$];
[{3-(prop-2-ynyl)cyclopent-1-enyl};H;CONH$_2$;2;CF$_3$];
[{cyclopent-2-enyl};H;CONH$_2$;2;CF$_3$];
[{3-(prop-1-ynyl)cyclopent-2-enyl};H;CONH$_2$;2;CF$_3$];
[{3-(prop-2-ynyl)cyclopent-2-enyl};H;CONH$_2$;2;CF$_3$];
[{cyclopent-3-enyl};H;CONH$_2$;2;CF$_3$];
[{3-(prop-1-ynyl)cyclopent-3-enyl};H;CONH$_2$;2;CF$_3$];
[{3-(prop-2-ynyl)cyclopent-3-enyl};H;CONH$_2$;2;CF$_3$];
[{3-ethynylcyclohex-1-enyl};H;CONH$_2$;2;CF$_3$];
[{3-(prop-1-ynyl)cyclohex-1-enyl};H;CONH$_2$;2;CF$_3$];
[{3-(prop-2-ynyl)cyclohex-1-enyl};H;CONH$_2$;2;CF$_3$];
[{4-fluorocyclohex-1-enyl};H;CONH$_2$;2;CF$_3$];
[{4-(prop-2-enyl)cyclohex-1-enyl};H;CONH$_2$;2;CF$_3$];
[{4-ethynylcyclohex-1-enyl};H;CONH$_2$;2;CF$_3$];
[{4-(prop-1-ynyl)cyclohex-1-enyl};H;CONH$_2$;2;CF$_3$];
[{4-(prop-2-ynyl)cyclohex-1-enyl};H;CONH$_2$;2;CF$_3$];
[{3-(prop-1-ynyl)cyclohex-2-enyl};H;CONH$_2$;2;CF$_3$];
[{3-(prop-2-ynyl)cyclohex-2-enyl};H;CONH$_2$;2;CF$_3$];
[{4-(prop-2-enyl)cyclohex-2-enyl};H;CONH$_2$;2;CF$_3$];
[{4-ethynylcyclohex-2-enyl};H;CONH$_2$;2;CF$_3$];
[{4-(prop-1-ynyl)cyclohex-2-enyl};H;CONH$_2$;2;CF$_3$];
[{4-(prop-2-ynyl)cyclohex-2-enyl};H;CONH$_2$;2;CF$_3$];
[{3-(prop-1-ynyl)cyclohex-3-enyl};H;CONH$_2$;2;CF$_3$];
[{3-(prop-2-ynyl)cyclohex-3-enyl};H;CONH$_2$;2;CF$_3$];
[{4-fluorocyclohex-3-enyl};H;CONH$_2$;2;CF$_3$];
[{4-(prop-2-enyl)cyclohex-3-enyl};H;CONH$_2$;2;CF$_3$];
[{4-ethynylcyclohex-3-enyl};H;CONH$_2$;2;CF$_3$];
[{4-(prop-1-ynyl)cyclohex-3-enyl};H;CONH$_2$;2;CF$_3$];
[{4-(prop-2-ynyl)cyclohex-3-enyl};H;CONH$_2$;2;CF$_3$];
[{3-(fluoromethyl)cyclopentyl};F;CONH$_2$;2;CF$_3$];
[{3-(difluoromethyl)cyclopentyl};F;CONH$_2$;2;CF$_3$];
[{3-(trifluoromethyl)cyclopentyl};F;CONH$_2$;2;CF$_3$];
[{3-ethynylcyclopentyl};F;CONH$_2$;2;CF$_3$];
[{3-(prop-1-ynyl)cyclopentyl};F;CONH$_2$;2;CF$_3$];
[{3-(prop-2-ynyl)cyclopentyl};F;CONH$_2$;2;CF$_3$];
[{3-(prop-2-ynyloxy)cyclopentyl};F;CONH$_2$;2;CF$_3$];
[{3-ethynylcyclohexyl};F;CONH$_2$;2;CF$_3$];
[{3-(prop-1-ynyl)cyclohexyl};F;CONH$_2$;2;CF$_3$];
[{3-(prop-2-ynyl)cyclohexyl};F;CONH$_2$;2;CF$_3$];
[{3-(prop-2-ynyloxy)cyclohexyl};F;CONH$_2$;2;CF$_3$];
[{4-fluorocyclohexyl};F;CONH$_2$;2;CF$_3$];
[{4,4-difluorocyclohexyl};F;CONH$_2$;2;CF$_3$];
[{4-ethynylcyclohexyl};F;CONH$_2$;2;CF$_3$];
[{4-(prop-1-ynyl)cyclohexyl};F;CONH$_2$;2;CF$_3$];
[{4-(prop-2-ynyl)cyclohexyl};F;CONH$_2$;2;CF$_3$];
[{4-(3-methoxyprop-1-ynyl)cyclohexyl};F;CONH$_2$;2;CF$_3$];
[{4-(3-dimethylaminoprop-1-ynyl)cyclohexyl};F;CONH$_2$;2;CF$_3$];
[{4-(4-methoxycarbonylbut-1-ynyl)cyclohexyl};F;CONH$_2$;2;CF$_3$];
[{cyclopent-1-enyl};F;CONH$_2$;2;CF$_3$];
[{3-(prop-1-ynyl)cyclopent-1-enyl};F;CONH$_2$;2;CF$_3$];
[{3-(prop-2-ynyl)cyclopent-1-enyl};F;CONH$_2$;2;CF$_3$];
[{cyclopent-2-enyl};F;CONH$_2$;2;CF$_3$];
[{3-(prop-1-ynyl)cyclopent-2-enyl};F;CONH$_2$;2;CF$_3$];
[{3-(prop-2-ynyl)cyclopent-2-enyl};F;CONH$_2$;2;CF$_3$];
[{cyclopent-3-enyl};F;CONH$_2$;2;CF$_3$];
[{3-(prop-1-ynyl)cyclopent-3-enyl};F;CONH$_2$;2;CF$_3$];
[{3-(prop-2-ynyl)cyclopent-3-enyl};F;CONH$_2$;2;CF$_3$];
[{3-ethynylcyclohex-1-enyl};F;CONH$_2$;2;CF$_3$];
[{3-(prop-1-ynyl)cyclohex-1-enyl};F;CONH$_2$;2;CF$_3$];
[{3-(prop-2-ynyl)cyclohex-1-enyl};F;CONH$_2$;2;CF$_3$];
[{4-fluorocyclohex-1-enyl};F;CONH$_2$;2;CF$_3$];
[{4-(prop-2-enyl)cyclohex-1-enyl};F;CONH$_2$;2;CF$_3$];
[{4-ethynylcyclohex-1-enyl};F;CONH$_2$;2;CF$_3$];
[{4-(prop-1-ynyl)cyclohex-1-enyl};F;CONH$_2$;2;CF$_3$];
[{4-(prop-2-ynyl)cyclohex-1-enyl};F;CONH$_2$;2;CF$_3$];
[{3-(prop-1-ynyl)cyclohex-2-enyl};F;CONH$_2$;2;CF$_3$];
[{3-(prop-2-ynyl)cyclohex-2-enyl};F;CONH$_2$;2;CF$_3$];
[{4-(prop-2-enyl)cyclohex-2-enyl};F;CONH$_2$;2;CF$_3$];
[{4-ethynylcyclohex-2-enyl};F;CONH$_2$;2;CF$_3$];
[{4-(prop-1-ynyl)cyclohex-2-enyl};F;CONH$_2$;2;CF$_3$];
[{4-(prop-2-ynyl)cyclohex-2-enyl};F;CONH$_2$;2;CF$_3$];
[{3-(prop-1-ynyl)cyclohex-3-enyl};F;CONH$_2$;2;CF$_3$];
[{3-(prop-2-ynyl)cyclohex-3-enyl};F;CONH$_2$;2;CF$_3$];
[{4-fluorocyclohex-3-enyl};F;CONH$_2$;2;CF$_3$];
[{4-(prop-2-enyl)cyclohex-3-enyl};F;CONH$_2$;2;CF$_3$];
[{4-ethynylcyclohex-3-enyl};F;CONH$_2$;2;CF$_3$];
[{4-(prop-1-ynyl)cyclohex-3-enyl};F;CONH$_2$;2;CF$_3$];
[{4-(prop-2-ynyl)cyclohex-3-enyl};F;CONH$_2$;2;CF$_3$];
[{3-(fluoromethyl)cyclopentyl};Cl;CONH$_2$;2;CF$_3$];
[{3-(difluoromethyl)cyclopentyl};Cl;CONH$_2$;2;CF$_3$];
[{3-(trifluoromethyl)cyclopentyl};Cl;CONH$_2$;2;CF$_3$];
[{3-ethynylcyclopentyl};Cl;CONH$_2$;2;CF$_3$];
[{3-(prop-1-ynyl)cyclopentyl};Cl;CONH$_2$;2;CF$_3$];
[{3-(prop-2-ynyl)cyclopentyl};Cl;CONH$_2$;2;CF$_3$];
[{3-(prop-2-ynyloxy)cyclopentyl};Cl;CONH$_2$;2;CF$_3$];
[{3-ethynylcyclohexyl};Cl;CONH$_2$;2;CF$_3$];
[{3-(prop-1-ynyl)cyclohexyl};Cl;CONH$_2$;2;CF$_3$];
[{3-(prop-2-ynyl)cyclohexyl};Cl;CONH$_2$;2;CF$_3$];
[{3-(prop-2-ynyloxy)cyclohexyl};Cl;CONH$_2$;2;CF$_3$];
[{4-fluorocyclohexyl};Cl;CONH$_2$;2;CF$_3$];
[{4,4-difluorocyclohexyl};Cl;CONH$_2$;2;CF$_3$];
[{4-ethynylcyclohexyl};Cl;CONH$_2$;2;CF$_3$];
[{4-(prop-1-ynyl)cyclohexyl};Cl;CONH$_2$;2;CF$_3$];
[{4-(prop-2-ynyl)cyclohexyl};Cl;CONH$_2$;2;CF$_3$];
[{4-(3-methoxyprop-1-ynyl)cyclohexyl};Cl;CONH$_2$;2;CF$_3$];
[{4-(3-dimethylaminoprop-1-ynyl)cyclohexyl};Cl;CONH$_2$;2;CF$_3$];
[{4-(4-methoxycarbonylbut-1-ynyl)cyclohexyl};Cl;CONH$_2$;2;CF$_3$];
[{cyclopent-1-enyl};Cl;CONH$_2$;2;CF$_3$];
[{3-(prop-1-ynyl)cyclopent-1-enyl};Cl;CONH$_2$;2;CF$_3$];
[{3-(prop-2-ynyl)cyclopent-1-enyl};Cl;CONH$_2$;2;CF$_3$];
[{cyclopent-2-enyl};Cl;CONH$_2$;2;CF$_3$];
[{3-(prop-1-ynyl)cyclopent-2-enyl};Cl;CONH$_2$;2;CF$_3$];
[{3-(prop-2-ynyl)cyclopent-2-enyl};Cl;CONH$_2$;2;CF$_3$];
[{cyclopent-3-enyl};Cl;CONH$_2$;2;CF$_3$];
[{3-(prop-1-ynyl)cyclopent-3-enyl};Cl;CONH$_2$;2;CF$_3$];
[{3-(prop-2-ynyl)cyclopent-3-enyl};Cl;CONH$_2$;2;CF$_3$];
[{3-ethynylcyclohex-1-enyl};Cl;CONH$_2$;2;CF$_3$];
[{3-(prop-1-ynyl)cyclohex-1-enyl};Cl;CONH$_2$;2;CF$_3$];
[{3-(prop-2-ynyl)cyclohex-1-enyl};Cl;CONH$_2$;2;CF$_3$];
[{4-fluorocyclohex-1-enyl};Cl;CONH$_2$;2;CF$_3$];
[{4-(prop-2-enyl)cyclohex-1-enyl};Cl;CONH$_2$;2;CF$_3$];
[{4-ethynylcyclohex-1-enyl};Cl;CONH$_2$;2;CF$_3$];
[{4-(prop-1-ynyl)cyclohex-1-enyl};Cl;CONH$_2$;2;CF$_3$];
[{4-(prop-2-ynyl)cyclohex-1-enyl};Cl;CONH$_2$;2;CF$_3$];

[{3-(prop-1-ynyl)cyclohex-2-enyl};Cl;CONH$_2$;2;CF$_3$];
[{3-(prop-2-ynyl)cyclohex-2-enyl};Cl;CONH$_2$;2;CF$_3$];
[{4-(prop-2-enyl)cyclohex-2-enyl};Cl;CONH$_2$;2;CF$_3$];
[{4-ethynylcyclohex-2-enyl};Cl;CONH$_2$;2;CF$_3$];
[{4-(prop-1-ynyl)cyclohex-2-enyl};Cl;CONH$_2$;2;CF$_3$];
[{4-(prop-2-ynyl)cyclohex-2-enyl};Cl;CONH$_2$;2;CF$_3$];
[{3-(prop-1-ynyl)cyclohex-3-enyl};Cl;CONH$_2$;2;CF$_3$];
[{3-(prop-2-ynyl)cyclohex-3-enyl};Cl;CONH$_2$;2;CF$_3$];
[{4-fluorocyclohex-3-enyl};Cl;CONH$_2$;2;CF$_3$];
[{4-(prop-2-enyl)cyclohex-3-enyl};Cl;CONH$_2$;2;CF$_3$];
[{4-ethynylcyclohex-3-enyl};Cl;CONH$_2$;2;CF$_3$];
[{4-(prop-1-ynyl)cyclohex-3-enyl};Cl;CONH$_2$;2;CF$_3$];
[{4-(prop-2-ynyl)cyclohex-3-enyl};Cl;CONH$_2$;2;CF$_3$];
[{3-(fluoromethyl)cyclopentyl};CH$_3$;CONH$_2$;2;CF$_3$];
[{3-(difluoromethyl)cyclopentyl};CH$_3$;CONH$_2$;2;CF$_3$];
[{3-(trifluoromethyl)cyclopentyl};CH$_3$;CONH$_2$;2;CF$_3$];
[{3-ethynylcyclopentyl};CH$_3$;CONH$_2$;2;CF$_3$];
[{3-(prop-1-ynyl)cyclopentyl};CH$_3$;CONH$_2$;2;CF$_3$];
[{3-(prop-2-ynyl)cyclopentyl};CH$_3$;CONH$_2$;2;CF$_3$];
[{3-(prop-2-ynyloxy)cyclopentyl};CH$_3$;CONH$_2$;2;CF$_3$];
[{3-ethynylcyclohexyl};CH$_3$;CONH$_2$;2;CF$_3$];
[{3-(prop-1-ynyl)cyclohexyl};CH$_3$;CONH$_2$;2;CF$_3$];
[{3-(prop-2-ynyl)cyclohexyl};CH$_3$;CONH$_2$;2;CF$_3$];
[{3-(prop-2-ynyloxy)cyclohexyl};CH$_3$;CONH$_2$;2;CF$_3$];
[{4-fluorocyclohexyl};CH$_3$;CONH$_2$;2;CF$_3$];
[{4,4-difluorocyclohexyl};CH$_3$;CONH$_2$;2;CF$_3$];
[{4-ethynylcyclohexyl};CH$_3$;CONH$_2$;2;CF$_3$];
[{4-(prop-1-ynyl)cyclohexyl};CH$_3$;CONH$_2$;2;CF$_3$];
[{4-(prop-2-ynyl)cyclohexyl};CH$_3$;CONH$_2$;2;CF$_3$];
[{4-(3-methoxyprop-1-ynyl)cyclohexyl};CH$_3$;CONH$_2$;2;CF$_3$];
[{4-(3-dimethylaminoprop-1-ynyl)cyclohexyl};CH$_3$;CONH$_2$;2;CF$_3$];
[{4-(4-methoxycarbonylbut-1-ynyl)cyclohexyl};CH$_3$;CONH$_2$;2;CF$_3$];
[{cyclopent-1-enyl};CH$_3$;CONH$_2$;2;CF$_3$];
[{3-(prop-1-ynyl)cyclopent-1-enyl};CH$_3$;CONH$_2$;2;CF$_3$];
[{3-(prop-2-ynyl)cyclopent-1-enyl};CH$_3$;CONH$_2$;2;CF$_3$];
[{cyclopent-2-enyl};CH$_3$;CONH$_2$;2;CF$_3$];
[{3-(prop-1-ynyl)cyclopent-2-enyl};CH$_3$;CONH$_2$;2;CF$_3$];
[{3-(prop-2-ynyl)cyclopent-2-enyl};CH$_3$;CONH$_2$;2;CF$_3$];
[{cyclopent-3-enyl};CH$_3$;CONH$_2$;2;CF$_3$];
[{3-(prop-1-ynyl)cyclopent-3-enyl};CH$_3$;CONH$_2$;2;CF$_3$];
[{3-(prop-2-ynyl)cyclopent-3-enyl};CH$_3$;CONH$_2$;2;CF$_3$];
[{3-ethynylcyclohex-1-enyl};CH$_3$;CONH$_2$;2;CF$_3$];
[{3-(prop-1-ynyl)cyclohex-1-enyl};CH$_3$;CONH$_2$;2;CF$_3$];
[{3-(prop-2-ynyl)cyclohex-1-enyl};CH$_3$;CONH$_2$;2;CF$_3$];
[{4-fluorocyclohex-1-enyl};CH$_3$;CONH$_2$;2;CF$_3$];
[{4-(prop-2-enyl)cyclohex-1-enyl};CH$_3$;CONH$_2$;2;CF$_3$];
[{4-ethynylcyclohex-1-enyl};CH$_3$;CONH$_2$;2;CF$_3$];
[{4-(prop-1-ynyl)cyclohex-1-enyl};CH$_3$;CONH$_2$;2;CF$_3$];
[{4-(prop-2-ynyl)cyclohex-1-enyl};CH$_3$;CONH$_2$;2;CF$_3$];
[{3-(prop-1-ynyl)cyclohex-2-enyl};CH$_3$;CONH$_2$;2;CF$_3$];
[{3-(prop-2-ynyl)cyclohex-2-enyl};CH$_3$;CONH$_2$;2;CF$_3$];
[{4-(prop-2-enyl)cyclohex-2-enyl};CH$_3$;CONH$_2$;2;CF$_3$];
[{4-ethynylcyclohex-2-enyl};CH$_3$;CONH$_2$;2;CF$_3$];
[{4-(prop-1-ynyl)cyclohex-2-enyl};CH$_3$;CONH$_2$;2;CF$_3$];
[{4-(prop-2-ynyl)cyclohex-2-enyl};CH$_3$;CONH$_2$;2;CF$_3$];
[{3-(prop-1-ynyl)cyclohex-3-enyl};CH$_3$;CONH$_2$;2;CF$_3$];
[{3-(prop-2-ynyl)cyclohex-3-enyl};CH$_3$;CONH$_2$;2;CF$_3$];
[{4-fluorocyclohex-3-enyl};CH$_3$;CONH$_2$;2;CF$_3$];
[{4-(prop-2-enyl)cyclohex-3-enyl};CH$_3$;CONH$_2$;2;CF$_3$];
[{4-ethynylcyclohex-3-enyl};CH$_3$;CONH$_2$;2;CF$_3$];
[{4-(prop-1-ynyl)cyclohex-3-enyl};CH$_3$;CONH$_2$;2;CF$_3$];
[{4-(prop-2-ynyl)cyclohex-3-enyl};CH$_3$;CONH$_2$;2;CF$_3$];
[{3-(fluoromethyl)cyclopentyl};CH$_3$;CONH$_2$;2;CF$_3$];
[{3-(difluoromethyl)cyclopentyl};CH$_3$;CONH$_2$;2;CF$_3$];
[{3-(trifluoromethyl)cyclopentyl};CH$_3$;CONH$_2$;2;CF$_3$];
[{3-ethynylcyclopentyl};CH$_3$;CONH$_2$;2;CF$_3$];
[{3-(prop-1-ynyl)cyclopentyl};CH$_3$;CONH$_2$;2;CF$_3$];
[{3-(prop-2-ynyl)cyclopentyl};CH$_3$;CONH$_2$;2;CF$_3$];
[{3-(prop-2-ynyloxy)cyclopentyl};CH$_3$;CONH$_2$;2;CF$_3$];
[{3-ethynylcyclohexyl};CH$_3$;CONH$_2$;2;CF$_3$];
[{3-(prop-1-ynyl)cyclohexyl};CH$_3$;CONH$_2$;2;CF$_3$];
[{3-(prop-2-ynyl)cyclohexyl};CH$_3$;CONH$_2$;2;CF$_3$];
[{3-(prop-2-ynyloxy)cyclohexyl};CH$_3$;CONH$_2$;2;CF$_3$];
[{4-fluorocyclohexyl};CH$_3$;CONH$_2$;2;CF$_3$];
[{4,4-difluorocyclohexyl};CH$_3$;CONH$_2$;2;CF$_3$];
[{4-ethynylcyclohexyl};CH$_3$;CONH$_2$;2;CF$_3$];
[{4-(prop-1-ynyl)cyclohexyl};CH$_3$;CONH$_2$;2;CF$_3$];
[{4-(prop-2-ynyl)cyclohexyl};CH$_3$;CONH$_2$;2;CF$_3$];
[{4-(3-methoxyprop-1-ynyl)cyclohexyl};CH$_3$;CONH$_2$;2;CF$_3$];
[{4-(3-dimethylaminoprop-1-ynyl)cyclohexyl};CH$_3$;CONH$_2$;2;CF$_3$];
[{4-(4-methoxycarbonylbut-1-ynyl)cyclohexyl};CH$_3$;CONH$_2$;2;CF$_3$];
[{cyclopent-1-enyl};CH$_3$;CONH$_2$;2;CF$_3$];
[{3-(prop-1-ynyl)cyclopent-1-enyl};CH$_3$;CONH$_2$;2;CF$_3$];
[{3-(prop-2-ynyl)cyclopent-1-enyl};CH$_3$;CONH$_2$;2;CF$_3$];
[{cyclopent-2-enyl};CH$_3$;CONH$_2$;2;CF$_3$];
[{3-(prop-1-ynyl)cyclopent-2-enyl};CH$_3$;CONH$_2$;2;CF$_3$];
[{3-(prop-2-ynyl)cyclopent-2-enyl};CH$_3$;CONH$_2$;2;CF$_3$];
[{cyclopent-3-enyl};CH$_3$;CONH$_2$;2;CF$_3$];
[{3-(prop-1-ynyl)cyclopent-3-enyl};CH$_3$;CONH$_2$;2;CF$_3$];
[{3-(prop-2-ynyl)cyclopent-3-enyl};CH$_3$;CONH$_2$;2;CF$_3$];
[{3-ethynylcyclohex-1-enyl};CH$_3$;CONH$_2$;2;CF$_3$];
[{3-(prop-1-ynyl)cyclohex-1-enyl};CH$_3$;CONH$_2$;2;CF$_3$];
[{3-(prop-2-ynyl)cyclohex-1-enyl};CH$_3$;CONH$_2$;2;CF$_3$];
[{4-fluorocyclohex-1-enyl};CH$_3$;CONH$_2$;2;CF$_3$];
[{4-(prop-2-enyl)cyclohex-1-enyl};CH$_3$;CONH$_2$;2;CF$_3$];
[{4-ethynylcyclohex-1-enyl};CH$_3$;CONH$_2$;2;CF$_3$];
[{4-(prop-1-ynyl)cyclohex-1-enyl};CH$_3$;CONH$_2$;2;CF$_3$];
[{4-(prop-2-ynyl)cyclohex-1-enyl};CH$_3$;CONH$_2$;2;CF$_3$];
[{3-(prop-1-ynyl)cyclohex-2-enyl};CH$_3$;CONH$_2$;2;CF$_3$];
[{3-(prop-2-ynyl)cyclohex-2-enyl};CH$_3$;CONH$_2$;2;CF$_3$];
[{4-(prop-2-enyl)cyclohex-2-enyl};CH$_3$;CONH$_2$;2;CF$_3$];
[{4-ethynylcyclohex-2-enyl};CH$_3$;CONH$_2$;2;CF$_3$];
[{4-(prop-1-ynyl)cyclohex-2-enyl};CH$_3$;CONH$_2$;2;CF$_3$];
[{4-(prop-2-ynyl)cyclohex-2-enyl};CH$_3$;CONH$_2$;2;CF$_3$];
[{3-(prop-1-ynyl)cyclohex-3-enyl};CH$_3$;CONH$_2$;2;CF$_3$];
[{3-(prop-2-ynyl)cyclohex-3-enyl};CH$_3$;CONH$_2$;2;CF$_3$];
[{4-fluorocyclohex-3-enyl};CH$_3$;CONH$_2$;2;CF$_3$];
[{4-(prop-2-enyl)cyclohex-3-enyl};CH$_3$;CONH$_2$;2;CF$_3$];
[{4-ethynylcyclohex-3-enyl};CH$_3$;CONH$_2$;2;CF$_3$];
[{4-(prop-1-ynyl)cyclohex-3-enyl};CH$_3$;CONH$_2$;2;CF$_3$];
[{4-(prop-2-ynyl)cyclohex-3-enyl};CH$_3$;CONH$_2$;2;CF$_3$];
[{3-(methoxyimino)cyclopentyl};H;H;0;CF$_3$];
[{3-(methoxyimino)cyclopentyl};H;H;2;CF$_3$];
[{3-(methoxyimino)cyclopentyl};H;H;0;C$_2$F$_5$];
[{3-(methoxyimino)cyclopentyl};H;H;2;C$_2$F$_5$];
[{3-(methoxyimino)cyclopentyl};H;CO$_2$CH$_3$;2;CF$_3$];
[{3-(methoxyimino)cyclopentyl};F;CO$_2$CH$_3$;2;CF$_3$];
[{3-(methoxyimino)cyclopentyl};Cl;CO$_2$CH$_3$;2;CF$_3$];
[{3-(methoxyimino)cyclopentyl};CH$_3$;CO$_2$CH$_3$;2;CF$_3$];
[{3-(methoxyimino)cyclopentyl};CH$_3$;CO$_2$CH$_3$;2;CF$_3$];
[{3-(methoxyimino)cyclopentyl};H;CN;2;CF$_3$];
[{3-(methoxyimino)cyclopentyl};F;CN;2;CH$_3$];
[{3-(methoxyimino)cyclopentyl};Cl;CN;2;CF$_3$];
[{3-(methoxyimino)cyclopentyl};CH$_3$;CN;2;CF$_3$];
[{3-(methoxyimino)cyclopentyl};H;CONH$_2$;2;CF$_3$];
[{3-(methoxyimino)cyclopentyl};F;CONH$_2$;2;CF$_3$];
[{3-(methoxyimino)cyclopentyl};Cl;CONH$_2$;2;CF$_3$];
[{3-(methoxyimino)cyclopentyl};CH$_3$;CONH$_2$;2;CF$_3$];

[{3-(methoxyimino)cyclopentyl};CH$_3$;CONH$_2$;2;CF$_3$];
[{3-(ethoxyimino)cyclopentyl};H;H;0;CF$_3$];
[{3-(ethoxyimino)cyclopentyl};H;H;2;CF$_3$];
[{3-(ethoxyimino)cyclopentyl};H;H;0;C$_2$F$_5$];
[{3-(ethoxyimino)cyclopentyl};H;H;2;C$_2$F$_5$];
[{3-(ethoxyimino)cyclopentyl};H;CO$_2$CH$_3$;2;CF$_3$];
[{3-(ethoxyimino)cyclopentyl};F;CO$_2$CH$_3$;2;CF$_3$];
[{3-(ethoxyimino)cyclopentyl};Cl;CO$_2$CH$_3$;2;CF$_3$];
[{3-(ethoxyimino)cyclopentyl};CH$_3$;CO$_2$CH$_3$;2;CF$_3$];
[{3-(ethoxyimino)cyclopentyl};CH$_3$;CO$_2$CH$_3$;2;CF$_3$];
[{3-(ethoxyimino)cyclopentyl};H;CN;2;CF$_3$];
[{3-(ethoxyimino)cyclopentyl};F;CN;2;CF$_3$];
[{3-(ethoxyimino)cyclopentyl};Cl;CN;2;CF$_3$];
[{3-(ethoxyimino)cyclopentyl};CH$_3$;CN;2;CF$_3$];
[{3-(ethoxyimino)cyclopentyl};H;CONH$_2$;2;CF$_3$];
[{3-(ethoxyimino)cyclopentyl};F;CONH$_2$;2;CF$_3$];
[{3-(ethoxyimino)cyclopentyl};Cl;CONH$_2$;2;CF$_3$];
[{3-(ethoxyimino)cyclopentyl};CH$_3$;CONH$_2$;2;CF$_3$];
[{3-(ethoxyimino)cyclopentyl};CH$_3$;CONH$_2$;2;CF$_3$];
[{3-(methoxyimino)cyclohexyl};H;H;0;CF$_3$];
[{3-(methoxyimino)cyclohexyl};H;H;2;CF$_3$];
[{3-(methoxyimino)cyclohexyl};H;H;0;C$_2$F$_5$];
[{3-(methoxyimino)cyclohexyl};H;H;2;C$_2$F$_5$];
[{3-(methoxyimino)cyclohexyl};H;CO$_2$CH$_3$;2;CF$_3$];
[{3-(methoxyimino)cyclohexyl};F;CO$_2$CH$_3$;2;CF$_3$];
[{3-(methoxyimino)cyclohexyl};Cl;CO$_2$CH$_3$;2;CF$_3$];
[{3-(methoxyimino)cyclohexyl};CH$_3$;CO$_2$CH$_3$;2;CF$_3$];
[{3-(methoxyimino)cyclohexyl};CH$_3$;CO$_2$CH$_3$;2;CF$_3$];
[{3-(methoxyimino)cyclohexyl};H;CN;2;CF$_3$];
[{3-(methoxyimino)cyclohexyl};F;CN;2;CF$_3$];
[{3-(methoxyimino)cyclohexyl};Cl;CN;2;CF$_3$];
[{3-(methoxyimino)cyclohexyl};CH$_3$;CN;2;CF$_3$];
[{3-(methoxyimino)cyclohexyl};H;CONH$_2$;2;CF$_3$];
[{3-(methoxyimino)cyclohexyl};F;CONH$_2$;2;CF$_3$];
[{3-(methoxyimino)cyclohexyl};Cl;CONH$_2$;2;CF$_3$];
[{3-(methoxyimino)cyclohexyl};CH$_3$;CONH$_2$;2;CF$_3$];
[{3-(methoxyimino)cyclohexyl};CH$_3$;CONH$_2$;2;CF$_3$];
[{3-(ethoxyimino)cyclohexyl};H;H;0;CF$_3$];
[{3-(ethoxyimino)cyclohexyl};H;H;2;CF$_3$];
[{3-(ethoxyimino)cyclohexyl};H;H;0;C$_2$F$_5$];
[{3-(ethoxyimino)cyclohexyl};H;H;2;C$_2$F$_5$];
[{3-(ethoxyimino)cyclohexyl};H;CO$_2$CH$_3$;2;CF$_3$];
[{3-(ethoxyimino)cyclohexyl};F;CO$_2$CH$_3$;2;CF$_3$];
[{3-(ethoxyimino)cyclohexyl};Cl;CO$_2$CH$_3$;2;CF$_3$];
[{3-(ethoxyimino)cyclohexyl};CH$_3$;CO$_2$CH$_3$;2;CF$_3$];
[{3-(ethoxyimino)cyclohexyl};CH$_3$;CO$_2$CH$_3$;2;CF$_3$];
[{3-(ethoxyimino)cyclohexyl};H;CN;2;CF$_3$];
[{3-(ethoxyimino)cyclohexyl};F;CN;2;CF$_3$];
[{3-(ethoxyimino)cyclohexyl};Cl;CN;2;CF$_3$];
[{3-(ethoxyimino)cyclohexyl};CH$_3$;CN;2;CF$_3$];
[{3-(ethoxyimino)cyclohexyl};H;CONH$_2$;2;CF$_3$];
[{3-(ethoxyimino)cyclohexyl};F;CONH$_2$;2;CF$_3$];
[{3-(ethoxyimino)cyclohexyl};Cl;CONH$_2$;2;CF$_3$];
[{3-(ethoxyimino)cyclohexyl};CH$_3$;CONH$_2$;2;CF$_3$];
[{3-(ethoxyimino)cyclohexyl};CH$_3$;CONH$_2$;2;CF$_3$];
[{4-(methoxyimino)cyclohexyl};H;H;0;CF$_3$];
[{4-(methoxyimino)cyclohexyl};H;H;2;CF$_3$];
[{4-(methoxyimino)cyclohexyl};H;H;0;C$_2$F$_5$];
[{4-(methoxyimino)cyclohexyl};H;H;2;C$_2$F$_5$];
[{4-(methoxyimino)cyclohexyl};H;CO$_2$CH$_3$;2;CF$_3$];
[{4-(methoxyimino)cyclohexyl}F;CO$_2$CH$_3$;2;CF$_3$];
[{4-(methoxyimino)cyclohexyl};Cl;CO$_2$CH$_3$;2;CF$_3$];
[{4-(methoxyimino)cyclohexyl};CH$_3$;CO$_2$CH$_3$;2;CF$_3$];
[{4-(methoxyimino)cyclohexyl};CH$_3$;CO$_2$CH$_3$;2;CF$_3$];
[{4-(methoxyimino)cyclohexyl};H;CN;2;CF$_3$];
[{4-(methoxyimino)cyclohexyl};F;CN;2;CF$_3$];
[{4-(methoxyimino)cyclohexyl};Cl;CN;2;CF$_3$];
[{4-(methoxyimino)cyclohexyl};CH$_3$;CN;2;CF$_3$];
[{4-(methoxyimino)cyclohexyl};H;CONH$_2$;2;CF$_3$];
[{4-(methoxyimino)cyclohexyl};F;CONH$_2$;2;CF$_3$];
[{4-(methoxyimino)cyclohexyl};Cl;CONH$_2$;2;CF$_3$];
[{4-(methoxyimino)cyclohexyl};CH$_3$;CONH$_2$;2;CF$_3$];
[{4-(methoxyimino)cyclohexyl};CH$_3$;CONH$_2$;2;CF$_3$];
[{4-(ethoxyimino)cyclohexyl};H;H;0;CF$_3$];
[{4-(ethoxyimino)cyclohexyl};H;H;2;CF$_3$];
[{4-(ethoxyimino)cyclohexyl};H;H;0;C$_2$F$_5$];
[{4-(ethoxyimino)cyclohexyl};H;H;2;C$_2$F$_5$];
[{4-(ethoxyimino)cyclohexyl}H;CO$_2$CH$_3$;2;CF$_3$];
[{4-(ethoxyimino)cyclohexyl};F;CO$_2$CH$_3$;2;CF$_3$];
[{4-(ethoxyimino)cyclohexyl};Cl;CO$_2$CH$_3$;2;CF$_3$];
[{4-(ethoxyimino)cyclohexyl};CH$_3$;'CO$_2$CH$_3$;2;CF$_3$];
[{4-(ethoxyimino)cyclohexyl};CH$_3$;CO$_2$CH$_3$;2;CF$_3$];
[{4-(ethoxyimino)cyclohexyl};H;CN;2;CF$_3$];
[{4-(ethoxyimino)cyclohexyl};F;CN;2;CF$_3$];
[{4-(ethoxyimino)cyclohexyl};Cl;CN;2;CF$_3$];
[{4-(ethoxyimino)cyclohexyl};CH$_3$;CN;2;CF$_3$];
[{4-(ethoxyimino)cyclohexyl};H;CONH$_2$;2;CF$_3$];
[{4-(ethoxyimino)cyclohexyl};F; CONH$_2$;2;CF$_3$];
[{4-(ethoxyimino)cyclohexyl};Cl;CONH$_2$;2;CF$_3$];
[{4-(ethoxyimino)cyclohexyl};CH$_3$;CONH$_2$;2;CF$_3$];
[{4-(ethoxyimino)cyclohexyl};CH$_3$;CONH$_2$;2;CF$_3$]

Next, Formulation Examples are shown. The term "part(s)" means part(s) by weight. The compounds of the present invention are represented by the compound numbers as described above.

Formulation Example 1

Nine parts of any one of the present compounds (1) to (67) is dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 2

Five parts of the present compound (1) and 4 parts of a compound selected from the following group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

The group [A]:

aluminum phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos;

alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb;

acrinathrin, allethrin, benfluthrin, beta-cyfluthrin, bifenthrin, cycloprothrin, cyfluthrin, cyhalothrin, empenthrin, deltamethrin, esfenvalerate, ethofenprox, fenvalerate, flucythrinate, flufenoprox, flumethrin, fluvalinate, halfenprox, imiprothrin, prallethrin, pyrethrins, resmethrin, sigma-cypermethrin, silafluofen, tefluthrin, tralomethrin, transfluthrin, tetramethrin, lambda-cyhalothrin, gamma-cyhalothrin, furamethrin, taufluvalinate, 2,3,5,6-tetrafluoro-4-methylbenzyl 2,2-dimethyl-3-(1-propenyl)cyclopropanecarboxylate, 2,3,5,6-tetrafluoro-4-(methoxymethyl)benzyl 2,2-dimethyl-3-(2-methyl-1-propenyl)cyclopropanecarboxylate, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl 2,2,3,3-tetramethylcyclopropanecarboxylate;

cartap, bensultap, thiocyclam, monosultap, bisultap;

imidacloprid, nitenpyram, acetamiprid, thiamethoxam, thiacloprid;

chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, triazuron;

acetoprole, fipronil, vaniliprole, pyriprole, pyrafluprole;

chromafenozide, halofenozide, methoxyfenozide, tebufenozide;

aldrin, dieldrin, dienochlor, endosulfan, methoxychlor;

nicotine sulfate;

avermectin-B, bromopropylate, buprofezin, chlorphenapyr, cyromazine, D-D (1,3-dichloropropene), emamectin-benzoate, fenazaquin, flupyrazofos, hydroprene, methoprene, indoxacarb, metoxadiazone, milbemycin-A, pymetrozine, pyridalyl, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, protrifenbute, spiromesifen, sulfur, metaflumizone, spirotetramat, pyrifluquinazone, chlorantraniliprole, tralopyril, a compound represented by the following formula (A):

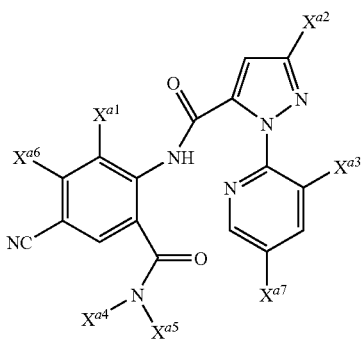

wherein $X^{a1}$ represents methyl, chlorine, bromine or fluorine, $X^{a2}$ represents fluorine, chlorine, bromine, C1-C4 haloalkyl or C1-C4 haloalkoxy, $X^{a3}$ represents fluorine, chlorine or bromine, $X^{a4}$ represents optionally substituted C1-C4 alkyl, optionally substituted C3-C4 alkenyl, optionally substituted C3-C4 alkynyl, optionally substituted C3-C5 cycloalkyl or hydrogen, $X^{a5}$ represents hydrogen or methyl, $X^{a6}$ represents hydrogen, fluorine or chlorine, and $X^{a7}$ represents hydrogen, fluorine or chlorine;

a compound represented by the following formula (B):

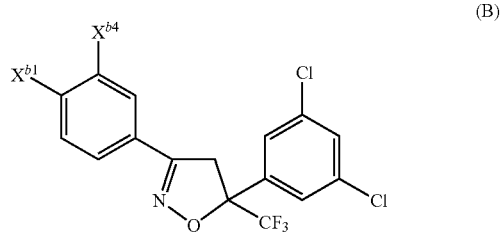

wherein $X^{b1}$ represents) $X^{b2}$—NH—C(=O), $X^{b2}$—C(=O)—NH—C$_2$, $X^{b3}$—S(O), optionally substituted pyrrol-1-yl, optionally substituted imidazol-1-yl, optionally substituted pyrazol-1-yl, or optionally substituted 1,2,4-triazol-1-yl, $X^{b2}$ represents optionally substituted C1-C4 haloalkyl such as 2,2,2-trifluoroethyl or optionally substituted C3-C6 cycloalkyl such as cyclopropyl, $X^{b3}$ represents optionally substituted C1-C4 alkyl such as methyl, and $X^{b4}$ represents hydrogen, chroline, cyano or methyl;

a compound represented by the following formula (C):

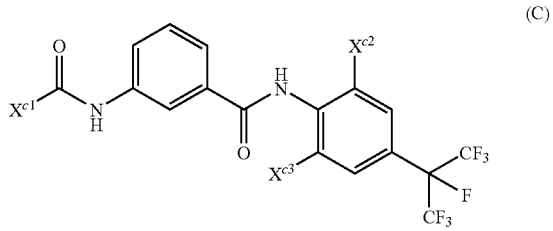

wherein $X^{c1}$ represents optionally substituted C1-C4 alkyl such as 3,3,3-trifluoropropyl, optionally substituted C1-C4 alkoxy such as 2,2,2-trichloroethoxy or optionally substituted phenyl such as 4-cyanophenyl, $X^{c2}$ represents methyl or trifluoromethylthio, and $X^{c3}$ represents methyl or halogen;

acequinocyl, amitraz, benzoximate, bifenazate, bromopropylate, chinomethionate, chlorobenzilate, CPCBS (chlorfenson), clofentezine, cyflumetofen, kelthane (dicofol), fenbutatin oxide, fenothiocarb, fenpyroximate, fluacrypyrim, fluproxyfen, hexythiazox, propargite (BPPS), pyridaben, pyrimidifen, tebufenpyrad, tetradifon, spirodiclofen, spiromesifen, spirotetramat, amidoflumet, and cyenopyrafen.

Formulation Example 3

Five parts of the present compound (4) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 4

Five parts of the present compound (6) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 5

Five parts of the present compound (7) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 6

Five parts of the present compound (11) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 7

Five parts of the present compound (12) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 8

Five parts of the present compound (13) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 9

Five parts of the present compound (18c) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 10

Five parts of the present compound (18t) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 11

Five parts of the present compound (20) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 12

Five parts of the present compound (21) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 13

Five parts of the present compound (22) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 14

Five parts of the present compound (26t) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 15

Five parts of the present compound (26c) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 16

Five parts of the present compound (29) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 17

Five parts of the present compound (30) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 18

Five parts of the present compound (31) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 19

Five parts of the present compound (32) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 20

Five parts of the present compound (33) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 21

Five parts of the present compound (34) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 22

Five parts of the present compound (35) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 23

Five parts of the present compound (40) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 24

Five parts of the present compound (43) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 25

Five parts of the present compound (44) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 26

Five parts of the present compound (45) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 27

Five parts of the present compound (51t) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 28

Five parts of the present compound (51c) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 29

Five parts of the present compound (52) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 30

Five parts of the present compound (55) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 31

Five parts of the present compound (59) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 32

Five parts of the present compound (60) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 33

Five parts of SORPOL 5060 (registered trade name for TOHO Chemical Industry Co., LTD.) is added to 40 parts of any one of the present compounds (1) to (67) and mixed thoroughly. Then, 32 parts of CARPLEX #80 (registered trade name for Shionogi & Co., Ltd., synthetic anhydrous silicon oxide fine powder) and 23 parts of 300 mesh diatomaceous earth are added thereto and mixed with a juice mixer to obtain a wettable powder.

Formulation Example 34

Three parts of any one of the present compounds (1) to (67), 5 parts of synthetic hydrous silicon oxide fine powder, 5 parts of sodium dodecylbenzenesulfonate, 30 parts of bentonite and 57 parts of clay are mixed by stirring thoroughly. To this mixture an appropriate amount of water is added. The mixture is further stirred, granulated with a granulator, and then air-dried to obtain a granule.

Formulation Example 35

Four point five parts of any one of the present compounds (1) to (67), 1 part of synthetic hydrous silicon oxide fine powder, 1 part of Dorires B (manufactured by Sankyo) as a flocculant, and 7 parts of clay are mixed thoroughly with a mortar and then by stirring with a juice mixer. To the resultant mixture 86.5 parts of cut clay is added and mixed by stirring thoroughly to obtain a dust.

Formulation Example 36

Ten parts of any one of the present compounds (1) to (67), 35 parts of white carbon containing 50% by weight of polyoxyethylene alkylether sulfate ammonium salt relative to the white carbon, and 55 parts of water are mixed and then finely-divided by a wet grinding method to obtain a formulation.

Formulation Example 37

Zero point five part of any one of the present compounds (1) to (67) is dissolved in 10 parts of dichloromethane. This solution is mixed with 89.5 parts of Isopar M (isoparaffin: registered trade name for Exxon Chemical) to obtain an oil solution.

Formulation Example 38

Zero point one part of any one of the present compounds (1) to (67) and 49.9 parts of NEO-THIOZOL (Chuo Kasei Co., Ltd.) are placed in an aerosol can. An aerosol valve is fitted to the can and the can is then charged with 25 parts of dimethyl ether and 25 parts of LPG. An actuator is fitted to the can to obtain an oily aerosol.

Formulation Example 39

An aerosol container is charged with 0.6 parts of any one of the present compounds (1) to (67), 0.01 part of BHT, 5 parts of xylene, a mixture of 3.39 parts of a deodorized kerosine and 1 part of an emulsifying agent [Atmos 300 (registered trade name for Atmos Chemical Ltd.)] and 50 parts of distilled water. A valve part is attached to the container and the container is then charged with 40 parts of a propellant (LPG) through the valve under increased pressure to obtain an aqueous aerosol.

Formulation Example 40

Five parts of any one of the present compounds (1) to (67) is dissolved in 80 parts of diethylene glycol monoethyl ether. Thereto 15 parts of propylene carbonate is mixed to obtain a spot-on liquid formulation.

Formulation Example 41

Ten parts of any one of the present compounds (1) to (67) is dissolved in 70 parts of diethylene glycol monoethyl ether. Thereto 20 parts of 2-octyldodecanol is mixed to obtain a pour-on liquid formulation.

Formulation Example 42

To 0.5 parts of any one of the present compounds (1) to (67) are added 60 parts of NIKKOL TEALS-42 (a 42% aqueous solution of triethanolamine lauryl sulfate, Nikko Chemicals) and 20 parts of propylene glycol. The mixture is stirred well to obtain a homogeneous solution. Thereto 19.5 parts of water is added and mixed by stirring thoroughly to obtain a homogeneous shampoo formulation.

Formulation Example 43

A porous ceramic plate with a length of 4.0 cm, a width of 0.4 cm and a thickness of 1.2 cm is impregnated with a solution of 0.1 g of any one of the present compounds (1) to (67) in 2 ml of propylene glycol to obtain a heating-type smoking pesticide.

Formulation Example 44

Five parts of any one of the present compounds (1) to (67) and 95 parts of an ethylene-methyl methacrylate copolymer (the proportion of methyl methacrylate in the copolymer: 10% by weight, ACRYFT WD301, Sumitomo Chemical) are melted and kneaded in a sealed pressure kneader (Moriyama Manufacturing Co., Ltd.). The obtained kneaded product is extruded through a molding die using an extruder to obtain a molded bar with a length of 15 cm and a diameter of 3

Formulation Example 45

Five parts of any one of the present compounds (1) to (67) and 95 parts of a flexible polyvinyl chloride resin are melted and kneaded in a sealed pressure kneader (Moriyama Manufacturing Co., Ltd.). The obtained kneaded product is extruded through a molding die using an extruder to obtain a molded bar with a length of 15 cm and a diameter of 3 mm.

Next, effectiveness of the compound of the present invention as the active ingredient of a pesticidal composition is shown by Test Examples.

Test Example 1

A formulation of any one of the present compounds (1), (2), (4), (5), (7), (11), (12), (13), (18t), (18c), (19), (20), (21), (22), (25t), (25c), (26t), (26c), (27), (29), (30), (31), (32), (33), (34), (35), (36), (38), (40), (41), (43), (47), (49), (50), (55) and (56) obtained according to Formulation Example 36 was diluted so that the active ingredient concentration was 500 ppm to obtain a test solution.

At the same time, 50 g of culture soil, Bonsol No. 2 (manufactured by Sumitomo Chemical Co., Ltd.) was put into a polyethylene cup, and 10 to 15 seeds of rice were planted therein. The rice plants were grown until the second foliage leaf was developed, and then cut so as to have the same height of 5 cm. The test solution was sprayed on the rice paints in an amount of 20 ml/cup. After the test solution sprayed on the rice plants was dried, the rice plants were placed in a plastic cup for the purpose of preventing test worms from escaping. Thirty first-instar larvae of brown rice planthopper were released into the cup, and the cup was sealed with a lid. Then the cup was placed in a greenhouse at 25° C. for 6 days. Then, the number of parasitic brown rice planthoppers on the rice plants was examined.

As a result, on the plants treated with any one of the present compounds (1), (2), (4), (5), (7), (11), (12), (13), (18t), (18c), (19), (20), (21), (22), (25t), (25c), (26t), (26c), (27), (29), (30), (31), (32), (33), (34), (35), (36), (38), (40), (41), (43), (47), (49), (50), (55) and (56), the number of the parasitic pests was 3 or smaller.

Test Example 2

A formulation of any one of the present compounds (2), (4), (5), (7), (11), (12), (13), (18t), (18c), (19), (20), (21), (22), (25t), (25c), (26t), (26c), (27), (29), (30), (31), (32), (33), (34), (35), (38), (43), (47), (49), (50), (55) and (56) obtained according to Formulation Example 36 was diluted so that the active ingredient concentration was 55.6 ppm to obtain a test solution.

At the same time, 50 g of culture soil, Bonsol No. 2 (manufactured by Sumitomo Chemical Co., Ltd.) was put into a polyethylene cup with five holes of 5 mm diameter at the bottom, and 10 to 15 seeds of rice were planted therein. The rice plants were grown until the second foliage leaf was developed, and then treated with 45 ml of the test solution by allowing the plants to absorb the test solution from the bottom of the cup. The rice plants were placed in a greenhouse at 25° C. for 6 days and then cut into the same height of 5 cm. Thirty first-instar larvae of brown rice planthopper were released into the greenhouse at 25° C. and left for 6 days. Then, the number of parasitic brown rice planthoppers on the rice plants was examined.

As a result, on the plants treated with any one of the present compounds (2), (4), (5), (7), (11), (12), (13), (18t), (18c), (19), (20), (21), (22), (25t), (25c), (26t), (26c), (27), (29), (30), (31), (32), (33), (34), (35), (38), (43), (47), (49), (50), (55) and (56), the number of the parasitic pests was 3 or smaller.

Test Example 3

A formulation of any one of the present compounds (4), (5), (7), (11), (12), (13), (18t), (18c), (19), (20), (22), (25t), (26t), (26c), (28), (29), (30), (31), (32), (33), (34), (35), (39), (40), (41), (43), (49) and (50) obtained according to Formulation Example 36 was diluted with water so that the active ingredient concentration was 500 ppm to obtain a test solution.

At the same time, a cucumber was planted in a polyethylene cup and was grown until the first foliage leaf was developed. About 20 cotton aphids were placed on the cucumber so that they could be parasitic on the cucumber. One day after, 20 ml/cup of the test solution was sprayed on the cucumber. Six days after spraying, the number of cotton aphids was examined.

As a result, on the plant treated with any one of the present compounds (4), (5), (7), (11), (12), (13), (18t), (18c), (19), (20), (22), (25t), (26t), (26c), (28), (29), (30), (31), (32), (33), (34), (35), (39), (40), (41), (43), (49) and (50), the number of the parasitic pests was 3 or smaller.

Test Example 4

A formulation of any one of the present compounds (1), (4), (5), (7), (11), (12), (13), (18t), (18c), (19), (20), (21), (22), (24), (25t), (25c), (26t), (26c), (27), (29), (30), (31), (32), (33), (34), (35), (40), (41), (43), (49), (50) and (55) obtained according to Formulation Example 36 was diluted with water so that the active ingredient concentration was 500 ppm to obtain a test solution.

A filter paper having a diameter of 5.5 cm was spread on the bottom of a polyethylene cup having a diameter of 5.5 cm and 0.7 ml of the test solution was added dropwise onto the filter paper. As a bait 30 mg of sucrose was uniformly placed on the filter paper. Into the polyethylene cup, 10 female imagoes of *Musca domestica* were released and the cup was sealed with a lid. After 24 hours, the number of surviving *Musca domestica* was examined and the death rate of the pest was calculated.

As a result, the treatments with any one of the present compounds (1), (4), (5), (7), (11), (12), (13), (18t), (18c), (19), (20), (21), (22), (24), (25t), (25c), (26t), (26c), (27), (29), (30), (31), (32), (33), (34), (35), (40), (41), (43), (49), (50) and (55) showed a pest death rate of 90% or more.

Test Example 5

A formulation of any one of the present compounds (4), (5), (7), (12), (13), (18t), (18c), (22), (25t), (25c), (26t), (26c), (29), (30), (31), (32), (33), (34), (40), (41), (43), (49) and (55) obtained according to Formulation Example 36 was diluted with water so that the active ingredient concentration was 500 ppm to obtain a test solution.

A filter paper having a diameter of 5.5 cm was spread on the bottom of a polyethylene cup having a diameter of 5.5 cm and 0.7 ml of the test solution was added dropwise onto the filter paper. As a bait 30 mg of sucrose was uniformly placed on the filter paper. Into the polyethylene cup, 2 male imagoes of *Blattalla germanica* were released and the cup was sealed with a lid. After 6 days, the number of surviving *Blattalla germanica* was examined and the death rate of the pest was calculated.

As a result, the treatments with any one of the present compounds (4), (5), (7), (12), (13), (18t), (18c), (22), (25t), (25c), (26t), (26c), (29), (30), (31), (32), (33), (34), (40), (41), (43), (49) and (55) showed a pest death rate of 100%.

Test Example 6

A formulation of any one of the present compounds (7), (11), (12), (13), (17), (18t), (18c), (22), (24), (25t), (25c), (26t), (26c), (27), (29), (33), (34), (35), (36), (38), (40), (41), (43), (47), (49), (50) and (55) obtained according to Formulation Example 36 was diluted with water so that the active ingredient concentration was 500 ppm to obtain a test solution.

To 100 mL of ion-exchanged water, 0.7 ml of the test solution was added (active ingredient concentration: 3.5 ppm). Into the solution, 20 last-instar larvae of *Culex pipiens* pallens were released. One day after, the number of surviving *Culex pipiens* pallens was examined and the death rate of the pest was calculated.

As a result, the treatments with any one of the present compounds (7), (11), (12), (13), (17), (18t), (18c), (22), (24), (25t), (25c), (26t), (26c), (27), (29), (33), (34), (35), (36), (38), (40), (41), (43), (47), (49), (50) and (55) showed a pest death rate of 95% or more.

Test Example 7

Five milligrams of any one of the present compounds (4), (7), (18t), (22), (25t), (26t), (29), (30), (31), (32), (33), (34), (35), (40), (41), (42), (43), (44) and (55) was dissolved in 10 mL of acetone. One milliliter of the acetone solution was uniformly applied on one side of a filter paper (TOYO No. 2; 5×10 cm), so that the filter paper having a surface area of 50 cm$^2$ was treated with 100 mg/m$^2$ of the present compound. After drying, the filter paper was folded in two and its edges were clipped to make a pouch. Test ticks (non-blood-sucking nymphal ticks, *Haemaphysalis longicornis*, 10 ticks/group) were put into the pouch, and the pouch was sealed with clips. Two days after, the number of surviving ticks was examined and the death rate was calculated.

As a result, the treatments with any one of the present compounds (4), (7), (18t), (22), (25t), (26t), (29), (30), (31), (32), (33), (34), (35), (40), (41), (42), (43), (44) and (55) showed a pest death rate of 90%.

INDUSTRIAL APPLICABILITY

The compound of the present invention has an excellent controlling effect on arthropod pests, and thus it is useful as an active ingredient for a pesticidal composition.

The invention claimed is:
1. A halogen-containing organosulfur compound represented by the formula (I):

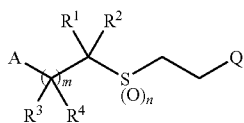

(I)

wherein m represents 0, 1 or 2, n represents 0, 1 or 2,
A represents a C3-C7 cycloalkyl group optionally substituted with a group selected from the groups E1 to E3, or a C5-C7 cycloalkenyl group optionally substituted with a group selected from the groups E1 to E3;
Q represents a C1-C5 haloalkyl group containing at least one fluorine atom;
$R^1$ and $R^3$ are the same as or different from each other, and represent a C1-C4 chain hydrocarbon group optionally substituted with a halogen atom, a halogen atom, or a hydrogen atom;
$R^2$ and $R^4$ are the same as or different from each other, and represent a C1-C4 chain hydrocarbon group optionally substituted with a halogen atom, —C(=G)R$^5$, a cyano group, a halogen atom, or a hydrogen atom;
G represents an oxygen atom or a sulfur atom;
$R^5$ represents a C1-C4 alkyl group optionally substituted with a halogen atom, a hydroxyl group, a C1-C4 alkoxy group optionally substituted with a halogen atom, a C3-C6 alkenyloxy group optionally substituted with a halogen atom, a C3-C6 alkynyloxy group optionally substituted with a halogen atom, an amino group, a C1-C4 alkylamino group optionally substituted, with a halogen atom, a di(C1-C4 alkyl)amino group optionally substituted with a halogen atom, a C2-C5 cyclic amino group, or a hydrogen atom;
the group E1 is a group of monovalent substituents consisting of a C1-C6 chain hydrocarbon group optionally substituted with a group selected from the group L, a C3-C6 cycloalkyl group optionally substituted with a halogen atom, —OR$^6$, —SR$^6$, —S(=O)R$^6$, —S(=O)$_2$R$^6$, —C(=O)R$^7$, —OC(=O)R$^8$, a halogen atom, a cyano group, and a hydroxyl group;
the group E2 is a group of bivalent substituents of which two valences are derived from one atom, consisting of =O, =NO—R$^6$, =C=CH$_2$, and =C(R$^{11}$)R$^{12}$;
the group E3 is a group of bivalent substituents of which two valences are derived from different atoms, consisting of a C2-C6 alkylene group optionally substituted with a group selected from the group L, a C4-C6 alkenylene group optionally substituted with a group selected from the group L, -G-T$^1$-G-, and -G-T$^1$-G-T$^2$-; wherein T$^1$ and T$^2$ are the same as or different from each other, and represent a methylene group or an ethylene group;
the group L consists of a hydroxyl group, a C1-C4 alkoxy group optionally substituted with a halogen atom, a C3-C6 alkenyloxy group optionally substituted with a halogen atom, a C3-C6 alkynyloxy group optionally substituted with a halogen atom, —N(R$^9$)R$^{10}$, a C2-C5 cyclic amino group, —C(=O)R$^7$, —OC(=O)R$^8$ and a halogen atom;
R$^6$ represents a C1-C4 chain hydrocarbon group optionally substituted with a group selected from the group L, or a C3-C6 cycloalkyl group optionally substituted with a group selected from the group L;
R$^7$ represents a hydroxyl group, a C1-C4 alkoxy group optionally substituted with a halogen atom, a C3-C6 alkenyloxy group optionally substituted with a halogen atom, a C3-C6 alkynyloxy group optionally substituted with a halogen atom, an amino group, a C1-C4 alkylamino group optionally substituted with a halogen atom, a di(C1-C4 alkyl)amino group optionally substituted with a halogen atom, a C2-C5 cyclic amino group, a C1-C4 alkyl group optionally substituted with a halogen atom, or a hydrogen atom;
R$^8$ represents a C1-C4 alkoxy group optionally substituted with a halogen atom, a C3-C6 alkenyloxy group optionally substituted with a halogen atom, a C3-C6 alkynyloxy group optionally substituted with a halogen atom, an amino group, a C1-C4 alkylamino group optionally substituted with a halogen atom, a di(C1-C4 alkyl) amino group optionally substituted With a halogen atom, a C2-C5 cyclic amino group, a C1-C4 alkyl group optionally substituted with a halogen atom, or a hydrogen atom;
R$^9$ and R$^{10}$ are the same as or different, from each other, and represent a C1-C4 alkyl group optionally substituted with a halogen atom, a C3-C6 alkenyl group optionally substituted with a halogen atom, a C3-C6 alkynyl group optionally substituted with a halogen atom, a C3-C6 cycloalkyl group optionally substituted with a halogen atom, a phenyl group optionally substituted with a halogen atom, or a hydrogen atom; and
R$^{11}$ and R$^{12}$ are the same as or different from each other, and represent a C1-C4 alkoxy group optionally substituted with a halogen atom, a C1-C4 chain hydrocarbon group optionally substituted, with a halogen atom, a halogen atom, or a hydrogen atom.

2. The halogen-containing organosulfur compound according to claim 1, wherein Q is a C1-C3 haloalkyl group containing at least one fluorine atom.

3. The halogen-containing organosulfur compound according to claim 1, wherein Q is a C1-C5 fluoroalkyl group.

4. The halogen-containing organosulfur compound according to claim 1, wherein Q is a C1-C3 fluoroalkyl group.

5. The halogen-containing organosulfur compound according to any one of claims 1 to 4, wherein m is 0.

6. The halogen-containing organosulfur compound according to any one of claims 1 to 4, wherein m is 1.

7. The halogen-containing organosulfur compound according to claim 1, wherein n is 0.

8. The halogen-containing organosulfur compound according to claim 1, wherein n is 1.

9. The halogen-containing organosulfur compound according to claim 1, wherein n is 2.

10. The halogen-containing organosulfur compound according to claim 1, wherein $R^2$ is a hydrogen atom.

11. The halogen-containing organosulfur compound according to claim 1, wherein $R^2$ is a C1-C4 alkyl group.

12. The halogen-containing organosulfur compound according to claim 1, wherein $R^2$ is a cyano group.

13. The halogen-Containing organosulfur compound according to claim 1, wherein $R^2$ is —C(=G)$R^5$.

14. The halogen-containing organosulfur compound according to claim 1, wherein $R^2$ is —C(=G)$R^5$, G is an oxygen atom, and $R^5$ is an amino group, a C1-C4 alkylamino group optionally substituted with a halogen atom, a di(C1-C4 alkyl)amino group optionally substituted with a halogen atom, or a C2-C5 cyclic amino group.

15. The halogen-containing organosulfur compound according to claim 1, wherein $R^2$ is —C(=G)$R^5$, G is an oxygen atom, and $R^5$ is an amino group.

16. The halogen-containing organosulfur compound according to claim 1, wherein $R^1$ is a hydrogen atom, or a C1-C4 alkyl group optionally substituted with a halogen atom.

17. The halogen-containing organosulfur compound according to claim 1, wherein $R^1$ is a halogen atom.

18. The halogen-containing organosulfur compound according to claim 1, wherein A is a cyclohexyl group optionally substituted with a group selected from the groups E1 to E3, or a cyclohexenyl group optionally substituted with a group selected from the groups E1 to E3.

19. The halogen-containing organosulfur compound according to claim 1, wherein A is a cyclohexyl or cyclohexenyl group which is optionally substituted with a monovalent group selected from the group consisting of a C2-C6 alkynyl group optionally substituted with a group selected from the group L, a C2-C6 alkynyl group optionally substituted with a group selected from the group L, a halogen atom, and a cyano group.

20. The halogen-containing organosulfur compound according to claim 1, wherein A is a cyclohexyl group optionally substituted with a group selected from the group E2.

21. A pesticidal composition which comprises the halogen-containing organosulfur compound according to claim 1 as an active ingredient.

22. A method of controlling an arthropod pest which comprises applying an effective amount of the halogen-containing organosulfur compound according to claim 1 to the arthropod pest or a place where the arthropod pest inhabits.

* * * * *